US007129040B2

(12) United States Patent
Steck et al.

(10) Patent No.: US 7,129,040 B2
(45) Date of Patent: Oct. 31, 2006

(54) TUMOR SUPPRESSOR DESIGNATED TS10Q23.3

(76) Inventors: Peter Steck, 5421 Holly St., Bellaire, TX (US) 77401; Mark A. Pershouse, 4065 McDermed Dr., Houston, TX (US) 77025; Samar A. Jasser, 9411 Kristin Dr., Houston, TX (US) 77031; Alfred W. K. Yung, 4141 Byron St., Houston, TX (US) 77005; Sean V. Tavtigian, 557 E. 1st Ave., #3, Salt Lake City, UT (US) 84103

( * ) Notice: Subject to any disclaimer, the term of this patent is extended or adjusted under 35 U.S.C. 154(b) by 0 days.

(21) Appl. No.: 10/979,642

(22) Filed: Nov. 1, 2004

(65) Prior Publication Data

US 2005/0147995 A1    Jul. 7, 2005

Related U.S. Application Data

(60) Continuation of application No. 10/299,003, filed on Nov. 19, 2002, which is a division of application No. 09/140,749, filed on Aug. 26, 1998, now Pat. No. 6,482,795, which is a continuation-in-part of application No. 08/791,115, filed on Jan. 30, 1997, now Pat. No. 6,262,242.

(60) Provisional application No. 60/083,563, filed on Apr. 30, 1998, provisional application No. 60/057,750, filed on Aug. 26, 1997.

(51) Int. Cl.
*C12Q 1/68* (2006.01)
*G01N 33/53* (2006.01)
*G01N 33/48* (2006.01)
*G01N 33/566* (2006.01)

(52) U.S. Cl. ............................... 435/4; 435/6; 435/7.1; 436/64; 436/501

(58) Field of Classification Search .................... 435/4, 435/6, 7.1; 436/501, 64
See application file for complete search history.

(56) References Cited

U.S. PATENT DOCUMENTS 6,287,854 B1 * 9/2001 Spurr et al. .............. 435/320.1

FOREIGN PATENT DOCUMENTS

WO    WO 97/15686    5/1997
WO    WO 98/33907    8/1998

OTHER PUBLICATIONS

GenBank Accession No. U93051.
GenBank Accession No. U92437.
GenBank Accession No. U92436.
GenBank Accession No. U92435.
GenBank Accession No. W30684.

Arch, E.M. et al., "Deletion of *PTEN* in a Patient with Bannayan-Riley-Ruvalcaba Syndrome Suggests Allelism with Cowden Disease," *Am. J. Med. Genets.*, 1997; 71:489-93.
Albarosa, R. et al., "Deletion mapping of gliomas suggest the presence of two small regions for candidate tumor-suppressor genes in a 17-cM interval on chromosome 10q," *Am J Hum Genet.*, 1996 58:1260-67.
Bork, P., "Powers and Pitfalls in Sequence Analysis," *Genome Research*, 2000; 10:398-400.
Carter, B.S. et al., "Allelic loss of chromosomes 16q and 10q in human prostate cancer," *Proc. Nat. Acad. Sci. USA*, 1990; 87:8751-55.
Fujimoto, M. et al., "Loss of Heterozygosity on Chromosome 10 in Human Glioblastoma Multiforme," *Genomics*, 1989; 4:210-14.
Fults, D. et al., "Molecular Cytogenetic Analysis of a t(7;10) in a Human Glioblastoma Cell Line," *Cancer Genet. Cytogenet.*, 1995; 81:118-24.
Gray, I.C. et al., "Loss of the chromosomal region 10q23-25 in prostate cancer," *Cancer Res.*, 1995; 55:4800-3.
Guldberg, P. et al., "Disruption of the *MMAC1/PTEN* Gene by Deletion or Mutation is a Frequent Event in Malignant Melanoma," *Cancer Res.*, 1997; 57:3660-63.
Herbst, R.A. et al., "Loss of Heterozygosity for 10q22-10qter in Malignant Melanoma Progression," *Cancer Res.*, 1994; 54:3111-14.
Ittmann, M., "Allelic loss on chromosome 10 in prostate adenocarcinoma," *Cancer Res.*, 1996; 56:2143-47.
James, C.D. et al., "Clonal genomic alterations in glioma malignancy stages," *Cancer Res.*, 1988; 48:5546-51.
Karlbom, A.E. et al., Loss of heterozygosity in malignant gliomas involves at least three distinct regions on chromosome 10,: *Hum. Genet.*, 1993; 92:169-74.
Kimmelman, A.C. et al., "Loss of Heterozygosity of Chromosome 10p in Human Gliomas," *Genomics*, 1996; 34:250-54.

(Continued)

*Primary Examiner*—Karen A. Canella
(74) *Attorney, Agent, or Firm*—Jonathan A. Baker; Jay Z. Zhang; Myriad Genetics IP Department

(57) ABSTRACT

A specific region of chromosome 10 (10q23.3) has been implicated by series of studies to contain a tumor suppressor gene involved in gliomas, as well as a number of other human cancers. One gene within this region was identified, and the corresponding coding region of the gene represents a novel 47 kD protein. A domain of this product has an exact match to the conserved catalytic domain of protein tyrosine phosphatases, indicating a possible functional role in phosphorylation events. Sequence analyses demonstrated the a number of exons of the gene were deleted in tumor cell lines used to define the 10q23.3 region, leading to the classification of this gene as a tumor suppressor. Further analyses have demonstrated the presence of a number of mutations in the gene in both glioma and prostate carcinoma cells. Methods for diagnosing and treating cancers related to this tumor suppressor, designated as TS10q23.3, also are disclosed.

49 Claims, 43 Drawing Sheets

OTHER PUBLICATIONS

Klein, J., "Self-nonself discrimination, histoincompatability, and the concept of immunology," *Immunogenetics*, 1999; 50:116-123.

Lacombe, L. et al., "Microsatellite Instability and Deletion Analysis of Chromosome 10 in Human Prostate Cancer," *Int. J. Cancer (Pred. Oncol.)*, 1996; 69:110-13.

Li, D-M. et al., "TEP1, Encoded by a candidate Tumor Suppressor Locus, is a Novel Protein Tyrosine Phosphatase Regulated by Transforming Growth Factor $\exists^1$," *Cancer Res.*, 1997; 57:2124-29.

Li, J. et al., "PTEN, a Putative Protein Tyrosine Phosphatase Gene Mutated in Human Brain, Breast, and Prostate Cancer," *Science*, 1997; 275:1943-47.

Liaw, D. et al., "Germline mutations of the *PTEN* gene in Cowden disease, an inherited breast and thyroid cancer syndrome," *Nature Genet.*, 1997; 16:64-67.

Marsh, D.J. et al., "Germline mutations in *PTEN* are present in Bannayan-Zonana syndrome," *Nature Genet.*, 1997; 16:333-34.

Matthews & Van Holde, *Biochemistry* (textbook), 2nd Ed., pp. 165-171 (1996).

Matthews, B., "Genetic and Structural Analysis of the Protein Stability Problem," *Perspective in Biochemistry*, 1989; 1:6-9.

Murakami, Y.S. et al., "Suppression of the malignant phenotype of human prostate cancer cell line PPC-1 by introduction of normal fragments of human chromosome 10," *Cancer Res.*, 1996; 56:2157-60.

Nelen, M.R. et al., "Germline mutations in the *PTEN/MMAC1* gene in patients with Cowden disease," *Human Mol. Genets.*, 1997; 6:1383-87.

Paul, W.E., ed., *Fundamental Immunology* (textbook), 3rd Ed., pp. 249-251. (1993).

Wilson et al., "2.2 Mb of contiguous nucleotide sequence from chromosome III of *C. elegans*," *Nature*, 1994; 368:32-38.

Pershouse, M.A. et al. Abstract 400, "Allelic mapping of a tumor suppressing region on chromosome 10q in human glioblastomas," *Am. J. Human Genets.*, 57:Suppl. Oct. 1995.

Pershouse, M.A. et al. Abstract 1043, "Functional Localization of Tumor Suppressor Genes on Chromosome 10 in Human Glioblastoma," *Proc. Amer. Assoc. Cancer Res.*, 1994; 35:174.

Pershouse, M.A. et al., "Analysis of the functional role of chromosome 10 loss in human glioblastomas," *Cancer Res.*, 1993; 53:5043-50.

Proft et al., "Identification and characterization of hitherto unknown *Mycoplasma* pneumonia proteins," *Molecular Microbiology*, 1994; 13(2):337-348.

Rasheed, B.K. et al., "Chromosome 10 deletion mapping in human gliomas: a common deletion region in 10q25," *Oncogene*, 1995; 10:2243-46.

Rhei, E. et al., " Mutation Analysis of the Putative Tumor Suppressor Gene *PTEN/MMAC1* in Primary Breast Carcinomas," *Cancer Res.*, 1997; 57:3657-59.

Ristori et al., "Compositional bias and mimicry toward the nonself proteome in immunodominant T cell epitopes of self and nonself antigens," *FASEB Journal*, 2000; 14:431-438.

Sanchez, Y. et al., "Tumor Suppression and apoptosis of human prostate carcinoma mediated by a genetic locus within human chromosome 10pter-q11," *Proc. Nat. Acad. Sci. USA*, 1996; 93:2551-56.

Steck, P.A. et al., "Identification of a candidate tumour suppressor gene, *MMAC1*, at chromosome 10q23.3 that is mutated in multiple advanced cancers," *Nature Genets.*, 1997; 15:356-62.

Steck, P.A. et al., "Two Tumor Suppressive Loci on Chromosome 10 Involved in Human Gliobastomas," *Genes, Chromosomes & Cancer*, 1995; 12:255-61.

Steck, P.A. et al. Abstract D-605, "Functional Roles of and Localization of Chromosome 10 Deletions in Human Glioblastomas," *J. Cell. Biochem.*, Suppl. 18A, p. 211 (Jan. 4-23, 1994).

Tashiro, H. et al., "Muttions in *PTEN* are Frequent in Endometrial Carcinoma but Rare in Other Common Gynecological Malignancies," *Cancer Res.*, 1997; 57:3935-40.

Teng, D. H-F. et al., "*MMAC1/PTEN* mutations in primary tumor specimens and tumor cell lines," *Cancer Res.*, 1997; 57:5221-25.

Trybus, T.M. et al., "Distinct Areas of Allelic Loss on Chromosomal Regions 10p and 10q in Human Prostate Cancer," *Cancer Res.*, 1996; 56:2263-67.

Watling, C.J. et al., "Loss of Heterozygosity Analysis of Chromosomes 9, 10 and 17 in Gliomas in Families," *Can. J. Neurol. Sci.*, 1995; 22:17-21.

* cited by examiner

```
CCCCCTCGCCCCGGCGCGGTCCCGTCCGCGCCTCTCGCTCCCCTCGGTCTCTTCCGAGGCGCCGGCTCCCGGCGGCGGAGGGGG   100
GCAGGCCGGCGGGCGCTGATGTGGCAGGACTCTTTATGCGCTGCGGGCAGGATACCGCTCGGCGCTGGGACGCGCTGCTCTCCTCTC   200
AGCTGCAGCCATGATGGAAGTTGAGAGTTGAGAGCCGCTGTGAGGGAGGAGATGAGAGACGGGCCGGCGCGCCGCGCCCCGGA     300
CCCTCTCAGCGCCTGTGAGCAGCCGCGGGGCAGCCCTGGGGAGCCCGGCTGGGCCGGGCGGGGCGTTCTCGCCTCTTCGT        400
TTCTAACCGTGCAGCCTCTTCCTCGGCTTCCTGGAAAGGAAGTGAAGCTGCGGCGCCCGGCTGAGCCGGGAGCCCGGGCGCGG    500
GCACCTCCCGCTCCTGGAGCGGGGAGAGTTGGTCTCTCTCCCCTTCTACTGCCTCCAACACGGCCTCCGGAGGGTCAGTCACCATTT 600
AGGGCTGGGAACGCCGGAGAGTTGGTCTCTCTCCCCTTGCCCCAGGCCTCCGGCCCACATCCAGGACCCGGCGGTTTTAAA       700
CCCGTCCGCCCGCCACCCCCGTGGCCAGGCCTCTGGCTGCTGAGGAGAAGCAGGCCAGCCGTTCGGAGGATTATTCGTCTCCCATTCGCT 800
GCGCTGCCAGGCCTCTGGCTGCTGAGGAGAAGCAGGCCAAGTCAGGCCATTCCATCCTGCAACCATCCAGCAGCCATTACCCGGCTGCGGTCCAGA 900
AAGCGGGCAGAGCGAGGGGCATCAGCTACCGCCAGTCAGCCAAGTCAGAGCCATTCCATCCTGCAGAGAAGCCCCGCCAGCAGCTTCTGCCATCT 1000
CCTCCTTTTCTTCCAGCAGCCTCCCAGACATGACAGCCATCATCAAAGAGATCGTTAGCAGAACAAACAAAGGAGATATCAAGAGGATGGATTCGAC 1100

AGACTTGACCTATATTTATCCAAACATTATTGCTATGGGATTTCCTGCAGAAAGACTTGAAGGCTATACAGGAACAATATTGATGATGTAGTAAGGT 1200

TTGGATTCAAAGCATAAAAACCATTACAAGATATACAAGATCTTTGTGCTGAAAGACATTATGACACCGCCAAATTTAATTGCAGAGTTGCACAATATCC 1300

TTGAAGACCATAACCCACCACCACCAGCTAGAACTTATCAAACCCCTTTTGTGAAGATCTTGACCAATGGCTAAGTGAAGATGACAATCATGTTGCAGCAATT 1400

CTGTAAAGCTGGAAAGGACCAGAGACGAACTGGTGTAATGATATGTCATATTATTATTACATCGGGGCAAATTTTAAAGGCACAAGAGGCCCTAGATTTCTATG 1500

GAAGTAAGGACCAGAGACAAAAGGGAGTAACTATTCCCAGTCAGAGGCGCTATGTGTATTATTATTATAGCTACCTGTTAAAGAATCATCTGGATTATAG 1600

CAGTGGCACTGTTGTTTCACAAGATGATGTTTGAAACTATTCCAATGTTCAGTGGCGAACTTGCAATCCTCAGTTTGTGGTCTGCCAGCTAAAGGTG 1700
```

FIG. 6A

```
GATATATTCCTCCCAATTCAGGACCCACACGACGGGAAGAGACAAGTTCATGTACTTTGAGTTCCCTCAGCCGTTACCTGTGTGTGGTGATATCAAAGTAG  1800

TTCTTCCACAAACAGAACAAGATGCTAAAAAGGACAAAATGTTTCACTTTTGGGTAAATACATTCTTCATACCAGGACCAGAGAGAAACCTCAGAAAAA   1900

TAGAAAATGGAAGTCTATGTGATCAAGAATCGATAGCATTTGCAGTATAGAGCGTGCAGATAATGACAAGGAATATCTAGTACTTACTTTAACAAAA    2000

TGATCTTGACAAAGCAAATAAAGACAAAGCCAACCGATACTTTTCTCCAAATTTAAGGTGAAGCTGTACTTCACAAAAACAGTAGAGGAGCCGTCAA    2100

CCAGAGGGCTAGCAGTTCAACTTCTGTAACACCAGATGTTAGTGACAATGAACCTGATCATTATAGATATTCTGACACCACTGACTCTGATCCAGAGAA   2200

AACCTTTGATGAAGATCAGCATCACACAAATTACACAAAGTCTGAATTTTTTTTATCAAGAGGGATAAAACACCATGAAAATAAACTTGAATAAACTG    2300
AATGGACCCTTTTTTTTAATGGCAATAGGACATTGTGTCAGATTATAGGAACAATTCTCTTTCCTGACCAATCTTGTTGTTTTACCCTATA           2400
TCCACAGGGTTTGACACTTGTGTCCAGTTGTGTAGCTGTGTCATGTAGCCTTTGTGTCAAAGGACATTTAAAATTCAAT                      2500
GGATTAATAAAGATGGCACTTTCCCGTTTTATTCCCAGTTTTATAAAAAGTGGAGACAGACGACTGATGTGTATACGTAGGAATTTTTTCCTTTGTGTTCT  2600
CACCAACTGAAGTGGCTAAAGAGCTTTGTGATATACTTGGTCACATCCTGTGGCAACAGATAAGTTTGCAGTGTGGCTAAGAGAG                 2700
TTCCGAAAGGTTTGCTACCATTCTAATGCATGTATTCGGGTTAGGGCAATGCTCAGAAGGGGAATGCTCAGAAAGGAAATAATTTATGCTCACTGCTGTTTGAC  2800
TATACCATCTCCAGCTATTTACACACCTTTCTTTAGCATGCTACAGTTGGACATTCGGAACATTCGGGTACAGGAATCTGTATTGGGTACAGGAATGACTTAAT  2900
GCATTTTTTTAAAGCATATAAAATAATTGGTGCTAGAAAGGCAGCTAAAGAACAGCAACAATGACTGAATCTCTGCAACATCTTAAGAT            3000
ACAAATGAAGGGATATAAAAATAATTCATAGGTAAGAAACACAGCAACAATGACTAACCATATAAATGTGGAGGCTATCAACAAAGAATGGGCTTG      3100
ACATTATAAAAAATTGACAATGATTTATTAAATATGTTTTCTCAATTGTAAAAAAAA
```

| | | 50 | | 60 | | 70 | | 80 | | 90 | | 100 | | 110 | | 120 | | 130 | |
|---|---|---|---|---|---|---|---|---|---|---|---|---|---|---|---|---|---|---|---|
| 6 C6.1.HUMAN | | GATATCA | AGAGGATGGA | | TTCGACTTAG | | ACTTGACCTA | | TATTTATCCA | | AACATTATTG | | CTATGGGATT | | TCCTTGCAGAA | | AGACTTGAAG | GCG |
| 3 C6.1.MOUSE | | GATATCA | AGAGGATGGA | | TTCGACTTAG | | ACTTGACCTA | | TATTTATCCA | | AATATTATTG | | CTATGGGATT | | TCCTTGCAGAA | | AGACTTGAAG | GTG |
| 37 C6.1.DOG | | GCTACCA | GGAGGATGGG | | TTCGACTTGG | | ACTTGACCTA | | TATTTATCCC | | AACATTATTG | | CTATGGGGTT | | TCCTTGCAGAA | | AGACTTGAAG | GCG |
| 38 NT.COMP | | * * | * | | * | | | | * | | * | | * | | | | | * |
| 44 HUMAN.PEP | | Y Q | E D G | | F D L D | | L T Y | | I Y P | | N I I A | | M G F | | P A E | | R L E G | V |
| 46 MOUSE.PEP | | Y Q | E D G | | F D L D | | L T Y | | I Y P | | N I I A | | M G F | | P A E | | R L E G | V |
| 39 DOG.PEP | | Y Q | E D G | | F D L D | | L T Y | | I Y P | | N I I A | | M G F | | P A E | | R L E G | V |
| 48 PEP.COMP | | | | | | | | | | | | | | | | | | | * |
| 15 TS10q23.3.PEP | | Y Q | E D G | | F D L D | | L T Y | | I Y P | | N I I A | | M G F | | P A E | | R L E G | V |
| | | 140 | | 150 | | 160 | | 170 | | 180 | | 190 | | 200 | | 210 | | 220 | |
| 6 C6.1.HUMAN | | TATACAG | GAACAATATT | | GATGATTGCA | | TAAGGTTTTT | | GGATTCAAAG | | CATAAAAACC | | ATTACAAGAT | | ATACAATCTT | | TGTGCTGAAA | GAC |
| 3 C6.1.MOUSE | | TATACAG | GAACAATATT | | GATGATGTAG | | TAAGGTTTTT | | GGATTCAAAG | | CATAAAAACC | | ATTACAAGAT | | ATACAATCTA | | TGTGCTGAGA | GAC |
| 37 C6.1.DOG | | TATACAG | GAACAATATT | | GATGATGTAG | | TAAGGTTTTT | | GGATTCAAAG | | CATAAAAACC | | ATTACAAGAT | | ATACAATCTG | | TGTGCTGAAA | GAC |
| 38 NT.COMP | | | | | | | | | | | | | | * | | | | | |
| 44 HUMAN.PEP | | Y R | N N I | | D D V V | | R F L | | D S K | | H K N H | | Y K I | | C A E R | H |
| 46 MOUSE.PEP | | Y R | N N I | | D D V V | | R F L | | D S K | | H K N H | | Y K I | | C A E R | H |
| 39 DOG.PEP | | Y R | N N I | | D D V V | | R F L | | D S K | | H K N H | | Y K I | | C A E R | H |
| 48 PEP.COMP | | | | | | | | | | | | | | | | | | | |
| 15 TS10q23.3.PEP | | Y R | N N I | | D D V V | | R F L | | D S K | | H K N H | | Y K I | | C A E R | H |
| | | 230 | | 240 | | 250 | | 260 | | 270 | | 280 | | 290 | | 300 | | 310 | |
| 6 C6.1.HUMAN | | ATTATGA | CACCGCCAAA | | TTTAATTGCA | | GAGTTGCACA | | ATATCCTTTT | | GAAGACCATA | | ACCCACCACA | | GCTAGAACTT | | ATCAAACCTT | TTT |
| 3 C6.1.MOUSE | | ATTATGA | CACCGCCAAA | | TTTAACTGCA | | GAGTTGCACA | | GTATCCTTTT | | GAAGACCATA | | ACCCACCACA | | GCTAGAACTA | | ATCAAACCCT | TCT |
| 37 C6.1.DOG | | ATTATGA | TACCCCCAAA | | TTTAACTGCA | | GAGTTGCACA | | GTATCCTTTT | | GAAGACCATA | | ATCCACCACA | | GCTAGAACTG | | ATCAAACCCT | TTT |
| 38 NT.COMP | | | | | | | | | | | | | | * | | | | | * |
| 44 HUMAN.PEP | | Y D | T A K | | F N C R | | V A Q | | Y P F | | E D H N | | P P Q | | L E L | | I K P F | C |
| 46 MOUSE.PEP | | Y D | T A K | | F N C R | | V A Q | | Y P F | | E D H N | | P P Q | | L E L | | I K P F | C |
| 39 DOG.PEP | | Y D | T A K | | F N C R | | V A Q | | Y P F | | E D H N | | P P Q | | L E L | | I K P F | C |
| 48 PEP.COMP | | | | | | | | | | | | | | | | | | | |
| 15 TS10q23.3.PEP | | Y D | T A K | | F N C R | | V A Q | | Y P F | | E D H N | | P P Q | | L E L | | I K P F | C |
| | | 320 | | 330 | | 340 | | 350 | | 360 | | 370 | | 380 | | 390 | | 400 | |
| 6 C6.1.HUMAN | | GTGAAGA | TCTTGACCAA | | TGGCTAAGTG | | AAGATGACAA | | TCATGTTGCA | | GCAATTCACT | | ACCCACCACA | | GTAAAGCTGG | | AAAGGGACGA | ACTGGTGTAA |
| 3 C6.1.MOUSE | | GTGAAGA | TCTTGACCAA | | TGGCTAAGTG | | AAGATGACAA | | TCATGTGGCA | | GCAATTCACT | | ACCCACCACA | | GTAAAGCTGG | | AAAGGGACGG | ACTGGTGTAA |
| 37 C6.1.DOG | | GTGAAGA | TCCTTGACCAA | | TGGCTAAGTG | | AAGATGACAA | | TCATGTTGCA | | GCAATTCACT | | ATCCACCACA | | GTAAAGCTGG | | AAAGGGACGA | ACTGGTGTAA |
| 38 NT.COMP | | | | | | | | | | | | | | | | | | | |
| 44 HUMAN.PEP | | E D | L D Q | | W L S E | | D D N | | H V A | | A I H C | | P P Q | | K A G | | K G R | T G V M |
| 46 MOUSE.PEP | | E D | L D Q | | W L S E | | D D N | | H V A | | A I H C | | P P Q | | K A G | | K G R | T G V M |
| 39 DOG.PEP | | E D | L D Q | | W L S E | | D D N | | H V A | | A I H C | | P P Q | | K A G | | K G R | T G V M |
| 48 PEP.COMP | | | | | | | | | | | | | | | | | | | |
| 15 TS10q23.3.PEP | | E D | L D Q | | W L S E | | D D N | | H V A | | A I H C | | P P Q | | K A G | | K G R | T G V M |

| | 1490 | 1500 | 1510 | 1520 | 1530 | 1540 | 1550 | 1560 | 1570 |
|---|---|---|---|---|---|---|---|---|---|
| 6 C6.1.HUMAN | GCACTTT | CCCGTTTTAT | TCCAGTTTTA | TAAAAAGTGG | AGACAGACTG | ATGTGTATAC | GTAGGAATTT | TTTCCTTTTG | TGTTCTGTCA CCA |
| 3 C6.1.MOUSE | ↓ | | | | | | | | |
| 37 C6.1.DOG | | | | | | | | | |
| 38 NT.COMP | ↓↓↓↓↓ | | | | | | | | |
| 44 HUMAN.PEP | | | | | | | | | |
| 46 MOUSE.PEP | | | | | | | | | |
| 39 DOG.PEP | | | | | | | | | |
| 48 PEP.COMP | | | | | | | | | |
| 15 TS10q23.3.PEP | | | | | | | | | |

| | 1580 | 1590 | 1600 | 1610 | 1620 | 1630 | 1640 | 1650 | 1660 |
|---|---|---|---|---|---|---|---|---|---|
| 6 C6.1.HUMAN | ACTGAAS | TGGCTAAAGA | GCTTTGTGAT | ATACTGGTTC | ACATCCTACC | CCTTTGCACT | TGTCGCAACA | GATAAGTTTG | CAGTTGGCTA AGA |
| 3 C6.1.MOUSE | ↓ | | | | | | | | |
| 37 C6.1.DOG | | | | | | | | | |
| 38 NT.COMP | ↓↓↓↓↓ | | | | | | | | |
| 44 HUMAN.PEP | | | | | | | | | |
| 46 MOUSE.PEP | | | | | | | | | |
| 39 DOG.PEP | | | | | | | | | |
| 48 PEP.COMP | | | | | | | | | |
| 15 TS10q23.3.PEP | | | | | | | | | |

| | 1670 | 1680 | 1690 | 1700 | 1710 | 1720 | 1730 | 1740 | 1750 |
|---|---|---|---|---|---|---|---|---|---|
| 6 C6.1.HUMAN | GAGGTTT | CCGAAAGGTT | TTGCTACCAT | TCTAATGCAT | GTATTGGGGT | TAGGGCAATG | GAGGGGAATG | CTCAGAAAGG | AAATAATTTT ATG |
| 3 C6.1.MOUSE | ↓ | | | | | | | | |
| 37 C6.1.DOG | | | | | | | | | |
| 38 NT.COMP | ↓↓↓↓↓ | | | | | | | | |
| 44 HUMAN.PEP | | | | | | | | | |
| 46 MOUSE.PEP | | | | | | | | | |
| 39 DOG.PEP | | | | | | | | | |
| 48 PEP.COMP | | | | | | | | | |
| 15 TS10q23.3.PEP | | | | | | | | | |

| | 1760 | 1770 | 1780 | 1790 | 1800 | 1810 | 1820 | 1830 | 1840 |
|---|---|---|---|---|---|---|---|---|---|
| 6 C6.1.HUMAN | CTGGACT | CTGGACCATA | TACCATCTCC | AGCTATTTAC | ACACACCTTT | CTTTAGCAIG | CTACAGTTAT | TAATCTGGAC | ATTCCAGGAA TTG |
| 3 C6.1.MOUSE | ↓ | | | | | | | | |
| 37 C6.1.DOG | | | | | | | | | |
| 38 NT.COMP | ↓↓↓↓↓ | | | | | | | | |
| 44 HUMAN.PEP | | | | | | | | | |
| 46 MOUSE.PEP | | | | | | | | | |
| 39 DOG.PEP | | | | | | | | | |
| 48 PEP.COMP | | | | | | | | | |
| 15 TS10q23.3.PEP | | | | | | | | | |

| | 1850 | 1860 | 1870 | 1880 | 1890 | 1900 | 1910 | 1920 | 1930 |
|---|---|---|---|---|---|---|---|---|---|
| 6 C6.1.HUMAN | GCCGCTG | TCACTGCTG | TTGTTGCCC | ATTTTTTTT | AAAGCATATT | GGTCCTAGAA | AAGCCAGCTA | AAGGAAGTGA | ATCTGTATTG GGG |
| 3 C6.1.MOUSE | ↓ | ↓ | | | | | | | --- |
| 37 C6.1.DOG | | | | | | | | | |
| 38 NT.COMP | ↓↓↓↓ | | | | | | | | |
| 44 HUMAN.PEP | | | | | | | | | |
| 46 MOUSE.PEP | | | | | | | | | |
| 39 DOG.PEP | | | | | | | | | |
| 48 PEP.COMP | | | | | | | | | |
| 15 TS10q23.3.PEP | | | | | | | | | |

| | 1940 | 1950 | 1960 | 1970 | 1980 | 1990 | 2000 | 2010 | 2020 |
|---|---|---|---|---|---|---|---|---|---|
| 6 C6.1.HUMAN | TACAGGA | ATGAACCTTC | TGCAACATCT | TAAGATCCAC | AAATGAAGGG | ATATAAAAAT | AATGTCATAG | GTAAGAAACA | CAGCAACAAT GAC |
| 3 C6.1.MOUSE | ↓ | | | | | | | | --- |
| 37 C6.1.DOG | | | | | | | | | |
| 38 NT.COMP | ↓↓↓↓↓ | | | | | | | | |
| 44 HUMAN.PEP | | | | | | | | | |
| 46 MOUSE.PEP | | | | | | | | | |
| 39 DOG.PEP | | | | | | | | | |
| 48 PEP.COMP | | | | | | | | | |
| 15 TS10q23.3.PEP | | | | | | | | | |

| | 2030 | 2040 | 2050 | 2060 | 2070 | 2080 | 2090 | 2100 | 2110 |
|---|---|---|---|---|---|---|---|---|---|
| 6 C6.1.HUMAN | TTAACCA | TATAAATGTG | GAGGCTATCA | ACAAAGAATG | GGCTTGAAAC | ATTATAAAAA | TTGACAATGA | TTTATTAAAT | ATGTTTCTC AAT |
| 3 C6.1.MOUSE | ↓↓ | | | | | | | | --- |
| 37 C6.1.DOG | | | | | | | | | |
| 38 NT.COMP | ↓↓↓↓↓ | | | | | | | | |
| 44 HUMAN.PEP | | | | | | | | | |
| 46 MOUSE.PEP | | | | | | | | | |
| 39 DOG.PEP | | | | | | | | | |
| 48 PEP.COMP | | | | | | | | | |
| 15 TS10q23.3.PEP | | | | | | | | | |

| | 2120 | 2130 | 2140 | 2150 | 2160 | 2170 | 2180 | 2190 | 2200 |
|---|---|---|---|---|---|---|---|---|---|
| 6 C6.1.HUMAN | TCTAAAA | AAAAAA | | | | | | | |
| 3 C6.1.MOUSE | ↓↓ | --- | | | | | | | |
| 37 C6.1.DOG | | | | | | | | | |
| 38 NT.COMP | ↓↓↓↓↓ | | | | | | | | |
| 44 HUMAN.PEP | | | | | | | | | |
| 46 MOUSE.PEP | | | | | | | | | |
| 39 DOG.PEP | | | | | | | | | |
| 48 PEP.COMP | | | | | | | | | |
| 15 TS10q23.3.PEP | | | | | | | | | |

FIG. 9I

| | | -1030 | -1020 | -1010 | -1000 | -990 | -980 | -970 | -960 | -950 | |
|---|---|---|---|---|---|---|---|---|---|---|---|
| 1 | CA6.CG01.IAIA | CCTC | CCCTCCCCG | GCCGGTTCC | GTCCGCCTCT | CGCTCGCCTC | CCGCCCCCTC | TCGGTCTTCC | GAGGCGCCCG | GGCTCCCCGC | GCCGCG ↑↑↑↑↑↑ |
| 2 | CA6.CG01.IAXBIB | | | | | | | | | | |
| 3 | CA6.CG01.IBXCIC | | | | | | | | | | |
| 4 | CA6.CG01.ICXDID | | | | | | | | | | |
| 5 | CA6.CG01.IDXEIE | | | | | | | | | | |
| 6 | CA6.CG01.IEXFIF | | | | | | | | | | |
| 7 | CA6.CG01.IFXGIG | | | | | | | | | | |
| 8 | CA6.CG01.IGXHIH | | | | | | | | | | |
| 9 | CA6.CG01.IHXI | | | | | | | | | | |

| | | -940 | -930 | -920 | -910 | -900 | -890 | -880 | -870 | -860 | |
|---|---|---|---|---|---|---|---|---|---|---|---|
| 1 | CA6.CG01.IAIA | GCCG | AGGGGCCCCG | CAGGCCCGCG | GGCGGTGATG | GCCTGCAGGACT | CTTTATCGCC | TGGGGCAGGA | TACGCGCTCG | CCGCCTCAGGC | GCCGACT ↑↑↑↑↑↑ |
| 2 | CA6.CG01.IAXBIB | | | | | | | | | | |
| 3 | CA6.CG01.IBXCIC | | | | | | | | | | |
| 4 | CA6.CG01.ICXDID | | | | | | | | | | |
| 5 | CA6.CG01.IDXEIE | | | | | | | | | | |
| 6 | CA6.CG01.IEXFIF | | | | | | | | | | |
| 7 | CA6.CG01.IFXGIG | | | | | | | | | | |
| 8 | CA6.CG01.IGXHIH | | | | | | | | | | |
| 9 | CA6.CG01.IHXI | | | | | | | | | | |

| | | -850 | -840 | -830 | -820 | -810 | -800 | -790 | -780 | -770 | |
|---|---|---|---|---|---|---|---|---|---|---|---|
| 1 | CA6.CG01.IAIA | GCGC | TCAGTTCTCT | CCTCTCGGAA | GCTGCAGCCA | TGATGGAAGT | TTGAGAGTTG | AGCCGCTGTG | AGGCGAGGCC | CGGCTCAGGC | GAGCGA ↑↑↑↑↑↑ |
| 2 | CA6.CG01.IAXBIB | | | | | | | | | | |
| 3 | CA6.CG01.IBXCIC | | | | | | | | | | |
| 4 | CA6.CG01.ICXDID | | | | | | | | | | |
| 5 | CA6.CG01.IDXEIE | | | | | | | | | | |
| 6 | CA6.CG01.IEXFIF | | | | | | | | | | |
| 7 | CA6.CG01.IFXGIG | | | | | | | | | | |
| 8 | CA6.CG01.IGXHIH | | | | | | | | | | |
| 9 | CA6.CG01.IHXI | | | | | | | | | | |

| | | -760 | -750 | -740 | -730 | -720 | -710 | -700 | -690 | -680 | |
|---|---|---|---|---|---|---|---|---|---|---|---|
| 1 | CA6.CG01.IAIA | GATG | AGAGACGGCG | GCGGCCGGCG | CCCGGAGCCC | CCTCTCAGCCC | CTGTGAGCAG | CCGCGGGGCC | AGCCCCTCG | GGGAGCCGGC | CGGGCCT ↑↑↑↑↑↑ |
| 2 | CA6.CG01.IAXBIB | | | | | | | | | | |
| 3 | CA6.CG01.IBXCIC | | | | | | | | | | |
| 4 | CA6.CG01.ICXDID | | | | | | | | | | |
| 5 | CA6.CG01.IDXEIE | | | | | | | | | | |
| 6 | CA6.CG01.IEXFIF | | | | | | | | | | |
| 7 | CA6.CG01.IFXGIG | | | | | | | | | | |
| 8 | CA6.CG01.IGXHIH | | | | | | | | | | |
| 9 | CA6.CG01.IHXI | | | | | | | | | | |

|   |              | -670       | -660       | -650       | -640       | -630       | -620       | -610       | -600       | -590       |
|---|--------------|------------|------------|------------|------------|------------|------------|------------|------------|------------|
| 1 | CA6.CG01.XA1A | GCGG | CGGCGGCAGC | GGCGGCCGTTT | CTCGCCCCCT | TCTCGTCTTT | CAGCCTCTG | CTCCGCTTCT | CCTCGGCTTCT | AAGGTG ↑↑↑↑↑↑ |
| 2 | CA6.CG01.IAXB1B |         |            |            |            |            |            |            |            |            |
| 3 | CA6.CG01.IBXC1C |         |            |            |            |            |            |            |            |            |
| 4 | CA6.CG01.ICXD1D |         |            |            |            |            |            |            |            |            |
| 5 | CA6.CG01.IDXE1E |         |            |            |            |            |            |            |            |            |
| 6 | CA6.CG01.IEXF1F |         |            |            |            |            |            |            |            |            |
| 7 | CA6.CG01.IFXG1G |         |            |            |            |            |            |            |            |            |
| 8 | CA6.CG01.IGXH1H |         |            |            |            |            |            |            |            |            |
| 9 | CA6.CG01.IHXI   |         |            |            |            |            |            |            |            |            |

|   |              | -580       | -570       | -560       | -550       | -540       | -530       | -520       | -510       | -500       |
|---|--------------|------------|------------|------------|------------|------------|------------|------------|------------|------------|
| 1 | CA6.CG01.XA1A | GAAG | CCGTGGGCTC | GGGCGGGAAGC | CGGCTGAGGC | GCGGTCTGAAG | GGGGTCTGAG | CGGGCGGCGGC | ACCTCCCGCT | CCTGAGCCG | GGGGAGAAG  CGGGCG ↑↑↑↑↑↑ |
| 2 | CA6.CG01.IAXB1B |         |            |            |            |            |            |            |            |            |
| 3 | CA6.CG01.IBXC1C |         |            |            |            |            |            |            |            |            |
| 4 | CA6.CG01.ICXD1D |         |            |            |            |            |            |            |            |            |
| 5 | CA6.CG01.IDXE1E |         |            |            |            |            |            |            |            |            |
| 6 | CA6.CG01.IEXF1F |         |            |            |            |            |            |            |            |            |
| 7 | CA6.CG01.IFXG1G |         |            |            |            |            |            |            |            |            |
| 8 | CA6.CG01.IGXH1H |         |            |            |            |            |            |            |            |            |
| 9 | CA6.CG01.IHXI   |         |            |            |            |            |            |            |            |            |

|   |              | -490       | -480       | -470       | -460       | -450       | -440       | -430       | -420       | -410       |
|---|--------------|------------|------------|------------|------------|------------|------------|------------|------------|------------|
| 1 | CA6.CG01.XA1A | CGGC | GGCGGCCCG | GGCGGCTCCAC | GCCGCTAGGAG | CTTCCAGGGAG | GGGGTCTGAAG | TGGCTGTGTCA | CCATTCCAG | GGCTGGGAAC | GCCGAGAGT  TGGTCT ↑↑↑↑↑↑ |
| 2 | CA6.CG01.IAXB1B |    | g       | aattaatagt | tagtacgtgg | atcttcaaa | tatcaaagt | tttcagttg | gagac      | atagccagct  cttaaa |
| 3 | CA6.CG01.IBXC1C |    |          |            |            |            |            |            | atgggaaaat | gatgtctgaa  ttttca |
| 4 | CA6.CG01.ICXD1D |         |            |            |            |            |            |            |            |            |
| 5 | CA6.CG01.IDXE1E |         |            |            |            |            |            |            |            |            |
| 6 | CA6.CG01.IEXF1F |         |            |            |            |            |            |            |            |            |
| 7 | CA6.CG01.IFXG1G |         |            |            |            |            |            |            |            |            |
| 8 | CA6.CG01.IGXH1H |         |            |            |            |            |            |            |            |            |
| 9 | CA6.CG01.IHXI   |         |            |            |            |            |            |            |            |            |

|   |              | -400       | -390       | -380       | -370       | -360       | -350       | -340       | -330       | -320       |
|---|--------------|------------|------------|------------|------------|------------|------------|------------|------------|------------|
| 1 | CA6.CG01.XA1A | CTCC | CCTTCTACTG | CCTCCAACAC | GGGGCCGGCCG | CTCTCTTTT | GCGGCGGCCG | ATCCAGGGAC | CCGGGCCCGGT | TTTAAACCTC | CCGTCCGCCG  TGGTCT ↑↑↑↑ |
| 2 | CA6.CG01.IAXB1B | tctg | acttccagat | tttcactgtg | tcttcttt  | tctgtaagt | gttgccttt | ttagccatga | aaattagaa | gttgaactct  tgtcttt |
| 3 | CA6.CG01.IBXC1C | gggt | tatttttaag | agtacttgat | tagacgtc   | ttgtaaatct | ctatgagcta | ggtacttg  | cactaaatgc | taatgctttt  taaaga |
| 4 | CA6.CG01.ICXD1D |         |            |            |            |            |            |            |            | at         |
| 5 | CA6.CG01.IDXE1E |         |            |            |            |            |            |            |            |            |
| 6 | CA6.CG01.IEXF1F |         |            |            |            |            |            |            |            |            |
| 7 | CA6.CG01.IFXG1G |         |            |            |            |            |            |            |            |            |
| 8 | CA6.CG01.IGXH1H |         |            |            |            |            |            |            |            |            |
| 9 | CA6.CG01.IHXI   |         |            |            |            |            |            |            |            |            |

| | 410 | 420 | 430 | 440 | 450 | 460 | 470 | 480 | 490 | |
|---|---|---|---|---|---|---|---|---|---|---|
| 1 CA6.CG01.XAIA | tagg | cttaaaatcc | tagagtggat | ttattcagtt | aaattattc | acactaagat | gtnatgact | aatactgtat | attttatgt | agacca |
| 2 CA6.CG01.IAXBIB | ttat | cctgtgtctc | tagagctatt | gactgaaaaa | gctgttaggg | catctctaa | ctgtacatca | cctaagttat | ttaaaattgc | tgaatt |
| 3 CA6.CG01.IBXCIC | taaa | agtatgaaa | ggatataac | | | | | | | |
| 4 CA6.CG01.ICXDID | NNNN | NNNNNNNNN | NNNNNNNNNN | NNNNNNNNNN | NNNNNNNNNN | NNNNNNNNN | NNNNNNNNN | NNNNNNNNNN | NNNNNNNNNN | NNNNNN |
| 5 CA6.CG01.IDXEIE | agcc | caatttctga | ctagatgtat | ggagaacct | gtccc | | | | | |
| 6 CA6.CG01.IEXFIF | ttag | catgggacca | atatttaaa | aattttggt | ctataggtag | aaatgagatc | tgtctgtgg | tcttatgtag | tgacacaaac | cac |
| 7 CA6.CG01.IFXGIG | gtca | aaaagctgc | attttccctt | ttcctaatc | ttgtgtgttt | gctgaaatct | ggggcaaagg | tgcgggaggg | ggctaaatga | ctggga |
| 8 CA6.CG01.IGXHIH | cttt | ttgtgtcaaa | aggacattta | aattcaatt | aggattaata | aagatggcac | ttccccagtt | tattccagtt | ttataaaaag | tggaga |
| 9 CA6.CG01.IHXI | | | | | | | | | | |
| | 500 | 510 | 520 | 530 | 540 | 550 | 560 | 570 | 580 | |

| | 590 | 600 | 610 | 620 | 630 | 640 | 650 | 660 | 670 | |
|---|---|---|---|---|---|---|---|---|---|---|
| 1 CA6.CG01.XAIA | aatt | ttaaggtacc | actgtgcata | tgtntaccaa | ctacctgaag | aantatttgg | ttgtacnag | anatatataa | aggatcgct | nggtgt |
| 2 CA6.CG01.IAXBIB | aagt | ggctgctt | gtctangaca | gnnttttaag | gactgccac | ctgattgata | gaactagttg | accttatctt | taacttttg | ttttct |
| 3 CA6.CG01.IBXCIC | | | | | | | | | | |
| 4 CA6.CG01.ICXDID | NNNN | NNNNNNNNN | NNNNNNNNN | NNNNNNNNNN | NNNNNNNNN | NNNNNNNNNN | NNNNNNNNN | NNNNNNNNNN | NNNNNNNNN | NNNNNNN |
| 5 CA6.CG01.IDXEIE | | | | | | | | | | |
| 6 CA6.CG01.IEXFIF | tatg | aagtaggaat | gggagaggaa | agaaatagat | gggaactcag | tcatttggga | atgattcata | tggaatgttt | ttactgctt | ttcaca |
| 7 CA6.CG01.IFXGIG | caga | ctgatgtgta | tacgtgagga | ttttttcctt | tgtgtctg | tcaccaactg | aagtgggctaa | agagcttgr | gatatactgg | |
| 8 CA6.CG01.IGXHIH | | | | | | | | | | |
| 9 CA6.CG01.IHXI | | | | | | | | | | |
| | | | | | | | | | | |

| | | | | | | | | | | |
|---|---|---|---|---|---|---|---|---|---|---|
| 1 CA6.CG01.XAIA | tcca | aggctaatcc | agtttataa | ttttgcataa | tttcctaact | gcgaatatca | tttatttana | acaatttatt | ctccag | |
| 2 CA6.CG01.IAXBIB | tttg | acttggant | aaaangttga | aaaggtaaaa | ggaagga | | | | | |
| 3 CA6.CG01.IBXCIC | NNNN | Ntcctccctc | cccaccctca | gtcnctggaa | aacaggtttt | aaagatagtt | gctaatcctt | atttcttcta | aattttta | |
| 4 CA6.CG01.ICXDID | | | | | | | | | | |
| 5 CA6.CG01.IDXEIE | | | | | | | | | | |
| 6 CA6.CG01.IEXFIF | tcct | accccttttgc | actgtggca | acagataagt | ttgcagttgg | ctaagagagg | tttccgaaag | gttt | | |
| 7 CA6.CG01.IFXGIG | | | | | | | | | | |
| 8 CA6.CG01.IGXHIH | | | | | | | | | | |
| 9 CA6.CG01.IHXI | | | | | | | | | | |

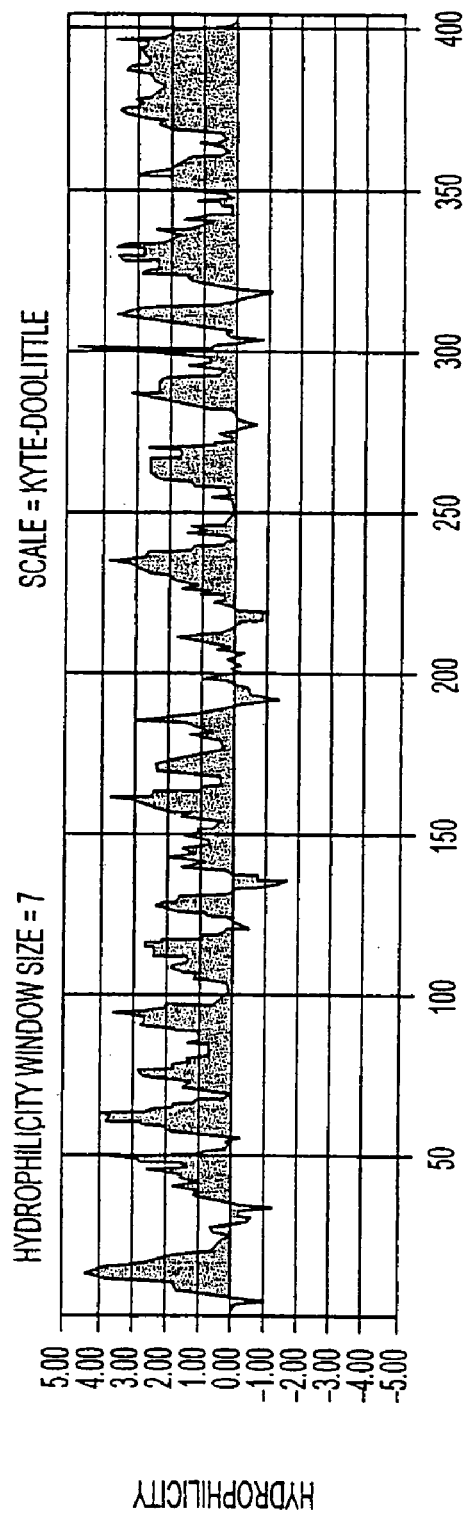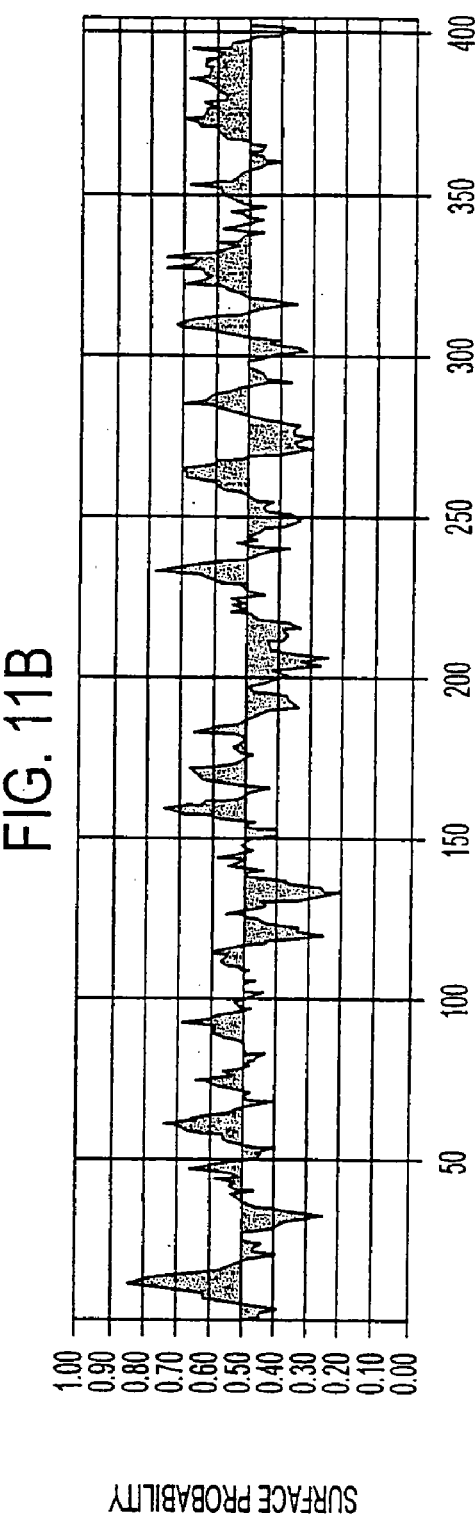

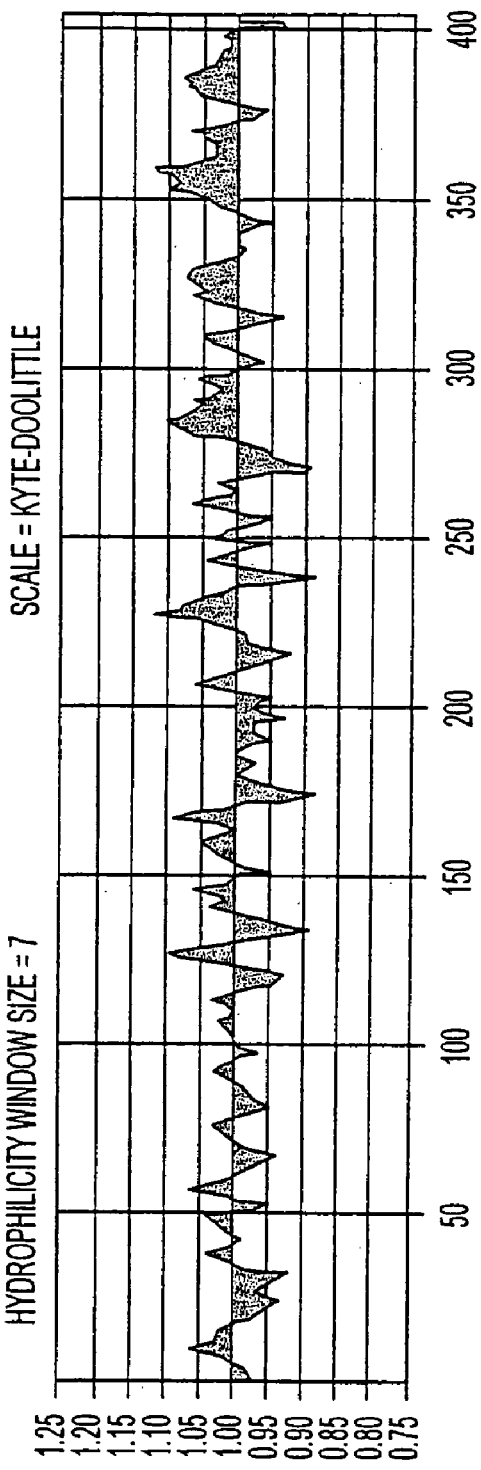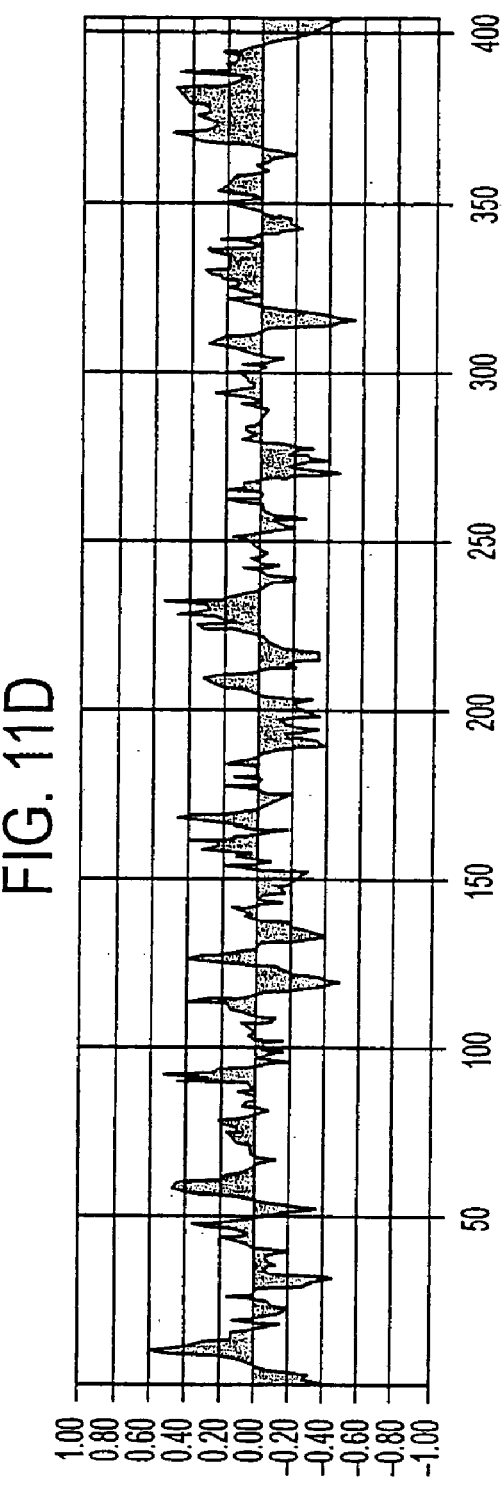

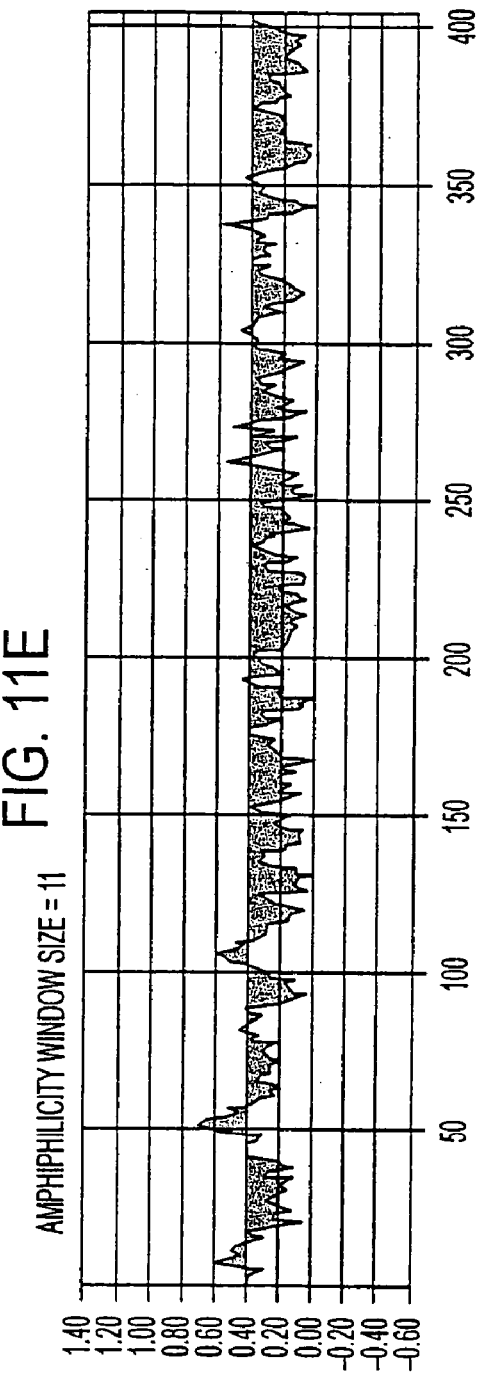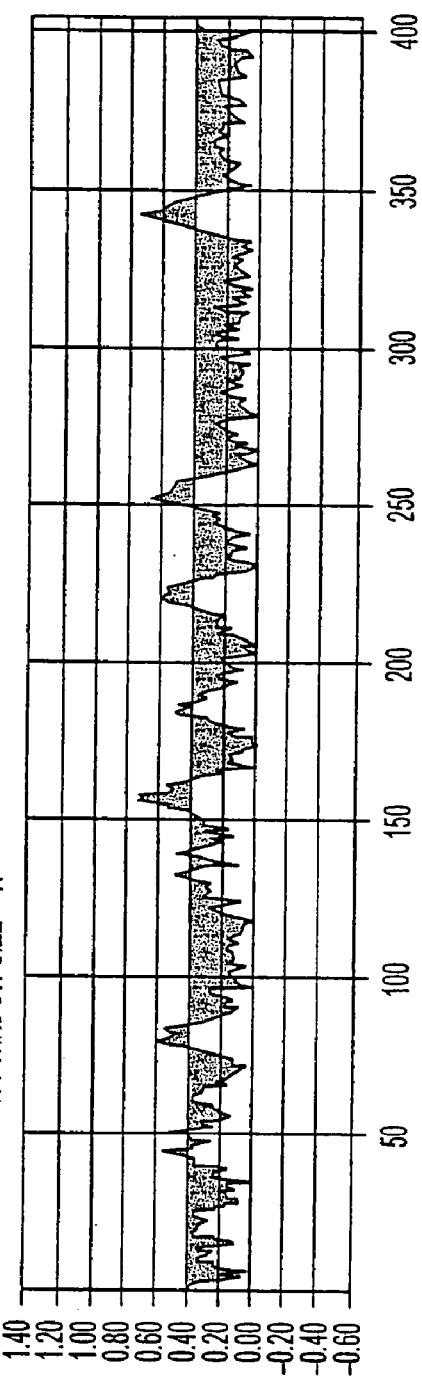

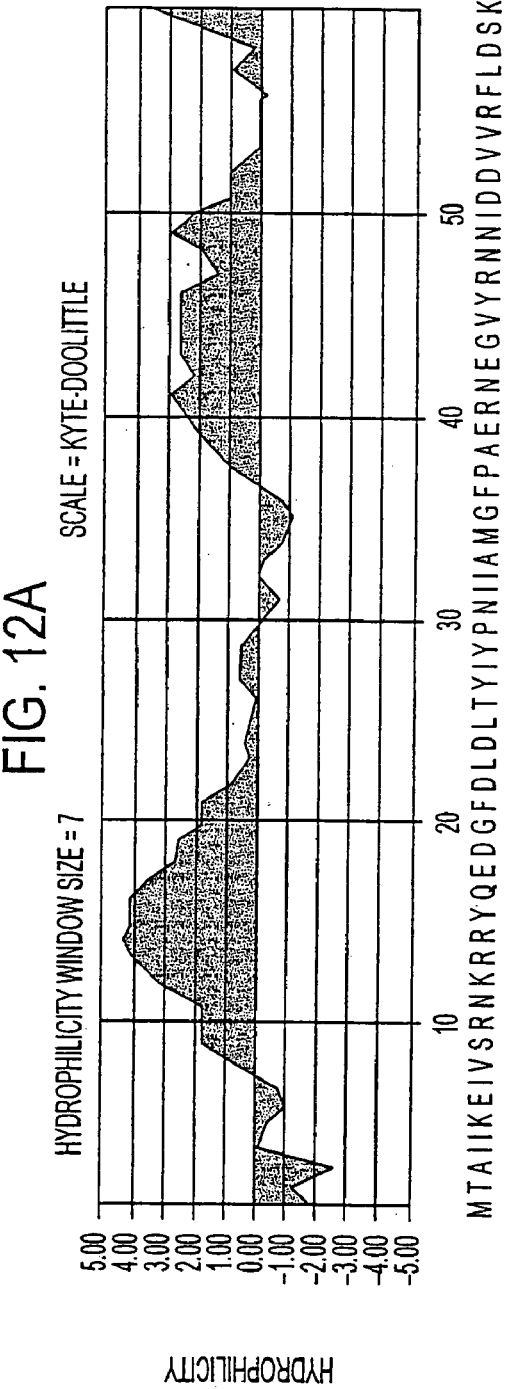
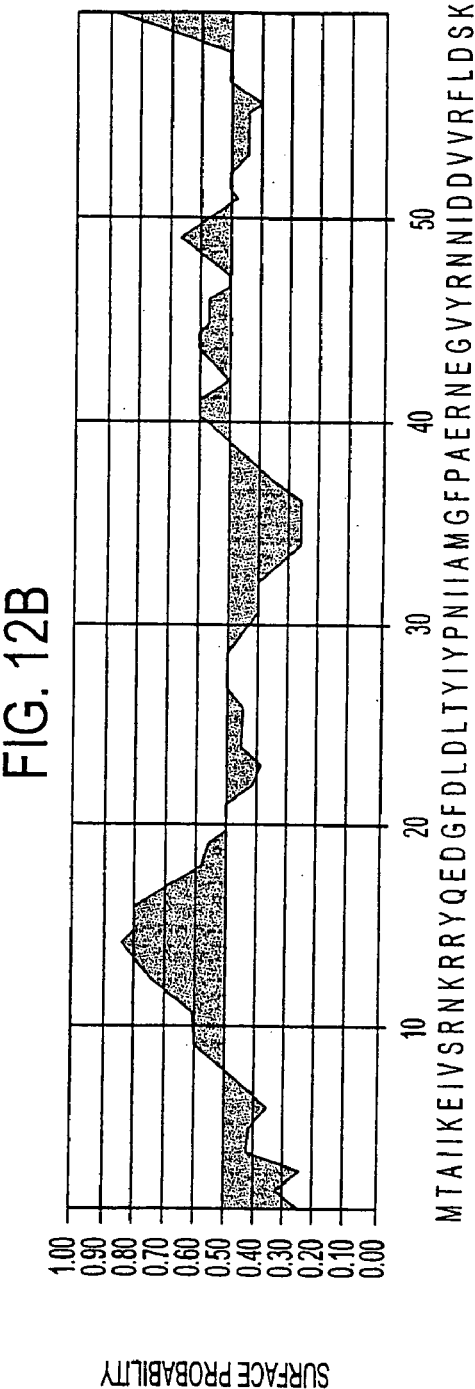

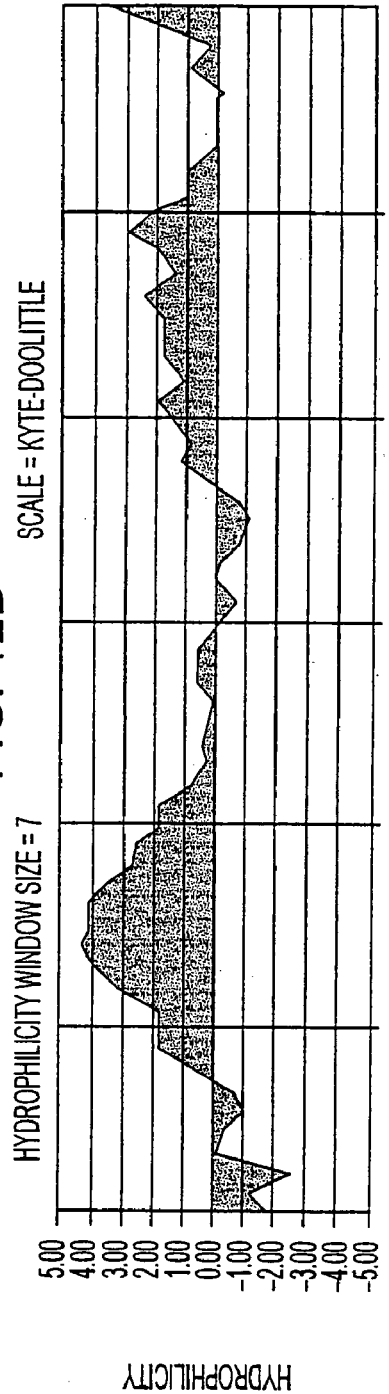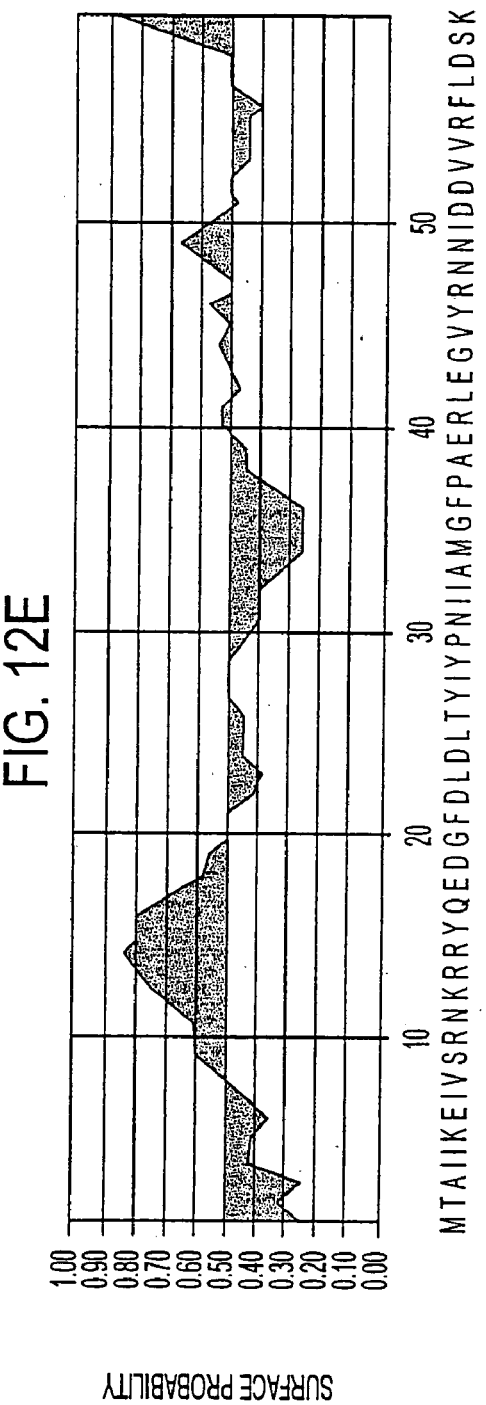

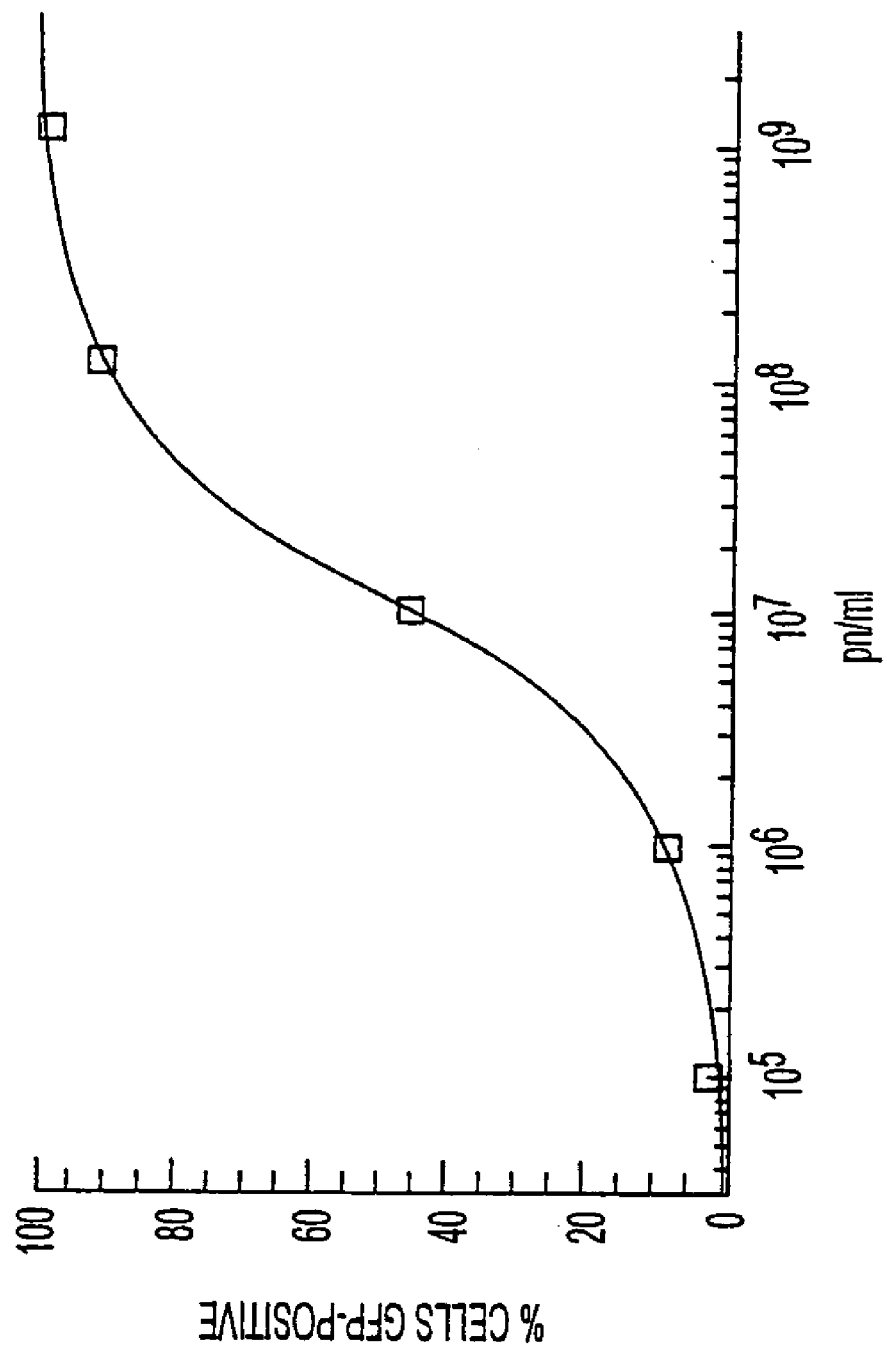

SEQUENCE LISTING

<160> NUMBER OF SEQ ID NOS: 64

<210> SEQ ID NO 1
<211> LENGTH: 3160
<212> TYPE: DNA
<213> ORGANISM: Homo sapiens
<220> FEATURE:
<221> NAME/KEY: CDS
<222> LOCATION: (1035)..(2243)

<400> SEQUENCE: 1

```
cctcccctcg cccggcgcgg tcccgtccgc ctctcgctcg cctcccgcct ccccctcggtc     60 ttccgaggcg cccgggctcc cggcgcggcg gcggagggg cgggcaggcc ggcggcggt      120 gatgtggcag gactctttat gcgctgcggc aggatacgcg ctcggcgctg ggacgcgact      180
gcgctcagtt ctctcctctc ggaagctgca gccatgatgg aagtttgaga gttgagccgc      240
tgtgaggcga ggccgggctc aggcgaggga gatgagagac ggcggcggcc gcggcccgga      300
gcccctctca gcgcctgtga gcagccgcgg gggcagcgcc ctcggggagc cggccggcct      360
gcggcggcgg cagcggcggc gtttctcgcc tcctcttcgt cttttctaac cgtgcagcct      420
cttcctcggc ttctcctgaa agggaaggtg gaagccgtgg gctcgggcgg gagccggctg      480
aggcgcggcg gcggcggcgg cggcacctcc cgctcctgga gcggggggga gaagcggcgg      540
```

-continued

```
cggcggcggc cgcggcggct gcagctccag ggaggggggtc tgagtcgcct gtcaccattt      600
ccagggctgg gaacgccgga gagttggtct ctcccttct actgcctcca acacggcggc        660
ggcggcggcg gcacatccag ggacccgggc cggttttaaa cctcccgtcc gccgccgccg      720 cacccccgt ggcccgggct ccggaggccg ccggcggagg cagccgttcg gaggattatt       780
cgtcttctcc ccattccgct gccgccgctg ccaggcctct ggctgctgag gagaagcagg      840
cccagtcgct gcaaccatcc agcagccgcc gcagcagcca ttacccggct gcggtccaga      900
gccaagcggc ggcagagcga ggggcatcag ctaccgccaa gtccagagcc atttccatcc      960
tgcagaagaa gccccgccac cagcagcttc tgccatctct ctcctccttt ttcttcagcc     1020
```

```
acaggctccc agac atg aca gcc atc atc aaa gag atc gtt agc aga aac      1070
              Met Thr Ala Ile Ile Lys Glu Ile Val Ser Arg Asn
                1               5                  10 aaa agg aga tat caa gag gat gga ttc gac tta gac ttg acc tat att      1118
Lys Arg Arg Tyr Gln Glu Asp Gly Phe Asp Leu Asp Leu Thr Tyr Ile
           15                  20                  25 tat cca aac att att gct atg gga ttt cct gca gaa aga ctt gaa ggc      1166
Tyr Pro Asn Ile Ile Ala Met Gly Phe Pro Ala Glu Arg Leu Glu Gly
        30                  35                  40 gta tac agg aac aat att gat gat gta gta agg ttt ttg gat tca aag      1214
Val Tyr Arg Asn Asn Ile Asp Asp Val Val Arg Phe Leu Asp Ser Lys
 45                 50                  55                  60 cat aaa aac cat tac aag ata tac aat ctt tgt gct gaa aga cat tat      1262
His Lys Asn His Tyr Lys Ile Tyr Asn Leu Cys Ala Glu Arg His Tyr
            65                  70                  75 gac acc gcc aaa ttt aat tgc aga gtt gca caa tat cct ttt gaa gac      1310
Asp Thr Ala Lys Phe Asn Cys Arg Val Ala Gln Tyr Pro Phe Glu Asp
        80                  85                  90 cat aac cca cca cag cta gaa ctt atc aaa ccc ttt tgt gaa gat ctt      1358
His Asn Pro Pro Gln Leu Glu Leu Ile Lys Pro Phe Cys Glu Asp Leu
        95                 100                 105 gac caa tgg cta agt gaa gat gac aat cat gtt gca gca att cac tgt      1406
Asp Gln Trp Leu Ser Glu Asp Asp Asn His Val Ala Ala Ile His Cys
    110                 115                 120 aaa gct gga aag gga cga act ggt gta atg ata tgt gca tat tta tta      1454
Lys Ala Gly Lys Gly Arg Thr Gly Val Met Ile Cys Ala Tyr Leu Leu
125                 130                 135                 140 cat cgg ggc aaa ttt tta aag gca caa gag gcc cta gat ttc tat ggg      1502
His Arg Gly Lys Phe Leu Lys Ala Gln Glu Ala Leu Asp Phe Tyr Gly
                145                 150                 155 gaa gta agg acc aga gac aaa aag gga gta act att ccc agt cag agg      1550
Glu Val Arg Thr Arg Asp Lys Lys Gly Val Thr Ile Pro Ser Gln Arg
            160                 165                 170 cgc tat gtg tat tat agc tac ctg tta aag aat cat ctg gat tat          1598
Arg Tyr Val Tyr Tyr Ser Tyr Leu Leu Lys Asn His Leu Asp Tyr
        175                 180                 185 aga cca gtg gca ctg ttg ttt cac aag atg atg ttt gaa act att cca      1646
Arg Pro Val Ala Leu Leu Phe His Lys Met Met Phe Glu Thr Ile Pro
        190                 195                 200 atg ttc agt ggc gga act tgc aat cct cag ttt gtg gtc tgc cag cta      1694
Met Phe Ser Gly Gly Thr Cys Asn Pro Gln Phe Val Val Cys Gln Leu
205                 210                 215                 220 aag gtg aag ata tat tcc tcc aat tca gga ccc aca cga cgg gaa gac      1742
Lys Val Lys Ile Tyr Ser Ser Asn Ser Gly Pro Thr Arg Arg Glu Asp
                225                 230                 235 aag ttc atg tac ttt gag ttc cct cag ccg tta cct gtg tgt ggt gat      1790
Lys Phe Met Tyr Phe Glu Phe Pro Gln Pro Leu Pro Val Cys Gly Asp
            240                 245                 250
```

```
atc aaa gta gag ttc ttc cac aaa cag aac aag atg cta aaa aag gac      1838
Ile Lys Val Glu Phe Phe His Lys Gln Asn Lys Met Leu Lys Lys Asp
        255                 260                 265 aaa atg ttt cac ttt tgg gta aat aca ttc ttc ata cca gga cca gag      1886
Lys Met Phe His Phe Trp Val Asn Thr Phe Phe Ile Pro Gly Pro Glu
    270                 275                 280 gaa acc tca gaa aaa gta gaa aat gga agt cta tgt gat caa gaa atc      1934
Glu Thr Ser Glu Lys Val Glu Asn Gly Ser Leu Cys Asp Gln Glu Ile
285                 290                 295                 300 gat agc att tgc agt ata gag cgt gca gat aat gac aag gaa tat cta      1982
Asp Ser Ile Cys Ser Ile Glu Arg Ala Asp Asn Asp Lys Glu Tyr Leu
                305                 310                 315 gta ctt act tta aca aaa aat gat ctt gac aaa gca aat aaa gac aaa      2030
Val Leu Thr Leu Thr Lys Asn Asp Leu Asp Lys Ala Asn Lys Asp Lys
            320                 325                 330 gcc aac cga tac ttt tct cca aat ttt aag gtg aag ctg tac ttc aca      2078
Ala Asn Arg Tyr Phe Ser Pro Asn Phe Lys Val Lys Leu Tyr Phe Thr
        335                 340                 345 aaa aca gta gag gag ccg tca aat cca gag gct agc agt tca act tct      2126
Lys Thr Val Glu Glu Pro Ser Asn Pro Glu Ala Ser Ser Ser Thr Ser
    350                 355                 360 gta aca cca gat gtt agt gac aat gaa cct gat cat tat aga tat tct      2174
Val Thr Pro Asp Val Ser Asp Asn Glu Pro Asp His Tyr Arg Tyr Ser
365                 370                 375                 380 gac acc act gac tct gat cca gag aat gaa cct ttt gat gaa gat cag      2222
Asp Thr Thr Asp Ser Asp Pro Glu Asn Glu Pro Phe Asp Glu Asp Gln
                385                 390                 395 cat aca caa att aca aaa gtc tgaatttttt tttatcaaga gggataaaac         2273
His Thr Gln Ile Thr Lys Val
                400 accatgaaaa taaacttgaa taaactgaaa atggaccttt ttttttttaa tggcaatagg    2333 acattgtgtc agattaccag ttataggaac aattctcttt tcctgaccaa tcttgtttta    2393 ccctatacat ccacagggtt ttgacacttg ttgtccagtt gaaaaaaggt tgtgtagctg    2453 tgtcatgtat atacctttt gtgtcaaaag gacatttaaa attcaattag gattaataaa     2513 gatggcactt tcccgtttta ttccagtttt ataaaaagtg gagacagact gatgtgtata    2573 cgtaggaatt ttttccttt gtgttctgtc accaactgaa gtggctaaag gctttgtga     2633 tatactggtt cacatcctac ccctttgcac ttgtggcaac agataagttt gcagttggct    2693 aagagaggtt tccgaaaggt tttgctacca ttctaatgca tgtattcggg ttagggcaat    2753 ggagggaat gctcagaaag gaaataattt tatgctggac tctggaccat ataccatctc    2813 cagctattta cacacccctt tctttagcat gctacagtta ttaatctgga cattcgagga    2873 attggccgct gtcactgctt gttgtttgcg catttttttt taaagcatat tggtgctaga    2933 aaaggcagct aaaggaagtg aatctgtatt ggggtacagg aatgaacctt ctgcaacatc    2993 ttaagatcca caaatgaagg gatataaaaa taatgtcata ggtaagaaac acagcaacaa    3053 tgacttaacc atataaatgt ggaggctatc aacaaagaat gggcttgaaa cattataaaa    3113 attgacaatg atttattaaa tatgttttct caattgtaaa aaaaaaa                  3160

<210> SEQ ID NO 2
<211> LENGTH: 403
<212> TYPE: PRT
<213> ORGANISM: Homo sapiens

<400> SEQUENCE: 2
```

```
Met Thr Ala Ile Ile Lys Glu Ile Val Ser Arg Asn Lys Arg Tyr
 1               5                  10                  15

Gln Glu Asp Gly Phe Asp Leu Asp Thr Tyr Ile Tyr Pro Asn Ile
                20                  25                  30

Ile Ala Met Gly Phe Pro Ala Glu Arg Leu Glu Gly Val Tyr Arg Asn
            35                  40                  45

Asn Ile Asp Asp Val Val Arg Phe Leu Asp Ser Lys His Lys Asn His
        50                  55                  60

Tyr Lys Ile Tyr Asn Leu Cys Ala Glu Arg His Tyr Asp Thr Ala Lys
 65                  70                  75                  80

Phe Asn Cys Arg Val Ala Gln Tyr Pro Phe Glu Asp His Asn Pro Pro
                85                  90                  95

Gln Leu Glu Leu Ile Lys Pro Phe Cys Glu Asp Leu Asp Gln Trp Leu
            100                 105                 110

Ser Glu Asp Asp Asn His Val Ala Ala Ile His Cys Lys Ala Gly Lys
            115                 120                 125

Gly Arg Thr Gly Val Met Ile Cys Ala Tyr Leu Leu His Arg Gly Lys
            130                 135                 140

Phe Leu Lys Ala Gln Glu Ala Leu Asp Phe Tyr Gly Glu Val Arg Thr
145                 150                 155                 160

Arg Asp Lys Lys Gly Val Thr Ile Pro Ser Gln Arg Arg Tyr Val Tyr
                165                 170                 175

Tyr Tyr Ser Tyr Leu Leu Lys Asn His Leu Asp Tyr Arg Pro Val Ala
            180                 185                 190

Leu Leu Phe His Lys Met Met Phe Glu Thr Ile Pro Met Phe Ser Gly
            195                 200                 205

Gly Thr Cys Asn Pro Gln Phe Val Val Cys Gln Leu Lys Val Lys Ile
    210                 215                 220

Tyr Ser Ser Asn Ser Gly Pro Thr Arg Arg Glu Asp Lys Phe Met Tyr
225                 230                 235                 240

Phe Glu Phe Pro Gln Pro Leu Pro Val Cys Gly Asp Ile Lys Val Glu
                245                 250                 255

Phe Phe His Lys Gln Asn Lys Met Leu Lys Asp Lys Met Phe His
            260                 265                 270

Phe Trp Val Asn Thr Phe Phe Ile Pro Gly Pro Glu Glu Thr Ser Glu
            275                 280                 285

Lys Val Glu Asn Gly Ser Leu Cys Asp Gln Glu Ile Asp Ser Ile Cys
    290                 295                 300

Ser Ile Glu Arg Ala Asp Asn Asp Lys Glu Tyr Leu Val Leu Thr Leu
305                 310                 315                 320

Thr Lys Asn Asp Leu Asp Lys Ala Asn Lys Asp Lys Ala Asn Arg Tyr
                325                 330                 335

Phe Ser Pro Asn Phe Lys Val Lys Leu Tyr Phe Thr Lys Thr Val Glu
                340                 345                 350

Glu Pro Ser Asn Pro Glu Ala Ser Ser Thr Ser Val Thr Pro Asp
            355                 360                 365

Val Ser Asp Asn Glu Pro Asp His Tyr Arg Tyr Ser Asp Thr Thr Asp
            370                 375                 380

Ser Asp Pro Glu Asn Glu Pro Phe Asp Glu Asp Gln His Thr Gln Ile
385                 390                 395                 400

Thr Lys Val

<210> SEQ ID NO 3
```

```
<211> LENGTH: 39
<212> TYPE: PRT
<213> ORGANISM: Homo sapiens

<400> SEQUENCE: 3

Ser Pro Arg Pro Ala Arg Ser Arg Pro Leu Ala Arg Leu Pro Pro
 1               5                  10                  15

Pro Leu Gly Leu Pro Arg Arg Pro Gly Ser Arg Arg Gly Gly Gly
            20                  25                  30

Gly Gly Gln Ala Gly Gly Arg
        35

<210> SEQ ID NO 4
<211> LENGTH: 40
<212> TYPE: PRT
<213> ORGANISM: Homo sapiens

<400> SEQUENCE: 4

Cys Gly Arg Thr Leu Tyr Ala Leu Arg Gln Asp Thr Arg Ser Ala Leu
 1               5                  10                  15

Gly Arg Asp Cys Ala Gln Phe Ser Pro Leu Gly Ser Cys Ser His Asp
            20                  25                  30

Gly Ser Leu Arg Val Glu Pro Leu
        35                  40

<210> SEQ ID NO 5
<211> LENGTH: 9
<212> TYPE: PRT
<213> ORGANISM: Homo sapiens

<400> SEQUENCE: 5

Gly Glu Ala Gly Leu Arg Arg Gly Arg
 1               5

<210> SEQ ID NO 6
<211> LENGTH: 14
<212> TYPE: PRT
<213> ORGANISM: Homo sapiens

<400> SEQUENCE: 6

Glu Thr Ala Ala Ala Ala Ala Arg Ser Pro Ser Gln Arg Leu
 1               5                  10

<210> SEQ ID NO 7
<211> LENGTH: 43
<212> TYPE: PRT
<213> ORGANISM: Homo sapiens

<400> SEQUENCE: 7

Ala Ala Ala Gly Ala Ala Pro Ser Gly Ser Arg Pro Ala Cys Gly Gly
 1               5                  10                  15

Gly Ser Gly Gly Val Ser Arg Leu Leu Phe Val Phe Ser Asn Arg Ala
            20                  25                  30

Ala Ser Ser Ser Ala Ser Pro Glu Arg Glu Gly
        35                  40

<210> SEQ ID NO 8
<211> LENGTH: 597
<212> TYPE: PRT
<213> ORGANISM: Homo sapiens

<400> SEQUENCE: 8
```

-continued

```
Ser Arg Gly Leu Gly Arg Glu Pro Ala Glu Arg Arg Arg Arg
 1               5                  10                  15

Arg His Leu Pro Leu Leu Glu Arg Gly Gly Glu Ala Ala Ala Ala
                 20                  25                  30

Ala Ala Ala Ala Ala Ala Pro Gly Arg Gly Ser Glu Ser Pro Val Thr
             35                  40                  45

Ile Ser Arg Ala Gly Asn Ala Gly Glu Leu Val Ser Pro Leu Leu Leu
 50                  55                  60

Pro Pro Thr Arg Arg Arg Arg Arg His Ile Gln Gly Pro Gly Pro
 65                  70                  75                  80

Val Leu Asn Leu Pro Ser Ala Ala Ala Pro Pro Val Ala Arg Ala
                 85                  90                  95

Pro Glu Ala Ala Gly Gly Gly Ser Arg Ser Glu Asp Tyr Ser Ser Ser
             100                 105                 110

Pro His Ser Ala Ala Ala Ala Arg Pro Leu Ala Ala Glu Glu Lys
         115                 120                 125

Gln Ala Gln Ser Leu Gln Pro Ser Ser Ser Arg Arg Ser Ser His Tyr
     130                 135                 140

Pro Ala Ala Val Gln Ser Gln Ala Ala Ala Glu Arg Gly Ala Ser Ala
145                 150                 155                 160

Thr Ala Lys Ser Arg Ala Ile Ser Ile Leu Gln Lys Lys Pro Arg His
                 165                 170                 175

Gln Gln Leu Leu Pro Ser Leu Ser Ser Phe Phe Ser His Arg Leu
                 180                 185                 190

Pro Asp Met Thr Ala Ile Ile Lys Glu Ile Val Ser Arg Asn Lys Arg
         195                 200                 205

Arg Tyr Gln Glu Asp Gly Phe Asp Leu Asp Leu Thr Tyr Ile Tyr Pro
     210                 215                 220

Asn Ile Ile Ala Met Gly Phe Pro Ala Glu Arg Leu Glu Gly Val Tyr
225                 230                 235                 240

Arg Asn Asn Ile Asp Asp Val Val Arg Phe Leu Asp Ser Lys His Lys
                 245                 250                 255

Asn His Tyr Lys Ile Tyr Asn Leu Cys Ala Glu Arg His Tyr Asp Thr
         260                 265                 270

Ala Lys Phe Asn Cys Arg Val Ala Gln Tyr Pro Phe Glu Asp His Asn
     275                 280                 285

Pro Pro Gln Leu Glu Leu Ile Lys Pro Phe Cys Glu Asp Leu Asp Gln
290                 295                 300

Trp Leu Ser Glu Asp Asp Asn His Val Ala Ala Ile His Cys Lys Ala
305                 310                 315                 320

Gly Lys Gly Arg Thr Gly Val Met Ile Cys Ala Tyr Leu Leu His Arg
                 325                 330                 335

Gly Lys Phe Leu Lys Ala Gln Glu Ala Leu Asp Phe Tyr Gly Glu Val
             340                 345                 350

Arg Thr Arg Asp Lys Lys Gly Val Thr Ile Pro Ser Gln Arg Arg Tyr
         355                 360                 365

Val Tyr Tyr Tyr Ser Tyr Leu Leu Lys Asn His Leu Asp Tyr Arg Pro
     370                 375                 380

Val Ala Leu Leu Phe His Lys Met Met Phe Glu Thr Ile Pro Met Phe
385                 390                 395                 400

Ser Gly Gly Thr Cys Asn Pro Gln Phe Val Val Cys Gln Leu Lys Val
                 405                 410                 415

Lys Ile Tyr Ser Ser Asn Ser Gly Pro Thr Arg Arg Glu Asp Lys Phe
```

-continued

```
                420              425              430
    Met Tyr Phe Glu Phe Pro Gln Pro Leu Pro Val Cys Gly Asp Ile Lys
            435                  440                  445

Val Glu Phe Phe His Lys Gln Asn Lys Met Leu Lys Lys Asp Lys Met
            450                  455                  460

Phe His Phe Trp Val Asn Thr Phe Phe Ile Pro Gly Pro Glu Glu Thr
    465                  470                  475                  480

Ser Glu Lys Val Glu Asn Gly Ser Leu Cys Asp Gln Glu Ile Asp Ser
                    485                  490                  495

Ile Cys Ser Ile Glu Arg Ala Asp Asn Asp Lys Glu Tyr Leu Val Leu
                500                  505                  510

Thr Leu Thr Lys Asn Asp Leu Asp Lys Ala Asn Lys Asp Lys Ala Asn
            515                  520                  525

Arg Tyr Phe Ser Pro Asn Phe Lys Val Lys Leu Tyr Phe Thr Lys Thr
    530                  535                  540

Val Glu Glu Pro Ser Asn Pro Glu Ala Ser Ser Ser Thr Ser Val Thr
    545                  550                  555                  560

Pro Asp Val Ser Asp Asn Glu Pro Asp His Tyr Arg Tyr Ser Asp Thr
                    565                  570                  575

Thr Asp Ser Asp Pro Glu Asn Glu Pro Phe Asp Glu Asp Gln His Thr
                580                  585                  590

Gln Ile Thr Lys Val
            595
```

<210> SEQ ID NO 9
<211> LENGTH: 1962
<212> TYPE: DNA
<213> ORGANISM: Mus musculus
<220> FEATURE:
<221> NAME/KEY: CDS
<222> LOCATION: (751)..(1959)

<400> SEQUENCE: 9

```
gcgagggaga tgagagacgg cggcggccac ggcccagagc ccctctcagc gcctgtgagc    60
agccgcgggg gcagcgccct cggggagccg gccgggcggc ggcggcggca gcggcggcgg   120
gcctcgcctc ctcgtcgtct gttctaaccg ggcagcttct gagcagcttc ggagagagac   180
ggtggaagaa gccgtgggct cgagcgggag ccggcgcagg ctcggcggct gcacctcccg   240
ctcctggagc gggggggaga agcggcggcg gcggccgcgg ctccggggag ggggtcggag   300
tcgcctgtca ccattgccag ggctgggaac gccggagagt tgctctctcc ccttctcctg   360
cctccaacac ggcggcggcg gcggcggcac gtccagggac ccgggccggt gttaagcctc   420
ccgtccgccg ccgccgcacc cccctggcc cgggctccgg aggccgccgg aggaggcagc    480
cgctgcgagg attatccgtc ttctccccat tccgctgcct cggctgccag gcctctggct   540
gctgaggaga agcaggccca gtctctgcaa ccatccagca gccgccgcag cagccattac   600
ccggctgcgg tccagggcca agcggcagca gagcgagggg catcagcgac cgccaagtcc   660
agagccattt ccatcctgca gaagaagcct cgccaccagc agcttctgcc atctctctcc   720
tcctttttct tcagccacag gctcccagac atg aca gcc atc atc aaa gag atc    774
                                   Met Thr Ala Ile Ile Lys Glu Ile
                                     1               5 gtt agc aga aac aaa agg aga tat caa gag gat gga ttc gac tta gac   822
Val Ser Arg Asn Lys Arg Arg Tyr Gln Glu Asp Gly Phe Asp Leu Asp
         10                  15                  20 ttg acc tat att tat cca aat att att gct atg gga ttt cct gca gaa   870
```

-continued

```
Leu Thr Tyr Ile Tyr Pro Asn Ile Ile Ala Met Gly Phe Pro Ala Glu
 25                  30                  35                  40 aga ctt gaa ggt gta tac agg aac aat att gat gat gta gta agg ttt      918
Arg Leu Glu Gly Val Tyr Arg Asn Asn Ile Asp Asp Val Val Arg Phe
                     45                  50                  55 ttg gat tca aag cat aaa aac cat tac aag ata tac aat cta tgt gct      966
Leu Asp Ser Lys His Lys Asn His Tyr Lys Ile Tyr Asn Leu Cys Ala
                 60                  65                  70 gag aga cat tat gac acc gcc aaa ttt aac tgc aga gtt gca cag tat     1014
Glu Arg His Tyr Asp Thr Ala Lys Phe Asn Cys Arg Val Ala Gln Tyr
             75                  80                  85 cct ttt gaa gac cat aac cca cca cag cta gaa ctt atc aaa ccc ttc     1062
Pro Phe Glu Asp His Asn Pro Pro Gln Leu Glu Leu Ile Lys Pro Phe
         90                  95                 100 tgt gaa gat ctt gac caa tgg cta agt gaa gat gac aat cat gtt gca     1110
Cys Glu Asp Leu Asp Gln Trp Leu Ser Glu Asp Asp Asn His Val Ala
105                 110                 115                 120 gca att cac tgt aaa gct gga aag gga cgg act ggt gta atg att tgt     1158
Ala Ile His Cys Lys Ala Gly Lys Gly Arg Thr Gly Val Met Ile Cys
                125                 130                 135 gca tat tta ttg cat cgg ggc aaa ttt tta aag gca caa gag gcc cta     1206
Ala Tyr Leu Leu His Arg Gly Lys Phe Leu Lys Ala Gln Glu Ala Leu
            140                 145                 150 gat ttt tat ggg gaa gta agg acc aga gac aaa aag gga gtc aca att     1254
Asp Phe Tyr Gly Glu Val Arg Thr Arg Asp Lys Lys Gly Val Thr Ile
        155                 160                 165 ccc agt cag agg cgc tat gta tat tat tat agc tac ctg cta aaa aat     1302
Pro Ser Gln Arg Arg Tyr Val Tyr Tyr Tyr Ser Tyr Leu Leu Lys Asn
170                 175                 180 cac ctg gat tac aga ccc gtg gca ctg ctg ttt cac aag atg atg ttt     1350
His Leu Asp Tyr Arg Pro Val Ala Leu Leu Phe His Lys Met Met Phe
185                 190                 195                 200 gaa act att cca atg ttc agt ggc gga act tgc aat cct cag ttt gtg     1398
Glu Thr Ile Pro Met Phe Ser Gly Gly Thr Cys Asn Pro Gln Phe Val
                205                 210                 215 gtc tgc cag cta aag gtg aag ata tat tcc tcc aat tca gga ccc acg     1446
Val Cys Gln Leu Lys Val Lys Ile Tyr Ser Ser Asn Ser Gly Pro Thr
            220                 225                 230 cgg cgg gag gac aag ttc atg tac ttt gag ttc cct cag cca ttg cct     1494
Arg Arg Glu Asp Lys Phe Met Tyr Phe Glu Phe Pro Gln Pro Leu Pro
        235                 240                 245 gtg tgt ggt gat atc aaa gta gag ttc ttc cac aaa cag aac aag atg     1542
Val Cys Gly Asp Ile Lys Val Glu Phe Phe His Lys Gln Asn Lys Met
250                 255                 260 ctc aaa aag gac aaa atg ttt cac ttt tgg gta aat acg ttc ttc ata     1590
Leu Lys Lys Asp Lys Met Phe His Phe Trp Val Asn Thr Phe Phe Ile
265                 270                 275                 280 cca gga cca gag gaa acc tca gaa aaa gtg gaa aat gga agt ctt tgt     1638
Pro Gly Pro Glu Glu Thr Ser Glu Lys Val Glu Asn Gly Ser Leu Cys
                285                 290                 295 gat cag gaa atc gat agc att tgc agt ata gag cgt gca gat aat gac     1686
Asp Gln Glu Ile Asp Ser Ile Cys Ser Ile Glu Arg Ala Asp Asn Asp
            300                 305                 310 aag gag tat ctt gta ctc acc cta aca aaa aac gat ctt gac aaa gca     1734
Lys Glu Tyr Leu Val Leu Thr Leu Thr Lys Asn Asp Leu Asp Lys Ala
        315                 320                 325 aac aaa gac aag gcc aac cga tac ttc tct cca aat ttt aag gtg aaa     1782
Asn Lys Asp Lys Ala Asn Arg Tyr Phe Ser Pro Asn Phe Lys Val Lys
330                 335                 340
```

-continued

```
cta tac ttt aca aaa aca gta gag gag cca tca aat cca gag gct agc    1830
Leu Tyr Phe Thr Lys Thr Val Glu Glu Pro Ser Asn Pro Glu Ala Ser
345                 350                 355                 360 agt tca act tct gtg act cca gat gtt agt gac aat gaa cct gat cat    1878
Ser Ser Thr Ser Val Thr Pro Asp Val Ser Asp Asn Glu Pro Asp His
                365                 370                 375 tat aga tat tct gac acc act gac tct gat cca gag aat gaa cct ttt    1926
Tyr Arg Tyr Ser Asp Thr Thr Asp Ser Asp Pro Glu Asn Glu Pro Phe
            380                 385                 390 gat gaa gat cag cat tca caa att aca aaa gtc tga                    1962
Asp Glu Asp Gln His Ser Gln Ile Thr Lys Val
            395                 400
```

<210> SEQ ID NO 10
<211> LENGTH: 403
<212> TYPE: PRT
<213> ORGANISM: Mus musculus

<400> SEQUENCE: 10

```
Met Thr Ala Ile Ile Lys Glu Ile Val Ser Arg Asn Lys Arg Arg Tyr
 1               5                  10                  15

Gln Glu Asp Gly Phe Asp Leu Asp Leu Thr Tyr Ile Tyr Pro Asn Ile
             20                  25                  30

Ile Ala Met Gly Phe Pro Ala Glu Arg Leu Glu Gly Val Tyr Arg Asn
         35                  40                  45

Asn Ile Asp Asp Val Val Arg Phe Leu Asp Ser Lys His Lys Asn His
     50                  55                  60

Tyr Lys Ile Tyr Asn Leu Cys Ala Glu Arg His Tyr Asp Thr Ala Lys
 65                  70                  75                  80

Phe Asn Cys Arg Val Ala Gln Tyr Pro Phe Glu Asp His Asn Pro Pro
                 85                  90                  95

Gln Leu Glu Leu Ile Lys Pro Phe Cys Glu Asp Leu Asp Gln Trp Leu
            100                 105                 110

Ser Glu Asp Asp Asn His Val Ala Ala Ile His Cys Lys Ala Gly Lys
        115                 120                 125

Gly Arg Thr Gly Val Met Ile Cys Ala Tyr Leu Leu His Arg Gly Lys
    130                 135                 140

Phe Leu Lys Ala Gln Glu Ala Leu Asp Phe Tyr Gly Glu Val Arg Thr
145                 150                 155                 160

Arg Asp Lys Lys Gly Val Thr Ile Pro Ser Gln Arg Arg Tyr Val Tyr
                165                 170                 175

Tyr Tyr Ser Tyr Leu Leu Lys Asn His Leu Asp Tyr Arg Pro Val Ala
            180                 185                 190

Leu Leu Phe His Lys Met Met Phe Glu Thr Ile Pro Met Phe Ser Gly
        195                 200                 205

Gly Thr Cys Asn Pro Gln Phe Val Val Cys Gln Leu Lys Val Lys Ile
    210                 215                 220

Tyr Ser Ser Asn Ser Gly Pro Thr Arg Arg Glu Asp Lys Phe Met Tyr
225                 230                 235                 240

Phe Glu Phe Pro Gln Pro Leu Pro Val Cys Gly Asp Ile Lys Val Glu
                245                 250                 255

Phe Phe His Lys Gln Asn Lys Met Leu Lys Lys Asp Lys Met Phe His
            260                 265                 270

Phe Trp Val Asn Thr Phe Phe Ile Pro Gly Pro Glu Glu Thr Ser Glu
        275                 280                 285

Lys Val Glu Asn Gly Ser Leu Cys Asp Gln Glu Ile Asp Ser Ile Cys
```

-continued

```
                        290                 295                 300
Ser Ile Glu Arg Ala Asp Asn Asp Lys Glu Tyr Leu Val Leu Thr Leu
305                 310                 315                 320

Thr Lys Asn Asp Leu Asp Lys Ala Asn Lys Asp Lys Ala Asn Arg Tyr
                325                 330                 335

Phe Ser Pro Asn Phe Lys Val Lys Leu Tyr Phe Thr Lys Thr Val Glu
                340                 345                 350

Glu Pro Ser Asn Pro Glu Ala Ser Ser Thr Ser Val Thr Pro Asp
                355                 360                 365

Val Ser Asp Asn Glu Pro Asp His Tyr Arg Tyr Ser Asp Thr Thr Asp
                370                 375                 380

Ser Asp Pro Glu Asn Glu Pro Phe Asp Glu Asp Gln His Ser Gln Ile
385                 390                 395                 400

Thr Lys Val

<210> SEQ ID NO 11
<211> LENGTH: 14
<212> TYPE: PRT
<213> ORGANISM: Mus musculus

<400> SEQUENCE: 11

Glu Thr Ala Ala Ala Thr Ala Gln Ser Pro Ser Gln Arg Leu
1               5                   10

<210> SEQ ID NO 12
<211> LENGTH: 36
<212> TYPE: PRT
<213> ORGANISM: Mus musculus

<400> SEQUENCE: 12

Ala Ala Ala Gly Ala Ala Pro Ser Gly Ser Arg Pro Gly Gly Gly Gly
1               5                   10                  15

Gly Ser Gly Gly Gly Pro Arg Leu Leu Val Val Cys Ser Asn Arg Ala
                20                  25                  30

Ala Ser Glu Gln
            35

<210> SEQ ID NO 13
<211> LENGTH: 17
<212> TYPE: PRT
<213> ORGANISM: Mus musculus

<400> SEQUENCE: 13

Glu Arg Asp Gly Gly Arg Ser Arg Gly Leu Glu Arg Glu Pro Ala Gln
1               5                   10                  15

Ala

<210> SEQ ID NO 14
<211> LENGTH: 17
<212> TYPE: PRT
<213> ORGANISM: Mus musculus

<400> SEQUENCE: 14

Arg Arg Leu His Leu Pro Leu Leu Glu Arg Gly Gly Glu Ala Ala Ala
1               5                   10                  15

Ala

<210> SEQ ID NO 15
<211> LENGTH: 559
```

```
<212> TYPE: PRT
<213> ORGANISM: Mus musculus

<400> SEQUENCE: 15

Pro Gly Arg Gly Ser Glu Ser Pro Val Thr Ile Ala Arg Ala Gly Asn
 1               5                  10                  15

Ala Gly Glu Leu Leu Ser Pro Leu Leu Leu Pro Pro Thr Arg Arg Arg
             20                  25                  30

Arg Arg Arg His Val Gln Gly Pro Gly Pro Val Leu Ser Leu Pro Ser
         35                  40                  45

Ala Ala Ala Ala Pro Pro Leu Ala Arg Ala Pro Glu Ala Ala Gly Gly
     50                  55                  60

Gly Ser Arg Cys Glu Asp Tyr Pro Ser Ser Pro His Ser Ala Ala Ser
 65                  70                  75                  80

Ala Ala Arg Pro Leu Ala Ala Glu Glu Lys Gln Ala Gln Ser Leu Gln
                 85                  90                  95

Pro Ser Ser Arg Arg Ser Ser His Tyr Pro Ala Ala Val Gln Gly
                100                 105                 110

Gln Ala Ala Glu Arg Gly Ala Ser Ala Thr Ala Lys Ser Arg Ala
            115                 120                 125

Ile Ser Ile Leu Gln Lys Lys Pro Arg His Gln Gln Leu Leu Pro Ser
130                 135                 140

Leu Ser Ser Phe Phe Phe Ser His Arg Leu Pro Asp Met Thr Ala Ile
145                 150                 155                 160

Ile Lys Glu Ile Val Ser Arg Asn Lys Arg Arg Tyr Gln Glu Asp Gly
                165                 170                 175

Phe Asp Leu Asp Leu Thr Tyr Ile Tyr Pro Asn Ile Ile Ala Met Gly
            180                 185                 190

Phe Pro Ala Glu Arg Leu Glu Gly Val Tyr Arg Asn Asn Ile Asp Asp
        195                 200                 205

Val Val Arg Phe Leu Asp Ser Lys His Lys Asn His Tyr Lys Ile Tyr
    210                 215                 220

Asn Leu Cys Ala Glu Arg His Tyr Asp Thr Ala Lys Phe Asn Cys Arg
225                 230                 235                 240

Val Ala Gln Tyr Pro Phe Glu Asp His Asn Pro Pro Gln Leu Glu Leu
                245                 250                 255

Ile Lys Pro Phe Cys Glu Asp Leu Asp Gln Trp Leu Ser Glu Asp Asp
            260                 265                 270

Asn His Val Ala Ala Ile His Cys Lys Ala Gly Lys Gly Arg Thr Gly
        275                 280                 285

Val Met Ile Cys Ala Tyr Leu Leu His Arg Gly Lys Phe Leu Lys Ala
    290                 295                 300

Gln Glu Ala Leu Asp Phe Tyr Gly Glu Val Arg Thr Arg Asp Lys Lys
305                 310                 315                 320

Gly Val Thr Ile Pro Ser Gln Arg Arg Tyr Val Tyr Tyr Tyr Ser Tyr
                325                 330                 335

Leu Leu Lys Asn His Leu Asp Tyr Arg Pro Val Ala Leu Leu Phe His
            340                 345                 350

Lys Met Met Phe Glu Thr Ile Pro Met Phe Ser Gly Gly Thr Cys Asn
        355                 360                 365

Pro Gln Phe Val Val Cys Gln Leu Lys Val Lys Ile Tyr Ser Ser Asn
    370                 375                 380

Ser Gly Pro Thr Arg Arg Glu Asp Lys Phe Met Tyr Phe Glu Phe Pro
385                 390                 395                 400
```

```
Gln Pro Leu Pro Val Cys Gly Asp Ile Lys Val Glu Phe Phe His Lys
                405                 410                 415
Gln Asn Lys Met Leu Lys Lys Asp Lys Met Phe His Phe Trp Val Asn
            420                 425                 430
Thr Phe Phe Ile Pro Gly Pro Glu Glu Thr Ser Glu Lys Val Glu Asn
        435                 440                 445
Gly Ser Leu Cys Asp Gln Glu Ile Asp Ser Ile Cys Ser Ile Glu Arg
    450                 455                 460
Ala Asp Asn Asp Lys Glu Tyr Leu Val Leu Thr Leu Thr Lys Asn Asp
465                 470                 475                 480
Leu Asp Lys Ala Asn Lys Asp Lys Ala Asn Arg Tyr Phe Ser Pro Asn
                485                 490                 495
Phe Lys Val Lys Leu Tyr Phe Thr Lys Thr Val Glu Glu Pro Ser Asn
            500                 505                 510
Pro Glu Ala Ser Ser Ser Thr Ser Val Thr Pro Asp Val Ser Asp Asn
        515                 520                 525
Glu Pro Asp His Tyr Arg Tyr Ser Asp Thr Thr Asp Ser Asp Pro Glu
    530                 535                 540
Asn Glu Pro Phe Asp Glu Asp Gln His Ser Gln Ile Thr Lys Val
545                 550                 555
```

```
<210> SEQ ID NO 16
<211> LENGTH: 1291
<212> TYPE: DNA
<213> ORGANISM: Canis familiaris
<220> FEATURE:
<221> NAME/KEY: CDS
<222> LOCATION: (109)..(1290)

<400> SEQUENCE: 16
ccgcccgccg ccaggcccgg ggccgcctgc agcctgcgga ggaggccgcg ccgcccgccg      60
ctcctgccgt ctctctcctc cttcctctcc agccaccggc tcccagac atg aca gcc     117
                                                    Met Thr Ala
                                                      1 atc atc aag gag atc gtc agc aga aac aaa agg cgc tac cag gag gat     165
Ile Ile Lys Glu Ile Val Ser Arg Asn Lys Arg Arg Tyr Gln Glu Asp
  5                  10                  15 ggg ttc gac ttg gac ttg acc tat att tat ccc aac att att gct atg     213
Gly Phe Asp Leu Asp Leu Thr Tyr Ile Tyr Pro Asn Ile Ile Ala Met
 20                  25                  30                  35 ggg ttt cct gca gaa aga ctt gaa ggc gta tac agg aac aat att gat     261
Gly Phe Pro Ala Glu Arg Leu Glu Gly Val Tyr Arg Asn Asn Ile Asp
                 40                  45                  50 gat gta gta agg ttt ttg gat tca aag cat aaa aac cat tac aag ata     309
Asp Val Val Arg Phe Leu Asp Ser Lys His Lys Asn His Tyr Lys Ile
             55                  60                  65 tac aat ctg tgt gct gaa aga cat tat gat acc gcc aaa ttt aac tgc     357
Tyr Asn Leu Cys Ala Glu Arg His Tyr Asp Thr Ala Lys Phe Asn Cys
         70                  75                  80 aga gtt gca cag tat cct ttt gaa gac cat aat cca cca cag cta gaa     405
Arg Val Ala Gln Tyr Pro Phe Glu Asp His Asn Pro Pro Gln Leu Glu
     85                  90                  95 ctt atc aaa ccc ttt tgt gaa gat ctt gac caa tgg cta agt gaa gat     453
Leu Ile Lys Pro Phe Cys Glu Asp Leu Asp Gln Trp Leu Ser Glu Asp
100                 105                 110                 115 gac aat cat gtt gca gca att cac tgt aaa gct gga aag gga cga act     501
Asp Asn His Val Ala Ala Ile His Cys Lys Ala Gly Lys Gly Arg Thr
                 120                 125                 130
```

```
ggt gta atg att tgt gca tat tta tta cat cgg ggc aaa ttt cta aag       549
Gly Val Met Ile Cys Ala Tyr Leu Leu His Arg Gly Lys Phe Leu Lys
        135                 140                 145 gca caa gag gcc cta gat ttc tat ggg gaa gta agg acc aga gac aaa       597
Ala Gln Glu Ala Leu Asp Phe Tyr Gly Glu Val Arg Thr Arg Asp Lys
150                 155                 160 aag gga gta act att ccc agt cag agg cgc tat gtg tat tat tat agc       645
Lys Gly Val Thr Ile Pro Ser Gln Arg Arg Tyr Val Tyr Tyr Tyr Ser
        165                 170                 175 tac ctg tta aag aat cat ctg gat tat aga cca gtg gca ctg ttg ttt       693
Tyr Leu Leu Lys Asn His Leu Asp Tyr Arg Pro Val Ala Leu Leu Phe
180                 185                 190                 195 cac aag atg atg ttt gaa act att cca atg ttc agt ggc gga act tgc       741
His Lys Met Met Phe Glu Thr Ile Pro Met Phe Ser Gly Gly Thr Cys
            200                 205                 210 aat cct cag ttt gtg gtc tgc cag cta aag gtg aag atc tat tcc tcc       789
Asn Pro Gln Phe Val Val Cys Gln Leu Lys Val Lys Ile Tyr Ser Ser
        215                 220                 225 aat tca gga ccc aca cga cgg gaa gac aag ttc atg tac ttt gag ttc       837
Asn Ser Gly Pro Thr Arg Arg Glu Asp Lys Phe Met Tyr Phe Glu Phe
230                 235                 240 cct cag cca ttg cct gtg tgc ggt gac atc aaa gta gag ttc ttc cac       885
Pro Gln Pro Leu Pro Val Cys Gly Asp Ile Lys Val Glu Phe Phe His
        245                 250                 255 aaa cag aac aag atg cta aaa aag gac aaa atg ttt cac ttt tgg gta       933
Lys Gln Asn Lys Met Leu Lys Lys Asp Lys Met Phe His Phe Trp Val
260                 265                 270                 275 aac aca ttc ttc ata cca gga cca gag gaa acc tca gaa aaa gta gaa       981
Asn Thr Phe Phe Ile Pro Gly Pro Glu Glu Thr Ser Glu Lys Val Glu
            280                 285                 290 aat gga agt cta tgt gat caa gaa att gat agt att tgc agt ata gaa      1029
Asn Gly Ser Leu Cys Asp Gln Glu Ile Asp Ser Ile Cys Ser Ile Glu
        295                 300                 305 cgt gca gat aat gac aag gaa tat cta gta ctc act tta aca aaa aat      1077
Arg Ala Asp Asn Asp Lys Glu Tyr Leu Val Leu Thr Leu Thr Lys Asn
310                 315                 320 gat ctc gac aaa gca aat aaa gac aag gcc aac cga tat ttt tct cca      1125
Asp Leu Asp Lys Ala Asn Lys Asp Lys Ala Asn Arg Tyr Phe Ser Pro
        325                 330                 335 aat ttt aag gtg aag ctg tac ttc aca aaa act gta gag gag cca tca      1173
Asn Phe Lys Val Lys Leu Tyr Phe Thr Lys Thr Val Glu Glu Pro Ser
340                 345                 350                 355 aac ccg gag gct agc agt tca act tct gtg acg cca gat gtt agt gac      1221
Asn Pro Glu Ala Ser Ser Ser Thr Ser Val Thr Pro Asp Val Ser Asp
            360                 365                 370 aat gaa cct gat cat tat aga tat tct gac acc act gac tct gac cca      1269
Asn Glu Pro Asp His Tyr Arg Tyr Ser Asp Thr Thr Asp Ser Asp Pro
        375                 380                 385 gag aat gaa ccc ttt gat gaa g                                        1291
Glu Asn Glu Pro Phe Asp Glu
390

<210> SEQ ID NO 17
<211> LENGTH: 394
<212> TYPE: PRT
<213> ORGANISM: Canis familiaris

<400> SEQUENCE: 17

Met Thr Ala Ile Ile Lys Glu Ile Val Ser Arg Asn Lys Arg Arg Tyr
1               5                   10                  15
```

```
Gln Glu Asp Gly Phe Asp Leu Asp Leu Thr Tyr Ile Tyr Pro Asn Ile
             20                  25                  30

Ile Ala Met Gly Phe Pro Ala Glu Arg Leu Glu Gly Val Tyr Arg Asn
         35                  40                  45

Asn Ile Asp Asp Val Val Arg Phe Leu Asp Ser Lys His Lys Asn His
     50                  55                  60

Tyr Lys Ile Tyr Asn Leu Cys Ala Glu Arg His Tyr Asp Thr Ala Lys
 65                  70                  75                  80

Phe Asn Cys Arg Val Ala Gln Tyr Pro Phe Glu Asp His Asn Pro Pro
                 85                  90                  95

Gln Leu Glu Leu Ile Lys Pro Phe Cys Glu Asp Leu Asp Gln Trp Leu
            100                 105                 110

Ser Glu Asp Asp Asn His Val Ala Ala Ile His Cys Lys Ala Gly Lys
        115                 120                 125

Gly Arg Thr Gly Val Met Ile Cys Ala Tyr Leu Leu His Arg Gly Lys
    130                 135                 140

Phe Leu Lys Ala Gln Glu Ala Leu Asp Phe Tyr Gly Glu Val Arg Thr
145                 150                 155                 160

Arg Asp Lys Lys Gly Val Thr Ile Pro Ser Gln Arg Arg Tyr Val Tyr
                165                 170                 175

Tyr Tyr Ser Tyr Leu Leu Lys Asn His Leu Asp Tyr Arg Pro Val Ala
            180                 185                 190

Leu Leu Phe His Lys Met Met Phe Glu Thr Ile Pro Met Phe Ser Gly
        195                 200                 205

Gly Thr Cys Asn Pro Gln Phe Val Val Cys Gln Leu Lys Val Lys Ile
    210                 215                 220

Tyr Ser Ser Asn Ser Gly Pro Thr Arg Arg Glu Asp Lys Phe Met Tyr
225                 230                 235                 240

Phe Glu Phe Pro Gln Pro Leu Pro Val Cys Gly Asp Ile Lys Val Glu
                245                 250                 255

Phe Phe His Lys Gln Asn Lys Met Leu Lys Lys Asp Lys Met Phe His
            260                 265                 270

Phe Trp Val Asn Thr Phe Phe Ile Pro Gly Pro Glu Glu Thr Ser Glu
        275                 280                 285

Lys Val Glu Asn Gly Ser Leu Cys Asp Gln Glu Ile Asp Ser Ile Cys
    290                 295                 300

Ser Ile Glu Arg Ala Asp Asn Asp Lys Glu Tyr Leu Val Leu Thr Leu
305                 310                 315                 320

Thr Lys Asn Asp Leu Asp Lys Ala Asn Lys Asp Lys Ala Asn Arg Tyr
                325                 330                 335

Phe Ser Pro Asn Phe Lys Val Lys Leu Tyr Phe Thr Lys Thr Val Glu
            340                 345                 350

Glu Pro Ser Asn Pro Glu Ala Ser Ser Thr Ser Val Thr Pro Asp
        355                 360                 365

Val Ser Asp Asn Glu Pro Asp His Tyr Arg Tyr Ser Asp Thr Thr Asp
370                 375                 380

Ser Asp Pro Glu Asn Glu Pro Phe Asp Glu
385                 390

<210> SEQ ID NO 18
<211> LENGTH: 430
<212> TYPE: PRT
<213> ORGANISM: Canis familiaris
```

<400> SEQUENCE: 18

```
Pro Pro Ala Ala Arg Pro Gly Ala Ala Cys Ser Leu Arg Arg Pro
  1               5                  10                  15

Arg Arg Pro Pro Leu Leu Pro Ser Leu Ser Ser Phe Leu Ser Ser His
             20                  25                  30

Arg Leu Pro Asp Met Thr Ala Ile Ile Lys Glu Ile Val Ser Arg Asn
         35                  40                  45

Lys Arg Arg Tyr Gln Glu Asp Gly Phe Asp Leu Asp Leu Thr Tyr Ile
     50                  55                  60

Tyr Pro Asn Ile Ile Ala Met Gly Phe Pro Ala Glu Arg Leu Glu Gly
 65                  70                  75                  80

Val Tyr Arg Asn Asn Ile Asp Asp Val Val Arg Phe Leu Asp Ser Lys
                 85                  90                  95

His Lys Asn His Tyr Lys Ile Tyr Asn Leu Cys Ala Glu Arg His Tyr
            100                 105                 110

Asp Thr Ala Lys Phe Asn Cys Arg Val Ala Gln Tyr Pro Phe Glu Asp
            115                 120                 125

His Asn Pro Pro Gln Leu Glu Leu Ile Lys Pro Phe Cys Glu Asp Leu
        130                 135                 140

Asp Gln Trp Leu Ser Glu Asp Asp Asn His Val Ala Ala Ile His Cys
145                 150                 155                 160

Lys Ala Gly Lys Gly Arg Thr Gly Val Met Ile Cys Ala Tyr Leu Leu
                165                 170                 175

His Arg Gly Lys Phe Leu Lys Ala Gln Glu Ala Leu Asp Phe Tyr Gly
            180                 185                 190

Glu Val Arg Thr Arg Asp Lys Lys Gly Val Thr Ile Pro Ser Gln Arg
            195                 200                 205

Arg Tyr Val Tyr Tyr Tyr Ser Tyr Leu Leu Lys Asn His Leu Asp Tyr
        210                 215                 220

Arg Pro Val Ala Leu Leu Phe His Lys Met Met Phe Glu Thr Ile Pro
225                 230                 235                 240

Met Phe Ser Gly Gly Thr Cys Asn Pro Gln Phe Val Val Cys Gln Leu
                245                 250                 255

Lys Val Lys Ile Tyr Ser Ser Asn Ser Gly Pro Thr Arg Arg Glu Asp
            260                 265                 270

Lys Phe Met Tyr Phe Glu Phe Pro Gln Pro Leu Pro Val Cys Gly Asp
        275                 280                 285

Ile Lys Val Glu Phe Phe His Lys Gln Asn Lys Met Leu Lys Lys Asp
        290                 295                 300

Lys Met Phe His Phe Trp Val Asn Thr Phe Phe Ile Pro Gly Pro Glu
305                 310                 315                 320

Glu Thr Ser Glu Lys Val Glu Asn Gly Ser Leu Cys Asp Gln Glu Ile
                325                 330                 335

Asp Ser Ile Cys Ser Ile Glu Arg Ala Asp Asn Asp Lys Glu Tyr Leu
            340                 345                 350

Val Leu Thr Leu Thr Lys Asn Asp Leu Asp Lys Ala Asn Lys Asp Lys
            355                 360                 365

Ala Asn Arg Tyr Phe Ser Pro Asn Phe Lys Val Lys Leu Tyr Phe Thr
        370                 375                 380

Lys Thr Val Glu Glu Pro Ser Asn Pro Glu Ala Ser Ser Ser Thr Ser
385                 390                 395                 400

Val Thr Pro Asp Val Ser Asp Asn Glu Pro Asp His Tyr Arg Tyr Ser
                405                 410                 415
```

```
Asp Thr Thr Asp Ser Asp Pro Glu Asn Glu Pro Phe Asp Glu
        420                 425                 430

<210> SEQ ID NO 19
<211> LENGTH: 1257
<212> TYPE: DNA
<213> ORGANISM: Homo sapiens

<400> SEQUENCE: 19
cctcccctcg cccggcgcgg tcccgtccgc ctctcgctcg cctccgcct  cccctcggtc      60 ttccgaggcg cccgggctcc cggcgcggcg gcggaggggg cgggcaggcc ggcgggcggt     120
gatgtggcag gactctttat gcgctgcggc aggatacgcg ctcggcgctg ggacgcgact     180
gcgctcagtt ctctcctctc ggaagctgca gccatgatgg aagtttgaga gttgagccgc     240
tgtgaggcga ggccgggctc aggcgaggga gatgagagac ggcggcggcc gcggcccgga     300 gccctctca gcgcctgtga gcagccgcg gggcagcgcc ctcggggagc cggccggcct       360
gcggcggcgg cagcggcggc gtttctcgcc tcctcttcgt cttttctaac cgtgcagcct     420
cttcctcggc ttctcctgaa agggaaggtg gaagccgtgg gctcgggcgg gagccggctg     480
aggcgcggcg gcggcggcg cggcacctcc cgctcctgga gcggggggga gaagcggcgg     540
cggcggcggc cgcggcggct gcagctccag ggaggggtc tgagtcgcct gtcaccattt      600
ccagggctgg gaacgccgga gagttggtct ctccccttct actgcctcca acacggcggc    660
ggcggcggcg gcacatccag ggacccgggc cggttttaaa cctcccgtcc gccgccgccg    720
caccccccgt ggcccgggct ccggaggccg ccggcggagg cagccgttcg gaggattatt    780
cgtcttctcc ccattccgct gccgccgctg ccaggcctct ggctgctgag gagaagcagg     840
cccagtcgct gcaaccatcc agcagccgcc gcagcagcca ttacccggct gcggtccaga    900
gccaagcggc ggcagagcga ggggcatcag ctaccgccaa gtccagagcc atttccatcc    960
tgcagaagaa gccccgccac cagcagcttc tgccatctct ctcctccttt tcttcagcc    1020 acaggctccc agacatgaca gccatcatca aagagatcgt tagcagaaac aaaaggagat    1080
atcaagagga tggattcgac ttagacttga cctgtatcca tttctgcggc tgctcctctt    1140 taccttctg tcactctctt agaacgtggg agtagacgga tgcgaaaatg tccgtagttt     1200
gggtgactat aacatttaac cctggtcagg ttgctaggtc atatattttg tgtttcc       1257

<210> SEQ ID NO 20
<211> LENGTH: 1084
<212> TYPE: DNA
<213> ORGANISM: Homo sapiens

<400> SEQUENCE: 20
gagacatagc cagctcttaa atctgacttc cagattttca ctgtgtcttc ttttttctgt      60
aacgtgttgc cttttttagc catgaaaaat tagaagttga actcttgtct tttcaggcag     120
gtgtcaattt tggggttttg ttttgatttt tggttttga cataaagtac tttagttctg      180
tgatgtataa accgtgagtt tctgtttttc tcatatacct gaatactgtc catgtggaag     240
ttacctttta tctttaccag tattaacaca taaatggtta tacataaata cattgaccac     300
cttttattac tccagctata gtggggaaag ctttcttttc ataactagct aatgttttaa     360
aaagtattct tttagtttga ttgctgcata tttcagatat ttctttcctt aactaaagta     420
ctcagatatt tatccaaaca ttattgctat gggatttcct gcagaaagac ttgaaggcgt     480
atacaggaac aatattgatg atgtagtaag gtaagaatgc tttgattttc tatttcaaat     540
```

| | |
|---|---|
| attgatgttt atattcatgt tgtgttttca tttagaaaag atttctaagc cacagaaaaa | 600 |
| gatactttgt gatgtaaact attattgtag tgctctataa tcatttttg gcttaccgta | 660 |
| cctaatggac ttcaggggga tacagttcat tgataagaa ctgaccttat acattacata | 720 |
| atcaggtact tatgtgatat catttcctgg actccataaa atgctggtca ccaggtttaa | 780 |
| tacctggatt ccattacagt gtgattttg tcttatttca tagttgggga ttaggcttaa | 840 |
| aatcctagag tggatttatt cagttaaatt tattcacact aagatgtgat gactaatact | 900 |
| gtatatttt atgtagacca aattttaagg taccactgtg catatgttac caactacctg | 960 |
| aagaatattt ggttggtaca gaatatataa aggaatcgct ggtgttccaa ggctaatcca | 1020 |
| gttttataat tttgcataat ttcctaactg cgaatatcat ttatttaaac aatttattct | 1080 |
| ccag | 1084 |

<210> SEQ ID NO 21
<211> LENGTH: 1104
<212> TYPE: DNA
<213> ORGANISM: Homo sapiens

<400> SEQUENCE: 21

| | |
|---|---|
| gaattaatag ttagtacgtg gatctttcaa atatcaaaag ttttcagttt gatgggaaaa | 60 |
| tgatgtctga atttcaggg ttatttttaa gagtacttga ttatgactgt cttgtaaatc | 120 |
| tctatgagct aggtatactt gcactaaatg ctaatgcttt ttaaagaagt tatgtcttaa | 180 |
| tattcagtct cattatgtta ggttgaagat agaagattat gaaatatttc tctgaaaagc | 240 |
| tctggttta cttcagattg tataaatctg tgtaatgtaa taattattta agaatgacat | 300 |
| gattactact ctaaacccat agaagggta tttgttggat tatttatttt cacttaaatg | 360 |
| gtatttgaga ttaggaaaaa gaaaatctgt cttttggttt ttcttgatag tattaatgta | 420 |
| atttcaaatg ttagctcatt tttgttaatg gtggcttttt gtttgtttgt tttgttttaa | 480 |
| ggtttttgga ttcaaagcat aaaaaccatt acaagatata caatctgtaa gtatgttttc | 540 |
| ttatttgtat gcttgcaaat atcttctaaa acaactatta agtgaaagtt atctgcttgt | 600 |
| tagagtgagg tagagttaaa gatacatttt aacagaattg tattcctaaa ccgattaagt | 660 |
| caagaagtcc aagagcattg ttagatcatt tagaaagtgt agtgatgagg taaaacattg | 720 |
| ttggcacaga ttcatgttac ttgatctgct ttaaatgact tggcatctag cccatatttg | 780 |
| agcccataac cgtgtggtaa tttgaagtgt aattcacagt agagcttctg ttaaagcact | 840 |
| aatagcatct tccatggagg tatacttcag agtgaatata attttgttta tcctgtgtct | 900 |
| ctagagctat tgactgaaaa agctgttagg gcattctcta actgtacatc acctaagtta | 960 |
| tttaaaattg ctgaattaag tggcttgtct tgtctagaca gattttaagg actgcccacc | 1020 |
| tgattgatag aactagttga ccttatcttt aacttttgt tttcttttga cttgggataa | 1080 |
| aagttgaaaa ggtaaaagga agga | 1104 |

<210> SEQ ID NO 22
<211> LENGTH: 656
<212> TYPE: DNA
<213> ORGANISM: Homo sapiens

<400> SEQUENCE: 22

| | |
|---|---|
| ttgcatacac ttaatctttt aagctttggt tttattatta taatatgggg gtgataacag | 60 |
| tatctactta atagaattct tgttattaac atgaaataat taatgttaaa cacagcataa | 120 |

```
tatgtgtcac attataaaga ttcaggcaat gtttgttagt attagtactt ttttttcttc      180
ctaagtgcaa aagataactt tatatcactt ttaaactttt cttttagttg tgctgaaaga      240
cattatgaca ccgccaaatt taattgcaga ggtaggtatg aatgtactgt actatgttgt      300
ataacttaaa cccgatagac tgtatcttac tgtcataaca ataatgagtc atccagatta      360
tcgagtgaga tacatattta tcttaagaat tatctttaaa aatttcaaaa attttaattt      420
tactgttgtg ttttaggaaa aagtattgca taaagctatt aatattgtca ggaagactaa      480
agtgcagcat agactaagca atcaggaaaa ttcctagact aaaaatagta taaggagagg      540
gtttacctac tatttgaggc agttggtcta atagtaagca atcacaggga ggaaagcaga      600
aactacttaa ctcttctgtg ttgaggaatg acataaaagg tatgaaagga tataac         656
```

<210> SEQ ID NO 23
<211> LENGTH: 808
<212> TYPE: DNA
<213> ORGANISM: Homo sapiens
<220> FEATURE:
<221> NAME/KEY: misc_feature
<222> LOCATION: (1)..(808)
<223> OTHER INFORMATION: n is unknown

<400> SEQUENCE: 23

```
atacattatt tttctctgga atccagtgtt tcttttaaat acctgttaag tttgtatgca       60
acatttctaa agttacctac ttgttaatta aaaattcaag ggttttttttt tcttattctg     120 aggttatctt tttaccacag ttgcacaata tcctttgaa gaccataacc caccacagct       180
agaacttatc aaacccttttt gtgaagatct tgaccaatgg ctaagtgaag atgacaatca    240
tgttgcagca attcactgta aagctggaaa gggacgaact ggtgtaatga tatgtgcata     300
tttattacat cggggcaaat ttttaaaggc acaagaggcc ctagatttct atggggaagt     360
aaggaccaga gacaaaaagg taagttattt tttgatgttt ttccttttcct cttcctggat    420 ctgagaattt attggaaaac agattttggg tttcttttttt tcnnnnnnnn nnnnnnnnnn   480
nnnnnnnnnn nnnnnnnnnn nnnnnnnnnn nnnnnnnnnn nnnnnnnnnn nnnnnnnnnn    540
nnnnnnnnnn nnnnnnnnnn nnnnnnnnnn nnnnnnnnnn nnnnnnnnnn nnnnnnnnnn    600
nnnnnnnnnn nnnnnnnnnn nnnnnnnnnn nnnnnnnnnn nnnnnnnnnn nnnnnnnnnn    660
nnnnnnnnnn nnnnnnnnnn nnnnnnnnnn nnnnnnnnnn nnnnnnnnnn nnnnnnnnnn    720
nnnnnnnnnn ntcctccctc cccaccctca gtcnctggaa aacaggtttt aaagatagtt    780
gctaatcctt atttcttcta aattttta                                        808
```

<210> SEQ ID NO 24
<211> LENGTH: 670
<212> TYPE: DNA
<213> ORGANISM: Homo sapiens

<400> SEQUENCE: 24

```
atatgataat tgttttaagg gaggagagtt attctgatat ccttgtattg atattgctct       60
tatttattat tgagctggat ttaagtatta atcatttaag gtcaaatttc taatgtataa     120
tatgttctta aatggctacg acccagttac catagcaatt tagtgaaata actataatgg    180
aacatttttt ttcaatttgg cttctctttt ttttctgtcc accagggagt aactattccc    240
agtcagaggc gctatgtgta ttattatagc tacctgttaa agaatcatct ggattataga    300
ccagtggcac tgttgtttca caagatgatg tttgaaacta ttccaatgtt cagtggcgga    360
acttgcagta agtgcttgga aattctcatc cttccatgta ttggaacagt tttcttaacc    420
```

```
atatctagaa gtttacataa aaatttagaa aagaaattta ccacatttga aatttatgca      480
ggagactata tttctgaagc atttgaacaa attaattagc tttgttgttc aactcattgg      540
gctaaagaag ccaaaagcaa tgggttttaa tgtagtcgaa gccaaattat atttatgaaa      600
gaaatattct gtgttataac ccaccaaata cagcccaatt tctgactaga tgtatggaag      660
aacctgtccc                                                             670
```

<210> SEQ ID NO 25
<211> LENGTH: 661
<212> TYPE: DNA
<213> ORGANISM: Homo sapiens

<400> SEQUENCE: 25

```
atatttttat ttcatttatt tcagttgatt tgcttgagat caagattgca gatacagaat       60
ccatatttcg tgtatattgc tgatattaat cattaaaatc gttttttgaca gtttgacagt     120 taaaggcatt tcctgtgaaa taatactggt atgtatttaa ccatgcagat cctcagtttg     180
tggtctgcca gctaaaggtg aagatatatt cctccaattc aggacccaca cgacgggaag     240
acaagttcat gtactttgag ttccctcagc cgttacctgt gtgtggtgat atcaaagtag     300
agttcttcca caaacagaac aagatgctaa aaaaggtttg tactttactt tcattgggag     360 aaaatatccaa aataaggaca gattaaaagc tatattttat tttatgacat gtaaggaact     420
ataatttgtt ttctattaga tctgcaggtg ttttgcttac tctggcattg gtgagacatt     480
ataagggtaa ataatcctgt ttgaaggaaa aggccttatg gcattgtaac attagaggaa     540
tttttcttaa caaggatggt taactgagaa gaaattagca tgggaccaat attttaaaaa     600
tttttggtct ataggtagaa atgagatctg ttctgtggtc ttatgtagtg acacaaacca     660
c                                                                      661
```

<210> SEQ ID NO 26
<211> LENGTH: 739
<212> TYPE: DNA
<213> ORGANISM: Homo sapiens

<400> SEQUENCE: 26

```
gtgttcacct ttattcagaa tatcaaatga tagtttatttt tgttgacttt ttgcaaatgt       60
ttaacatagg tgacagattt tcttttttaa aaaataaaa catcattaat taaatatgtc      120
atttcatttc ttttttcttt ctttttttttt ttttttttagg acaaaatgtt tcacttttgg     180
gtaaatacat tcttcatacc aggaccagag gaaacctcag aaaaagtaga aatggaagt      240 ctatgtgatc aagaaatcga tagcatttgc agtatagagc gtgcagataa tgacaaggaa     300
tatctagtac ttactttaac aaaaaatgat cttgacaaag caaataaaga caaagccaac     360
cgatactttt ctccaaattt taaggtcagt taaattaaac attttgtggg ggttggtgac     420
ttgtatgtat gtgatgtgtg tttaattcta ggagtacagc tgatgaagaa cttgcttgac     480
aagtttttaa cttatgtatt atttcgaagc agtgtttacg tagcagtaac atgaaagttt     540
ctaataaaat acccaatgta cacagcgtca aaaagctgc attttttcctt ttcctaattc     600 tttgttgttt gctgaaatct ggggcaaagg tgcgggaggg ggctaaatga ctgggatatg     660
aagtaggaat gggagaggaa agaaatagat gggaactcag tcatttggga atgattcata     720
tggaatgttt ttactgctt                                                    739
```

<210> SEQ ID NO 27

<211> LENGTH: 970
<212> TYPE: DNA
<213> ORGANISM: Homo sapiens

<400> SEQUENCE: 27

| | |
|---|---|
| atgagccaag atcatgccac tgcactccag cttggcaaca gagcaagact cttgtctcca | 60 |
| gaaatagaaa ataaataaat tgtattaaca tcctgatagt ttatctgtct agtacctagc | 120 |
| aagaagaaa atgttgaaca tcttaagaag agggtcattt aaaaggcctc ttaaaagatc | 180 |
| atgtttgtta cagtgcttaa aaattaatat gttcatctgc aaaatggaat aaaaaatctg | 240 |
| ttaaaaatat atttcactaa atagtttaag atgagtcata tttgtgggtt ttcattttaa | 300 |
| attttctttc tctaggtgaa gctgtacttc acaaaaacag tagaggagcc gtcaaatcca | 360 |
| gaggctagca gttcaacttc tgtaacacca gatgttagtg acaatgaacc tgatcattat | 420 |
| agatattctg acaccactga ctctgatcca gagaatgaac cttttgatga agatcagcat | 480 |
| acacaaatta caaagtctg aattttttt tatcaagagg gataaaacac catgaaaata | 540 |
| aacttgaata aactgaaaat ggacctttt ttttttaatg gcaataggac attgtgtcag | 600 |
| attaccagtt ataggaacaa ttctctttc ctgaccaatc ttgttttacc ctatacatcc | 660 |
| acagggtttt gacacttgtt gtccagttga aaaaggttg tgtagctgtg tcatgtatat | 720 |
| accttttgt gtcaaaagga catttaaaat tcaattagga ttaataaaga tggcactttc | 780 |
| ccgttttatt ccagttttat aaaaagtgga gacagactga tgtgtatacg taggaatttt | 840 |
| ttccttttgt gttctgtcac caactgaagt ggctaaagag cttttgtgata tactggttca | 900 |
| catcctaccc ctttgcactt gtggcaacag ataagtttgc agttggctaa gagaggtttc | 960 |
| cgaaaggttt | 970 |

<210> SEQ ID NO 28
<211> LENGTH: 11
<212> TYPE: PRT
<213> ORGANISM: Homo sapiens

<400> SEQUENCE: 28

Ile His Cys Lys Ala Gly Lys Gly Arg Thr Gly
 1               5                  10

<210> SEQ ID NO 29
<211> LENGTH: 11
<212> TYPE: PRT
<213> ORGANISM: Artificial Sequence
<220> FEATURE:
<221> NAME/KEY: SITE
<222> LOCATION: (1)
<223> OTHER INFORMATION: This amino acid residue is either Ile or Val.
<220> FEATURE:
<221> NAME/KEY: SITE
<222> LOCATION: (10)
<223> OTHER INFORMATION: This amino acid residue is either Ser or Thr.
<220> FEATURE:
<221> NAME/KEY: SITE
<222> LOCATION: (4)
<223> OTHER INFORMATION: This can be any amino acid residue.
<220> FEATURE:
<221> NAME/KEY: SITE
<222> LOCATION: (7)..(8)
<223> OTHER INFORMATION: These can be any amino acid residues
<220> FEATURE:
<223> OTHER INFORMATION: Description of Artificial Sequence:Conserved
      catalytic domain of a protein tyrosine
      phosphatase.

<400> SEQUENCE: 29

```
Xaa His Cys Xaa Ala Gly Xaa Xaa Arg Xaa Gly
 1               5                  10
```

<210> SEQ ID NO 30
<211> LENGTH: 60
<212> TYPE: PRT
<213> ORGANISM: Homo sapiens

<400> SEQUENCE: 30

```
Met Thr Ala Ile Ile Lys Glu Ile Val Ser Arg Asn Lys Arg Tyr
 1               5                  10                  15

Gln Glu Asp Gly Phe Asp Leu Asp Leu Thr Tyr Ile Tyr Pro Asn Ile
            20                  25                  30

Ile Ala Met Gly Phe Pro Ala Glu Arg Asn Glu Gly Val Tyr Arg Asn
        35                  40                  45

Asn Ile Asp Asp Val Val Arg Phe Leu Asp Ser Lys
        50                  55              60
```

<210> SEQ ID NO 31
<211> LENGTH: 60
<212> TYPE: PRT
<213> ORGANISM: Homo sapiens

<400> SEQUENCE: 31

```
Met Thr Ala Ile Ile Lys Glu Ile Val Ser Arg Asn Lys Arg Tyr
 1               5                  10                  15

Gln Glu Asp Gly Phe Asp Leu Asp Leu Thr Tyr Ile Tyr Pro Asn Ile
            20                  25                  30

Ile Ala Met Gly Phe Pro Ala Glu Arg Leu Glu Gly Val Tyr Arg Asn
        35                  40                  45

Asn Ile Asp Asp Val Val Arg Phe Leu Asp Ser Lys
        50                  55              60
```

<210> SEQ ID NO 32
<211> LENGTH: 60
<212> TYPE: PRT
<213> ORGANISM: Homo sapiens

<400> SEQUENCE: 32

```
Met Thr Ala Ile Ile Lys Glu Ile Val Ser Arg Asn Lys Arg Tyr
 1               5                  10                  15

Gln Glu Asp Gly Phe Asp Leu Asp Leu Thr Tyr Ile Tyr Pro Asn Ile
            20                  25                  30

Ile Ala Met Glu Phe Pro Ala Glu Arg Leu Glu Gly Val Tyr Arg Asn
        35                  40                  45

Asn Ile Asp Asp Val Val Arg Phe Leu Asp Ser Lys
        50                  55              60
```

<210> SEQ ID NO 33
<211> LENGTH: 40
<212> TYPE: DNA
<213> ORGANISM: Homo sapiens

<400> SEQUENCE: 33
gttttcccag tcacgacgag gtgacagatt ttcttttta        40

<210> SEQ ID NO 34
<211> LENGTH: 38
<212> TYPE: DNA
<213> ORGANISM: Homo sapiens -continued

```
<400> SEQUENCE: 34
aggaaacagc tatgaccatt cggttggctt tgtctttta                               38

<210> SEQ ID NO 35
<211> LENGTH: 37
<212> TYPE: DNA
<213> ORGANISM: Homo sapiens

<400> SEQUENCE: 35
gttttcccag tcacgacgca tttgcagtat agagcgt                                 37

<210> SEQ ID NO 36
<211> LENGTH: 38
<212> TYPE: DNA
<213> ORGANISM: Homo sapiens

<400> SEQUENCE: 36
aggaaacagc tatgaccata gctgtactcc tagaatta                                38

<210> SEQ ID NO 37
<211> LENGTH: 24
<212> TYPE: DNA
<213> ORGANISM: Homo sapiens

<400> SEQUENCE: 37 tttttttta ggacaaaatg tttc                                                24

<210> SEQ ID NO 38
<211> LENGTH: 23
<212> TYPE: DNA
<213> ORGANISM: Homo sapiens

<400> SEQUENCE: 38
aattcagact tttgtaattt gtg                                                23

<210> SEQ ID NO 39
<211> LENGTH: 20
<212> TYPE: DNA
<213> ORGANISM: Homo sapiens

<400> SEQUENCE: 39
tcctttttct tcagccacag                                                    20

<210> SEQ ID NO 40
<211> LENGTH: 20
<212> TYPE: DNA
<213> ORGANISM: Homo sapiens

<400> SEQUENCE: 40
attgctgcaa catgattgtc                                                    20

<210> SEQ ID NO 41
<211> LENGTH: 19
<212> TYPE: DNA
<213> ORGANISM: Homo sapiens

<400> SEQUENCE: 41
tgacaatcat gttgcagca                                                     19

<210> SEQ ID NO 42
<211> LENGTH: 23
<212> TYPE: DNA
<213> ORGANISM: Homo sapiens
```

```
<400> SEQUENCE: 42
tttattttca tggtgtttta tcc                                               23

<210> SEQ ID NO 43
<211> LENGTH: 22
<212> TYPE: DNA
<213> ORGANISM: Homo sapiens

<400> SEQUENCE: 43
cttcagccac aggctcccag ac                                                22

<210> SEQ ID NO 44
<211> LENGTH: 18
<212> TYPE: DNA
<213> ORGANISM: Homo sapiens

<400> SEQUENCE: 44
ggtgttttat ccctcttg                                                     18

<210> SEQ ID NO 45
<211> LENGTH: 32
<212> TYPE: DNA
<213> ORGANISM: Homo sapiens

<400> SEQUENCE: 45
cgggatccat gacagccatc atcaaagaga tc                                     32

<210> SEQ ID NO 46
<211> LENGTH: 25
<212> TYPE: DNA
<213> ORGANISM: Homo sapiens

<400> SEQUENCE: 46
cggaattctc agactttgt aattg                                              25

<210> SEQ ID NO 47
<211> LENGTH: 20
<212> TYPE: DNA
<213> ORGANISM: Homo sapiens

<400> SEQUENCE: 47
atcctcagtt tgtggtctgc                                                   20

<210> SEQ ID NO 48
<211> LENGTH: 20
<212> TYPE: DNA
<213> ORGANISM: Homo sapiens

<400> SEQUENCE: 48
gagcgtgcag ataatgacaa                                                   20

<210> SEQ ID NO 49
<211> LENGTH: 403
<212> TYPE: PRT
<213> ORGANISM: Mus musculus

<400> SEQUENCE: 49

Met Thr Ala Ile Ile Lys Glu Ile Val Ser Arg Asn Lys Arg Arg Tyr
 1               5                  10                  15

Gln Glu Asp Gly Phe Asp Leu Asp Leu Thr Tyr Ile Tyr Pro Asn Ile
             20                  25                  30
```

```
Ile Ala Met Gly Phe Pro Ala Glu Arg Leu Glu Gly Val Tyr Arg Asn
         35                  40                  45

Asn Ile Asp Asp Val Val Arg Phe Leu Asp Ser Lys His Lys Asn His
    50                  55                  60

Tyr Lys Ile Tyr Asn Leu Cys Ala Glu Arg His Tyr Asp Thr Ala Lys
65                  70                  75                  80

Phe Asn Cys Arg Val Ala Gln Tyr Pro Phe Glu Asp His Asn Pro Pro
                85                  90                  95

Gln Leu Glu Leu Ile Lys Pro Phe Cys Glu Asp Leu Asp Gln Trp Leu
            100                 105                 110

Ser Glu Asp Asp Asn His Val Ala Ala Ile His Cys Lys Ala Gly Lys
        115                 120                 125

Gly Arg Thr Gly Val Met Ile Cys Ala Tyr Leu Leu His Arg Gly Lys
130                 135                 140

Phe Leu Lys Ala Gln Glu Ala Leu Asp Phe Tyr Gly Glu Val Arg Thr
145                 150                 155                 160

Arg Asp Lys Lys Gly Val Thr Ile Pro Ser Gln Arg Arg Tyr Val Tyr
                165                 170                 175

Tyr Tyr Ser Tyr Leu Leu Lys Asn His Leu Asp Tyr Arg Pro Val Ala
            180                 185                 190

Leu Leu Phe His Lys Met Met Phe Glu Thr Ile Pro Met Phe Ser Gly
        195                 200                 205

Gly Thr Cys Asn Pro Gln Phe Val Cys Gln Leu Lys Val Lys Ile
    210                 215                 220

Tyr Ser Ser Asn Ser Gly Pro Thr Arg Arg Glu Asp Lys Phe Met Tyr
225                 230                 235                 240

Phe Glu Phe Pro Gln Pro Leu Pro Val Cys Gly Asp Ile Lys Val Glu
                245                 250                 255

Phe Phe His Lys Gln Asn Lys Met Leu Lys Lys Asp Lys Met Phe His
            260                 265                 270

Phe Trp Val Asn Thr Phe Phe Ile Pro Gly Pro Glu Glu Thr Ser Glu
        275                 280                 285

Lys Val Glu Asn Gly Ser Leu Cys Asp Gln Glu Ile Asp Ser Ile Cys
    290                 295                 300

Ser Ile Glu Arg Ala Asp Asn Asp Lys Glu Tyr Leu Val Leu Thr Leu
305                 310                 315                 320

Thr Lys Asn Asp Leu Asp Lys Ala Asn Lys Asp Lys Ala Asn Arg Tyr
                325                 330                 335

Phe Ser Pro Asn Phe Lys Val Lys Leu Tyr Phe Thr Lys Thr Val Glu
            340                 345                 350

Glu Pro Ser Asn Pro Glu Ala Ser Ser Thr Ser Val Thr Pro Asp
        355                 360                 365

Val Ser Asp Asn Glu Pro Asp His Tyr Arg Tyr Ser Asp Thr Thr Asp
370                 375                 380

Ser Asp Pro Glu Asn Glu Pro Phe Asp Glu Asp Gln His Ser Gln Ile
385                 390                 395                 400

Thr Lys Val

<210> SEQ ID NO 50
<211> LENGTH: 75
<212> TYPE: PRT
<213> ORGANISM: Mus musculus

<400> SEQUENCE: 50
```

```
Pro Pro Leu Ala Arg Arg Gly Pro Val Arg Leu Ser Leu Ala Ser Arg
 1               5                  10                  15

Leu Pro Ser Val Phe Arg Gly Ala Arg Ala Pro Gly Ala Ala Ala Glu
                 20                  25                  30

Gly Ala Gly Arg Pro Ala Gly Gly Asp Val Ala Gly Leu Phe Met Arg
             35                  40                  45

Cys Gly Arg Ile Arg Ala Arg Arg Trp Asp Ala Thr Ala Leu Ser Ser
     50                  55                  60

Leu Leu Ser Glu Ala Ala Ala Met Met Glu Val
 65              70                  75

<210> SEQ ID NO 51
<211> LENGTH: 238
<212> TYPE: PRT
<213> ORGANISM: Homo sapiens

<400> SEQUENCE: 51

Ala Ala Ala Gly Ala Ala Pro Ser Gly Ser Arg Pro Ala Cys Gly Gly
 1               5                  10                  15

Gly Ser Gly Gly Val Ser Arg Leu Leu Phe Val Phe Ser Asn Arg Ala
                 20                  25                  30

Ala Ser Ser Ala Ser Pro Glu Arg Glu Gly Gly Ser Arg Gly Leu
             35                  40                  45

Gly Arg Glu Pro Ala Glu Ala Arg Arg Arg Arg Arg His Leu Pro
     50                  55                  60

Leu Leu Glu Arg Gly Gly Glu Ala Ala Ala Ala Ala Ala Ala Ala Ala
 65              70                  75                  80

Ala Ala Pro Gly Arg Gly Ser Glu Ser Pro Val Thr Ile Ser Arg Ala
                 85                  90                  95

Gly Asn Ala Gly Glu Leu Val Ser Pro Leu Leu Pro Pro Thr Arg
             100                 105                 110

Arg Arg Arg Arg His Ile Gln Gly Pro Gly Pro Val Leu Asn Leu
     115                 120                 125

Pro Ser Ala Ala Ala Pro Pro Val Ala Arg Ala Pro Glu Ala Ala
     130                 135                 140

Gly Gly Gly Ser Arg Ser Glu Asp Tyr Ser Ser Pro His Ser Ala
145                 150                 155                 160

Ala Ala Ala Arg Pro Leu Ala Ala Glu Glu Lys Gln Ala Gln Ser
                 165                 170                 175

Leu Gln Pro Ser Ser Arg Arg Ser Ser His Tyr Pro Ala Ala Val
             180                 185                 190

Gln Ser Gln Ala Ala Ala Glu Arg Gly Ala Ser Ala Thr Ala Lys Ser
         195                 200                 205

Arg Ala Ile Ser Ile Leu Gln Lys Lys Pro Arg His Gln Gln Leu Leu
 210                 215                 220

Pro Ser Leu Ser Ser Phe Phe Phe Ser His Arg Leu Pro Asp
225                 230                 235

<210> SEQ ID NO 52
<211> LENGTH: 194
<212> TYPE: PRT
<213> ORGANISM: Mus musculus

<400> SEQUENCE: 52

Ser Glu Arg Asp Gly Gly Arg Ser Arg Gly Leu Glu Arg Glu Pro Ala
 1               5                  10                  15
```

-continued

```
Gln Ala Arg Arg Leu His Leu Pro Leu Leu Glu Arg Gly Gly Glu Ala
             20                  25                  30

Ala Ala Ala Ala Ala Ala Pro Gly Arg Gly Ser Glu Ser Pro Val Thr
         35                  40                  45

Ile Ala Arg Ala Gly Asn Ala Gly Glu Leu Leu Ser Pro Leu Leu Leu
     50                  55                  60

Pro Pro Thr Arg Arg Arg Arg Arg His Val Gln Gly Pro Gly Pro
 65                  70                  75                  80

Val Leu Ser Leu Pro Ser Ala Ala Ala Pro Pro Leu Ala Arg Ala
             85                  90                  95

Pro Glu Ala Ala Gly Gly Ser Arg Cys Glu Asp Tyr Pro Ser Ser
        100                 105                 110

Pro His Ser Ala Ala Ser Ala Ala Arg Pro Leu Ala Ala Glu Glu Lys
        115                 120                 125

Gln Ala Gln Ser Leu Gln Pro Ser Ser Arg Arg Ser Ser His Tyr
    130                 135                 140

Pro Ala Val Gln Gly Gln Ala Ala Glu Arg Gly Ala Ser Ala
145                 150                 155                 160

Thr Ala Lys Ser Arg Ala Ile Ser Ile Leu Gln Lys Lys Pro Arg His
                165                 170                 175

Gln Gln Leu Leu Pro Ser Leu Ser Ser Phe Phe Ser His Arg Leu
            180                 185                 190

Pro Asp

<210> SEQ ID NO 53
<211> LENGTH: 36
<212> TYPE: PRT
<213> ORGANISM: Canis familiaris

<400> SEQUENCE: 53

Pro Pro Ala Ala Arg Pro Gly Ala Ala Cys Ser Leu Arg Arg Pro
  1               5                  10                  15

Arg Arg Pro Pro Leu Leu Pro Ser Leu Ser Ser Phe Leu Ser Ser His
             20                  25                  30

Arg Leu Pro Asp
         35

<210> SEQ ID NO 54
<211> LENGTH: 1396
<212> TYPE: DNA
<213> ORGANISM: Canis familiaris
<220> FEATURE:
<221> NAME/KEY: CDS
<222> LOCATION: (109)..(1317)

<400> SEQUENCE: 54
ccgcccgccg ccaggcccgg ggccgcctgc agcctgcgga ggaggccgcg ccgcccgccg      60
ctcctgccgt ctctctcctc cttcctctcc agccaccggc tcccagac atg aca gcc    117
                                                   Met Thr Ala
                                                     1 atc atc aag gag atc gtc agc aga aac aaa agg cgc tac cag gag gat    165
Ile Ile Lys Glu Ile Val Ser Arg Asn Lys Arg Arg Tyr Gln Glu Asp
     5                  10                  15 ggg ttc gac ttg gac ttg acc tat att tat ccc aac att att gct atg    213
Gly Phe Asp Leu Asp Leu Thr Tyr Ile Tyr Pro Asn Ile Ile Ala Met
 20                  25                  30                  35 ggg ttt cct gca gaa aga ctt gaa ggc gta tac agg aac aat att gat    261
Gly Phe Pro Ala Glu Arg Leu Glu Gly Val Tyr Arg Asn Asn Ile Asp
```

```
                40                        45                        50
gat gta gta agg ttt ttg gat tca aag cat aaa aac cat tac aag ata      309
Asp Val Val Arg Phe Leu Asp Ser Lys His Lys Asn His Tyr Lys Ile
             55                        60                        65 tac aat ctg tgt gct gaa aga cat tat gat acc gcc aaa ttt aac tgc      357
Tyr Asn Leu Cys Ala Glu Arg His Tyr Asp Thr Ala Lys Phe Asn Cys
         70                        75                        80 aga gtt gca cag tat cct ttt gaa gac cat aat cca cca cag cta gaa      405
Arg Val Ala Gln Tyr Pro Phe Glu Asp His Asn Pro Pro Gln Leu Glu
             85                        90                        95 ctt atc aaa ccc ttt tgt gaa gat ctt gac caa tgg cta agt gaa gat      453
Leu Ile Lys Pro Phe Cys Glu Asp Leu Asp Gln Trp Leu Ser Glu Asp
100                       105                       110                       115 gac aat cat gtt gca gca att cac tgt aaa gct gga aag gga cga act      501
Asp Asn His Val Ala Ala Ile His Cys Lys Ala Gly Lys Gly Arg Thr
                     120                       125                       130 ggt gta atg att tgt gca tat tta tta cat cgg ggc aaa ttt cta aag      549
Gly Val Met Ile Cys Ala Tyr Leu Leu His Arg Gly Lys Phe Leu Lys
                 135                       140                       145 gca caa gag gcc cta gat ttc tat ggg gaa gta agg acc aga gac aaa      597
Ala Gln Glu Ala Leu Asp Phe Tyr Gly Glu Val Arg Thr Arg Asp Lys
             150                       155                       160 aag gga gta act att ccc agt cag agg cgc tat gtg tat tat tat agc      645
Lys Gly Val Thr Ile Pro Ser Gln Arg Arg Tyr Val Tyr Tyr Tyr Ser
         165                       170                       175 tac ctg tta aag aat cat ctg gat tat aga cca gtg gca ctg ttg ttt      693
Tyr Leu Leu Lys Asn His Leu Asp Tyr Arg Pro Val Ala Leu Leu Phe
180                       185                       190                       195 cac aag atg atg ttt gaa act att cca atg ttc agt ggc gga act tgc      741
His Lys Met Met Phe Glu Thr Ile Pro Met Phe Ser Gly Gly Thr Cys
                     200                       205                       210 aat cct cag ttt gtg gtc tgc cag cta aag gtg aag atc tat tcc tcc      789
Asn Pro Gln Phe Val Val Cys Gln Leu Lys Val Lys Ile Tyr Ser Ser
                 215                       220                       225 aat tca gga ccc aca cga cgg gaa gac aag ttc atg tac ttt gag ttc      837
Asn Ser Gly Pro Thr Arg Arg Glu Asp Lys Phe Met Tyr Phe Glu Phe
             230                       235                       240 cct cag cca ttg cct gtg tgc ggt gac atc aaa gta gag ttc ttc cac      885
Pro Gln Pro Leu Pro Val Cys Gly Asp Ile Lys Val Glu Phe Phe His
         245                       250                       255 aaa cag aac aag atg cta aaa aag gac aaa atg ttt cac ttt tgg gta      933
Lys Gln Asn Lys Met Leu Lys Lys Asp Lys Met Phe His Phe Trp Val
260                       265                       270                       275 aac aca ttc ttc ata cca gga cca gag gaa acc tca gaa aaa gta gaa      981
Asn Thr Phe Phe Ile Pro Gly Pro Glu Glu Thr Ser Glu Lys Val Glu
                     280                       285                       290 aat gga agt cta tgt gat caa gaa att gat agt att tgc agt ata gaa     1029
Asn Gly Ser Leu Cys Asp Gln Glu Ile Asp Ser Ile Cys Ser Ile Glu
                 295                       300                       305 cgt gca gat aat gac aag gaa tat cta gta ctc act tta aca aaa aat     1077
Arg Ala Asp Asn Asp Lys Glu Tyr Leu Val Leu Thr Leu Thr Lys Asn
             310                       315                       320 gat ctc gac aaa gca aat aaa gac aag gcc aac cga tat ttt tct cca     1125
Asp Leu Asp Lys Ala Asn Lys Asp Lys Ala Asn Arg Tyr Phe Ser Pro
         325                       330                       335 aat ttt aag gtg aag ctg tac ttc aca aaa act gta gag gag cca tca     1173
Asn Phe Lys Val Lys Leu Tyr Phe Thr Lys Thr Val Glu Glu Pro Ser
340                       345                       350                       355 aac ccg gag gct agc agt tca act tct gtg acg cca gat gtt agt gac     1221
```

-continued

| | | | | | | | | | | | | |
|---|---|---|---|---|---|---|---|---|---|---|---|---|
| Asn | Pro | Glu | Ala | Ser | Ser | Thr | Ser | Val | Thr | Pro | Asp | Val | Ser | Asp |
| | | | 360 | | | | | 365 | | | | 370 |

```
aat gaa cct gat cat tat aga tat tct gac acc act gac tct gac cca   1269
Asn Glu Pro Asp His Tyr Arg Tyr Ser Asp Thr Thr Asp Ser Asp Pro
            375                 380                 385 gag aat gaa ccc ttt gat gaa gat cag cac aca caa atc aca aaa gtc   1317
Glu Asn Glu Pro Phe Asp Glu Asp Gln His Thr Gln Ile Thr Lys Val
        390                 395                 400 tgaattttt ttaatcaaga gggataaaac accatgaaaa caaacttgaa taaactgaaa   1377
ttggaccttt tttttttaa                                                1396
```

<210> SEQ ID NO 55
<211> LENGTH: 403
<212> TYPE: PRT
<213> ORGANISM: Canis familiaris

<400> SEQUENCE: 55

Met Thr Ala Ile Ile Lys Glu Ile Val Ser Arg Asn Lys Arg Arg Tyr
1               5                   10                  15

Gln Glu Asp Gly Phe Asp Leu Asp Leu Thr Tyr Ile Tyr Pro Asn Ile
            20                  25                  30

Ile Ala Met Gly Phe Pro Ala Glu Arg Leu Glu Gly Val Tyr Arg Asn
        35                  40                  45

Asn Ile Asp Asp Val Val Arg Phe Leu Asp Ser Lys His Lys Asn His
    50                  55                  60

Tyr Lys Ile Tyr Asn Leu Cys Ala Glu Arg His Tyr Asp Thr Ala Lys
65                  70                  75                  80

Phe Asn Cys Arg Val Ala Gln Tyr Pro Phe Glu Asp His Asn Pro Pro
                85                  90                  95

Gln Leu Glu Leu Ile Lys Pro Phe Cys Glu Asp Leu Asp Gln Trp Leu
            100                 105                 110

Ser Glu Asp Asp Asn His Val Ala Ala Ile His Cys Lys Ala Gly Lys
        115                 120                 125

Gly Arg Thr Gly Val Met Ile Cys Ala Tyr Leu Leu His Arg Gly Lys
    130                 135                 140

Phe Leu Lys Ala Gln Glu Ala Leu Asp Phe Tyr Gly Glu Val Arg Thr
145                 150                 155                 160

Arg Asp Lys Lys Gly Val Thr Ile Pro Ser Gln Arg Arg Tyr Val Tyr
                165                 170                 175

Tyr Tyr Ser Tyr Leu Leu Lys Asn His Leu Asp Tyr Arg Pro Val Ala
            180                 185                 190

Leu Leu Phe His Lys Met Met Phe Glu Thr Ile Pro Met Phe Ser Gly
        195                 200                 205

Gly Thr Cys Asn Pro Gln Phe Val Val Cys Gln Leu Lys Val Lys Ile
    210                 215                 220

Tyr Ser Ser Asn Ser Gly Pro Thr Arg Arg Glu Asp Lys Phe Met Tyr
225                 230                 235                 240

Phe Glu Phe Pro Gln Pro Leu Pro Val Cys Gly Asp Ile Lys Val Glu
                245                 250                 255

Phe Phe His Lys Gln Asn Lys Met Leu Lys Lys Asp Lys Met Phe His
            260                 265                 270

Phe Trp Val Asn Thr Phe Phe Ile Pro Gly Pro Glu Glu Thr Ser Glu
        275                 280                 285

Lys Val Glu Asn Gly Ser Leu Cys Asp Gln Glu Ile Asp Ser Ile Cys
    290                 295                 300

-continued

```
Ser Ile Glu Arg Ala Asp Asn Asp Lys Glu Tyr Leu Val Leu Thr Leu
305                 310                 315                 320

Thr Lys Asn Asp Leu Asp Lys Ala Asn Lys Asp Lys Ala Asn Arg Tyr
            325                 330                 335

Phe Ser Pro Asn Phe Lys Val Lys Leu Tyr Phe Thr Lys Thr Val Glu
                340                 345                 350

Glu Pro Ser Asn Pro Glu Ala Ser Ser Thr Ser Val Thr Pro Asp
            355                 360                 365

Val Ser Asp Asn Glu Pro Asp His Tyr Arg Tyr Ser Asp Thr Thr Asp
    370                 375                 380

Ser Asp Pro Glu Asn Glu Pro Phe Asp Glu Asp Gln His Thr Gln Ile
385                 390                 395                 400

Thr Lys Val
```

<210> SEQ ID NO 56
<211> LENGTH: 2160
<212> TYPE: DNA
<213> ORGANISM: Mus musculus
<220> FEATURE:
<221> NAME/KEY: CDS
<222> LOCATION: (949)..(2157)

<400> SEQUENCE: 56

```
ggcgccctgc tctcccggcg gggcggcgga gggggcgggc tggccggcgc acggtgatgt      60
ggcgggactc tttgtgcact gcggcaggat acgcgcttgg gcgtcgggac gcggctgcgc     120
tcagctctct cctctcggaa gctgcagcca tgatggaagt ttgagagttg agccgctgtg     180
aggccaggcc cggcgcaggc gagggagatg agagacggcg gcggccacgg cccagagccc     240
ctctcagcgc ctgtgagcag ccgcgggggc agcgccctcg gggagccggc cgggcggcgg     300
cggcggcagc ggcggcgggc ctcgcctcct cgtcgtctgt tctaaccggg cagcttctga     360
gcagcttcgg agagagacgg tggaagaagc cgtgggctcg agcgggagcc ggcgcaggct     420
cggcggctgc acctcccgct cctggagcgg ggggagaag cggcggcggc ggccgcggct     480
ccggggaggg ggtcggagtc gcctgtcacc attgccaggg ctgggaacgc cggagagttg     540
ctctctcccc ttctcctgcc tccaacacgg cggcggcggc ggcggcacgt ccagggaccc     600
gggccggtgt taagcctccc gtccgccgcc gccgcacccc ccctggcccg ggctccggag     660
gccgccggag gaggcagccg ctgcgaggat tatccgtctt ctccccattc cgctgcctcg     720
gctgccaggc ctctggctgc tgaggagaag caggcccagt tctctgcaacc atccagcagc     780 cgccgcagca gccattaccc ggctgcggtc cagggccaag cggcagcaga gcgaggggca     840
tcagcgaccg ccaagtccag agccatttcc atcctgcaga agaagcctcg ccaccagcag     900
cttctgccat ctctctcctc cttttcttc agccacaggc tcccagac atg aca gcc      957
                                                    Met Thr Ala
                                                      1 atc atc aaa gag atc gtt agc aga aac aaa agg aga tat caa gag gat     1005
Ile Ile Lys Glu Ile Val Ser Arg Asn Lys Arg Arg Tyr Gln Glu Asp
  5                  10                  15 gga ttc gac tta gac ttg acc tat att tat cca aat att att gct atg     1053
Gly Phe Asp Leu Asp Leu Thr Tyr Ile Tyr Pro Asn Ile Ile Ala Met
 20                  25                  30                  35 gga ttt cct gca gaa aga ctt gaa ggt gta tac agg aac aat att gat     1101
Gly Phe Pro Ala Glu Arg Leu Glu Gly Val Tyr Arg Asn Asn Ile Asp
         40                  45                  50 gat gta gta agg ttt ttg gat tca aag cat aaa aac cat tac aag ata     1149
```

```
Asp Val Val Arg Phe Leu Asp Ser Lys His Lys Asn His Tyr Lys Ile
             55                  60                  65 tac aat cta tgt gct gag aga cat tat gac acc gcc aaa ttt aac tgc      1197
Tyr Asn Leu Cys Ala Glu Arg His Tyr Asp Thr Ala Lys Phe Asn Cys
         70                  75                  80 aga gtt gca cag tat cct ttt gaa gac cat aac cca cca cag cta gaa      1245
Arg Val Ala Gln Tyr Pro Phe Glu Asp His Asn Pro Pro Gln Leu Glu
     85                  90                  95 ctt atc aaa ccc ttc tgt gaa gat ctt gac caa tgg cta agt gaa gat      1293
Leu Ile Lys Pro Phe Cys Glu Asp Leu Asp Gln Trp Leu Ser Glu Asp
100                 105                 110                 115 gac aat cat gtt gca gca att cac tgt aaa gct gga aag gga cgg act      1341
Asp Asn His Val Ala Ala Ile His Cys Lys Ala Gly Lys Gly Arg Thr
             120                 125                 130 ggt gta atg att tgt gca tat tta ttg cat cgg ggc aaa ttt tta aag      1389
Gly Val Met Ile Cys Ala Tyr Leu Leu His Arg Gly Lys Phe Leu Lys
             135                 140                 145 gca caa gag gcc cta gat ttt tat ggg gaa gta agg acc aga gac aaa      1437
Ala Gln Glu Ala Leu Asp Phe Tyr Gly Glu Val Arg Thr Arg Asp Lys
         150                 155                 160 aag gga gtc aca att ccc agt cag agg cgc tat gta tat tat tat agc      1485
Lys Gly Val Thr Ile Pro Ser Gln Arg Arg Tyr Val Tyr Tyr Tyr Ser
     165                 170                 175 tac ctg cta aaa aat cac ctg gat tac aga ccc gtg gca ctg ctg ttt      1533
Tyr Leu Leu Lys Asn His Leu Asp Tyr Arg Pro Val Ala Leu Leu Phe
180                 185                 190                 195 cac aag atg atg ttt gaa act att cca atg ttc agt ggc gga act tgc      1581
His Lys Met Met Phe Glu Thr Ile Pro Met Phe Ser Gly Gly Thr Cys
             200                 205                 210 aat cct cag ttt gtg gtc tgc cag cta aag gtg aag ata tat tcc tcc      1629
Asn Pro Gln Phe Val Val Cys Gln Leu Lys Val Lys Ile Tyr Ser Ser
             215                 220                 225 aat tca gga ccc acg cgg cgg gag gac aag ttc atg tac ttt gag ttc      1677
Asn Ser Gly Pro Thr Arg Arg Glu Asp Lys Phe Met Tyr Phe Glu Phe
         230                 235                 240 cct cag cca ttg cct gtg tgt ggt gat atc aaa gta gag ttc ttc cac      1725
Pro Gln Pro Leu Pro Val Cys Gly Asp Ile Lys Val Glu Phe Phe His
     245                 250                 255 aaa cag aac aag atg ctc aaa aag gac aaa atg ttt cac ttt tgg gta      1773
Lys Gln Asn Lys Met Leu Lys Lys Asp Lys Met Phe His Phe Trp Val
260                 265                 270                 275 aat acg ttc ttc ata cca gga cca gag gaa acc tca gaa aaa gtg gaa      1821
Asn Thr Phe Phe Ile Pro Gly Pro Glu Glu Thr Ser Glu Lys Val Glu
             280                 285                 290 aat gga agt ctt tgt gat cag gaa atc gat agc att tgc agt ata gag      1869
Asn Gly Ser Leu Cys Asp Gln Glu Ile Asp Ser Ile Cys Ser Ile Glu
             295                 300                 305 cgt gca gat aat gac aag gag tat ctt gta ctc acc cta aca aaa aac      1917
Arg Ala Asp Asn Asp Lys Glu Tyr Leu Val Leu Thr Leu Thr Lys Asn
         310                 315                 320 gat ctt gac aaa gca aac aaa gac aag gcc aac cga tac ttc tct cca      1965
Asp Leu Asp Lys Ala Asn Lys Asp Lys Ala Asn Arg Tyr Phe Ser Pro
     325                 330                 335 aat ttt aag gtg aaa cta tac ttt aca aaa aca gta gag gag cca tca      2013
Asn Phe Lys Val Lys Leu Tyr Phe Thr Lys Thr Val Glu Glu Pro Ser
340                 345                 350                 355 aat cca gag gct agc agt tca act tct gtg act cca gat gtt agt gac      2061
Asn Pro Glu Ala Ser Ser Ser Thr Ser Val Thr Pro Asp Val Ser Asp
             360                 365                 370
```

```
aat gaa cct gat cat tat aga tat tct gac acc act gac tct gat cca    2109
Asn Glu Pro Asp His Tyr Arg Tyr Ser Asp Thr Thr Asp Ser Asp Pro
        375                 380                 385 gag aat gaa cct ttt gat gaa gat cag cat tca caa att aca aaa gtc    2157
Glu Asn Glu Pro Phe Asp Glu Asp Gln His Ser Gln Ile Thr Lys Val
        390                 395                 400 tga                                                                2160
```

<210> SEQ ID NO 57
<211> LENGTH: 403
<212> TYPE: PRT
<213> ORGANISM: Mus musculus

<400> SEQUENCE: 57

```
Met Thr Ala Ile Ile Lys Glu Ile Val Ser Arg Asn Lys Arg Arg Tyr
  1               5                  10                  15

Gln Glu Asp Gly Phe Asp Leu Asp Leu Thr Tyr Ile Tyr Pro Asn Ile
             20                  25                  30

Ile Ala Met Gly Phe Pro Ala Glu Arg Leu Glu Gly Val Tyr Arg Asn
         35                  40                  45

Asn Ile Asp Asp Val Val Arg Phe Leu Asp Ser Lys His Lys Asn His
     50                  55                  60

Tyr Lys Ile Tyr Asn Leu Cys Ala Glu Arg His Tyr Asp Thr Ala Lys
 65                  70                  75                  80

Phe Asn Cys Arg Val Ala Gln Tyr Pro Phe Glu Asp His Asn Pro Pro
                 85                  90                  95

Gln Leu Glu Leu Ile Lys Pro Phe Cys Glu Asp Leu Asp Gln Trp Leu
            100                 105                 110

Ser Glu Asp Asp Asn His Val Ala Ala Ile His Cys Lys Ala Gly Lys
        115                 120                 125

Gly Arg Thr Gly Val Met Ile Cys Ala Tyr Leu Leu His Arg Gly Lys
    130                 135                 140

Phe Leu Lys Ala Gln Glu Ala Leu Asp Phe Tyr Gly Glu Val Arg Thr
145                 150                 155                 160

Arg Asp Lys Lys Gly Val Thr Ile Pro Ser Gln Arg Arg Tyr Val Tyr
                165                 170                 175

Tyr Tyr Ser Tyr Leu Leu Lys Asn His Leu Asp Tyr Arg Pro Val Ala
            180                 185                 190

Leu Leu Phe His Lys Met Met Phe Glu Thr Ile Pro Met Phe Ser Gly
        195                 200                 205

Gly Thr Cys Asn Pro Gln Phe Val Cys Gln Leu Lys Val Lys Ile
    210                 215                 220

Tyr Ser Ser Asn Ser Gly Pro Thr Arg Arg Glu Asp Lys Phe Met Tyr
225                 230                 235                 240

Phe Glu Phe Pro Gln Pro Leu Pro Val Cys Gly Asp Ile Lys Val Glu
                245                 250                 255

Phe Phe His Lys Gln Asn Lys Met Leu Lys Lys Asp Lys Met Phe His
            260                 265                 270

Phe Trp Val Asn Thr Phe Phe Ile Pro Gly Pro Glu Thr Ser Glu
        275                 280                 285

Lys Val Glu Asn Gly Ser Leu Cys Asp Gln Glu Ile Asp Ser Ile Cys
    290                 295                 300

Ser Ile Glu Arg Ala Asp Asn Asp Lys Glu Tyr Leu Val Leu Thr Leu
305                 310                 315                 320

Thr Lys Asn Asp Leu Asp Lys Ala Asn Lys Asp Lys Ala Asn Arg Tyr
```

-continued

```
                    325                 330                 335
Phe Ser Pro Asn Phe Lys Val Lys Leu Tyr Phe Thr Lys Thr Val Glu
            340                 345                 350

Glu Pro Ser Asn Pro Glu Ala Ser Ser Thr Ser Val Thr Pro Asp
            355                 360                 365

Val Ser Asp Asn Glu Pro Asp His Tyr Arg Tyr Ser Asp Thr Thr Asp
370                 375                 380

Ser Asp Pro Glu Asn Glu Pro Phe Asp Glu Asp Gln His Ser Gln Ile
385                 390                 395                 400

Thr Lys Val

<210> SEQ ID NO 58
<211> LENGTH: 23
<212> TYPE: DNA
<213> ORGANISM: Homo sapiens

<400> SEQUENCE: 58
ctgcagaaag acttgaaggc gta                                          23

<210> SEQ ID NO 59
<211> LENGTH: 23
<212> TYPE: DNA
<213> ORGANISM: Homo sapiens

<400> SEQUENCE: 59
gccccgatgt aataaatatg cac                                          23

<210> SEQ ID NO 60
<211> LENGTH: 18
<212> TYPE: PRT
<213> ORGANISM: Mus musculus

<400> SEQUENCE: 60

Gly Ala Leu Leu Ser Arg Arg Gly Gly Gly Gly Gly Leu Ala Gly
1               5                   10                  15

Ala Arg

<210> SEQ ID NO 61
<211> LENGTH: 13
<212> TYPE: PRT
<213> ORGANISM: Mus musculus

<400> SEQUENCE: 61

Cys Gly Gly Thr Leu Cys Ala Leu Arg Gln Asp Thr Arg
1               5                   10

<210> SEQ ID NO 62
<211> LENGTH: 27
<212> TYPE: PRT
<213> ORGANISM: Mus musculus

<400> SEQUENCE: 62

Trp Ala Ser Gly Arg Gly Cys Ala Gln Leu Ser Pro Leu Gly Ser Cys
1               5                   10                  15

Ser His Asp Gly Ser Leu Arg Val Glu Pro Leu
            20                  25

<210> SEQ ID NO 63
<211> LENGTH: 9
<212> TYPE: PRT
<213> ORGANISM: Mus musculus
```

```
<400> SEQUENCE: 63

Gly Gln Ala Arg Arg Arg Gly Arg
  1               5

<210> SEQ ID NO 64
<211> LENGTH: 1212
<212> TYPE: DNA
<213> ORGANISM: Homo sapiens

<400> SEQUENCE: 64
aggacagcca tcatcaaaga gatcgttagc agaaacaaaa ggagatatca agaggatgga      60
ttcgacttag acttgaccta tatttatcta aacattattg ctatgggatt tcctgcagaa     120
agacttgaag gcgtatacag gaacaatatt gatgatgtag taaggttttt ggattcaaag     180
cataaaaacc attacaagat acacaatctt tgtgctgaaa gacattatga caccgccaaa     240
tctaattaca gagttgcgca atatccttt gaagaccata acccaccaca gctagaactt     300
atcaaaccct tttgtgaaga tcttgaccaa tggctaagtg aagatgacaa tcatgttgca     360
gcaattcact gtaaagctgg aaagggacga actggtataa tgatttatgc atatttatta     420
catcggggca aattttttaaa ggcacaagag gccctagatt tctatgggga agtaaggacc     480
agagacaaaa agggagtaac tattcccagt cagaggcgct atgtgtatta ctatagctac     540
ctggtaaaga atcatgtgga ttatagacca gtggcactgt tgtttcacaa gatgatgttt     600
gaaactattc caatgttcag tggcggaact tgcaatcctc agtttgtggt ctgccagcta     660
aaggtgaaga tgtattcctc caattcagga cccacacgat gggaggacaa gttcatgtat     720
tttgagttcc ctcagccgtt acctgtgtgt ggtgatatca aagtagagtt cttccacaaa     780
cagaacaaga tgctaaaaaa ggacaaaatg tttcactttt gggtaaatac attcttcata     840
ccaggaccag aggaaacctc agaaaaagta gaaaatggaa gtctatgtga tcaagaaatt     900
gatagcattt gcagtataga gcgtgcagat aatgacaagg agtatctagt acttacttta     960
acaaaaaatg atcttgacaa agcaaataaa gacaaagcca accgatactt ttctccaaat    1020
tttaaggtga agctgtactt cacaaaaaca gtagaggagc cgtcaaatcc agaggctagc    1080
agttcaactt ctgtaacacc agatgttagt gacaatgaac ctgatcatta tagatattct    1140
gacaccactg actctgatcc agagaatgaa ccttttgatg aagatcagca tacacaaatt    1200
acaaaagtct ga                                                        1212
```

TUMOR SUPPRESSOR DESIGNATED TS10Q23.3

CROSS-REFERENCE TO RELATED APPLICATIONS

The present application is continuation application Ser. No. 10/299,003, filed 19 Nov. 2002, which is a divisional of application Ser. No. 09/140,749 filed on 26 Aug. 1998 now U.S. Pat. No. 6,482,795, which in turn is a continuation-in-part of application Ser. No. 08/791,115, filed 30 Jan. 1997 now U.S. Pat. No. 6,262,242. The present application is further related to and claims priority under 35 USC § 119(e) to provisional patent application Ser. No. 60/057,750, filed 26 Aug. 1997 and patent application Ser. No. 60/083,563, filed 30 Apr. 1998. All of these applications are incorporated herein by reference.

BACKGROUND OF THE INVENTION

I. Field of the Invention

The present invention relates to the fields of oncology, genetics and molecular biology. More particular the invention relates to the identification, on human chromosome 10, of a tumor suppressor gene. Defects in this gene are associated with the development of cancers, such as gliomas.

II. Related Art

Oncogenesis was described by Foulds (1958) as a multi-step biological process, which is presently known to occur by the accumulation of genetic damage. On a molecular level, the multistep process of tumorigenesis involves the disruption of both positive and negative regulatory effectors (Weinberg, 1989). The molecular basis for human colon carcinomas has been postulated, by Vogelstein and coworkers (1990), to involve a number of oncogenes, tumor suppressor genes and repair genes. Similarly, defects leading to the development of retinoblastoma have been linked to another tumor suppressor gene (Lee et al., 1987). Still other oncogenes and tumor suppressors have been identified in a variety of other malignancies. Unfortunately, there remains an inadequate number of treatable cancers, and the effects of cancer are catastrophic—over half a million deaths per year in the United States alone.

One example of the devastating nature of cancer involves tumors arising from cells of the astrocytic lineage that are the most common primary tumors of the central nervous system (Russell & Rubinstein, 1989). The majority of these tumors occur in the adult population. Primary brain tumors also account for the most common solid cancer in the pediatric patient population and the second leading cause of cancer deaths in children younger than 15 years of age. An estimated 18,500 new cases of primary brain tumors were diagnosed in 1994 (Boring et al., 1994). Epidemiological studies show that the incidence of brain tumors is increasing and represents the third most common cause of cancer death among 18 to 35 year old patients. Due to their location within the brain and the typical infiltration of tumor cells into the surrounding tissue, successful therapeutic intervention for primary brain tumors often is limited. Unfortunately, about two-thirds of these afflicted individuals will succumb to the disease within two years. The most common intracranial tumors in adults arise from cells of the glial lineage and occur at an approximately frequency of 48% glioblastoma multiform (GBM), 21% astrocytomas (A) (anaplastic (AA) and low grade) and 9% ependymomas and oligodendrogliomas (Levin et al., 1993).

Genetic studies have implicated several genes, and their corresponding protein products, in the oncogenesis of primary brain tumors. Among the various reported alterations are: amplification of epidermal growth factor receptor and one of its ligands, transforming growth factor-alpha, N-myc; gli, altered splicing and expression of fibroblast growth factor receptors, and loss of function of p53, p16, Rb, neurofibromatosis genes 1 and 2, DCC, and putative tumor suppressor genes on chromosomes 4, 10, 17 (non-p53), 19, 22, and X (Wong et al., 1987; El-Azouzi et al., 1989; Nishi et al., 1991; James et al., 1988; Kamb et al., 1984; Henson et al., 1994; Yamaguchi et al., 1994; Bianchi et al., 1994; Ransom et al., 1992; Rasheed et al., 1992; Scheck and Coons, 1993; Von Demling et al., 1994; Rubio et al., 1994; Ritland et al., 1995).

The most frequent alterations include amplification of EGF-receptor (~40%), loss of function of p53 (~50%), p16 (~50%), Rb (~30%) and deletions on chromosome 10 (>90%). Furthermore, the grade or degree of histological malignancy of astrocytic tumors correlates with increased accumulation of genetic damage similar to colon carcinoma. Moreover, some changes appear to be relatively lineage- or grade-specific. For instance, losses to chromosome 19q occur predominantly in oligodendrogliomas, while deletions to chromosome 10 and amplification and mutation of the EGF-receptor occur mainly in GBMs. The deletion of an entire copy or segments of chromosome 10 is strongly indicated as the most common genetic event associated with the most common form of primary brain tumors, GBMs.

Cytogenetic and later allelic deletion studies on GBMs clearly have demonstrated frequent and extensive molecular genetic alterations associated with chromosome 10 (Bigner et al., 1988; Ransom et al., 1992; Rasheed et al., 1992; James et al., 1988: Fujimoto et al., 1989; Fults et al., 1990, 1993; Karlbom et al., 1993; Rasheed et al., 1995; Sonoda et al., 1996; Albarosa et al., 1996). Cytogenetic analyses have clearly shown the alteration of chromosome 10 as a common occurrence in GBMs, with 60% of tumors exhibiting alteration. Allelic deletion studies of GBMs have also revealed very frequent allelic imbalances associated with chromosome 10 (90%). However, the losses are so extensive and frequent that no chromosomal sublocalization of a consistent loss could be unequivocally defined by these analyses.

Several recent studies have implicated the region 10q25–26, specifically a 17 cM region from D10S190 to D10S216. A telomeric region from D10S587 to D10S216 was implicated by allelic deletion analysis using a series of low and high grade gliomas that exhibited only a partial loss of chromosome 10 (Rasheed et al., 1995). This region (~1 cM) was lost or noninformative in 11 GBM's, 4 AA's, 1 A and 1 oligodendroglioma, suggesting localization of a candidate region. This study also illustrated that deletions to chromosome 10 occur in lower grade gliomas. Albarosa et al. (1996) suggest a centromeric candidate region based on a small allelic deletion in a pediatric brain tumor from the makers D10S221 to D10S209. Steck and Saya, using a series of GBMs, have suggested two common regions of deletions, 10q26 and 10q24 (D10S192).

The short arm of chromosome 10 also has been implicated to contain another tumor suppressor gene. Studies first provided functional evidence of a tumor suppressor gene on 10p in glioma (Steck et al., 1995) which was later shown for prostate (Sanchez et al., 1995; Murakami et al., 1996). The latter study has implicated a 11 cM region between D10S1172 and D10S527. Allelic deletion studies of gliomas have shown extensive deletion on 10p, but again, no firm localization has been achieved (Karlbom et al., 1993; Kimmelman et al., 1996; these regions of chromosome 10 are shown to FIG. 1, below). Furthermore, the amplification of EGF-receptor has also been shown to occur almost exclusively in tumors that had deletions in chromosome 10, suggesting a possible link between these genetic alterations (Von Deimling et al., 1992).

Deletions on the long arm, particularly 10q24, also have been reported for prostate, renal, uterine, small-cell lung, endometrial carcinomas, meningioma and acute T-cell leukemias (Carter et al., 1990; Morita et al, 1991; Herbst et al., 1984; Jones et al., 1994; Rempel et al., 1993; Peiffer et al., 1995; Petersen et al., 1997). Recently, detailed studies on prostate carcinoma have shown that (1) the short and long arm of chromosome 10 strongly appear to contain tumor suppressor genes, and (2) the localization of the long arm suppressor gene maps to the 10q23–24 boundary (Gray et al., 1995; Ittmann, 1996, Trybus et al., 1996). The region of common deletion identified by these three groups is centered around D10S215 and extends about 10 cM (FIG. 1). The region overlaps with our candidate region, however, no further localization within the region was reported fro prostate carcinoma. The allelic losses associated with prostate carcinoma also appear to occur in only about 30–40% of the tumors examined. Furthermore, deletions are observed in more advance staged tumors, similar to GBMs, and may be related to metastatic ability (Nihei et al., 1995; Komiya et al., 1996). The combination of these results suggest that multiple human cancers implicate the region 10q23–24.

Differences in locations of the candidate regions suggest several possibilities. First, the presence of two or more tumor suppressor genes on 10q are possible. Second, not all deletions may effect the tumor suppressor gene locus. These alternatives are not mutually exclusive. In support of the latter possibility, a potential latent centromere was suggested to occur at 10q25 which may give rise to genetic alterations, particularly breakage (Vouillaire et al., 1993).

Despite all of this information, the identity of the gene (or genes) involved with the 10q23–24-related tumor suppression remained elusive. Without identification of a specific gene and deduction of the protein for which it codes, it is impossible to begin developing an effective therapy targeting this product. Thus, it is an important goal to isolate the tumor suppressor(s) located in this region and determine its structure and function.

SUMMARY OF THE INVENTION

Therefore, it is an objective of the present invention to provide a tumor suppressor, designated as TS10q23.3 (also referred to as MMAC or PTEN). It also is an objective to provide DNAs representing all or part of a gene encoding TS10q23.3. It also is an objective to provides methods for using these compositions.

In accordance with the foregoing objectives, there is provided, in one embodiment, a tumor suppressor designated as TS10q23.3. The polypeptide has, in one example, the amino acid sequence as set forth in SEQ ID NO:2; SEQ ID NO:10, SEQ ID NO:17, SEQ ID NO:49, SEQ ID NO:55 or SEQ ID NO:57. In a further example, the polypeptide has the amino acid sequence as set forth in SEQ ID NO:3, SEQ ID NO:4, SEQ ID NO:5, SEQ ID NO:6, SEQ ID NO:7, SEQ ID NO:8, SEQ ID NO:11, SEQ ID NO:12, SEQ ID NO:13, SEQ ID NO:14, SEQ ID NO:15, SEQ ID NO:18, SEQ ID NO:50, SEQ ID NO:51, SEQ ID NO:52, SEQ ID NO:53, SEQ ID NO:60, SEQ ID NO:61, SEQ ID NO:62, or SEQ ID NO:63, Also provided is an isolated peptide having between about 10 and about 50 consecutive residues of a tumor suppressor designated as TS10q23.3. The peptide may be conjugated to a carrier molecule, for example, KLH or BSA.

In another embodiment, there is provided a monoclonal antibody that binds immunologically to a tumor suppressor designated as TS10q23.3. The antibody may be non-cross reactive with other human polypeptides, or it may bind to non-human TS10q23.3, but not to human TS10q23.3. The antibody may further comprise a detectable label, such as a fluorescent label, a chemiluminescent label, a radiolabel or an enzyme. Also encompassed are hybridoma cells and cell lines producing such antibodies.

In another embodiment, there is included a polyclonal antisera, antibodies of which bind immunologically to a tumor suppressor designated as TS10q23.3. The antisera may be derived from any animal, but preferably is from other than human, mouse or dog.

In still another embodiment, there is provided an isolated nucleic acid comprising a region, or the complement thereof, encoding a tumor suppressor designated TS10q23.3 or an allelic variant or mutant thereof. The tumor suppressor coding region may be derived from any mammal but, in particular embodiments, is selected from murine, canine and human sequences. Mutations include deletion mutants, insertion mutants, frameshift mutants, nonsense mutants, missense mutants or splice mutants. In certain embodiments, the mutation comprises a homozygous deletion of one or more of the exons of the tumor suppressor. In specific embodiments, exons 3, 4, 5, 6, 7, 8, or 9 are deleted. In other embodiments exon 2 is deleted. In certain embodiments all of exons 3–9 are deleted. In other embodiments, exons 2–9 are deleted. In a particular embodiment, the tumor suppressor has the amino acid sequence of SEQ ID NO:2; SEQ ID NO:10, SEQ ID NO:17, SEQ ID NO:49, SEQ ID NO:55 or SEQ ID NO:57. The nucleic acid may have the sequence set forth in SEQ ID NO:1, SEQ ID NO:9, SEQ ID NO:16, SEQ ID NO:54, or SEQ ID NO:56 or a complement thereof. The nucleic acid may further have the sequence set forth in SEQ ID NO:19, SEQ ID NO:20, SEQ ID NO:21, SEQ ID NO:22, SEQ ID NO:23, SEQ ID NO:24, SEQ ID NO:25, SEQ ID NO:26, or SEQ ID NO:27 or a complement thereof. The nucleic acid may also have the sequence set forth in SEQ ID NO:64 or a complement thereof. The nucleic acid may be genomic DNA, complementary DNA or RNA.

In certain embodiments, the mutant is a splice mutant. In particular embodiments, the splice mutation is in exon 3, exon 8 or intron 2. In more specific embodiments, the splice mutation results in (i) a change from G to T at position +1 in exon 3, or (ii) a change from G to T at position +1 in exon 8 or (iii) a change from G to T at position −1 in intron 2.

In certain other embodiments, the mutant is a missense mutant. In particular embodiments, the missense mutation is in exon 2. In more specific embodiments, the missense mutation results in a change from T to G at position 46 of exon 2, leading to a change from LEU to ARG. In certain other embodiments, the missense mutation results in a change from G to A at position 28 of exon 2, leading to a change from a GLY to a GLU. In certain other embodiments, the mutation results in a change from C to T at position 53 of exon 2. In certain other embodiments, the missense mutation results in a change from CC to TT at positions 112 and 113 of exon 2, leading to a change from PRO to PHE at amino acid 38 of said tumor suppressor. In certain embodiments, the missense mutation is in exon 5. In specific embodiments, the missense mutation may results in a change from T to G at position 323 of exon 5, leading to a change from LEU to ARG at amino acid 108 of said tumor suppressor. In other specific embodiments, the missense mutation results in a change from T to C at position 331 of exon 5 leading to a change from TRP to ARG at amino acid 111 of said tumor suppressor. In certain other embodiments, the missense mutation results in a change from T to G at position 335 of exon 5 leading to a change from LEU to ARG at amino acid 112 of said tumor suppressor. In still other embodiments, the missense mutation results in a change from G to A at position 407 of exon 5, leading to a change from CYS to TYR at amino acid 136 of said tumor suppressor. In other exemplary missense embodiments, the missense mutation results in a change from T to C at position 455 of exon 5, leading to a change from LEU to PRO at amino acid 152 of said tumor suppressor. In yet other embodiments, the missense mutation is in exon 6. More specifically, the missense mutation results in a change from C to T at position 517 of exon 6, leading to a change from ARG to CYS at amino acid 173 of said tumor suppressor. In other specific embodiments, the missense mutation results in a change from G to C at position 518 of exon 6 leading to a change from ARG to a PRO at amino acid 173 of said tumor suppressor.

Yet other embodiments provide a nonsense mutant. In certain embodiments, the nonsense mutation is in exon 5. More specifically, the nonsense mutation results in a change from C to T at position 388 of exon 5, leading to a change from ARG to a STOP at codon 130 of said tumor suppressor. In other embodiments, the nonsense mutation is in exon 7. More specifically, the nonsense mutation results in a change from C to T at position 697 of exon 7, leading to a change from ARG to a STOP at codon 233 of said tumor suppressor. In certain embodiments, the nonsense mutation is in exon 8. More specifically, the nonsense mutation results in a change from C to T at position 202 of exon 8.

In still further embodiments of the present invention, there is contemplated a frameshift mutant. In particular embodiments, the framshift mutation is in exon 7. More specifically, the frameshift mutation is a deletion of A at position 705 of exon 7, leading to a truncated tumor suppressor expression. In particular embodiments, frameshift mutation results is a deletion of G at position 823 of exon 7, leading to a truncated tumor suppressor expression. In other embodiments, the frameshift mutation is an insertion of TT at position 98 in exon 7. In certain embodiments, the frameshift mutation is in exon 1. More specifically, the frameshift mutation is a deletion of AA at positions 16 and 17 of exon 1.

In additional embodiments, the nucleic acid comprises a complementary DNA and further comprises a promoter operably linked to the region, or the complement thereof, encoding the tumor suppressor. Additional elements include a polyadenylation signal and an origin of replication.

Viral vectors such as retrovirus, *adenovirus, herpesvirus*, vaccinia virus and adeno-associated virus also may be employed. The vector may be "naked" or packaged in a virus particle. Alternatively, the nucleic acid may comprise an expression vector packaged in a liposome.

Various sizes of nucleic acids are contemplated, but are not limiting: about 1212 bases, about 1500 bases, about 2000 bases, about 3500 bases, about 5000 bases, about 10,000 bases, about 15,000 bases, about 20,000 bases, about 25,000 bases, about 30,000 bases, about 35,000 bases, about 40,000 bases, about 45,000 bases, about 50,000 bases, about 75,000 bases and about 100,000 bases.

In yet another embodiment, there is provided an isolated oligonucleotide of between about 10 and about 50 consecutive bases of a nucleic acid, or complementary thereto, encoding a tumor suppressor designated as TS10q23.3. The oligonucleotide may be about 15 bases in length, about 17 bases in length, about 20 bases in length, about 25 bases in length or about 50 bases in length.

In another embodiment, there is provided a method of diagnosing a cancer comprising the steps of (i) obtaining a sample from a subject; and (ii) determining the expression a functional TS10q23.3 tumor suppressor in cells of the sample. The cancer may be brain, lung, liver, spleen, kidney, lymph node, small intestine, pancreas, blood cells, colon, stomach, breast, endometrium, prostate, testicle, ovary, skin, head and neck, esophagus, bone marrow and blood cancer. In preferred embodiments, the cancer is prostate cancer or breast cancer. In another preferred embodiment, cancer is a brain cancer, for example, a glioma. The sample is a tissue or fluid sample.

In one format, the method involves assaying for a nucleic acid from the sample. The method may further comprise subjecting the sample to conditions suitable to amplify the nucleic acid. Alternatively, the method may comprise contacting the sample with an antibody that binds immunologically to a TS10q23.3, for example, in an ELISA. The comparison, regardless of format, may include comparing the expression of TS10q23.3 with the expression of TS10q23.3 in non-cancer samples. The comparison may look at levels of TS10q23.3 expression. Alternatively, the comparison may involve evaluating the structure of the TS10q23.3 gene, protein or transcript. Such formats may include sequencing, wild-type oligonucleotide hybridization, mutant oligonucleotide hybridization, SSCP™ and RNase protection. Particular embodiments include evaluating wild-type or mutant oligonucleotide hybridization where the oligonucleotide is configured in an array on a chip or wafer.

In another embodiment, there is provided a method for altering the phenotype of a tumor cell comprising the step of contacting the cell with a tumor suppressor designated TS10q23.3 under conditions permitting the uptake of the tumor suppressor by the tumor cell. The tumor cell may be derived from a tissue such as brain, lung, liver, spleen, kidney, lymph node, small intestine, blood cells, pancreas, colon, stomach, breast, endometrium, prostate, testicle, ovary, skin, head and neck, esophagus, bone marrow and blood tissue. The phenotype may be selected from proliferation, migration, contact inhibition, soft agar growth or cell cycling. The tumor suppressor may be encapsulated in a liposome or free.

In another embodiment, there is provided a method for altering the phenotype of a tumor cell comprising the step of contacting the cell with a nucleic acid (i) encoding a tumor suppressor designated TS10q23.3 and (ii) a promoter active in the tumor cell, wherein the promoter is operably linked to the region encoding the tumor suppressor, under conditions permitting the uptake of the nucleic acid by the tumor cell. The phenotype may be proliferation, migration, contact inhibition, soft agar growth or cell cycling. The nucleic acid may be encapsulated in a liposome. If the nucleic acid is a viral vector such as retrovirus, *adenovirus*, adeno-associated virus, vaccinia virus and *herpesvirus*, it may be encapsulated in a viral particle.

In a further embodiment, there is provided a method for treating cancer comprising the step of contacting a tumor cell within a subject with a tumor suppressor designated TS10q23.3 under conditions permitting the uptake of the tumor suppressor by the tumor cell. The method may involve treating a human subject.

In still a further embodiment, there is provided a method for treating cancer comprising the step of contacting a tumor cell within a subject with a nucleic acid (i) encoding a tumor suppressor designated TS10q23.3 and (ii) a promoter active in the tumor cell, wherein the promoter is operably linked to the region encoding the tumor suppressor, under conditions permitting the uptake of the nucleic acid by the tumor cell. The subject may be a human.

In still yet a further embodiment, there is provided transgenic mammal in which both copies of the gene encoding TS10q23.3 are interrupted or replaced with another gene.

In an additional embodiment, there is provided a method of determining the stage of cancer comprising the steps of (i) obtaining a sample from a subject; and (ii) determining the expression a functional TS10q23.3 tumor suppressor in cells of the sample. The cancer may be a brain cancer and the stage is distinguished between low grade and glioma. The determining may comprise assaying for a TS10q23.3 nucleic acid or polypeptide in the sample.

In yet an additional example, there is provided a method of predicting tumor metastasis comprising the steps of (i) obtaining a sample from a subject; and (ii) determining the expression a functional TS10q23.3 tumor suppressor in cells of the sample. The cancer may be distinguished as metastatic and non-metastatic. The determining may comprise assaying for a TS10q23.3 nucleic acid or polypeptide in the sample.

In still yet an additional embodiment, there is provided a method of screening a candidate substance for anti-tumor activity comprising the steps of (i) providing a cell lacking functional TS10q23.3 polypeptide; (ii) contacting the cell with the candidate substance; and (iii) determining the effect of the candidate substance on the cell. The cell may be a tumor cell, for example, a tumor cell having a mutation in the coding region of TS10q23.3.7. The mutation may be a deletion mutant, an insertion mutant, a frameshift mutant, a nonsense mutant, a missense mutant or splice mutant. The determining may comprise comparing one or more characteristics of the cell in the presence of the candidate substance with characteristics of a cell in the absence of the candidate substance. The characteristic may be TS10q23.3 expression, phosphatase activity, proliferation, metastasis, contact inhibition, soft agar growth, cell cycle regulation, tumor formation, tumor progression and tissue invasion. The candidate substance may be a chemotherapeutic or radiotherapeutic agent or be selected from a small molecule library. The cell may be contacted in vitro or in vivo.

In still a further additional embodiment, there is provided a method of screening a candidate substance for anti-kinase activity comprising the steps of (i) providing a having TS10q23.3 polypeptide comprising at least one tyrosine kinase site; (ii) contacting the cell with the candidate substance; and (iii) determining the effect of the candidate substance on the phosphorylation of the site. The determining may comprise comparing one or more characteristics of the cell in the presence of the candidate substance with characteristics of a cell in the absence of the candidate substance. The characteristic may be phosphorylation status of TS10q23.3, TS10q23.3 expression, phosphatase activity, proliferation, metastasis, contact inhibition, soft agar growth, cell cycle regulation, tumor formation, tumor progression and tissue invasion. The candidate substance may be a chemotherapeutic or radiotherapeutic agent or be selected from a small molecule library. The cell may be contacted in vitro or in vivo.

In yet another embodiment, the present invention provides a method of diagnosing Cowden's Syndrome comprising the steps of obtaining a sample from a subject; and determining the expression a functional TS10q23.3 gene product in cells of the sample. In particularly preferred embodiments, the cells may be selected from the group consisting of breast, ovarian, thyroid and endometrial cells. In other embodiments, the sample may be a tissue or fluid sample. In other aspects of the invention the determining comprises assaying for a nucleic acid from the sample. In more preferred aspects, the method may further comprise subjecting the sample to conditions suitable to amplify the nucleic acid. In other embodiments, the method may further comprise the step of comparing the expression of TS10q23.3 with the expression of TS10q23.3 in non-Cowden's Syndrome samples. In particular embodiments, the comparison may involve evaluating the level of TS10q23.3 expression. In more particular embodiments, the Cowden's Syndrome sample comprises a mutation in the coding sequence of TS10q23.3. The mutation may be a frameshift mutation, a deletion mutation, an insertion mutation or a missense mutation. In more particular embodiments the mutation is in exon 7. In other particular embodiments, the mutation results in a premature termination of the TS10q23.3 gene product. In other embodiments, the deletion mutation is in exon 8. In certain embodiments the insertion is in exon 2. In particularly preferred embodiments, the mutation is an insertion of AT at base 791 of exon 7. In other particularly preferred embodiments, the mutation is a thirteen base pair deletion at base 915 of exon 8. In another preferred embodiment, the mutation is a three base pair insertion at base 137 of exon 2. More specifically the three base pair insertion results encodes for an ASN in the TS10q23.3 gene product.

In a further aspect, there is also provided a method of diagnosing a subject predisposed to breast cancer comprising the steps of obtaining a sample from a subject; and determining the expression a functional TS10q23.3 gene product in cells of the sample. In particular embodiments, the cells may be selected from the group consisting of breast, ovarian cells, thyroid cells and endometrial cells. In other embodiments, the sample is a tissue or fluid sample. In a particularly preferred aspect the method further comprises the step of comparing the expression of TS10q23.3 with the expression of TS10q23.3 in normal samples. In more defined aspects the sample comprises a mutation in the coding sequence of TS10Q23.3. The mutation may be a frameshift mutation, a deletion mutation, an insertion mutation or a missense mutation. In more particular embodiments the mutation is in exon 7. In other particular embodiments, the mutation results in a premature termination of the TS10q23.3 gene product. In other embodiments, the deletion mutation is in exon 8. In certain embodiments the insertion is in exon 2. In particularly preferred embodiments, the mutation is an insertion of AT at base 791 of exon 7. In other particularly preferred embodiments, the mutation is a thirteen base pair deletion at base 915 of exon 8. In another preferred embodiment, the mutation is a three base pair insertion at base 137 of exon 2. More specifically the three base pair insertion results encodes for an ASN in the TS10q23.3 gene product.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein:

FIG. 6.—Coding Sequence and 5'- and 3'-Flanking Regions of TS10q23.3. Coding region is in bold as is the first in frame stop codon.

FIG. 7.—Predicted Amino Acid Sequence of TS10q23.3 Product. Abbreviations are A, alanine; C, cysteine; D, aspartic acid; E, glutamic acid; F; phenylalanine; G, glycine; H, histidine; I, isoleucine; K, lysine; L, leucine; M, methionine; N, asparagine; P, proline; Q, glutamine; R, arginine; S, serine; T, threonine; V, valine; W, tryptophan; Y, tyrosine. Phosphatase consensus site is in bold; tyrosine phosphorylation sites are italicized and underlined.

FIG. 10.—Sequence of Exons and Surrounding Intronic Regions of TS10q23.3. The exons are denoted as capital letters starting at position one, and introns are designated lower case letters; except for the first exon where the initiation codon starts at position one and the 3' exon/intron boundary is at position 79 and 80, respectively. The lower case letter designate (Table 5) corresponds to the numbering of the sequence presented in this figure, except for the first exon. The mutations for U87 and U138 are at the first intron G residue [G+1>T] after the exon (exon 7 and 8, respectively). For T98G and KE, the point mutations are at positions 46 and 28 of exon 2, respectively. For LnCap cells, the mutation is a deletion of bases 16 and 17 in the first intron.

FIGS. 11A–G.—Analysis of Secondary Structures in TS1023.3. FIG. 11A: Hydrophilicity plot; FIG. 11B: Surface probability plot; FIG. 11C: Flexibility plot; FIG. 11D: Antigenic index plot; FIG. 11E: Amphiphilic helix plot; FIG. 11F: Amphiphilic sheet plot; FIG. 11G: Secondary structure plot.

FIGS. 12A–I.—Comparison of Predicted Characteristics in TS10q23.3 and Point Mutants T98G and KE. FIG. 12A: Hydrophilicity plot of residues 1–60 of wild-type polypeptide; FIG. 12B: Surface probability plot of residues 1–60 of wild-type polypeptide; FIG. 12C: Secondary structure plot of residues 1–60 of wild-type polypeptide; FIG. 12D: Hydrophilicity plot of residues 1–60 of KE mutant; FIG. 12E: Surface probability plot of residues 1–60 of KE mutant; FIG. 12F: Secondary structure plot of residues 1–60 of KE mutant; FIG. 12G: Hydrophilicity plot of residues 1–60 of T98G mutant; FIG. 12H: Surface probability plot of residues 1–60 of T98G mutant; FIG. 12I: Secondary structure plot of residues 1–60 of T98G mutant. The T98G mutation (Leu→Arg) at residue 42 results in the loss of proposed helix secondary structure of TS10q23.3. The mutation in KE at residue 36 (Gly→Glu) would significantly increase the length of the proposed helical structure in the region. Both mutations would affect the same helical structure. Also, minor changes in the hydrophilicity and surface probability arise.

FIG. 18. FACS infectivity assay. U87MG cells were infected with GFCB at the indicator/concentrations for 24 hr. The fraction of cells expressing green fluorescent protein was quantitated by flow cytometry. pn/ml: adenovirus particle numbers per ml.

FIG. 19A. $^3$H-thymidine uptake. FIG. 19B. Viable cell count assay. Error bars are S.D. (3 replicates). Pn/ml: adenovirus particle numbers per ml.

SEQUENCE SUMMARY

Figure 10C:
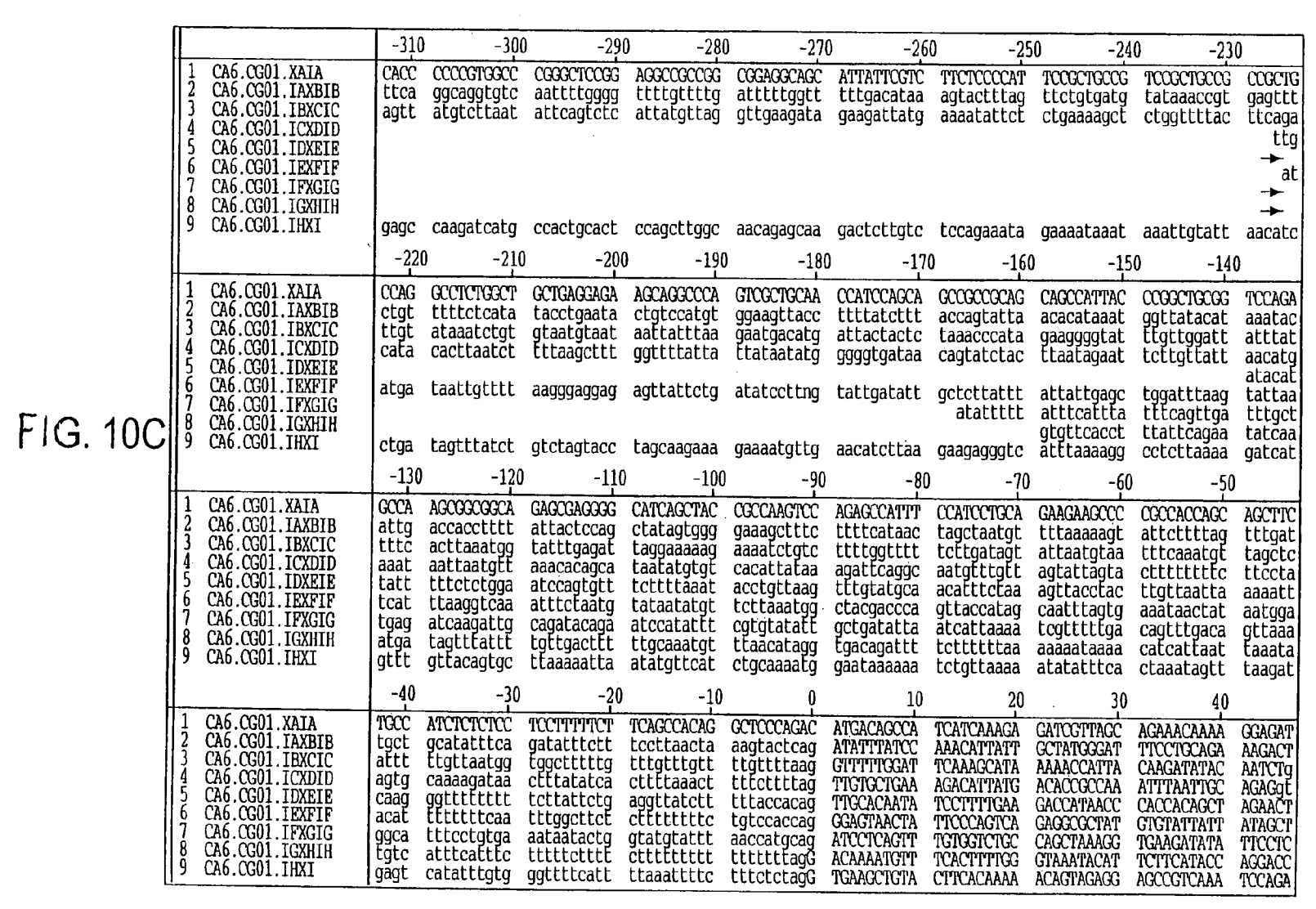
Figure 10D:
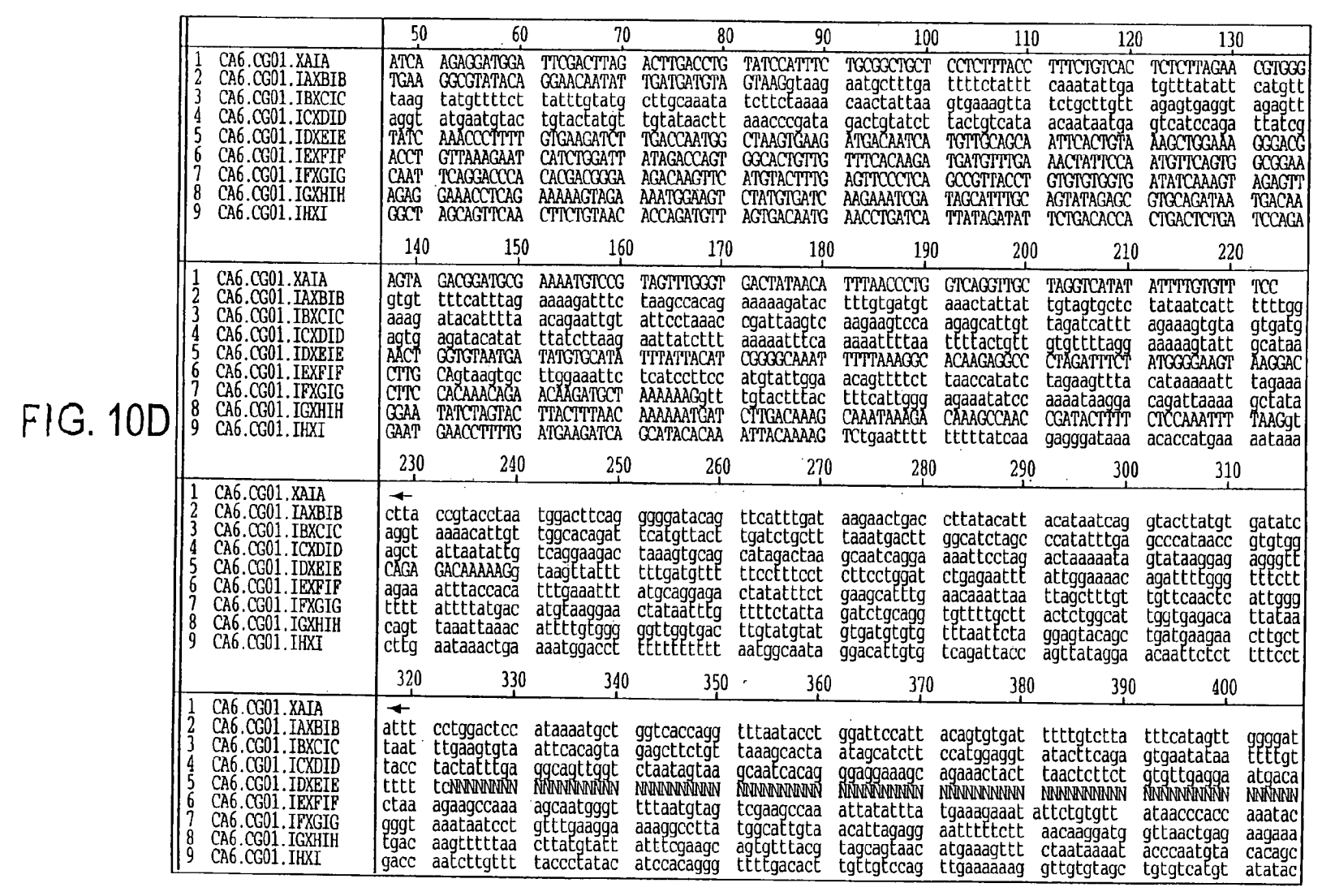
Figure 9C:
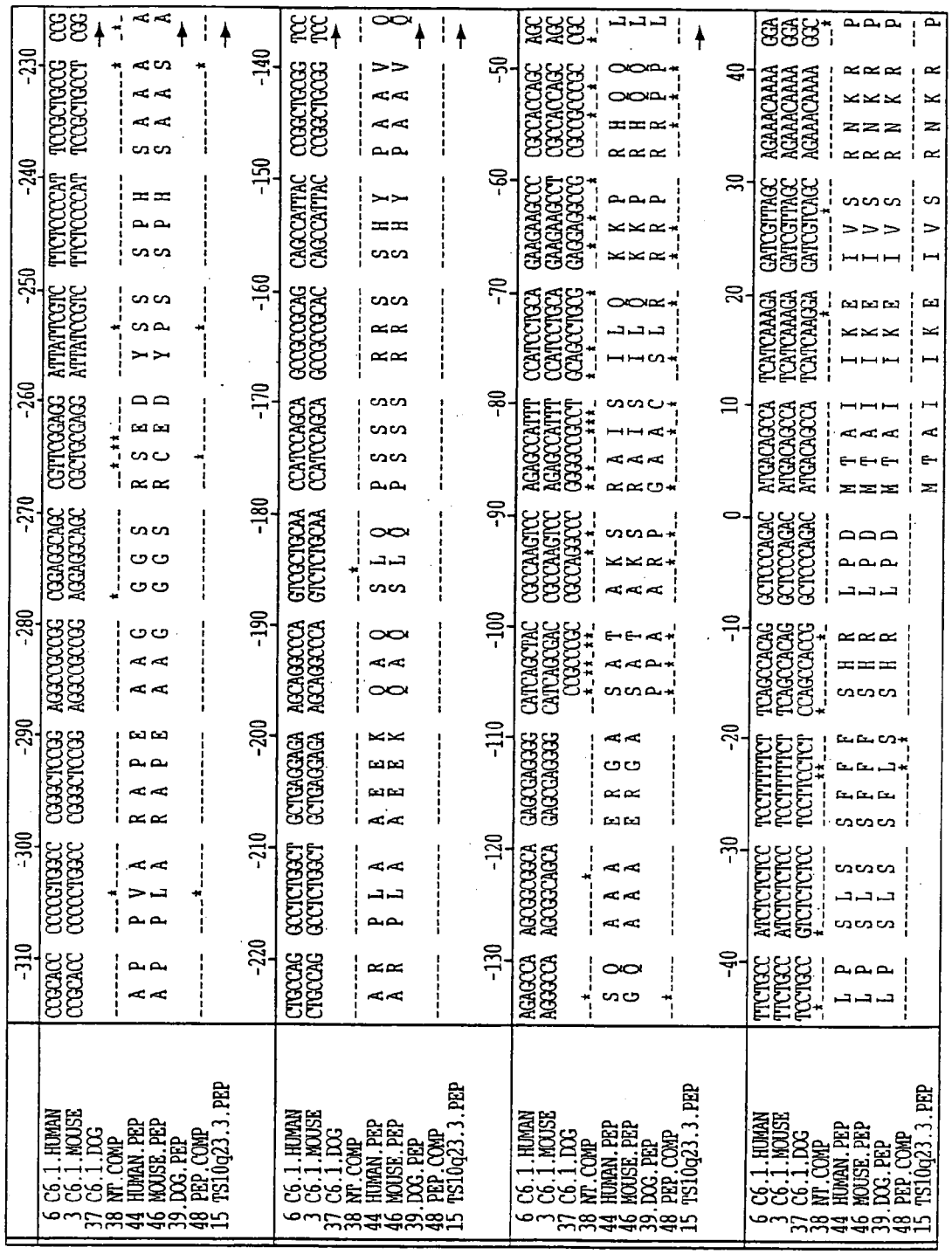
FIG. 9.—Homology Comparison of Human TS10q23.3 with Mouse and Dog Homologs. The initiation ATG codon and methionine amino acid are designated at the start (1) position. The termination codon is TGA (1210). Alterations between the human and mouse or dog sequences on the genomic or amino acid level are designated by a star in the sequence compared. The dog and human amino acid sequences are identical; the mouse sequence differed at position 398, where the mouse has a Serine, as opposed to a Threonine in dog and human.
Figure 11G:
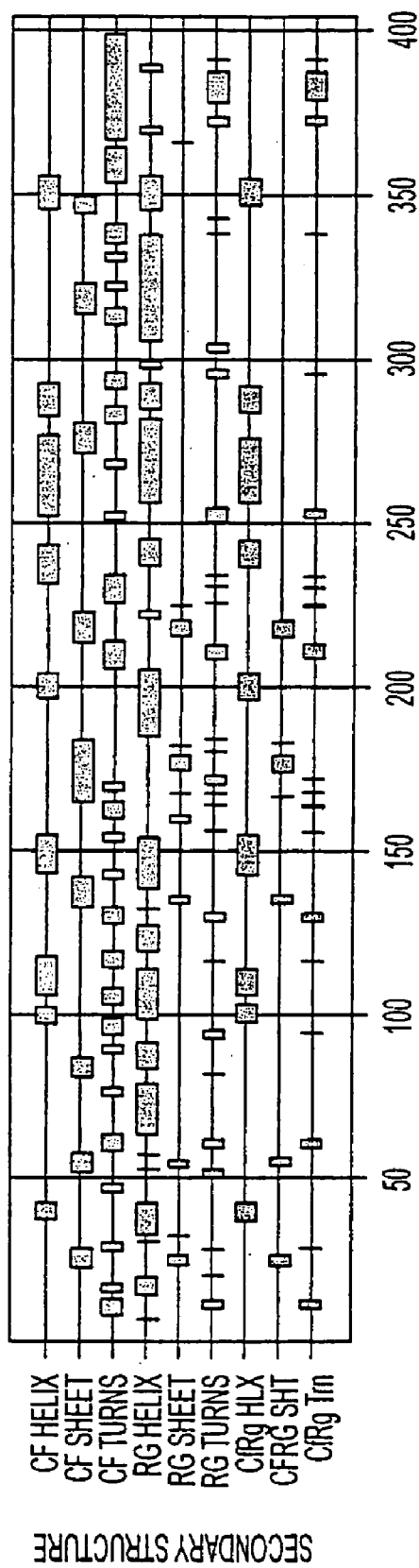
Figure 12C:
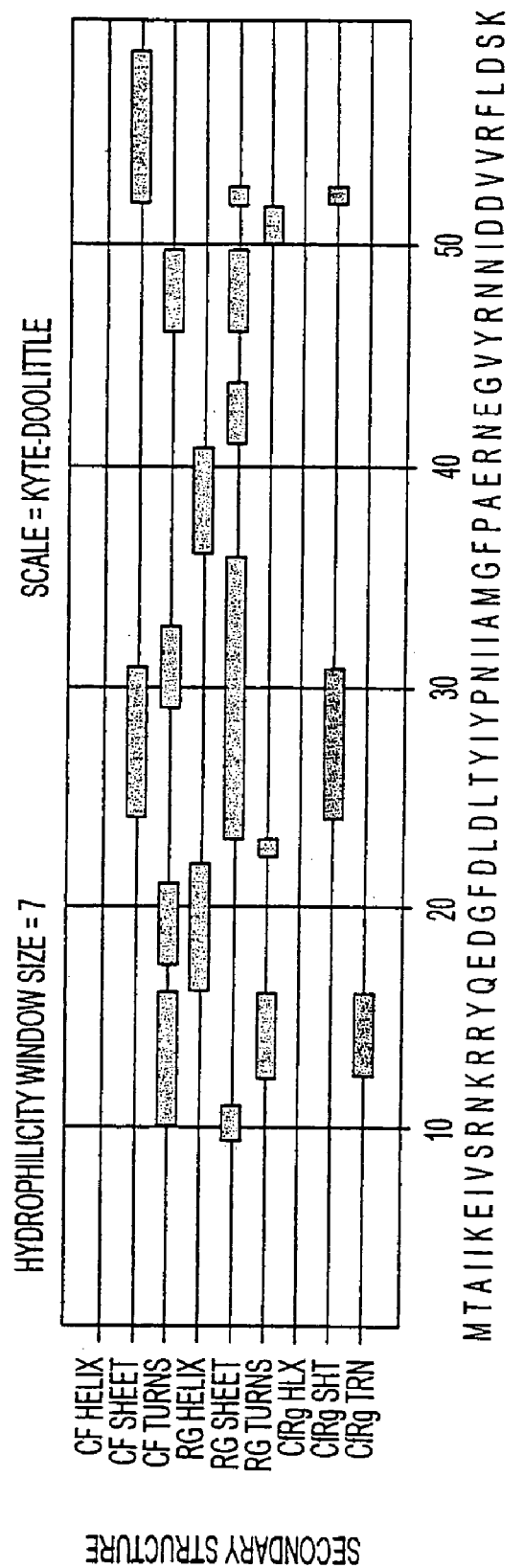
Figure 12F:
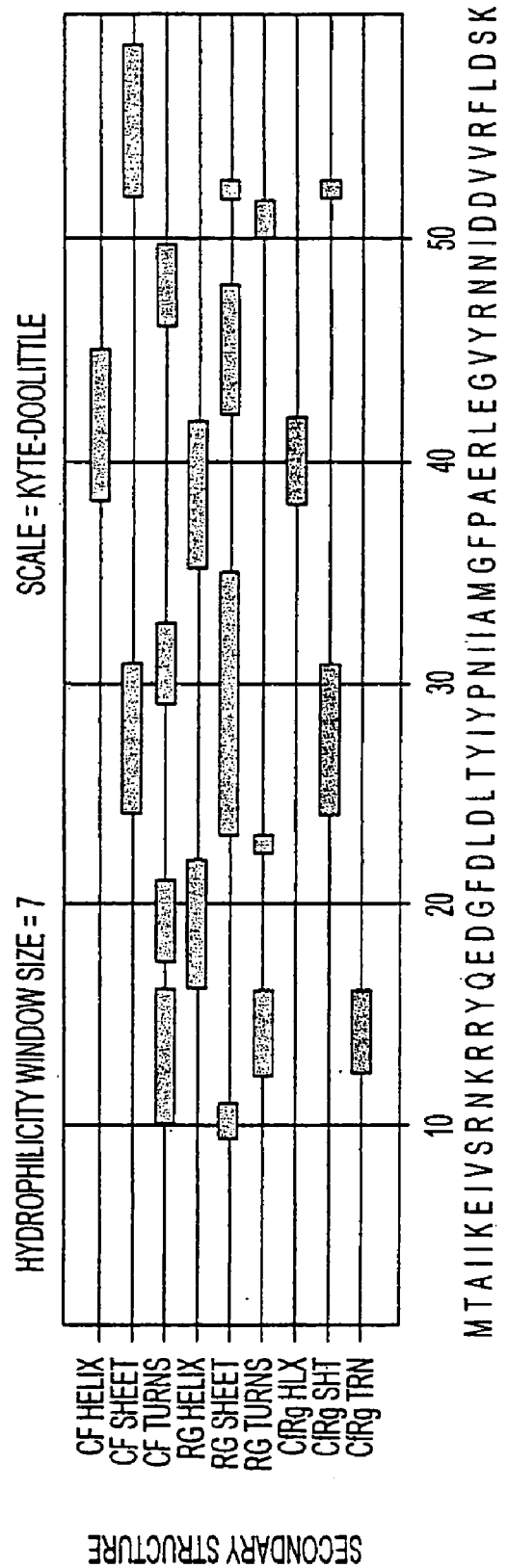
Figure 12G:
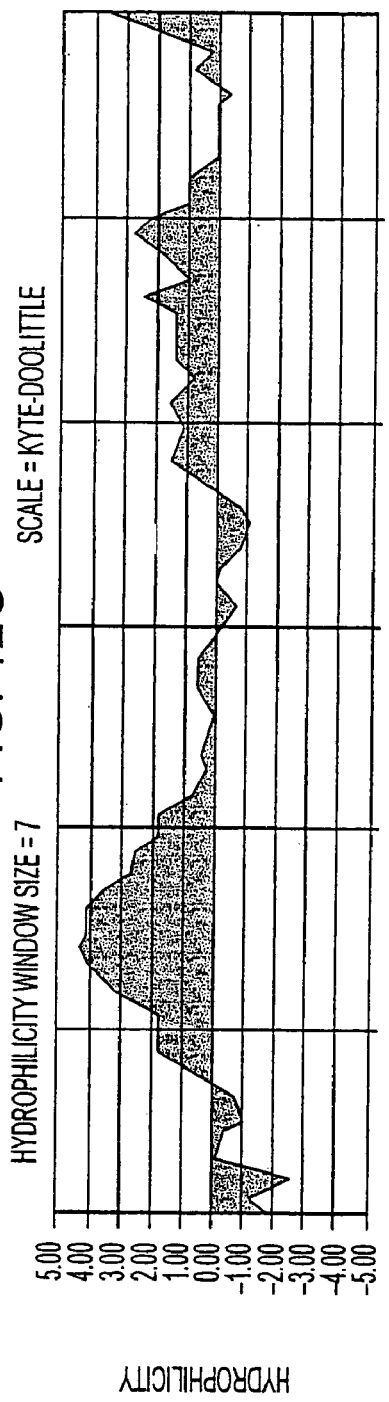
Figure 12H:
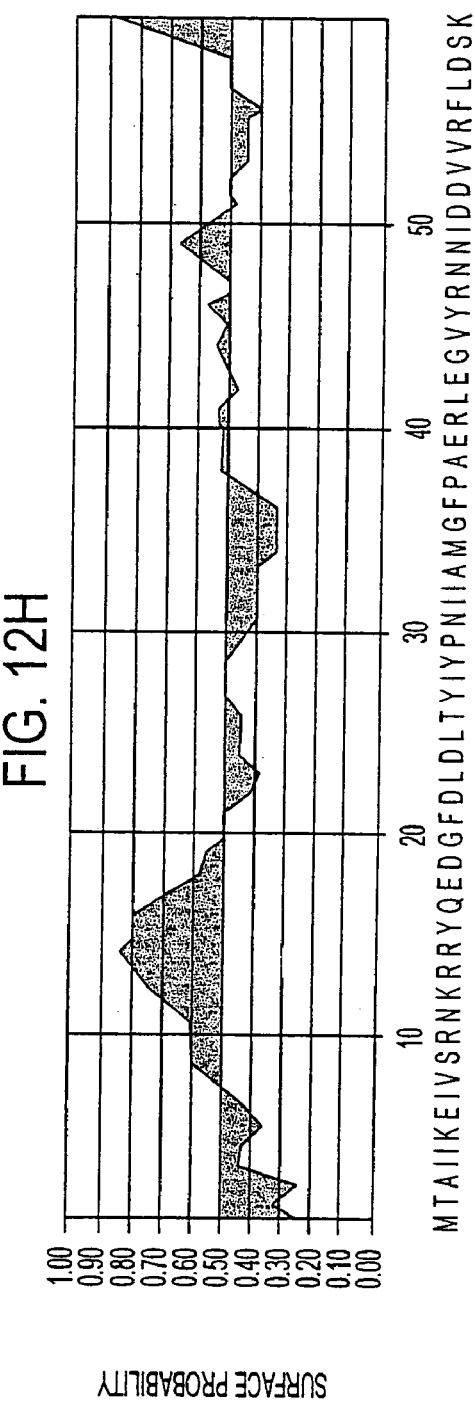
Figure 12I:
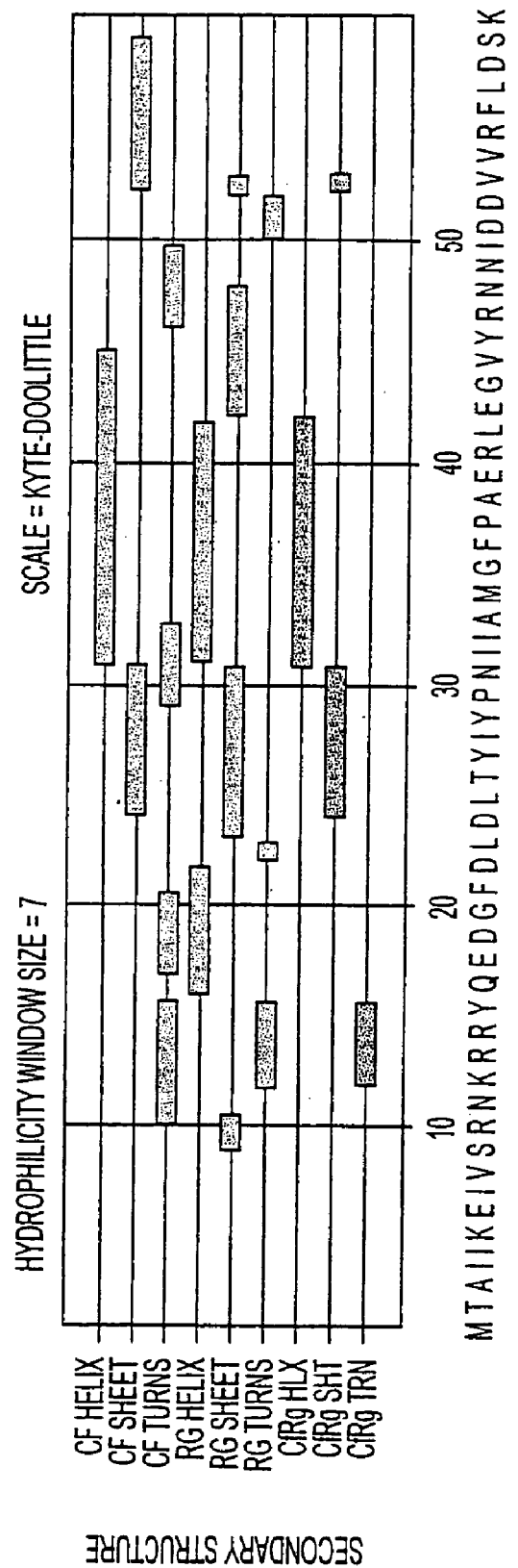
Figure 9A:
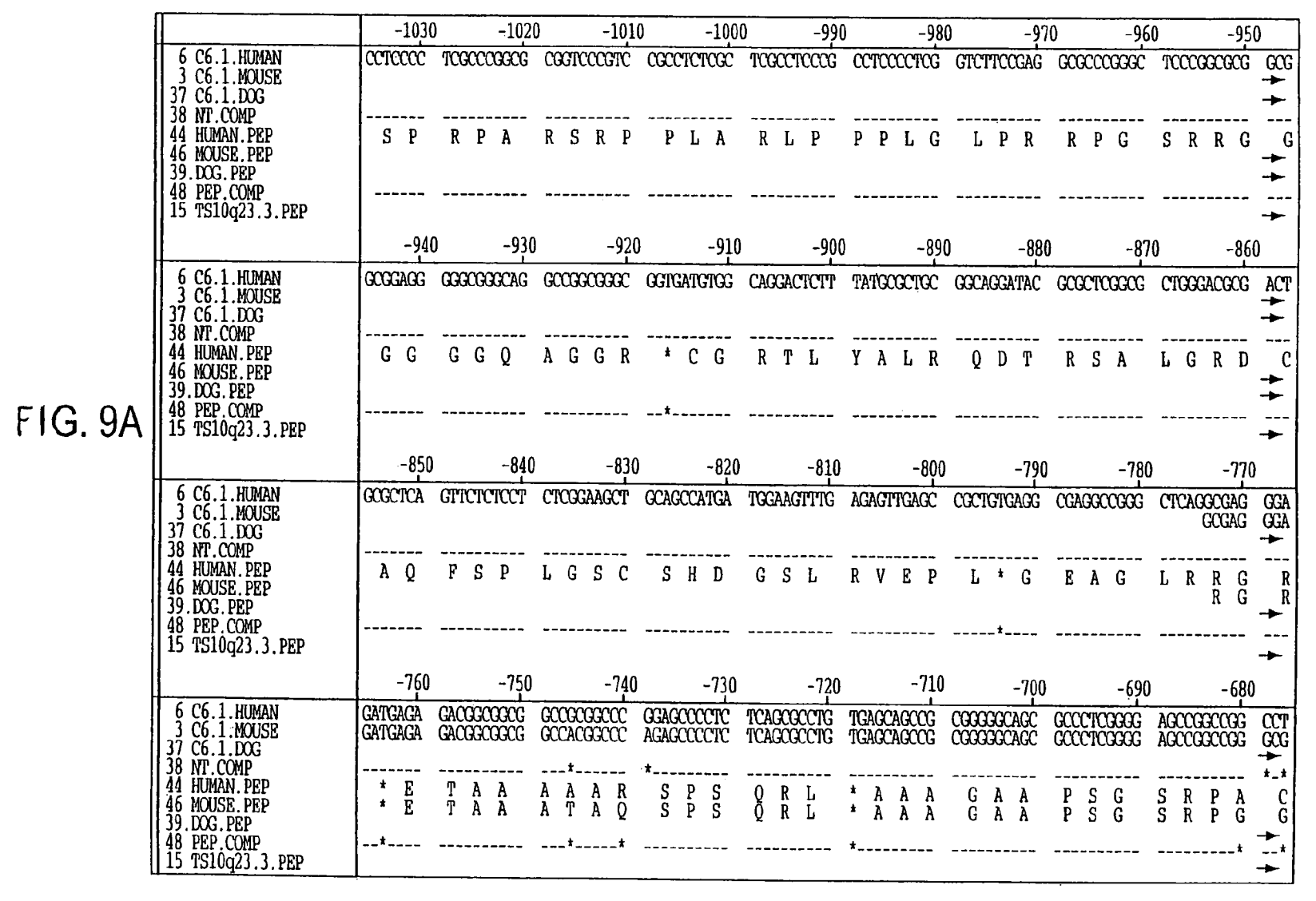
Figure 9B:
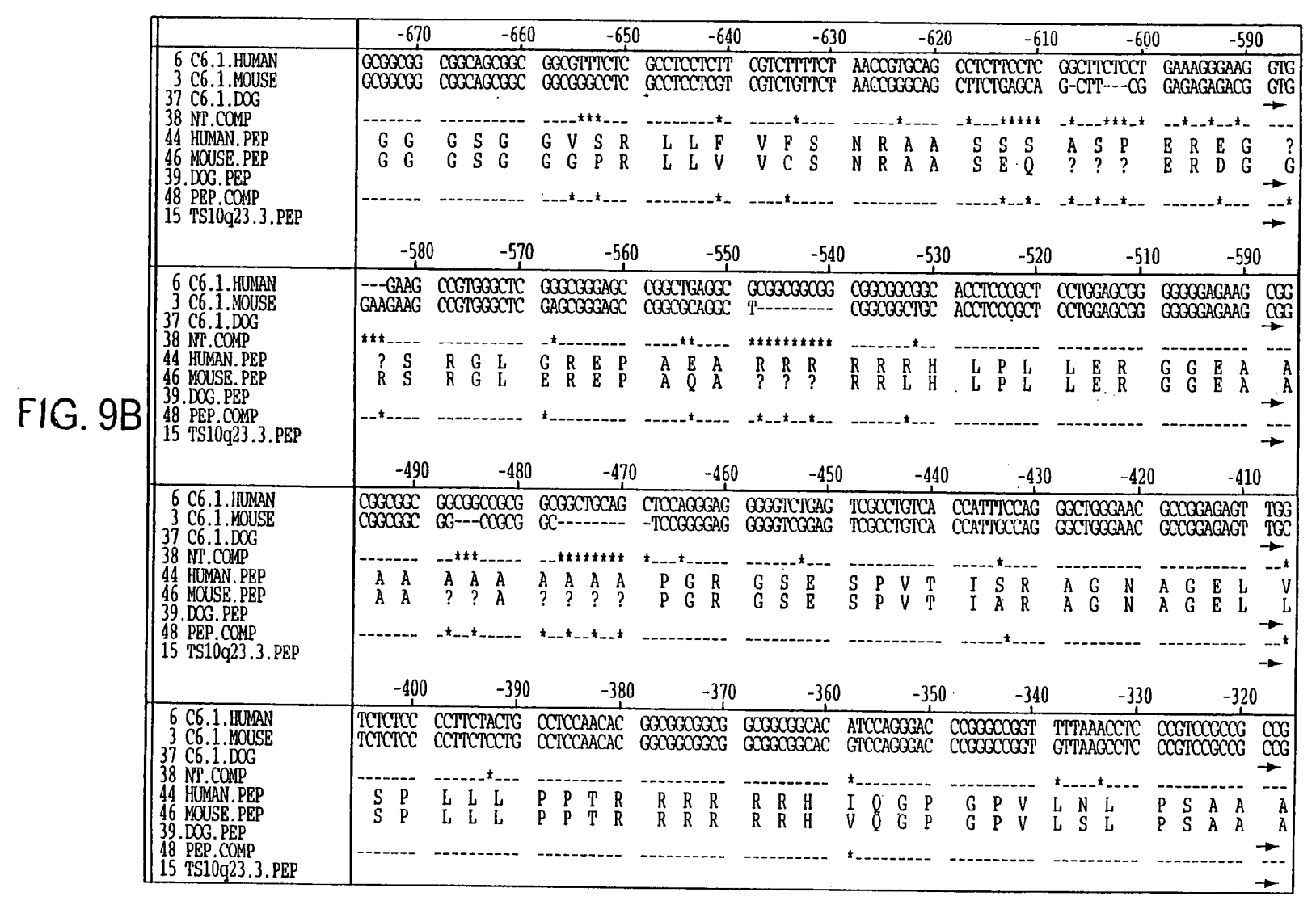
Figure 9E:
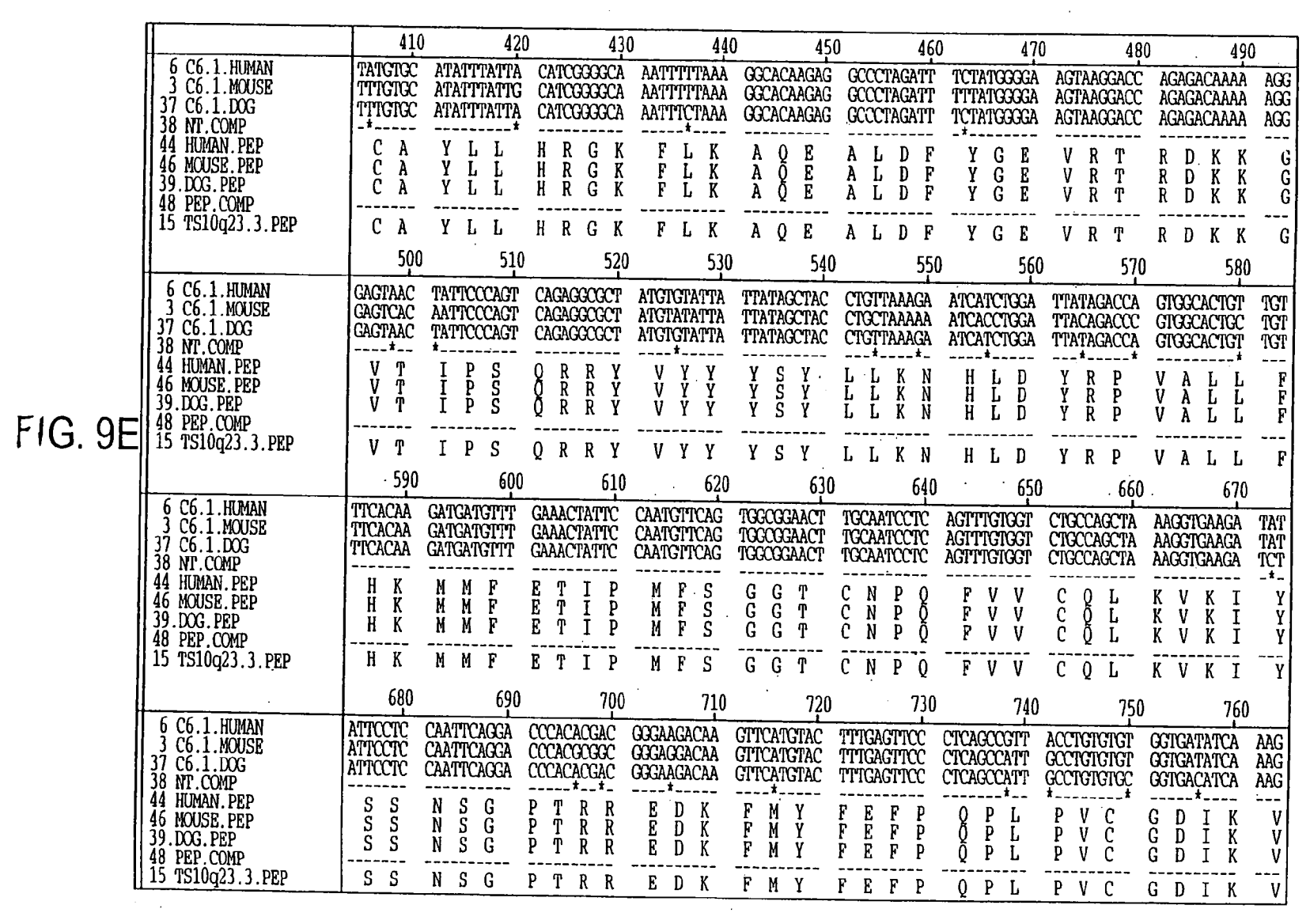
Figure 9F:
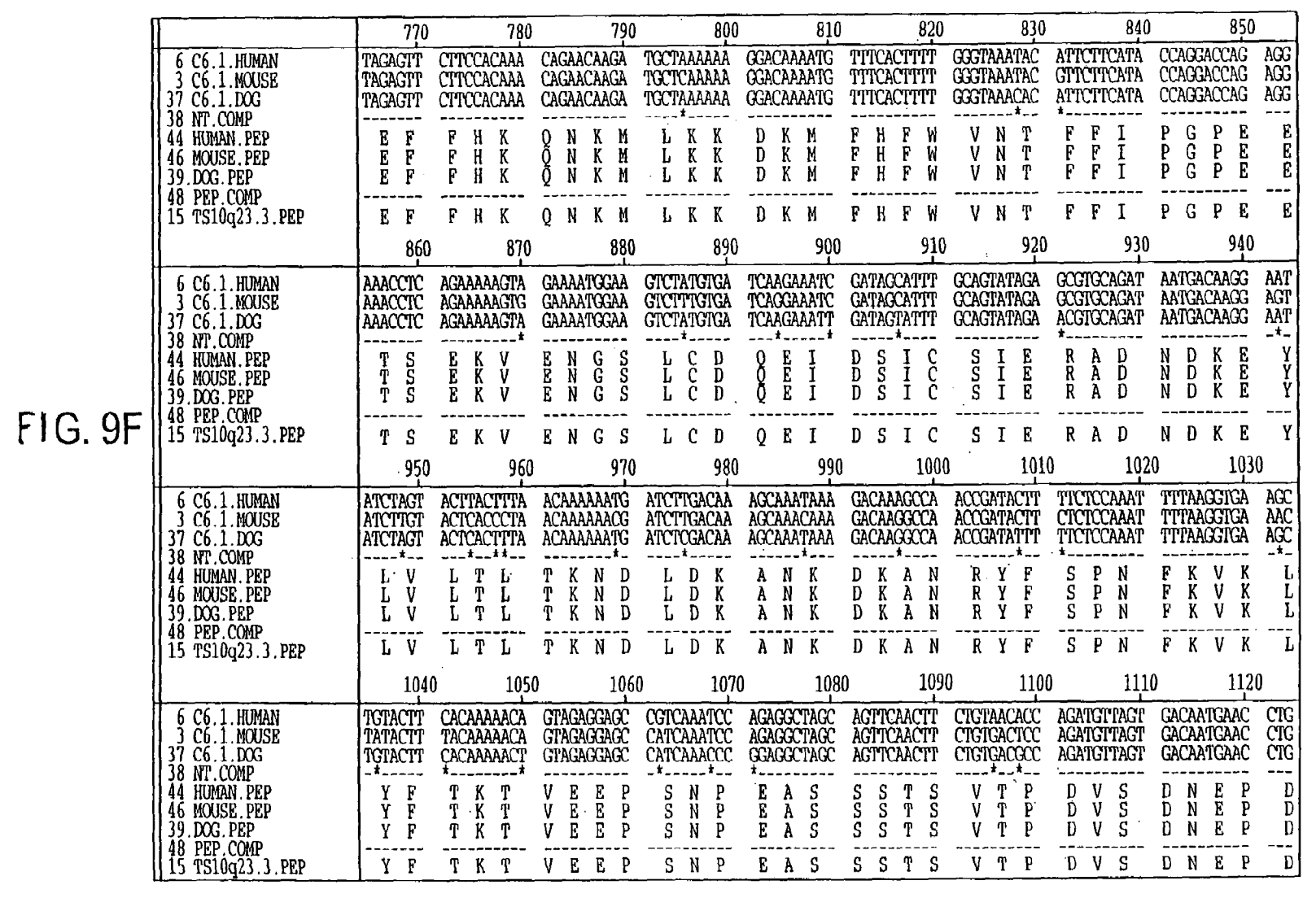
Figure 9G:
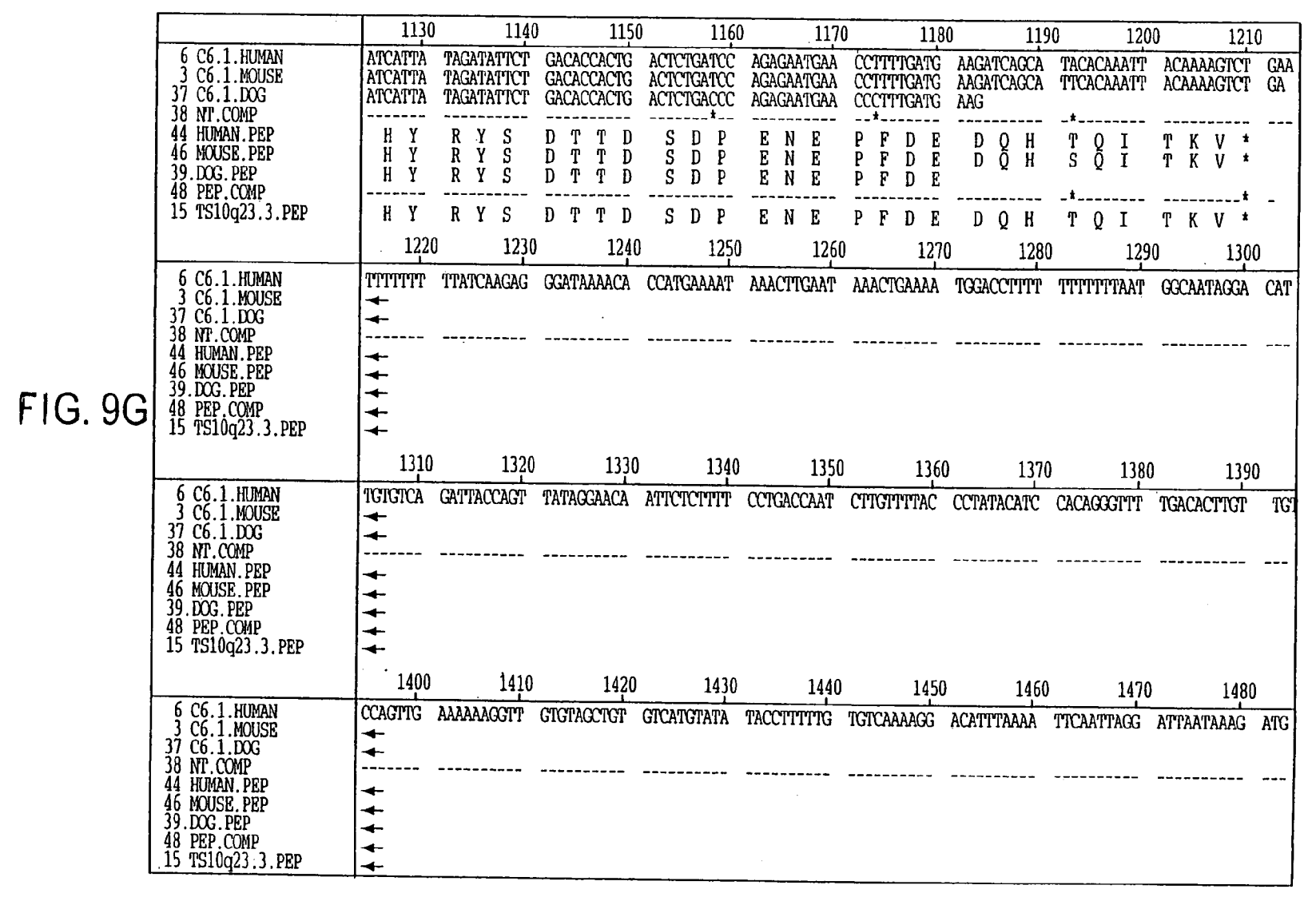

SEQ ID NO:1=human TS10q23.3 gene sequence (FIGS. 6 and 9); SEQ ID NO:2=human TS10q23.3 peptide sequence from CDS of SEQ ID NO:1; SEQ ID NO:3=translation of bases 3–119 of SEQ ID NO:1; SEQ ID NO:4=translation of bases 123–242 of SEQ ID NO:1; SEQ ID NO:5=translation of bases 246–272 of SEQ ID NO:1; SEQ ID NO:6=translation of bases 276–317 of SEQ ID NO:1; SEQ ID NO:7=translation of bases 321–449 of SEQ ID NO:1; SEQ ID NO:8=translation of bases 453–2243 of SEQ ID NO:1; SEQ ID NO:9=mouse TS10q23.3 gene sequence (FIG. 9); SEQ ID NO:10=mouse TS10q23.3 peptide sequence from CDS of SEQ ID NO:9; SEQ ID NO:11=translation of bases 14–55 of SEQ ID NO:9; SEQ ID NO:12=translation of bases 59–166 of SEQ ID NO:9; SEQ ID NO:13=translation of bases 172–222 of SEQ ID NO:9; SEQ ID NO:14=translation of bases 223–273 of SEQ ID NO:9; SEQ ID NO:15=translation of bases 283–1959 of SEQ ID NO:9; SEQ ID NO:16=dog TS10q23.3 gene sequence (FIG. 9); SEQ ID NO:17=dog TS10q23.3 peptide sequence from CDS of SEQ ID NO:16; SEQ ID NO:18=translation of bases 1–1290 of SEQ ID NO:16; SEQ ID NO:19=exon 1 (FIG. 10); SEQ ID NO:20=exon 2 (FIG. 10); SEQ ID NO:21=exon 3 (FIG. 10); SEQ ID NO:22=exon 4 (FIG. 10); SEQ ID NO:23=exon 5 (FIG. 10); SEQ ID NO:24=exon 6 (FIG. 10); SEQ ID NO:25=exon 7 (FIG. 10); SEQ ID NO:26=exon 8 (FIG. 10); SEQ ID NO:27=exon 9 (FIG. 10); SEQ ID NO:28=a motif from residues 88 to 98; SEQ ID NO:29=conserved catalytic domain of a protein tyrosine phosphatase (Denu et al., 1996); SEQ ID NO:30=residues 1–60 of wild-type TS10q23.3 polypeptide (FIGS. 12A–12C); SEQ ID NO:31=residues 1–60 of T98G mutant TS10q23.3 polypeptide (FIGS. 12D–12F); SEQ ID NO:32=residues 1–60 of KE mutant TS10q23.3 polypeptide (FIGS. 12G–12I); SEQ ID NO:33=CA6.ex8.FB primer; SEQ ID NO:34=CA6.ex8.RQ primer; SEQ ID NO:35: =CA6.ex8.FC primer; SEQ ID NO:36=CA6.ex8.RR primer; SEQ ID NO:37=nested primer used to obtain secondary amplicons exon 8 FB-RQ; SEQ ID NO:38=nested primer used to obtain secondary amplicons exon 9 FB-RR; SEQ ID NO:39=M5'F primer; SEQ ID NO:40=M5' R primer; SEQ ID NO:41=M3'F primer; SEQ ID NO:42:=F3'R primer; SEQ ID NO:43=primer in first round PCR™ in human fetal brain; SEQ ID NO:44=primer in first round PCR™ in human fetal brain; SEQ ID NO:45=primer in second round PCR™ in human fetal brain; SEQ ID NO:46=primer in second round PCR™ in human fetal brain; SEQ ID NO:47=primer used to generate a specific 303 bp product from the pseudogene and not TS10q23; SEQ ID NO:48=primer used to generate a specific 303 bp product from the pseudogene and not TS10q23; SEQ ID NO:49=mouse MMAC1 protein sequence; SEQ ID NO:50=peptide sequence; SEQ ID NO:51=translation of bases 321–1034 of SEQ ID NO:1; SEQ ID NO:52=translation of bases 169–750 of SEQ ID NO:9; SEQ ID NO:53=translation of bases 1–108 of SEQ ID NO:16; SEQ ID NO:54=dog MMAC1 gene sequence; SEQ ID NO:55=dog MMAC1 protein sequence from CDS of SEQ ID NO:54; SEQ ID NO:56=mouse MMAC gene sequence; SEQ ID NO:57=mouse MMAC1 protein sequence from CDS of SEQ ID NO:56; SEQ ID NO:58=primer MAC1.6f matching sequences in MMAC1 exon 2; SEQ ID NO:59=primer MAC 1.6r matching sequences in MMAC1 exon 5; SEQ ID NO:60=translation of bases 1–54 of SEQ ID NO:56; SEQ ID NO:61=translation of bases 58–96 of SEQ ID NO:56; SEQ ID NO:62=translation of bases 98–178 of SEQ ID NO:56; SEQ ID NO:63=translation of bases 182–208 of SEQ ID NO:56; SEQ ID NO:64=sequence of human TS10q23.3 pseudogene.

DETAILED DESCRIPTION OF THE PREFERRED EMBODIMENTS

I. The Present Invention

As stated above, a number of different groups have shown evidence of a tumor suppressing activity associated with the 10q region of human chromosome 10. Despite this considerable amount of work, the identity of the gene or genes responsible for this activity has not been determined. Previous investigations used a functional approach involving transfer of chromosomes or chromosomal fragments suspected of harboring tumor suppressor gene(s) into tumorigenic glioma cells. These efforts allowed definition of the biological activity of putative tumor suppressor gene(s) and aided in the localization of such activity. Chromosomes 2 and 10 were transferred into U251 glioma cells and chromosomes 2 and 10 into LG-11 cells. The LG-11 cells were shown to have no intact copies of chromosome 10 and the breakpoint was subsequently found to occur at 10q24. The transfer of chromosome 10 resulted in hybrid cells that displayed a suppressed phenotype, exhibiting a loss of tumorigenicity (no tumor formation) and loss of the ability to grow in soft agarose (50× to 1000× decrease; Pershouse et al., 1993). The hybrid's exponential growth rate was similar to the parental cell, although the hybrid cell's saturation density was significantly (10× to 20×) lower than the parental cells. The transfer of chromosome 2 resulted in hybrid cells that acted similar to the parental cells.

One objective of these studies was to localize the chromosome 10 suppressor gene by fragmentation of the neomycin-tagged chromosome 10 and, subsequently, to transfer the fragmented chromosome into glioma cells. However, the inventors observed that some of the hybrid cells had spontaneously undergone chromosomal rearrangements to yield hybrid cells retaining only various regions of the inserted chromosome 10 (Pershouse et al., 1993). The inventors then subcloned the hybrids and analyzed them, rather than initiate fragmentation studies (Steck et al., 1995). The retention of the inserted chromosome 10 or its fragments was tracked by informative RFLP markers and FISH analysis. Interestingly, only the inserted chromosome was subjected to rearrangement. The insertion of an entire copy of chromosome 10 resulted in inhibition of the hybrid cell's transformed property to proliferate in soft agarose and to form tumors in nude mice.

These two phenotypes now appear to be partially separable by the instant analysis. Some subclones (U251.N10.5a–j), which revealed a loss of a major portion of the long arm of chromosome 10, grew in soft agarose but failed to form tumors in nude mice, thus indicating that a tumor suppressive locus resides in the remaining portion of the chromosome (10pter to 10q11). In contrast, clones that retained a distal region of the long arm, 10q24 to 10q26, failed both to proliferate in soft agarose and in nude mice (see FIG. 4). This suggests another phenotypic suppressive region residing in the distal region of the chromosome. The lack of additional 10-associated material further would suggest that the remaining chromosome 10 material is responsible for the altered biological phenotype. These results implicate the presence of two phenotypically independent suppressive regions on chromosome 10 involved in glioma progression (Steck et al., 1995).

According to the present invention, the inventors now have used several independent strategies to localize a tumor suppressor gene, designated TS10q23.3, that is involved in gliomas, breast cancer, prostate cancer and other cancers. These approaches, described in greater detail in the following Examples, included (i) identification of homozygous deletions in a series of human glioma cell lines; (ii) determination of a consistent region(s) of retention in clones suppressed for tumorigenicity; and (iii) allelic deletion studies on various grades of glioma and corresponding normal samples. With the gene in hand, it now becomes possible to exploit the information encoded by the gene to develop novel diagnostic and therapeutic approaches related to human cancer.

II. The 10q23.3 Tumor Suppressor

According to the present invention, there has been identified a tumor suppressor, encoded by a gene in the 10q23.3 locus, and designated here as TS10q23.3. This molecule is capable of suppressing tumor phenotypes in various cancers. The term tumor suppressor is well-known to those of skill in the art. Examples of other tumors suppressors are p53, Rb and p16, to name a few. While these molecules are structurally distinct, they form a group of functionally-related molecules, of which TS10q23.3 is a member. The uses in which these other tumor suppressors now are being exploited are equally applicable here.

In addition to the entire TS10q23.3 molecule, the present invention also relates to fragments of the polypeptide that may or may not retain the tumor suppressing (or other) activity. Fragments, including the N-terminus of the molecule may be generated by genetic engineering of translation stop sites within the coding region (discussed below). Alternatively, treatment of the TS10q23.3 molecule with proteolytic enzymes, known as proteases, can produces a variety of N-terminal, C-terminal and internal fragments. Examples of fragments may include contiguous residues of the TS10q23.3. sequence given in FIG. 7 and FIG. 9, of 6, 7, 8, 9, 10, 11, 12, 13, 14, 15, 16, 17, 18, 19, 20, 21, 22, 23, 24, 25, 30, 35, 40, 45, 50, 55, 60, 65, 75, 80, 85, 90, 95, 100, 200, 300, 400 or more amino acids in length. These fragments may be purified according to known methods, such as precipitation (e.g., ammonium sulfate), HPLC, ion exchange chromatography, affinity chromatography (including immunoaffinity chromatography) or various size separations (sedimentation, gel electrophoresis, gel filtration).

A. Structural Features of the Polypeptide

The gene for TS10q23.3 encodes a 403 amino acid polypeptide. The predicted molecular weight of this molecule is 47,122, with a resulting pI of 5.86. Thus, at a minimum, this molecule may be used as a standard in assays where molecule weight and pI are being examined.

A phosphatase consensus site is located at residues 122–131, matching perfectly the tyrosine phosphatase (PTP) consensus sequence: [I/V]HCxAGxxR[S/T]G. Outside the active domains, sequences differ greatly. PTPs proceed through phosphoenzyme intermediates. The enzymatic reaction involves phosphoryl-cysteine intermediate formation after nucleophilic attack of the phosphorus atom of the substrate by the thiolate anion of cysteine. The reaction can be represented as a two-step chemical process: phosphoryl transfer to the enzyme accompanied by rapid release of dephosphorylated product; and hydrolysis of the thiol-phosphate intermediate concomitant with rapid release of phosphate. To form the catalytically competent component complex, the enzyme binds and reacts with the dianion of phosphate-containing substrate. On the enzyme, an aspartic acid must be protonated and the nucleophilic cysteine must be unprotonated (thiolate anion) for phosphoryl transfer to the enzyme. Also of note are potential tyrosine phosphorylation sites located at residues 233–240 and 308–315 and cAMP phosphorylation sites located at residues 128, 164, 223 and 335. Phosphatases are known to have kinase sites, and the phosphatase activity of these enzymes can be modulated by phosphorylation at these sites. Protein phosphatases generally are divided into two categories—serine/threonine phosphatases and tyrosine phosphatases. Certain of the tyrosine phosphatases also have activity against phosphoserine and phosphothreonine.

The interaction between kinases and phosphatases, and the various phosphorylation states of polypeptides, have been demonstrated as important features in cell physiology. Through a variety of different mechanisms, kinases and phosphatases act in different pathways within cells that are involved in signaling, energy storage and cell regulation. Since the identification of an intrinsic tyrosine kinase function in the transforming protein src (Collett & Erickson, 1978), the role of phosphorylation, particularly on tyrosine residues, has been demonstrated to be critical in the control of cellular proliferation and the induction of cancer (Hunter, 1991; Bishop, 1991). The roles that protein phosphatases play in growth regulation, as well as in many other biological and biochemical activities, have been correlated with the phosphorylation state of biologically important molecules (Cohen, 1994).

Based on its sequence, TS10q23.3 appears to encode a tyrosine phosphatase or dual specificity phosphatase with homology to the cytoskeleton associated proteins, chicken tensin and bovine auxilin (Steck et al., 1997; Li et al., 1997). The N-terminal half of TS10q23.3 is homologous to several phosphatases and its putative core phosphatase motif is present at residues 122–134 (Denu et al., 1996; Tonks and Neel, 1996). Thus, the N-terminal half of TS10q23.3 is homologous to several phosphatases and its putative core phosphatase motif is present at residues 122–134 (Denu et al., 1996; Tonks and Neel, 1996). Thus, the N-terminal region of TS10q23.3 may have enzymatic and cellular localization activities. The C-terminal portion of TS10q23.3 contains three potential tyrosine phosphorylation sites at residues 240, 315 and 336. If phosphorylated, tyrosine 315 would represent a potential SH2 binding site as there is a leucine residue located three residues C-terminal from the tyrosine (Songyang et al., 1995). Two potential serine phosphorylation sites are also present within the C-terminal half of TS10Q23.3. Serine residue 338 represents a potential Ca2+/calmodulin-dependent protein kinase II site, while serine 355 represents a potential caseine kinase II site (Hardie and Hanks, 1995). The last four C-terminal amino acids, ITKV, represent a potential PDZ binding domain (Fanning and Anderson, 1996; Saras and Heldin, 1996). PDZ domains are present in a variety of intracellular proteins and are thought to mediate protein-protein interactions by binding directly to the C-terminal ends of target proteins.

It also should be mentioned that the 60 or so amino acids of the N-terminus of the molecule show some homology to tensin, a cytoskeletal protein implicated in adhesion plaques. This suggests that TS10q23.3 may be involved in cell surface phenomena such as contact inhibition, invasion, migration or cell-to-cell signaling. TS10q23.3 point mutations identified in certain tumor cell lines affect secondary proposed structures in this region.

B. Functional Aspects

When the present application refers to the function of TS10q23.3 or "wild-type" activity, it is meant that the molecule in question has the ability to inhibit the transformation of a cell from a normally regulated state of proliferation to a malignant state, i.e., one associated with any sort of abnormal growth regulation, or to inhibit the transformation of a cell from an abnormal state to a highly malignant state, e.g., to prevent metastasis or invasive tumor growth. Other phenotypes that may be considered to be regulated by the normal TS10q23.3 gene product are angiogenesis, adhesion, migration, cell-to-cell signaling, cell growth, cell proliferation, density-dependent growth, anchorage-dependent growth and others. Determination of which molecules possess this activity may be achieved using assays familiar to those of skill in the art. For example, transfer of genes encoding TS10q23.3, or variants thereof, into cells that do not have a functional TS10q23.3 product, and hence exhibit impaired growth control, will identify, by virtue of growth suppression, those molecules having TS10q23.3 function.

As stated above, there is an indication that TS10q23.3 is a phosphatase. The portion of the protein located at residues 88 to 98 is a perfect match for the conserved catalytic domain of protein tyrosine phosphatase. Also, putative kinase targets are located in the molecule, which is another characteristic of phosphatases. Because other tumor suppressors have been identified with this type of activity, it will be desirable to determine the phosphatase function in the tumor suppressing role of TS10q23.3. This also may be a fruitful approach to developing screening assays for the absence of TS10q23.3 function or in the development of cancer therapies, for example, in targeting the phosphatase function of TS10q23.3, targeting the substrate upon which TS10q23.2 acts, and/or targeting the kinase or kinases which act upon TS10q23.3.

C. Variants of TS10q23.3

Amino acid sequence variants of the polypeptide can be substitutional, insertional or deletion variants. Deletion variants lack one or more residues of the native protein which are not essential for function or immunogenic activity, and are exemplified by the variants lacking a transmembrane sequence described above. Another common type of deletion variant is one lacking secretory signal sequences or signal sequences directing a protein to bind to a particular part of a cell. Insertional mutants typically involve the addition of material at a non-terminal point in the polypeptide. This may include the insertion of an immunoreactive epitope or simply a single residue. Terminal additions, called fusion proteins, are discussed below.

Substitutional variants typically contain the exchange of one amino acid for another at one or more sites within the protein, and may be designed to modulate one or more properties of the polypeptide, such as stability against proteolytic cleavage, without the loss of other functions or properties. Substitutions of this kind preferably are conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

In particular aspects it is contemplated that one of skill in the art will employ standard technologies well known to those of skill in the art to produce the mutants. Specifically contemplated will be N-terminal deletions, C-terminal deletions, internal deletions, as well as random and point mutagenesis.

N-terminal and C-terminal deletions are forms of deletion mutagenesis that take advantage for example, of the presence of a suitable single restriction site near the end of the C- or N-terminal region. The DNA is cleaved at the site and the cut ends are degraded by nucleases such as BAL31, exonuclease III, DNase I, and S1 nuclease. Rejoining the two ends produces a series of DNAs with deletions of varying size around the restriction site. Proteins expressed from such mutant can be assayed for apoptosis inhibiting and/or chaperone function as described throughout the specification. Similar techniques are employed in internal deletion mutants, however, in internal deletion mutants are generated by using two suitably placed restriction sites, thereby allowing a precisely defined deletion to be made, and the ends to be religated as above.

Also contemplated are partial digestions mutants. In such instances, one of skill in the art would employ a "frequent cutter", that cuts the DNA in numerous places depending on the length of reaction time. Thus, by varying the reaction conditions it will be possible to generate a series of mutants of varying size, which may then be screened for activity.

A random insertional mutation may also be performed by cutting the DNA sequence with a DNase I, for example, and inserting a stretch of nucleotides that encode, 3, 6, 9, 12 etc., amino acids and religating the end. Once such a mutation is made the mutants can be screened for various activities presented by the wild-type protein.

Once general areas of the gene are identified as encoding particular protein domains, point mutagenesis may be employed to identify with particularity which amino acid residues are important in particular activities associated with TS10Q23.3. Thus one of skill in the art will be able to generate single base changes in the DNA strand to result in an altered codon and a missense mutation.

The following is a discussion based upon changing of the amino acids of a protein to create an equivalent, or even an improved, second-generation molecule. For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid substitutions can be made in a protein sequence, and its underlying DNA coding sequence, and nevertheless obtain a protein with like properties. It is thus contemplated by the inventors that various changes may be made in the DNA sequences of genes without appreciable loss of their biological utility or activity, as discussed below. Table 1 shows the codons that encode particular amino acids.

In making such changes, the hydropathic index of amino acids may be considered. The importance of the hydropathic amino acid index in conferring interactive biologic function on a protein is generally understood in the art (Kyte & Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (Kyte & Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine *−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent and immunologically equivalent protein. In such changes, the substitution of amino acids whose hydrophilicity values are within ±2 is preferred, those that are within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

Another embodiment for the preparation of polypeptides according to the invention is the use of peptide mimetics. Mimetics are peptide-containing molecules that mimic elements of protein secondary structure. See, for example, Johnson et al., "Peptide Turn Mimetics" in *BIOTECHNOL-*

*OGY AND PHARMACY*, Pezzuto et al., Eds., Chapman and Hall, New York (1993). The underlying rationale behind the use of peptide mimetics is that the peptide backbone of proteins exists chiefly to orient amino acid side chains in such a way as to facilitate molecular interactions, such as those of antibody and antigen. A peptide mimetic is expected to permit molecular interactions similar to the natural molecule. These principles may be used, in conjunction with the principles outline above, to engineer second generation molecules having many of the natural properties of TS10q23.3, but with altered and even improved characteristics.

D. Domain Switching

As described in the examples, the present inventors have identified putative murine and canine homologs of the human TS10q23.3 gene. In addition, mutations have been identified in TS10q23.3 which are believed to alter its function. These studies are important for at least two reasons. First, they provide a reasonable expectation that still other homologs, allelic variants and mutants of this gene may exist in related species, such as rat, rabbit, monkey, gibbon, chimp, ape, baboon, cow, pig, horse, sheep and cat. Upon isolation of these homologs, variants and mutants, and in conjunction with other analyses, certain active or functional domains can be identified. Second, this will provide a starting point for further mutational analysis of the molecule. One way in which this information can be exploited is in "domain switching."

Domain switching involves the generation of chimeric molecules using different but, in this case, related polypeptides. By comparing the mouse, dog and human sequences for TS10q23.3 with the TS10q23.3 of other species, and with mutants and allelic variants of these polypeptides, one can make predictions as to the functionally significant regions of these molecules. It is possible, then, to switch related domains of these molecules in an effort to determine the criticality of these regions to TS10q23.3 function. These molecules may have additional value in that these "chimeras" can be distinguished from natural molecules, while possibly providing the same function.

Based on the sequence identity, at the amino acid level, of the mouse, dog and human sequences, it may be inferred that even small changes in the primary sequence of the molecule will affect function. Further analysis of mutations and their predicted effect on secondary structure will add to this understanding.

Another structural aspect of TS10q23.3 that provides fertile ground for domain switching experiments is the tyrosine phosphatase-like domain and the putative tyrosine phosphorylation sites. This domain may be substituted for other phosphatase domains in order to alter the specificity of this function. A further investigation of the homology between TS10q23.3 and other phosphatases is warranted by this observation.

E. Fusion Proteins

A specialized kind of insertional variant is the fusion protein. This molecule generally has all or a substantial portion of the native molecule, linked at the N- or C-terminus, to all or a portion of a second polypeptide. For example, fusions typically employ leader sequences from other species to permit the recombinant expression of a protein in a heterologous host. Another useful fusion includes the addition of a immunologically active domain, such as an antibody epitope, to facilitate purification of the fusion protein. Inclusion of a cleavage site at or near the fusion junction will facilitate removal of the extraneous polypeptide after purification. Other useful fusions include linking of functional domains, such as active sites from enzymes, glycosylation domains, cellular targeting signals or transmembrane regions.

One particular fusion of interest would include a deletion construct lacking the phosphatase site of TS10q23.3 but containing other regions that could bind the substrate molecule. Fusion to a polypeptide that can be used for purification of the substrate-TS10q23.3 complex would serve to isolated the substrate for identification and analysis.

Examples of fusion protein expression systems include the glutathione S-transferase (GST) system (Pharmacia, Piscataway, N.J.), the maltose binding protein system (NEB, Beverley, Mass.), the FLAG system (IBI, New Haven, Conn.), and the 6×His system (Qiagen, Chatsworth, Calif.). Some of these systems produce recombinant polypeptides bearing only a small number of additional amino acids, which are unlikely to affect the antigenic ability of the recombinant polypeptide. For example, both the FLAG system and the 6×His system add only short sequences, both of which are known to be poorly antigenic and which do not adversely affect folding of the polypeptide to its native conformation.

In still further systems, it is possible to create fusion protein constructs to enhance immunogenicity of a TS10q23.3 fusion construct to increase immunogenicity are well known to those of skill in the art, for example, a fusion of TS10q23.3 with a helper antigen such as hsp70 or peptide sequences such as from Diptheria toxin chain or a cytokine such as IL2 will be useful in eliciting an immune response. In other embodiments, fusion construct can be made which will enhance the targeting of the TS10q23.3 related compositions to a specific site or cell. For example, fusing TS10q23.3 or a TS10q23.3 type protein to a ligand will be an effective means to target the composition to a site expressing the receptor for such a ligand. In this manner the TS10q23.3 or TS10q23.3 related composition may be delivered into a cell via receptor mediated delivery. The TS10q23.3 protein can be attached covalently or fused to a ligand. This can be used as a mechanics for delivery into a cell. The ligand with the protein attached may then be internalized by a receptor bearing cell.

Other fusion systems produce polypeptide hybrids where it is desirable to excise the fusion partner from the desired polypeptide. In one embodiment, the fusion partner is linked to the recombinant TS10q23.3 polypeptide by a peptide sequence containing a specific recognition sequence for a protease. Examples of suitable sequences are those recognized by the Tobacco Etch Virus protease (Life Technologies, Gaithersburg, Md.) or Factor Xa (New England Biolabs, Beverley, Mass.).

F. Purification of Proteins

It will be desirable to purify TS10q23.3 or variants thereof. Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. A particularly efficient method of purifying peptides is fast protein liquid chromatography or even HPLC.

Certain aspects of the present invention concern the purification, and in particular embodiments, the substantial purification, of an encoded protein or peptide. The term "purified protein or peptide" as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "–fold purification number." The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

High Performance Liquid Chromatography (HPLC) is characterized by a very rapid separation with extraordinary resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

A particular type of affinity chromatography useful in the purification of carbohydrate containing compounds is lectin affinity chromatography. Lectins are a class of substances that bind to a variety of polysaccharides and glycoproteins. Lectins are usually coupled to agarose by cyanogen bromide. Conconavalin A coupled to Sepharose was the first material of this sort to be used and has been widely used in the isolation of polysaccharides and glycoproteins other lectins that have been include lentil lectin, wheat germ agglutinin which has been useful in the purification of N-acetyl glucosaminyl residues and *Helix pomatia* lectin. Lectins themselves are purified using affinity chromatography with carbohydrate ligands. Lactose has been used to purify lectins from castor bean and peanuts; maltose has been useful in extracting lectins from lentils and jack bean; N-acetyl-D galactosamine is used for purifying lectins from soybean; N-acetyl glucosaminyl binds to lectins from wheat germ; D-galactosamine has been used in obtaining lectins from clams and L-fucose will bind to lectins from lotus.

The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. One of the most common forms of affinity chromatography is immunoaffinity chromatography. The generation of antibodies that would be suitable for use in accord with the present invention is discussed below.

G. Synthetic Peptides

The present invention also describes smaller TS10q23.3-related peptides for use in various embodiments of the present invention. Because of their relatively small size, the peptides of the invention can also be synthesized in solution or on a solid support in accordance with conventional techniques. Various automatic synthesizers are commercially available and can be used in accordance with known protocols. See, for example, Stewart and Young, (1984); Tam et al., (1983); Merrifield, (1986); and Barany and Merrifield (1979), each incorporated herein by reference. Short peptide sequences, or libraries of overlapping peptides, usually from about 6 up to about 35 to 50 amino acids, which correspond to the selected regions described herein, can be readily synthesized and then screened in screening assays designed to identify reactive peptides. Alternatively, recombinant DNA technology may be employed wherein a nucleotide sequence which encodes a peptide of the invention is inserted into an expression vector, transformed or transfected into an appropriate host cell and cultivated under conditions suitable for expression.

U.S. Pat. No. 4,554,101 (incorporated herein by reference) also teaches the identification and preparation of epitopes from primary amino acid sequences on the basis of hydrophilicity. Through the methods disclosed in Hopp, one of skill in the art would be able to identify epitopes from within any amino acid sequence encoded by any of the DNA sequences disclosed herein.

H. Antigen Compositions

The present invention also provides for the use of TS10q23.3 proteins or peptides as antigens for the immunization of animals relating to the production of antibodies. It is envisioned that either TS10q23.3, or portions thereof, will be coupled, bonded, bound, conjugated or chemically-linked to one or more agents via linkers, polylinkers or derivatized amino acids. This may be performed such that a bispecific or multivalent composition or vaccine is produced. It is further envisioned that the methods used in the preparation of these compositions will be familiar to those of skill in the art and should be suitable for administration to animals, i.e., pharmaceutically acceptable. Preferred agents are the carriers are keyhole limpet hemocyannin (KLH) or bovine serum albumin (BSA).

III. Nucleic Acids

The present invention also provides, in another embodiment, genes encoding TS10q23.3. Genes for the human, canine and murine TS10q23.3 molecule have been identified. The present invention is not limited in scope to these genes, however, as one of ordinary skill in the could, using these nucleic acids, readily identify related homologs in various other species (e.g., rat, rabbit, monkey, gibbon, chimp, ape, baboon, cow, pig, horse, sheep, cat and other species). The finding of mouse and dog homologs for this gene makes it likely that other species more closely related to humans will, in fact, have a homolog as well.

In addition, it should be clear that the present invention is not limited to the specific nucleic acids disclosed herein. As discussed below, a "TS10q23.3 gene" may contain a variety of different bases and yet still produce a corresponding polypeptide that is functionally indistinguishable, and in some cases structurally, from the human and mouse genes disclosed herein.

Similarly, any reference to a nucleic acid should be read as encompassing a host cell containing that nucleic acid and, in some cases, capable of expressing the product of that nucleic acid. In addition to therapeutic considerations, cells expressing nucleic acids of the present invention may prove useful in the context of screening for agents that induce, repress, inhibit, augment, interfere with, block, abrogate, stimulate or enhance the function of TS10q23.3.

A. Nucleic Acids Encoding 10q23.3

The human gene disclosed in FIGS. 6 and 9, and the murine gene disclosed in FIG. 9 are TS10q23.3 genes of the present invention. Nucleic acids according to the present invention may encode an entire TS10q23.3 gene, a domain of TS10q23.3 that expresses a tumor suppressing or phosphatase function, or any other fragment of the TS10q23.3 sequences set forth herein. The nucleic acid may be derived from genomic DNA, i.e., cloned directly from the genome of a particular organism. In preferred embodiments, however, the nucleic acid would comprise complementary DNA (cDNA). Also contemplated is a cDNA plus a natural intron or an intron derived from another gene; such engineered molecules are sometime referred to as "mini-genes." At a minimum, these and other nucleic acids of the present invention may be used as molecular weight standards in, for example, gel electrophoresis.

The term "cDNA" is intended to refer to DNA prepared using messenger RNA (mRNA) as template. The advantage of using a cDNA, as opposed to genomic DNA or DNA polymerized from a genomic, non- or partially-processed RNA template, is that the cDNA primarily contains coding sequences of the corresponding protein. There may be times when the full or partial genomic sequence is preferred, such as where the non-coding regions are required for optimal expression or where non-coding regions such as introns are to be targeted in an antisense strategy.

It also is contemplated that a given TS10q23.3 from a given species may be represented by natural variants that have slightly different nucleic acid sequences but, nonetheless, encode the same protein (see Table 1 below).

As used in this application, the term "a nucleic acid encoding a TS10q23.3" refers to a nucleic acid molecule that has been isolated free of total cellular nucleic acid. In preferred embodiments, the invention concerns a nucleic acid sequence essentially as set forth in FIGS. 6 and 9. The term "as set forth in FIG. 6 or 9" means that the nucleic acid sequence substantially corresponds to a portion of FIG. 6 or 9. The term "functionally equivalent codon" is used herein to refer to codons that encode the same amino acid, such as the six codons for arginine or serine (Table 1, below), and also refers to codons that encode biologically equivalent amino acids, as discussed in the following pages.

TABLE 1

| Amino Acids | | | Codons | | | |
|---|---|---|---|---|---|---|
| Alanine | Ala | A | GCA | GCC | GCG | GCU |
| Cysteine | Cys | C | UGC | UGU | | |
| Aspartic acid | Asp | D | GAC | GAU | | |
| Glutamic acid | Glu | E | GAA | GAG | | |
| Phenylalanine | Phe | F | UUC | UUU | | |
| Glycine | Gly | G | GGA | GGC | GGG | GGU |
| Histidine | His | H | CAC | CAU | | |
| Isoleucine | Ile | I | AUA | AUC | AUU | |
| Lysine | Lys | K | AAA | AAG | | |

TABLE 1-continued

| Amino Acids | | | Codons | | | | | |
|---|---|---|---|---|---|---|---|---|
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

Allowing for the degeneracy of the genetic code, sequences that have at least about 50%, usually at least about 60%, more usually about 70%, most usually about 80%, preferably at least about 90% and most preferably about 95% of nucleotides that are identical to the nucleotides of FIG. 9 will be sequences that are "as set forth in FIG. 9." Sequences that are essentially the same as those set forth in FIG. 9 may also be functionally defined as sequences that are capable of hybridizing to a nucleic acid segment containing the complement of FIG. 9 under standard conditions.

The DNA segments of the present invention include those encoding biologically functional equivalent TS10q23.3 proteins and peptides, as described above. Such sequences may arise as a consequence of codon redundancy and amino acid functional equivalency that are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques or may be introduced randomly and screened later for the desired function, as described below.

B. Oligonucleotide Probes and Primers

Naturally, the present invention also encompasses DNA segments that are complementary, or essentially complementary, to the sequence set forth in FIGS. 6 and 9. Nucleic acid sequences that are "complementary" are those that are capable of base-pairing according to the standard Watson-Crick complementary rules. As used herein, the term "complementary sequences" means nucleic acid sequences that are substantially complementary, as may be assessed by the same nucleotide comparison set forth above, or as defined as being capable of hybridizing to the nucleic acid segment of FIGS. 6 and 9 under relatively stringent conditions such as those described herein. Such sequences may encode the entire TS10q23.3 protein or functional or non-functional fragments thereof.

Alternatively, the hybridizing segments may be shorter oligonucleotides. Sequences of 17 bases long should occur only once in the human genome and, therefore, suffice to specify a unique target sequence. Although shorter oligomers are easier to make and increase in vivo accessibility, numerous other factors are involved in determining the specificity of hybridization. Both binding affinity and sequence specificity of an oligonucleotide to its complementary target increases with increasing length. It is contemplated that exemplary oligonucleotides of 8, 9, 10, 11, 12, 13, 14, 15, 16, 17, 18, 19, 20, 25, 30, 35, 40, 45, 50, 55, 60, 65, 70, 75, 80, 85, 90, 95, 100 or more base pairs will be used, although others are contemplated. Longer polynucleotides encoding 250, 500, 1000, 1212, 1500, 2000, 2500, 3000 or 3431 bases and longer are contemplated as well. Such oligonucleotides will find use, for example, as probes in Southern and Northern blots and as primers in amplification reactions.

Suitable hybridization conditions will be well known to those of skill in the art. In certain applications, for example, substitution of amino acids by site-directed mutagenesis, it is appreciated that lower stringency conditions are required. Under these conditions, hybridization may occur even though the sequences of probe and target strand are not perfectly complementary, but are mismatched at one or more positions. Conditions may be rendered less stringent by increasing salt concentration and decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Thus, hybridization conditions can be readily manipulated, and thus will generally be a method of choice depending on the desired results.

In other embodiments, hybridization may be achieved under conditions of, for example, 50 mM Tris-HCl (pH 8.3), 75 mM KCl, 3 mM $MgCl_2$, 10 mM dithiothreitol, at temperatures between approximately 20° C. to about 37° C. Other hybridization conditions utilized could include approximately 10 mM Tris-HCl (pH 8.3), 50 mM KCl, 1.5 μM $MgCl_2$, at temperatures ranging from approximately 40° C. to about 72° C. Formamide and SDS also may be used to alter the hybridization conditions.

One method of using probes and primers of the present invention is in the search for genes related to TS10q23.3 or, more particularly, homologs of TS10q23.3 from other species. The existence of a murine homolog strongly suggests that other homologs of the human TS10q23.3 will be discovered in species more closely related, and perhaps more remote, than mouse. Normally, the target DNA will be a genomic or cDNA library, although screening may involve analysis of RNA molecules. By varying the stringency of hybridization, and the region of the probe, different degrees of homology may be discovered.

Another way of exploiting probes and primers of the present invention is in site-directed, or site-specific mutagenesis. Site-specific mutagenesis is a technique useful in the preparation of individual peptides, or biologically functional equivalent proteins or peptides, through specific mutagenesis of the underlying DNA. The technique further provides a ready ability to prepare and test sequence variants, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

The technique typically employs a bacteriophage vector that exists in both a single stranded and double stranded form. Typical vectors useful in site-directed mutagenesis include vectors such as the M13 phage. These phage vectors are commercially available and their use is generally well known to those skilled in the art. Double stranded plasmids are also routinely employed in site directed mutagenesis, which eliminates the step of transferring the gene of interest from a phage to a plasmid.

In general, site-directed mutagenesis is performed by first obtaining a single-stranded vector, or melting of two strands of a double stranded vector which includes within its sequence a DNA sequence encoding the desired protein. An oligonucleotide primer bearing the desired mutated sequence is synthetically prepared. This primer is then annealed with the single-stranded DNA preparation, taking into account the degree of mismatch when selecting hybridization conditions, and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as E. coli cells, and clones are selected that include recombinant vectors bearing the mutated sequence arrangement.

The preparation of sequence variants of the selected gene using site-directed mutagenesis is provided as a means of producing potentially useful species and is not meant to be limiting, as there are other ways in which sequence variants of genes may be obtained. For example, recombinant vectors encoding the desired gene may be treated with mutagenic agents, such as hydroxylamine, to obtain sequence variants.

C. Antisense Constructs

In some cases, mutant tumor suppressors may not be non-functional. Rather, they may have aberrant functions that cannot be overcome by replacement gene therapy, even where the "wild-type" molecule is expressed in amounts in excess of the mutant polypeptide. Antisense treatments are one way of addressing this situation. Antisense technology also may be used to "knock-out" function of TS10q23.3 in the development of cell lines or transgenic mice for research, diagnostic and screening purposes.

Antisense methodology takes advantage of the fact that nucleic acids tend to pair with "complementary" sequences. By complementary, it is meant that polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense polynucleotides, when introduced into a target cell, specifically bind to their target polynucleotide and interfere with transcription, RNA processing, transport, translation and/or stability. Antisense RNA constructs, or DNA encoding such antisense RNA's, may be employed to inhibit gene transcription or translation or both within a host cell, either in vitro or in vivo, such as within a host animal, including a human subject.

Antisense constructs may be designed to bind to the promoter and other control regions, exons, introns or even exon-intron boundaries of a gene. It is contemplated that the most effective antisense constructs will include regions complementary to intron/exon splice junctions. Thus, it is proposed that a preferred embodiment includes an antisense construct with complementarity to regions within 50–200 bases of an intron-exon splice junction. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

As stated above, "complementary" or "antisense" means polynucleotide sequences that are substantially complementary over their entire length and have very few base mismatches. For example, sequences of fifteen bases in length may be termed complementary when they have complementary nucleotides at thirteen or fourteen positions. Naturally, sequences which are completely complementary will be sequences which are entirely complementary throughout their entire length and have no base mismatches. Other sequences with lower degrees of homology also are contemplated. For example, an antisense construct which has limited regions of high homology, but also contains a non-homologous region (e.g., ribozyme; see below) could be designed. These molecules, though having less than 50% homology, would bind to target sequences under appropriate conditions.

It may be advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence.

D. Ribozymes

Another approach for addressing the "dominant negative" mutant tumor suppressor is through the use of ribozymes. Although proteins traditionally have been used for catalysis of nucleic acids, another class of macromolecules has emerged as useful in this endeavor. Ribozymes are RNA-protein complexes that cleave nucleic acids in a site-specific fashion. Ribozymes have specific catalytic domains that possess endonuclease activity (Kim and Cook, 1987; Gerlach et al., 1987; Forster and Symons, 1987). For example, a large number of ribozymes accelerate phosphoester transfer reactions with a high degree of specificity, often cleaving only one of several phosphoesters in an oligonucleotide substrate (Cook et al., 1981; Michel and Westhof, 1990; Reinhold-Hurek and Shub, 1992). This specificity has been attributed to the requirement that the substrate bind via specific base-pairing interactions to the internal guide sequence ("IGS") of the ribozyme prior to chemical reaction.

Ribozyme catalysis has primarily been observed as part of sequence-specific cleavage/ligation reactions involving nucleic acids (Cook et al., 1981). For example, U.S. Pat. No. 5,354,855 reports that certain ribozymes can act as endonucleases with a sequence specificity greater than that of known ribonucleases and approaching that of the DNA restriction enzymes. Thus, sequence-specific ribozyme-mediated inhibition of gene expression may be particularly suited to therapeutic applications (Scanlon et al., 1991; Sarver et al., 1990). Recently, it was reported that ribozymes elicited genetic changes in some cells lines to which they were applied; the altered genes included the oncogenes H-ras, c-fos and genes of HIV. Most of this work involved the modification of a target mRNA, based on a specific mutant codon that is cleaved by a specific ribozyme.

E. Vectors for Cloning, Gene Transfer and Expression

Within certain embodiments expression vectors are employed to express the TS10q23.3 polypeptide product, which can then be purified and, for example, be used to vaccinate animals to generate antisera or monoclonal antibody with which further studies may be conducted. In other embodiments, the expression vectors are used in gene therapy. Expression requires that appropriate signals be provided in the vectors, and which include various regulatory elements, such as enhancers/promoters from both viral and mammalian sources that drive expression of the genes of interest in host cells. Elements designed to optimize messenger RNA stability and translatability in host cells also are defined. The conditions for the use of a number of dominant drug selection markers for establishing permanent, stable cell clones expressing the products are also provided, as is an element that links expression of the drug selection markers to expression of the polypeptide.

(i) Regulatory Elements

Promoters. Throughout this application, the term "expression construct" is meant to include any type of genetic construct containing a nucleic acid coding for gene products in which part or all of the nucleic acid encoding sequence is capable of being transcribed. The transcript may be translated into a protein, but it need not be. In certain embodiments, expression includes both transcription of a gene and translation of mRNA into a gene product. In other embodiments, expression only includes transcription of the nucleic acid encoding genes of interest.

The nucleic acid encoding a gene product is under transcriptional control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7–20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30–110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

The particular promoter employed to control the expression of a nucleic acid sequence of interest is not believed to be important, so long as it is capable of directing the expression of the nucleic acid in the targeted cell. Thus, where a human cell is targeted, it is preferable to position the nucleic acid coding region adjacent to and under the control of a promoter that is capable of being expressed in a human cell. Generally speaking, such a promoter might include either a human or viral promoter.

In various embodiments, the human *cytomegalovirus* (CMV) immediate early gene promoter, the SV40 early promoter, the Rous sarcoma virus long terminal repeat, β-actin, rat insulin promoter and glyceraldehyde-3-phosphate dehydrogenase can be used to obtain high-level expression of the coding sequence of interest. The use of other viral or mammalian cellular or bacterial phage promoters which are well-known in the art to achieve expression of a coding sequence of interest is contemplated as well, provided that the levels of expression are sufficient for a given purpose. By employing a promoter with well-known properties, the level and pattern of expression of the protein of interest following transfection or transformation can be optimized.

Selection of a promoter that is regulated in response to specific physiologic or synthetic signals can permit inducible expression of the gene product. For example in the case where expression of a transgene, or transgenes when a multicistronic vector is utilized, is toxic to the cells in which the vector is produced in, it may be desirable to prohibit or reduce expression of one or more of the transgenes. Examples of transgenes that may be toxic to the producer cell line are pro-apoptotic and cytokine genes. Several inducible promoter systems are available for production of viral vectors where the transgene product may be toxic.

The ecdysone system (Invitrogen, Carlsbad, Calif.) is one such system. This system is designed to allow regulated expression of a gene of interest in mammalian cells. It consists of a tightly regulated expression mechanism that allows virtually no basal level expression of the transgene, but over 200-fold inducibility. The system is based on the heterodimeric ecdysone receptor of *Drosophila*, and when ecdysone or an analog such as muristerone A binds to the receptor, the receptor activates a promoter to turn on expression of the downstream transgene high levels of mRNA transcripts are attained. In this system, both monomers of the heterodimeric receptor are constitutively expressed from one vector, whereas the ecdysone-responsive promoter which drives expression of the gene of interest is on another plasmid. Engineering of this type of system into the gene transfer vector of interest would therefore be useful. Cotransfection of plasmids containing the gene of interest and the receptor monomers in the producer cell line would then allow for the production of the gene transfer vector without expression of a potentially toxic transgene. At the appropriate time, expression of the transgene could be activated with ecdysone or muristeron A.

Another inducible system that would be useful is the Tet-Off™ or Tet-On™ system (Clontech, Palo Alto, Calif.) originally developed by Gossen and Bujard (Gossen and Bujard, 1992; Gossen et al., 1995). This system also allows high levels of gene expression to be regulated in response to tetracycline or tetracycline derivatives such as doxycycline. In the Tet-On™ system, gene expression is turned on in the presence of doxycycline, whereas in the Tet-Off™ system, gene expression is turned on in the absence of doxycycline. These systems are based on two regulatory elements derived from the tetracycline resistance operon of E. coli. The tetracycline operator sequence to which the tetracycline repressor binds, and the tetracycline repressor protein. The gene of interest is cloned into a plasmid behind a promoter that has tetracycline-responsive elements present in it. A second plasmid contains a regulatory element called the tetracycline-controlled transactivator, which is composed, in the Tet-Off™ system, of the VP16 domain from the herpes simplex virus and the wild-type tertracycline repressor. Thus in the absence of doxycycline, transcription is constitutively on. In the Tet-On™ system, the tetracycline repressor is not wild type and in the presence of doxycycline activates transcription. For gene therapy vector production, the Tet-Off™ system would be preferable so that the producer cells could be grown in the presence of tetracycline or doxycycline and prevent expression of a potentially toxic transgene, but when the vector is introduced to the patient, the gene expression would be constituitively on.

In some circumstances, it may be desirable to regulate expression of a transgene in a gene therapy vector. For example, different viral promoters with varying strengths of activity may be utilized depending on the level of expression desired. In mammalian cells, the CMV immediate early promoter if often used to provide strong transcriptional activation. Modified versions of the CMV promoter that are less potent have also been used when reduced levels of expression of the transgene are desired. When expression of a transgene in hematopoetic cells is desired, retroviral promoters such as the LTRs from MLV or MMTV are often used. Other viral promoters that may be used depending on the desired effect include SV40, RSV LTR, HIV-1 and HIV-2 LTR, adenovirus promoters such as from the E1A, E2A, or MLP region, AAV LTR, cauliflower mosaic virus, HSV-TK, and avian sarcoma virus.

Similarly tissue specific promoters may be used to effect transcription in specific tissues or cells so as to reduce potential toxicity or undesirable effects to non-targeted tissues. For example, promoters such as the PSA, probasin, prostatic acid phosphatase or prostate-specific glandular kallikrein (hK2) may be used to target gene expression in the prostate. Similarly, the following promoters may be used to target gene expression in other tissues (Table 2).

TABLE 2

Tissue specific promoters

| Tissue | Promoter |
| --- | --- |
| Pancreas | insulin |
|  | elastin |
|  | amylase |
|  | pdr-1 pdx-1 |
|  | glucokinase |
| Liver | albumin PEPCK |
|  | HBV enhancer |
|  | alpha fetoprotein |
|  | apolipoprotein C |
|  | alpha-1 antitrypsin |

TABLE 2-continued

Tissue specific promoters

| Tissue | Promoter |
| --- | --- |
|  | vitellogenin, NF-AB |
|  | Transthyretin |
| Skeletal muscle | myosin H chain |
|  | muscle creatine kinase |
|  | dystrophin |
|  | calpain p94 |
|  | skeletal alpha-actin |
|  | fast troponin 1 |
| Skin | keratin K6 |
|  | keratin K1 |
| Lung | CFTR |
|  | human cytokeratin 18 (K18) |
|  | pulmonary surfactant proteins A, B and C |
|  | CC-10 |
|  | P1 |
| Smooth muscle | sm22 alpha |
|  | SM-alpha-actin |
| Endothelium | endothelin-1 |
|  | E-selectin |
|  | von Willebrand factor |
|  | TIE (Korhonen et al., 1995) |
|  | KDR/flk-1 |
| Melanocytes | tyrosinase |
| Adipose tissue | lipoprotein lipase (Zechner et al., 1988) |
|  | adipsin (Spiegelman et al., 1989) |
|  | acetyl-CoA carboxylase (Pape and Kim, 1989) |
|  | glycerophosphate dehydrogenase (Dani et al., 1989) |
|  | adipocyte P2 (Hunt et al., 1986) |
| Blood | β-globin |

In certain indications, it may be desirable to activate transcription at specific times after administration of the gene therapy vector. This may be done with such promoters as those that are hormone or cytokine regulatable. For example in gene therapy applications where the indication is a gonadal tissue where specific steroids are produced or routed to, use of androgen or estrogen regulated promoters may be advantageous. Such promoters that are hormone regulatable include MMTV, MT-1, ecdysone and RuBisco. Other hormone regulated promoters such as those responsive to thyroid, pituitary and adrenal hormones are expected to be useful in the present invention. Cytokine and inflammatory protein responsive promoters that could be used include K and T Kininogen (Kageyama et al., 1987), c-fos, TNF-alpha, C-reactive protein (Arcone et al., 1988), haptoglobin (Oliviero et al., 1987), serum amyloid A2, C/EBP alpha, IL-1, IL-6 (Poli and Cortese, 1989), Complement C3 (Wilson et al., 1990), IL-8, alpha-1 acid glycoprotein (Prowse and Baumann, 1988), alpha-1 antitypsin, lipoprotein lipase (Zechner et al., 1988), angiotensinogen (Ron et al., 1991), fibrinogen, c-jun (inducible by phorbol esters, TNF-alpha, UV radiation, retinoic acid, and hydrogen peroxide), collagenase (induced by phorbol esters and retinoic acid), metallothionein (heavy metal and glucocorticoid inducible), Stromelysin (inducible by phorbol ester, interleukin-1 and EGF), alpha-2 macroglobulin and alpha-1 antichymotrypsin.

It is envisioned that cell cycle regulatable promoters may be useful in the present invention. For example, in a bi-cistronic gene therapy vector, use of a strong CMV promoter to drive expression of a first gene such as p16 that arrests cells in the G1 phase could be followed by expression of a second gene such as p53 under the control of a promoter that is active in the G1 phase of the cell cycle, thus providing a "second hit" that would push the cell into apoptosis. Other promoters such as those of various cyclins, PCNA, galectin-3, E2F1, p53 and BRCA1 could be used.

Tumor specific promoters such as osteocalcin, hypoxia-responsive element (HRE), MAGE-4, CEA, alpha-fetoprotein, GRP78/BiP and tyrosinase may also be used to regulate gene expression in tumor cells. Other promoters that could be used according to the present invention include Lac-regulatable, chemotherapy inducible (e.g. MDR), and heat (hyperthermia) inducible promoters, radiation-inducible (e.g., EGR (Joki et al., 1995)), Alpha-inhibin, RNA pol III tRNA met and other amino acid promoters, U1 snRNA (Bartlett et al., 1996), MC-1, PGK, β-actin and α-globin. Many other promoters that may be useful are listed in Walther and Stein (1996).

It is envisioned that any of the above promoters alone or in combination with another may be useful according to the present invention depending on the action desired. In addition, this list of promoters is should not be construed to be exhaustive or limiting, those of skill in the art will know of other promoters that may be used in conjunction with the promoters and methods disclosed herein.

Enhancers. Enhancers are genetic elements that increase transcription from a promoter located at a distant position on the same molecule of DNA. Enhancers are organized much like promoters. That is, they are composed of many individual elements, each of which binds to one or more transcriptional proteins. The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Below is a list of promoters additional to the tissue specific promoters listed above, cellular promoters/enhancers and inducible promoters/enhancers that could be used in combination with the nucleic acid encoding a gene of interest in an expression construct (Table 3 and Table 4). Additionally, any promoter/enhancer combination (as per the Eukaryotic Promoter Data Base EPDB) could also be used to drive expression of the gene. Eukaryotic cells can support cytoplasmic transcription from certain bacterial promoters if the appropriate bacterial polymerase is provided, either as part of the delivery complex or as an additional genetic expression construct.

TABLE 3

ENHANCER/PROMOTER

Immunoglobulin Heavy Chain
Immunoglobulin Light Chain
T-Cell Receptor
HLA DQ α and DQ β
β-Interferon
Interleukin-2
Interleukin-2 Receptor
MHC Class II 5
MHC Class II HLA-DRα
β-Actin
Muscle Creatine Kinase
Prealbumin (Transthyretin)
Elastase I
Metallothionein
Collagenase
Albumin Gene
α-Fetoprotein TABLE 3-continued

ENHANCER/PROMOTER

τ-Globin
β-Globin
e-fos
c-HA-ras
Insulin
Neural Cell Adhesion Molecule (NCAM)
α1-Antitrypsin
H2B (TH2B) Histone
Mouse or Type I Collagen
Glucose-Regulated Proteins (GRP94 and GRP78)
Rat Growth Hormone
Human Serum Amyloid A (SAA)
Troponin I (TN I)
Platelet-Derived Growth Factor
Duchenne Muscular Dystrophy
SV40
Polyoma
Retroviruses
Papilloma Virus
Hepatitis B Virus
Human Immunodeficiency Virus
Cytomegalovirus
Gibbon Ape Leukemia Virus

TABLE 4

| Element | Inducer |
| --- | --- |
| MT II | Phorbol Ester (TPA) |
| | Heavy metals |
| MMTV (mouse mammary tumor virus) | Glucocorticoids |
| β-Interferon | poly(rI)X |
| | poly(rc) |
| Adenovirus 5 E2 | Ela |
| c-jun | Phorbol Ester (TPA), $H_2O_2$ |
| Collagenase | Phorbol Ester (TPA) |
| Stromelysin | Phorbol Ester (TPA), IL-1 |
| SV40 | Phorbol Ester (TPA) |
| Murine MX Gene | Interferon, Newcastle Disease Virus |
| GRP78 Gene | A23187 |
| α-2-Macroglobulin | IL-6 |
| Vimentin | Serum |
| MHC Class I Gene H-2 kB | Interferon |
| HSP70 | Ela, SV40 Large T Antigen |
| Proliferin | Phorbol Ester-TPA |
| Tumor Necrosis Factor | FMA |
| Thyroid Stimulating Hormone α Gene | Thyroid Hormone |
| Insulin E Box | Glucose |

Polyadenylation Signals. Where a cDNA insert is employed, one will typically desire to include a polyadenylation signal to effect proper polyadenylation of the gene transcript. The nature of the polyadenylation signal is not believed to be crucial to the successful practice of the invention, and any such sequence may be employed such as human or bovine growth hormone and SV40 polyadenylation signals. Also contemplated as an element of the expression cassette is a terminator. These elements can serve to enhance message levels and to minimize read through from the cassette into other sequences.

IRES. In certain embodiments of the invention, the use of internal ribosome entry site (IRES) elements is contemplated to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (*poliovirus* and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message.

Any heterologous open reading frame can be linked to IRES elements. This includes genes for secreted proteins, multi-subunit proteins, encoded by independent genes, intracellular or membrane-bound proteins and selectable markers. In this way, expression of several proteins can be simultaneously engineered into a cell with a single construct and a single selectable marker.

(ii) Selectable Markers

In certain embodiments of the invention, the cells contain nucleic acid constructs of the present invention, a cell may be identified in vitro or in vivo by including a marker in the expression construct. Such markers would confer an identifiable change to the cell permitting easy identification of cells containing the expression construct. Usually the inclusion of a drug selection marker aids in cloning and in the selection of transformants, for example, genes that confer resistance to neomycin, puromycin, hygromycin, DHFR, GPT, zeocin and histidinol are useful selectable markers. Alternatively, enzymes such as herpes simplex virus thymidine kinase (tk) or chloramphenicol acetyltransferase (CAT) may be employed. Immunologic markers also can be employed. The selectable marker employed is not believed to be important, so long as it is capable of being expressed simultaneously with the nucleic acid encoding a gene product. Further examples of selectable markers are well known to one of skill in the art.

(iii) Delivery of Expression Vectors

There are a number of ways in which expression vectors may introduced into cells. In certain embodiments of the invention, the expression construct comprises a virus or engineered construct derived from a viral genome. The ability of certain viruses to enter cells via receptor-mediated endocytosis, to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as gene vectors were DNA viruses including the papovaviruses (simian virus 40, bovine papilloma virus, and polyoma) (Ridgeway, 1988; Baichwal and Sugden, 1986) and adenoviruses (Ridgeway, 1988; Baichwal and Sugden, 1986). These have a relatively low capacity for foreign DNA sequences and have a restricted host spectrum. Furthermore, their oncogenic potential and cytopathic effects in permissive cells raise safety concerns. They can accommodate only up to 8 kb of foreign genetic material but can be readily introduced in a variety of cell lines and laboratory animals (Nicolas and Rubenstein, 1988; Temin, 1986). The vector may be capable of replicating inside the cells. Alternatively, the vector may be replication deficient and is replicated in helper cells prior to delivery. Suitable vectors are known, such as disclosed in U.S. Pat. No. 5,252,479 and PCT published application WO 93/07282 and U.S. Pat. Nos. 5,691,198; 5,747,469; 5,436,146 and 5,753,500.

Adenoviruses. One of the preferred methods for in vivo delivery involves the use of an adenovirus expression vector. "Adenovirus expression vector" is meant to include those constructs containing adenovirus sequences sufficient to (a) support packaging of the construct and (b) to express an antisense polynucleotide that has been cloned therein. In this context, expression does not require that the gene product be synthesized.

The expression vector comprises a genetically engineered form of adenovirus. Knowledge of the genetic organization of *adenovirus*, a 36 kb, linear, double-stranded DNA virus, allows substitution of large pieces of adenoviral DNA with foreign sequences up to 7 kb (Grunhaus and Horwitz, 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage. So far, adenoviral infection appears to be linked only to mild disease such as acute respiratory disease in humans.

Adenovirus is particularly suitable for use as a gene transfer vector because of its mid-sized genome, ease of manipulation, high titer, wide target cell range and high infectivity. Both ends of the viral genome contain 100–200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Renan, 1990). The products of the late genes, including the majority of the viral capsid proteins, are expressed only after significant processing of a single primary transcript issued by the major late promoter (MLP). The MLP, (located at 16.8 m.u.) is particularly efficient during the late phase of infection, and all the mRNA's issued from this promoter possess a 5'-tripartite leader (TPL) sequence which makes them preferred mRNA's for translation.

In a current system, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure.

Generation and propagation of the current adenovirus vectors, which are replication deficient, depend on a unique helper cell line, designated 293, which was transformed from human embryonic kidney cells by Ad5 DNA fragments and constitutively expresses E1 proteins (Graham et al., 1977). Since the E3 region is dispensable from the adenovirus genome (Jones and Shenk, 1978), the current adenovirus vectors, with the help of 293 cells, carry foreign DNA in either the E1, the D3 or both regions (Graham and Prevec, 1991). In nature, adenovirus can package approximately 105% of the wild-type genome (Ghosh-Choudhury et al., 1987), providing capacity for about 2 extra kb of DNA. Combined with the approximately 5.5 kb of DNA that is replaceable in the E1 and E3 regions, the maximum capacity of the current adenovirus vector is under 7.5 kb, or about 15% of the total length of the vector. More than 80% of the adenovirus viral genome remains in the vector backbone and is the source of vector-borne cytotoxicity. Also, the replication deficiency of the E1-deleted virus is incomplete. For example, leakage of viral gene expression has been observed with the currently available vectors at high multiplicities of infection (MOI) (Mulligan, 1993).

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human *adenovirus*. Such cells include, e.g., Vero cells or other monkey embryonic mesenchymal or epithelial cells. As stated above, the preferred helper cell line is 293.

Recently, Racher et al., (1995) disclosed improved methods for culturing 293 cells and propagating *adenovirus*. In one format, natural cell aggregates are grown by inoculating individual cells into 1 liter siliconized spinner flasks (Techne, Cambridge, UK) containing 100–200 ml of medium. Following stirring at 40 rpm, the cell viability is estimated with trypan blue. In another format, Fibra-Cel microcarriers (Bibby Sterlin, Stone, UK) (5 g/l) is employed as follows. A cell inoculum, resuspended in 5 ml of medium, is added to the carrier (50 ml) in a 250 ml Erlenmeyer flask and left stationary, with occasional agitation, for 1 to 4 h. The medium is then replaced with 50 ml of fresh medium and shaking initiated. For virus production, cells are allowed to grow to about 80% confluence, after which time the medium is replaced (to 25% of the final volume) and adenovirus added at an MOI of 0.05. Cultures are left stationary overnight, following which the volume is increased to 100% and shaking commenced for another 72 h.

Other than the requirement that the adenovirus vector be replication defective, or at least conditionally defective, the nature of the adenovirus vector is not believed to be crucial to the successful practice of the invention. The adenovirus may be of any of the 42 different known serotypes or subgroups A–F. Adenovirus type 5 of subgroup C is the preferred starting material in order to obtain the conditional replication-defective adenovirus vector for use in the present invention. This is because Adenovirus type 5 is a human adenovirus about which a great deal of biochemical and genetic information is known, and it has historically been used for most constructions employing adenovirus as a vector.

As stated above, the typical vector according to the present invention is replication defective and will not have an adenovirus E1 region. Thus, it will be most convenient to introduce the polynucleotide encoding the gene of interest at the position from which the E1-coding sequences have been removed. However, the position of insertion of the construct within the adenovirus sequences is not critical to the invention. The polynucleotide encoding the gene of interest may also be inserted in lieu of the deleted E3 region in E3 replacement vectors as described by Karlsson et al., (1986) or in the E4 region where a helper cell line or helper virus complements the E4 defect.

Adenovirus is easy to grow and manipulate and exhibits broad host range in vitro and in vivo. This group of viruses can be obtained in high titers, e.g., $10^9$–$10^{11}$ plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors.

Adenovirus vectors have been used in eukaryotic gene expression (Levrero et al., 1991; Gomez-Foix et al., 1992) and vaccine development (Grunhaus and Horwitz, 1992; Graham and Prevec, 1991). Recently, animal studies suggested that recombinant adenovirus could be used for gene therapy (Stratford-Perricaudet and Perricaudet, 1991; Stratford-Perricaudet et al., 1990; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and stereotactic inoculation into the brain (Le Gal La Salle et al., 1993).

Retroviruses. The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding a gene of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

A novel approach designed to allow specific targeting of retrovirus vectors was recently developed based on the chemical modification of a retrovirus by the chemical addition of lactose residues to the viral envelope. This modification could permit the specific infection of hepatocytes via sialoglycoprotein receptors.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

There are certain limitations to the use of retrovirus vectors in all aspects of the present invention. For example, retrovirus vectors usually integrate into random sites in the cell genome. This can lead to insertional mutagenesis through the interruption of host genes or through the insertion of viral regulatory sequences that can interfere with the function of flanking genes (Varmus et al., 1981). Another concern with the use of defective retrovirus vectors is the potential appearance of wild-type replication-competent virus in the packaging cells. This can result from recombination events in which the intact-sequence from the recombinant virus inserts upstream from the gag, pol, env sequence integrated in the host cell genome. However, new packaging cell lines are now available that should greatly decrease the likelihood of recombination (Markowitz et al., 1988; Hersdorffer et al., 1990).

Herpesvirus. Because herpes simplex virus (HSV) is neurotropic, it has generated considerable interest in treating nervous system disorders. Moreover, the ability of HSV to establish latent infections in non-dividing neuronal cells without integrating in to the host cell chromosome or otherwise altering the host cell's metabolism, along with the existence of a promoter that is active during latency makes HSV an attractive vector. And though much attention has focused on the neurotropic applications of HSV, this vector also can be exploited for other tissues given its wide host range.

Another factor that makes HSV an attractive vector is the size and organization of the genome. Because HSV is large, incorporation of multiple genes or expression cassettes is less problematic than in other smaller viral systems. In addition, the availability of different viral control sequences with varying performance (temporal, strength, etc.) makes it possible to control expression to a greater extent than in other systems. It also is an advantage that the virus has relatively few spliced messages, further easing genetic manipulations.

HSV also is relatively easy to manipulate and can be grown to high titers. Thus, delivery is less of a problem, both in terms of volumes needed to attain sufficient MOI and in a lessened need for repeat dosings. For a review of HSV as a gene therapy vector, see Glorioso et al. (1995).

HSV, designated with subtypes 1 and 2, are enveloped viruses that are among the most common infectious agents encountered by humans, infecting millions of human subjects worldwide. The large, complex, double-stranded DNA genome encodes for dozens of different gene products, some of which derive from spliced transcripts. In addition to virion and envelope structural components, the virus encodes numerous other proteins including a protease, a ribonucleotides reductase, a DNA polymerase, a ssDNA binding protein, a helicase/primase, a DNA dependent ATPase, a dUTPase and others.

HSV genes form several groups whose expression is coordinately regulated and sequentially ordered in a cascade fashion (Honess and Roizman, 1974; Honess and Roizman 1975; Roizman and Sears, 1995). The expression of α genes, the first set of genes to be expressed after infection, is enhanced by the virion protein number 16, or α-transducing factor (Post et al., 1981; Batterson and Roizman, 1983; Campbell et al., 1983). The expression of β genes requires functional α gene products, most notably ICP4, which is encoded by the α4 gene (DeLuca et al., 1985). γ genes, a heterogeneous group of genes encoding largely virion structural proteins, require the onset of viral DNA synthesis for optimal expression (Holland et al., 1980).

In line with the complexity of the genome, the life cycle of HSV is quite involved. In addition to the lytic cycle, which results in synthesis of virus particles and, eventually, cell death, the virus has the capability to enter a latent state in which the genome is maintained in neural ganglia until some as of yet undefined signal triggers a recurrence of the lytic cycle. Avirulent variants of HSV have been developed and are readily available for use in gene therapy contexts (U.S. Pat. No. 5,672,344).

Adeno-Associated Virus. Recently, adeno-associated virus (AAV) has emerged as a potential alternative to the more commonly used retroviral and adenoviral vectors. While studies with retroviral and adenoviral mediated gene transfer raise concerns over potential oncogenic properties of the former, and immunogenic problems associated with the latter, AAV has not been associated with any such pathological indications.

In addition, AAV possesses several unique features that make it more desirable than the other vectors. Unlike retroviruses, AAV can infect non-dividing cells; wild-type AAV has been characterized by integration, in a site-specific manner, into chromosome 19 of human cells (Kotin and Berns, 1989; Kotin et al., 1990; Kotin et al., 1991; Samulski et al., 1991); and AAV also possesses anti-oncogenic properties (Ostrove et al., 1981; Berns and Giraud, 1996). Recombinant AAV genomes are constructed by molecularly cloning DNA sequences of interest between the AAV ITRs, eliminating the entire coding sequences of the wild-type AAV genome. The AAV vectors thus produced lack any of the coding sequences of wild-type AAV, yet retain the property of stable chromosomal integration and expression of the recombinant genes upon transduction both in vitro and in vivo (Berns, 1990; Berns and Bohensky, 1987; Bertran et al., 1996; Kearns et al., 1996; Ponnazhagan et al., 1997a). Until recently, AAV was believed to infect almost all cell types, and even cross species barriers. However, it now has been determined that AAV infection is receptor-mediated (Ponnazhagan et al., 1996; Mizukami et al., 1996).

AAV utilizes a linear, single-stranded DNA of about 4700 base pairs. Inverted terminal repeats flank the genome. Two genes are present within the genome, giving rise to a number of distinct gene products. The first, the cap gene, produces three different virion proteins (VP), designated VP-1, VP-2 and VP-3. The second, the rep gene, encodes four non-structural proteins (NS). One or more of these rep gene products is responsible for transactivating AAV transcription. The sequence of AAV is provided by Srivastava et al. (1983), and in U.S. Pat. No. 5,252,479 (entire text of which is specifically incorporated herein by reference).

The three promoters in AAV are designated by their location, in map units, in the genome. These are, from left to right, p5, p19 and p40. Transcription gives rise to six transcripts, two initiated at each of three promoters, with one of each pair being spliced. The splice site, derived from map units 42–46, is the same for each transcript. The four non-structural proteins apparently are derived from the longer of the transcripts, and three virion proteins all arise from the smallest transcript.

AAV is not associated with any pathologic state in humans. Interestingly, for efficient replication, AAV requires "helping" functions from viruses such as herpes simplex virus I and II, cytomegalovirus, pseudorabies virus and, of course, adenovirus. The best characterized of the helpers is adenovirus, and many "early" functions for this virus have been shown to assist with AAV replication. Low level expression of AAV rep proteins is believed to hold AAV structural expression in check, and helper virus infection is thought to remove this block.

Vaccinia Virus. Vaccinia virus vectors have been used extensively because of the ease of their construction, relatively high levels of expression obtained, wide host range and large capacity for carrying DNA. Vaccinia contains a linear, double-stranded DNA genome of about 186 kb that exhibits a marked "A–T" preference. Inverted terminal repeats of about 10.5 kb flank the genome. The majority of essential genes appear to map within the central region, which is most highly conserved among poxviruses. Estimated open reading frames in vaccinia virus number from 150 to 200. Although both strands are coding, extensive overlap of reading frames is not common.

At least 25 kb can be inserted into the vaccinia virus genome (Smith and Moss, 1983). Prototypical vaccinia vectors contain transgenes inserted into the viral thymidine kinase gene via homologous recombination. Vectors are selected on the basis of a tk-phenotype. Inclusion of the untranslated leader sequence of encephalomyocarditis virus, the level of expression is higher than that of conventional vectors, with the transgenes accumulating at 10% or more of the infected cell's protein in 24 h (Elroy-Stein et al., 1989).

Non-Viral transfer. In order to effect expression of sense or antisense gene constructs, the expression construct must be delivered into a cell. This delivery may be accomplished in vitro, as in laboratory procedures for transforming cells lines, or in vivo or ex vivo, as in the treatment of certain disease states. One mechanism for delivery is via viral infection where the expression construct is encapsidated in an infectious viral particle.

Several non-viral methods for the transfer of expression constructs into cultured mammalian cells also are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979) and lipofectamine-DNA complexes, cell sonication (Fechheimer et al., 1987), gene bombardment using high velocity microprojectiles (Yang et al., 1990), and receptor-mediated transfection (Wu and Wu, 1987; Wu and Wu, 1988). Some of these techniques may be successfully adapted for in vivo or ex vivo use.

Once the expression construct has been delivered into the cell the nucleic acid encoding the gene of interest may be positioned and expressed at different sites. In certain embodiments, the nucleic acid encoding the gene may be stably integrated into the genome of the cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In yet another embodiment of the invention, the expression construct may simply consist of naked recombinant DNA or plasmids. Transfer of the construct may be performed by any of the methods mentioned above which physically or chemically permeabilize the cell membrane. This is particularly applicable for transfer in vitro but it may be applied to in vivo use as well. Dubensky et al. (1984) successfully injected polyomavirus DNA in the form of calcium phosphate precipitates into liver and spleen of adult and newborn mice demonstrating active viral replication and acute infection. Benvenisty and Neshif (1986) also demonstrated that direct intraperitoneal injection of calcium phosphate-precipitated plasmids results in expression of the transfected genes. It is envisioned that DNA encoding a gene of interest may also be transferred in a similar manner in vivo and express the gene product.

In still another embodiment of the invention for transferring a naked DNA expression construct into cells may involve particle bombardment. This method depends on the ability to accelerate DNA-coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

Selected organs including the liver, skin, and muscle tissue of rats and mice have been bombarded in vivo (Yang et al., 1990; Zelenin et al., 1991). This may require surgical exposure of the tissue or cells, to eliminate any intervening tissue between the gun and the target organ, i.e., ex vivo treatment. Again, DNA encoding a particular gene may be delivered via this method and still be incorporated by the present invention.

In a further embodiment of the invention, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated are lipofectamine-DNA complexes.

Liposome-mediated nucleic acid delivery and expression of foreign DNA in vitro has been very successful. Wong et al., (1980) demonstrated the feasibility of liposome-mediated delivery and expression of foreign DNA in cultured chick embryo, HeLa and hepatoma cells. Nicolau et al., (1987) accomplished successful liposome-mediated gene transfer in rats after intravenous injection.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention. Where a bacterial promoter is employed in the DNA construct, it also will be desirable to include within the liposome an appropriate bacterial polymerase.

Other expression constructs which can be employed to deliver a nucleic acid encoding a particular gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1990). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EPO 0273085).

In other embodiments, the delivery vehicle may comprise a ligand and a liposome. For example, Nicolau et al., (1987) employed lactosyl-ceramide, a galactose-terminal asialganglioside, incorporated into liposomes and observed an increase in the uptake of the insulin gene by hepatocytes. Thus, it is feasible that a nucleic acid encoding a particular gene also may be specifically delivered into a cell type such as lung, epithelial or tumor cells, by any number of receptor-ligand systems with or without liposomes. For example, epidermal growth factor (EGF) may be used as the receptor for mediated delivery of a nucleic acid encoding a gene in many tumor cells that exhibit upregulation of EGF receptor. Mannose can be used to target the mannose receptor on liver cells. Also, antibodies to CD5 (CLL), CD22 (lymphoma), CD25 (T-cell leukemia) and MAA (melanoma) can similarly be used as targeting moieties.

In certain embodiments, gene transfer may more easily be performed under ex vivo conditions. Ex vivo gene therapy refers to the isolation of cells from an animal, the delivery of a nucleic acid into the cells in vitro, and then the return of the modified cells back into an animal. This may involve the surgical removal of tissue/organs from an animal or the primary culture of cells and tissues.

Primary mammalian cell cultures may be prepared in various ways. In order for the cells to be kept viable while in vitro and in contact with the expression construct, it is necessary to ensure that the cells maintain contact with the correct ratio of oxygen and carbon dioxide and nutrients but are protected from microbial contamination. Cell culture techniques are well documented and are disclosed herein by reference (Freshner, 1992).

One embodiment of the foregoing involves the use of gene transfer to immortalize cells for the production of proteins. The gene for the protein of interest may be transferred as described above into appropriate host cells followed by culture of cells under the appropriate conditions. The gene for virtually any polypeptide may be employed in this manner. The generation of recombinant expression vectors, and the elements included therein, are discussed above. Alternatively, the protein to be produced may be an endogenous protein normally synthesized by the cell in question.

Examples of useful mammalian host cell lines are Vero and HeLa cells and cell lines of Chinese hamster ovary, W138, BHK, COS-7, 293, HepG2, NIH3T3, RIN and MDCK cells. In addition, a host cell strain may be chosen that modulates the expression of the inserted sequences, or modifies and process the gene product in the manner desired. Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to insure the correct modification and processing of the foreign protein expressed.

A number of selection systems may be used including, but not limited to, HSV thymidine kinase, hypoxanthine-guanine phosphoribosyltransferase and adenine phosphoribosyltransferase genes, in tk-, hgprt- or aprt-cells, respectively. Also, anti-metabolite resistance can be used as the basis of selection for dhfr, that confers resistance to; gpt, that confers resistance to mycophenolic acid; neo, that confers resistance to the aminoglycoside G418; and hygro, that confers resistance to hygromycin.

Animal cells can be propagated in vitro in two modes: as non-anchorage dependent cells growing in suspension throughout the bulk of the culture or as anchorage-dependent cells requiring attachment to a solid substrate for their propagation (i.e., a monolayer type of cell growth).

Non-anchorage dependent or suspension cultures from continuous established cell lines are the most widely used means of large scale production of cells and cell products. However, suspension cultured cells have limitations, such as tumorigenic potential and lower protein production than adherent T-cells.

Large scale suspension culture of mammalian cells in stirred tanks is a common method for production of recombinant proteins. Two suspension culture reactor designs are in wide use—the stirred reactor and the airlift reactor. The stirred design has successfully been used on an 8000 liter capacity for the production of interferon. Cells are grown in a stainless steel tank with a height-to-diameter ratio of 1:1 to 3:1. The culture is usually mixed with one or more agitators, based on bladed disks or marine propeller patterns. Agitator systems offering less shear forces than blades have been described. Agitation may be driven either directly or indirectly by magnetically coupled drives. Indirect drives reduce the risk of microbial contamination through seals on stirrer shafts.

The airlift reactor, also initially described for microbial fermentation and later adapted for mammalian culture, relies on a gas stream to both mix and oxygenate the culture. The gas stream enters a riser section of the reactor and drives circulation. Gas disengages at the culture surface, causing denser liquid free of gas bubbles to travel downward in the downcomer section of the reactor. The main advantage of this design is the simplicity and lack of need for mechanical mixing. Typically, the height-to-diameter ratio is 10:1. The airlift reactor scales up relatively easily, has good mass transfer of gases and generates relatively low shear forces.

The antibodies of the present invention are particularly useful for the isolation of antigens by immunoprecipitation. Immunoprecipitation involves the separation of the target antigen component from a complex mixture, and is used to discriminate or isolate minute amounts of protein. For the isolation of membrane proteins cells must be solubilized into detergent micelles. Nonionic salts are preferred, since other agents such as bile salts, precipitate at acid pH or in the presence of bivalent cations. Antibodies are and their uses are discussed further, below.

III. Generating Antibodies Reactive with TS10q23.3

In another aspect, the present invention contemplates an antibody that is immunoreactive with a TS10q23.3 molecule of the present invention, or any portion thereof. An antibody can be a polyclonal or a monoclonal antibody. In a preferred embodiment, an antibody is a monoclonal antibody. Means for preparing and characterizing antibodies are well known in the art (see, e.g., Howell and Lane, 1988).

Briefly, a polyclonal antibody is prepared by immunizing an animal with an immunogen comprising a polypeptide of the present invention and collecting antisera from that immunized animal. A wide range of animal species can be used for the production of antisera. Typically an animal used for production of anti-antisera is a non-human animal including rabbits, mice, rats, hamsters, pigs or horses. Because of the relatively large blood volume of rabbits, a rabbit is a preferred choice for production of polyclonal antibodies.

Antibodies, both polyclonal and monoclonal, specific for isoforms of antigen may be prepared using conventional immunization techniques, as will be generally known to those of skill in the art. A composition containing antigenic epitopes of the compounds of the present invention can be used to immunize one or more experimental animals, such as a rabbit or mouse, which will then proceed to produce specific antibodies against the compounds of the present invention. Polyclonal antisera may be obtained, after allowing time for antibody generation, simply by bleeding the animal and preparing serum samples from the whole blood.

It is proposed that the monoclonal antibodies of the present invention will find useful application in standard immunochemical procedures, such as ELISA and Western blot methods and in immunohistochemical procedures such as tissue staining, as well as in other procedures which may utilize antibodies specific to TS10q23.3-related antigen epitopes. Additionally, it is proposed that monoclonal antibodies specific to the particular TS10q23.3 of different species may be utilized in other useful applications.

In general, both polyclonal and monoclonal antibodies against TS10q23.3 may be used in a variety of embodiments. For example, they may be employed in antibody cloning protocols to obtain cDNAs or genes encoding other TS10q23.3. They may also be used in inhibition studies to analyze the effects of TS10q23.3 related peptides in cells or animals. Anti-TS10q23.3 antibodies will also be useful in immunolocalization studies to analyze the distribution of TS10q23.3 during various cellular events, for example, to determine the cellular or tissue-specific distribution of TS10q23.3 polypeptides under different points in the cell cycle. A particularly useful application of such antibodies is in purifying native or recombinant TS10q23.3, for example, using an antibody affinity column. The operation of all such immunological techniques will be known to those of skill in the art in light of the present disclosure.

Means for preparing and characterizing antibodies are well known in the art (see, e.g., Harlow and Lane, 1988; incorporated herein by reference). More specific examples of monoclonal antibody preparation are give in the examples below.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimide and bis-biazotized benzidine.

As also is well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster, injection may also be given. The process of boosting and titering is repeated until a suitable titer is achieved. When a desired level of immunogenicity is obtained, the immunized animal can be bled and the serum isolated and stored, and/or the animal can be used to generate mAbs.

MAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified TS10q23.3 protein, polypeptide or peptide or cell expressing high levels of TS10q23.3. The immunizing composition is administered in a manner effective to stimulate antibody producing cells. Rodents such as mice and rats are preferred animals, however, the use of rabbit, sheep frog cells is also possible. The use of rats may provide certain advantages (Goding, 1986), but mice are preferred, with the BALB/c mouse being most preferred as this is most routinely used and generally gives a higher percentage of stable fusions.

Following immunization, somatic cells with the potential for producing antibodies, specifically B-lymphocytes (B-cells), are selected for use in the mAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, 1986). For example, where the immunized animal is a mouse, one may use P3-X63/Ag8, P3-X63-Ag8.653, NS1/1.Ag 4 1, Sp210-Ag14, FO, NSO/U, MPC-11, MPC11-X45-GTG 1.7 and S194/5XX0 Bu1; for rats, one may use R210.RCY3, Y3-Ag 1.2.3, IR983F and 4B210; and U-266, GM1500-GRG2, LICR-LON-HMy2 and UC729–6 are all useful in connection with cell fusions.

Methods for generating hybrids of antibody-producing spleen or lymph node cells and myeloma cells usually comprise mixing somatic cells with myeloma cells in a 2:1 ratio, though the ratio may vary from about 20:1 to about 1:1, respectively, in the presence of an agent or agents (chemical or electrical) that promote the fusion of cell membranes. Fusion methods using Sendai virus have been described (Kohler and Milstein, 1975; 1976), and those using polyethylene glycol (PEG), such as 37% (v/v) PEG, by Gefter et al., (1977). The use of electrically induced fusion methods is also appropriate (Goding, 1986).

Fusion procedures usually produce viable hybrids at low frequencies, around $1\times10^{-6}$ to $1\times10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B-cells can operate this pathway, but they have a limited life span in culture and generally die within about two weeks. Therefore, the only cells that can survive in the selective media are those hybrids formed from myeloma and B-cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide mAbs. The cell lines may be exploited for mAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide mAbs in high concentration. The individual cell lines could also be cultured in vitro, where the mAbs are naturally secreted into the culture medium from which they can be readily obtained in high concentrations. mAbs produced by either means may be further purified, if desired, using filtration, centrifugation and various chromatographic methods such as HPLC or affinity chromatography.

The individual cell lines could also be cultured in vitro, where the MAbs are naturally secreted into the culture medium from which they can be readily obtained in high concentrations.

MAbs produced by either means may be further purified, if desired, using filtration, centrifugation and various chromatographic methods such as HPLC or affinity chromatography. Fragments of the monoclonal antibodies of the invention can be obtained from the purified monoclonal antibodies by methods which include digestion with enzymes, such as pepsin or papain, and/or by cleavage of disulfide bonds by chemical reduction. Alternatively, monoclonal antibody fragments encompassed by the present invention can be synthesized using an automated peptide synthesizer.

It also is contemplated that a molecular cloning approach may be used to generate monoclonals. For this, combinatorial immunoglobulin phagemid libraries are prepared from RNA isolated from the spleen of the immunized animal, and phagemids expressing appropriate antibodies are selected by panning using cells expressing the antigen and control cells e.g., normal-versus-tumor cells. The advantages of this approach over conventional hybridoma techniques are that approximately $10^4$ times as many antibodies can be produced and screened in a single round, and that new specificities are generated by H and L chain combination which further increases the chance of finding appropriate antibodies.

Humanized monoclonal antibodies are antibodies of animal origin that have been modified using genetic engineering techniques to replace constant region and/or variable region framework sequences with human sequences, while retaining the original antigen specificity. Such antibodies are commonly derived from rodent antibodies with specificity against human antigens. such antibodies are generally useful for in vivo therapeutic applications. This strategy reduces the host response to the foreign antibody and allows selection of the human effector functions.

The techniques for producing humanized immunoglobulins are well known to those of skill in the art. For example U.S. Pat. No. 5,693,762 discloses methods for producing, and compositions of, humanized immunoglobulins having one or more complementarity determining regions (CDR's). When combined into an intact antibody, the humanized immunoglobulins are substantially non-immunogenic in humans and retain substantially the same affinity as the donor immunoglobulin to the antigen, such as a protein or other compound containing an epitope.

Other U.S. patents, each incorporated herein by reference, that teach the production of antibodies useful in the present invention include U.S. Pat. No. 5,565,332, which describes the production of chimeric antibodies using a combinatorial approach; U.S. Pat. No. 4,816,567 which describes recombinant immunoglobin preparations and U.S. Pat. No. 4,867,973 which describes antibody-therapeutic agent conjugates.

U.S. Pat. No. 5,565,332 describes methods for the production of antibodies, or antibody fragments, which have the same binding specificity as a parent antibody but which have increased human characteristics. Humanized antibodies may be obtained by chain shuffling, perhaps using phage display technology, in as much as such methods will be useful in the present invention the entire text of U.S. Pat. No. 5,565,332 is incorporated herein by reference. Human antibodies may also be produced by transforming B cells with EBV and subsequent cloning of secretors as described by Hoon et al., (1993).

Antibody conjugates in which a TS10Q23.3 antibody is linked to a detectable label or a cytotoxic agent form further aspects of the invention. Diagnostic antibody conjugates may be used both in vitro diagnostics, as in a variety of immunoassays, and in vivo diagnostics, such as in imaging technology.

Certain antibody conjugates include those intended primarily for use in vitro, where the antibody is linked to a secondary binding ligand or to an enzyme (an enzyme tag) that will generate a colored product upon contact with a chromogenic substrate. Examples of suitable enzymes include urease, alkaline phosphatase, (horseradish) hydrogen peroxidase and glucose oxidase. Preferred secondary binding ligands are biotin and avidin or streptavidin compounds. The use of such labels is well known to those of skill in the art in light and is described, for example, in U.S. Pat. Nos. 3,817,837; 3,850,752; 3,939,350; 3,996,345; 4,277,437; 4,275,149 and 4,366,241; each incorporated herein by reference.

Radioactively labeled monoclonal antibodies of the present invention may be produced according to well-known methods in the art. For instance, monoclonal antibodies can be iodinated by contact with sodium or potassium iodide and a chemical oxidizing agent such as sodium hypochlorite, or an enzymatic oxidizing agent, such as lactoperoxidase. Monoclonal antibodies according to the invention may be labeled with technetium-$^{99m}$ by ligand exchange process, for example, by reducing pertechnate with stannous solution, chelating the reduced technetium onto a Sephadex column and applying the antibody to this column or by direct labeling techniques, e.g., by incubating pertechnate, a reducing agent such as $SNCl_2$, a buffer solution such as sodium-potassium phthalate solution, and the antibody.

Intermediary functional groups which are often used to bind radioisotopes which exist as metallic ions to antibody are diethylenetriaminepentaacetic acid (DTPA) and ethylene diaminetetracetic acid (EDTA). Fluorescent labels include rhodamine, fluorescein isothiocyanate and renographin.

IV. Diagnosing Cancers Involving TS10q23.3

The present inventors have determined that alterations in TS10q23.3 are associated with malignancy. Therefore, TS10q23.3 and the corresponding gene may be employed as a diagnostic or prognostic indicator of cancer. More specifically, point mutations, deletions, insertions or regulatory pertubations relating to TS10q23.3 may cause cancer or promote cancer development, cause or promoter tumor progression at a primary site, and/or cause or promote metastasis. Other phenomena associated with malignancy that may be affected by TS10q23.3 expression include angiogenesis and tissue invasion.

A. Genetic Diagnosis

One embodiment of the instant invention comprises a method for detecting variation in the expression of TS10q23.3. This may comprises determining that level of TS10q23.3 or determining specific alterations in the expressed product. Obviously, this sort of assay has importance in the diagnosis of related cancers. Such cancer may involve cancers of the brain (glioblastomas, medulloblastoma, astrocytoma, oligodendroglioma, ependymomas), lung, liver, spleen, kidney, pancreas, small intestine, blood cells, lymph node, colon, breast, endometrium, stomach, prostate, testicle, ovary, skin, head and neck, esophagus, bone marrow, blood or other tissue. In particular, the present invention relates to the diagnosis of gliomas.

The biological sample can be any tissue or fluid. Various embodiments include cells of the skin, muscle, facia, brain, prostate, breast, endometrium, lung, head & neck, pancreas, small intestine, blood cells, liver, testes, ovaries, colon, skin, stomach, esophagus, spleen, lymph node, bone marrow or kidney. Other embodiments include fluid samples such as peripheral blood, lymph fluid, ascites, serous fluid, pleural effusion, sputum, cerebrospinal fluid, lacrimal fluid, stool or urine.

Nucleic acid used is isolated from cells contained in the biological sample, according to standard methodologies (Sambrook et al., 1989). The nucleic acid may be genomic DNA or fractionated or whole cell RNA. Where RNA is used, it may be desired to convert the RNA to a complementary DNA. In one embodiment, the RNA is whole cell RNA; in another, it is poly-A RNA. Normally, the nucleic acid is amplified.

Depending on the format, the specific nucleic acid of interest is identified in the sample directly using amplification or with a second, known nucleic acid following amplification. Next, the identified product is detected. In certain applications, the detection may be performed by visual means (e.g., ethidium bromide staining of a gel). Alternatively, the detection may involve indirect identification of the product via chemiluminescence, radioactive scintigraphy of radiolabel or fluorescent label or even via a system using electrical or thermal impulse signals (Affymax Technology; Bellus, 1994).

Following detection, one may compare the results seen in a given patient with a statistically significant reference group of normal patients and patients that have TS10q23.3-related pathologies. In this way, it is possible to correlate the amount or kind of TS10q23.3 detected with various clinical states.

Various types of defects have been identified by the present inventors. Thus, "alterations" should be read as including deletions, insertions, point mutations and duplications. Point mutations result in stop codons, frameshift mutations or amino acid substitutions. Somatic mutations are those occurring in non-germline tissues. Germ-line tissue can occur in any tissue and are inherited. Mutations in and outside the coding region also may affect the amount of TS10q23.3 produced, both by altering the transcription of the gene or in destabilizing or otherwise altering the processing of either the transcript (mRNA) or protein.

A cell takes a genetic step toward oncogenic transformation when one allele of a tumor suppressor gene is inactivated due to inheritance of a germline lesion or acquisition of a somatic mutation. The inactivation of the other allele of the gene usually involves a somatic micromutation or chromosomal allelic deletion that results in loss of heterozygosity (LOH). Alternatively, both copies of a tumor suppressor gene may be lost by homozygous deletion.

The inventors' initial steps toward identifying new mutations in TS10q23.3 were to prescreen primary tumors and tumor cell lines (TCLs) for LOH within this region of 10q23. Primary tumor specimens and TCLs were examined for LOH using polymorphic short tandem repeat markers on chromosome 10 located near the TS10q23.3 locus (Table 6). In this panel of samples, the inventors observed LOH in primary tumor specimens at frequencies ranging from 20% in colon specimens to 75% in glioblastoma multiforms (GBMs), with an overall LOH frequency of ~49%. For TCLs with sample sizes greater than nine, the incidence of LOH varied from 28% (colon) to 82% (GBMs), with an overall frequency of ~46%.

Figure 13A:
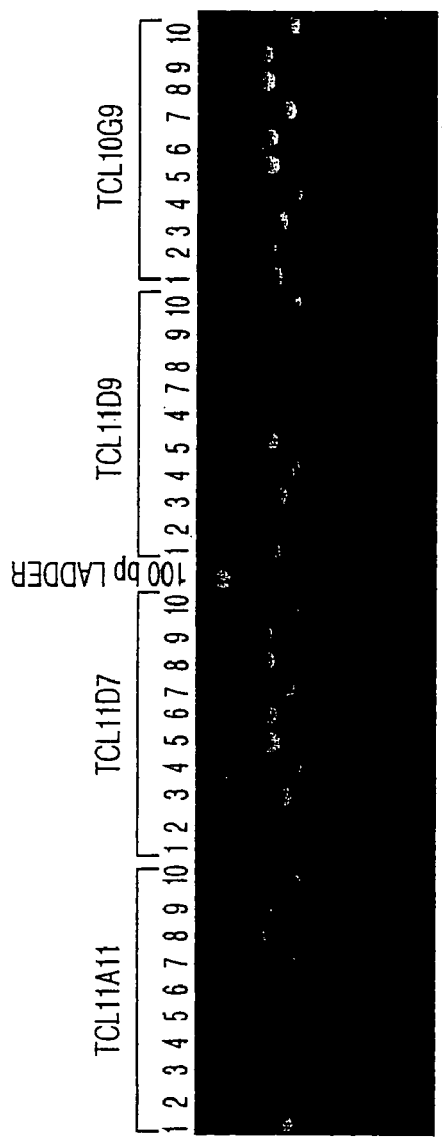
FIG. 13A. Homozygous deletion of the TS10Q23.3 gene in human tumor cell lines and TS10Q23.3 mRNA expression levels in primary glioblastomas. Shown are four cell lines, breast carcinoma TCL11A11, melanoma TCL11D7, melanoma TCL11D9 and leukemia TCL10G9 (control sample without homozygously deleted TS10Q23.3), each examined by PCR™ amplification using the following sequence tagged sites: (1) TS10Q23.3 exon 1, (2) TS10Q23.3 exon 2, (3) TS10Q23.3 exon 3, (4) TS10Q23.3 exon 4, (5) TS10Q23.3 exon 5, (6) TS10Q23.3 exon 6, (7) TS10Q23.3 exon 7, (8) TS10Q23.3 exon 8, (9) TS10Q23.3 exon 9, (10) control MKK4 exon 8.
Figure 13B:
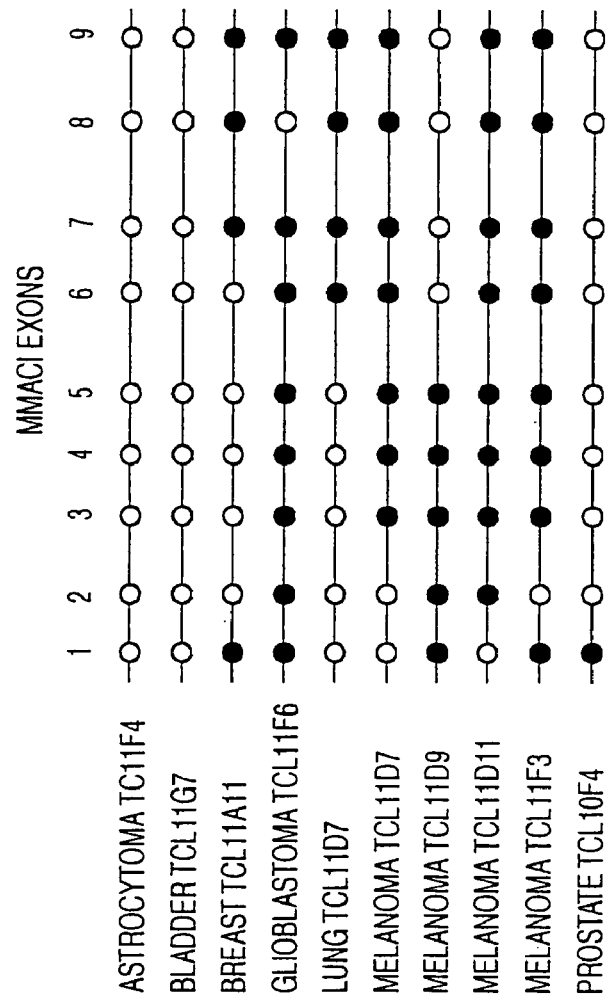
FIG. 13B. Homozygous deletion of the TS10Q23.3 gene in human tumor cell lines and TS10Q23.3 mRNA expression levels in primary glioblastomas. Schematic of the homozygous deletions observed in the TS10Q23.3 gene of TCLs screened. Closed circles represent exons that are not homozygously deleted while open circles represent exons that are lost.

In primary tumors exhibiting LOH surrounding the TS10q23.3 locus, the inventors detected a frameshift mutation in breast carcinoma, a nonsense mutation in pediatric GBM, a splicing variant in pediatric GBM and a missense variant in melanoma (Table 7). The inventors also investigated TCLs exhibited LOH, and identified ten homozygous deletions that affected the coding regions of TS10q23.3 (FIG. 13A and FIG. 13B). The homozygous deletions were present in TCLs from astrocytomas, bladder carcinoma, breast carcinoma, glioblastoma, lung carcinoma, melanoma, and prostate carcinoma. Whereas two of the cell lines had lost all nine TS10q23.3 exons, the other eight TCLs had homozygously deleted different coding portions of the gene. Analysis of the remaining TCLs revealed one frameshift, one nonsense and seven non-conservative missense variants (Table 7). These particular mutations may be targeted with oligonucleotides specifically designed to identify these mutations, or with antibodies that distinguish these markers from wild-type TS10q23.3.

It is contemplated that other mutations in the TS10q23.3 gene may be identified in accordance with the present invention. A variety of different assays are contemplated in this regard, including but not limited to, fluorescent in situ hybridization (FISH; U.S. Pat. No. 5,633,365 and U.S. Pat. No. 5,665,549, each incorporated herein by reference), direct DNA sequencing, PFGE analysis, Southern or Northern blotting, single-stranded conformation analysis (SSCA), RNAse protection assay, allele-specific oligonucleotide (ASO), dot blot analysis, denaturing gradient gel electrophoresis (e.g., U.S. Pat. No. 5,190,856 incorporated herein by reference), RFLP (e.g., U.S. Pat. No. 5,324,631 incorporated herein by reference) and PCR™-SSCP.

(i) Primers and Probes

The term primer, as defined herein, is meant to encompass any nucleic acid that is capable of priming the synthesis of a nascent nucleic acid in a template-dependent process. Typically, primers are oligonucleotides from ten to twenty base pairs in length, but longer sequences can be employed. Primers may be provided in double-stranded or single-stranded form, although the single-stranded form is preferred. Probes are defined differently, although they may act as primers. Probes, while perhaps capable of priming, are designed to binding to the target DNA or RNA and need not be used in an amplification process.

In preferred embodiments, the probes or primers are labeled with radioactive species ($^{32}P$, $^{14}C$, $^{35}S$, $^{3}H$, or other label), with a fluorophore (rhodamine, fluorescein) or a chemillumiscent (luciferase).

(ii) Template Dependent Amplification Methods

A number of template dependent processes are available to amplify the marker sequences present in a given template sample. One of the best known amplification methods is the polymerase chain reaction (referred to as PCR™) which is described in detail in U.S. Pat. Nos. 4,683,195, 4,683,202 and 4,800,159, and in Innis et al., 1990, each of which is incorporated herein by reference in its entirety.

Briefly, in PCR™, two primer sequences are prepared that are complementary to regions on opposite complementary strands of the marker sequence. An excess of deoxynucleoside triphosphates are added to a reaction mixture along with a DNA polymerase, e.g., Taq polymerase. If the marker sequence is present in a sample, the primers will bind to the marker and the polymerase will cause the primers to be extended along the marker sequence by adding on nucleotides. By raising and lowering the temperature of the reaction mixture, the extended primers will dissociate from the marker to form reaction products, excess primers will bind to the marker and to the reaction products and the process is repeated.

A reverse transcriptase PCR™ amplification procedure may be performed in order to quantify the amount of mRNA amplified. Methods of reverse transcribing RNA into cDNA are well known and described in Sambrook et al., 1989. Alternative methods for reverse transcription utilize thermostable, RNA-dependent DNA polymerases. These methods are described in WO 90/07641 filed Dec. 21, 1990. Polymerase chain reaction methodologies are well known in the art.

Another method for amplification is the ligase chain reaction ("LCR"), disclosed in EPO No. 320 308, incorporated herein by reference in its entirety. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR™, bound ligated units dissociate from the target and then serve as "target sequences" for ligation of excess probe pairs. U.S. Pat. No. 4,883,750 describes a method similar to LCR for binding probe pairs to a target sequence.

Qbeta Replicase, described in PCT Application No. PCT/US87/00880, may also be used as still another amplification method in the present invention. In this method, a replicative sequence of RNA that has a region complementary to that of a target is added to a sample in the presence of an RNA polymerase. The polymerase will copy the replicative sequence that can then be detected.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention, Walker et al. (1992a). Strand Displacement Amplification (SDA) is another method of carrying out isothermal amplification of nucleic acids which involves multiple rounds of strand displacement and synthesis, i.e., nick translation. See, U.S. Pat. Nos. 5,270,184 and 5,455,166 and Walker et al. (1992b) for SDA and Spargo et al. (1996) for thermophilic SDA.

Repair Chain Reaction (RCR), involves annealing several probes throughout a region targeted for amplification, followed by a repair reaction in which only two of the four bases are present. The other two bases can be added as biotinylated derivatives for easy detection. A similar approach is used in SDA. Target specific sequences can also be detected using a cyclic probe reaction (CPR). In CPR, a probe having 3' and 5' sequences of non-specific DNA and a middle sequence of specific RNA is hybridized to DNA that is present in a sample. Upon hybridization, the reaction is treated with RNase H, and the products of the probe identified as distinctive products that are released after digestion. The original template is annealed to another cycling probe and the reaction is repeated.

Still another amplification methods described in GB Application No. 2 202 328, and in PCT Application No. PCT/US89/01025, each of which is incorporated herein by reference in its entirety, may be used in accordance with the present invention. In the former application, "modified" primers are used in a PCR™-like, template- and enzyme-dependent synthesis. The primers may be modified by labeling with a capture moiety (e.g., biotin) and/or a detector moiety (e.g., enzyme). In the latter application, an excess of labeled probes are added to a sample. In the presence of the target sequence, the probe binds and is cleaved catalytically. After cleavage, the target sequence is released intact to be bound by excess probe. Cleavage of the labeled probe signals the presence of the target sequence.

Other nucleic acid amplification procedures include transcription-based amplification systems (TAS), including nucleic acid sequence based amplification (NASBA) and 3SR (Kwoh et al., 1989; Gingeras et al., PCT Application WO 88/10315, incorporated herein by reference in their entirety). See also, U.S. Pat. No. 5,409,818, Fahy et al. (1991) and Compton (1991) for 3SR and NASBA. In NASBA, the nucleic acids can be prepared for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer which has target specific sequences. Following polymerization, DNA/RNA hybrids are digested with RNase H while double stranded DNA molecules are heat denatured again. In either case the single stranded DNA is made fully double stranded by addition of second target specific primer, followed by polymerization. The double-stranded DNA molecules are then multiply transcribed by an RNA polymerase such as T7 or SP6. In an isothermal cyclic reaction, the RNA's are reverse transcribed into single stranded DNA, which is then converted to double stranded DNA, and then transcribed once again with an RNA polymerase such as T7 or SP6. The resulting products, whether truncated or complete, indicate target specific sequences.

Davey et al., EPO No. 329 822 (incorporated herein by reference in its entirety) disclose a nucleic acid amplification process involving cyclically synthesizing single-stranded RNA ("ssRNA"), ssDNA, and double-stranded DNA (dsDNA), which may be used in accordance with the present invention. The ssRNA is a template for a first primer oligonucleotide, which is elongated by reverse transcriptase (RNA-dependent DNA polymerase). The RNA is then removed from the resulting DNA:RNA duplex by the action of ribonuclease H (RNase H, an RNase specific for RNA in duplex with either DNA or RNA). The resultant ssDNA is a template for a second primer, which also includes the sequences of an RNA polymerase promoter (exemplified by T7 RNA polymerase) 5' to its homology to the template. This primer is then extended by DNA polymerase (exemplified by the large "Klenow" fragment of *E. coli* DNA polymerase 1), resulting in a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA.

Miller et al., PCT Application WO 89/06700 (incorporated herein by reference in its entirety) disclose a nucleic acid sequence amplification scheme based on the hybridization of a promoter/primer sequence to a target single-stranded DNA ("ssDNA") followed by transcription of many RNA copies of the sequence. This scheme is not cyclic, i.e., new templates are not produced from the resultant RNA transcripts. Other amplification methods include "RACE" and "one-sided PCR™" (Frohman, 1990; Ohara et al., 1989; each herein incorporated by reference in their entirety).

Methods based on ligation of two (or more) oligonucleotides in the presence of nucleic acid having the sequence of the resulting "di-oligonucleotide", thereby amplifying the di-oligonucleotide, may also be used in the amplification step of the present invention. Wu et al., (1989), incorporated herein by reference in its entirety.

(iii) Southern/Northern Blotting

Blotting techniques are well known to those of skill in the art. Southern blotting involves the use of DNA as a target, whereas Northern blotting involves the use of RNA as a target. Each provide different types of information, although cDNA blotting is analogous, in many aspects, to blotting or RNA species.

Briefly, a probe is used to target a DNA or RNA species that has been immobilized on a suitable matrix, often a filter of nitrocellulose. The different species should be spatially separated to facilitate analysis. This often is accomplished by gel electrophoresis of nucleic acid species followed by "blotting" on to the filter.

Subsequently, the blotted target is incubated with a probe (usually labeled) under conditions that promote denaturation and rehybridization. Because the probe is designed to base pair with the target, the probe will binding a portion of the target sequence under renaturing conditions. Unbound probe is then removed, and detection is accomplished as described above.

(iv) Separation Methods

It normally is desirable, at one stage or another, to separate the amplification product from the template and the excess primer for the purpose of determining whether specific amplification has occurred. In one embodiment, amplification products are separated by agarose, agarose-acrylamide or polyacrylamide gel electrophoresis using standard methods. See Sambrook et al., 1989.

Alternatively, chromatographic techniques may be employed to effect separation. There are many kinds of chromatography which may be used in the present invention: adsorption, partition, ion-exchange and molecular sieve, and many specialized techniques for using them including column, paper, thin-layer and gas chromatography (Freifelder, 1982).

(v) Detection Methods

Products may be visualized in order to confirm amplification of the marker sequences. One typical visualization method involves staining of a gel with ethidium bromide and visualization under UV light. Alternatively, if the amplification products are integrally labeled with radio- or fluorometrically-labeled nucleotides, the amplification products can then be exposed to x-ray film or visualized under the appropriate stimulating spectra, following separation.

In one embodiment, visualization is achieved indirectly. Following separation of amplification products, a labeled nucleic acid probe is brought into contact with the amplified marker sequence. The probe preferably is conjugated to a chromophore but may be radiolabeled. In another embodiment, the probe is conjugated to a binding partner, such as an antibody or biotin, and the other member of the binding pair carries a detectable moiety.

In one embodiment, detection is by a labeled probe. The techniques involved are well known to those of skill in the art and can be found in many standard books on molecular protocols. See Sambrook et al., 1989. For example, chromophore or radiolabel probes or primers identify the target during or following amplification.

One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

In addition, the amplification products described above may be subjected to sequence analysis to identify specific kinds of variations using standard sequence analysis techniques. Within certain methods, exhaustive analysis of genes is carried out by sequence analysis using primer sets designed for optimal sequencing (Pignon et al, 1994). The present invention provides methods by which any or all of these types of analyses may be used. Using the sequences disclosed herein, oligonucleotide primers may be designed to permit the amplification of sequences throughout the TS10q23.3 gene that may then be analyzed by direct sequencing.

(vi) Kit Components

All the essential materials and reagents required for detecting and sequencing TS10q23.3 and variants thereof may be assembled together in a kit. This generally will comprise preselected primers and probes. Also included may be enzymes suitable for amplifying nucleic acids including various polymerases (RT, Taq, Sequenase™ etc.), deoxynucleotides and buffers to provide the necessary reaction mixture for amplification. Such kits also generally will comprise, in suitable means, distinct containers for each individual reagent and enzyme as well as for each primer or probe.

(vii) Design and Theoretical Considerations for Relative Quantitative RT-PCR™

Reverse transcription (RT) of RNA to cDNA followed by relative quantitative PCR™ (RT-PCR™) can be used to determine the relative concentrations of specific mRNA species isolated from patients. By determining that the concentration of a specific mRNA species varies, it is shown that the gene encoding the specific mRNA species is differentially expressed.

In PCR™, the number of molecules of the amplified target DNA increase by a factor approaching two with every cycle of the reaction until some reagent becomes limiting. Thereafter, the rate of amplification becomes increasingly diminished until there is no increase in the amplified target between cycles. If a graph is plotted in which the cycle number is on the X axis and the log of the concentration of the amplified target DNA is on the Y axis, a curved line of characteristic shape is formed by connecting the plotted points. Beginning with the first cycle, the slope of the line is positive and constant. This is said to be the linear portion of the curve. After a reagent becomes limiting, the slope of the line begins to decrease and eventually becomes zero. At this point the concentration of the amplified target DNA becomes asymptotic to some fixed value. This is said to be the plateau portion of the curve.

The concentration of the target DNA in the linear portion of the PCR™ amplification is directly proportional to the starting concentration of the target before the reaction began. By determining the concentration of the amplified products of the target DNA in PCR™ reactions that have completed the same number of cycles and are in their linear ranges, it is possible to determine the relative concentrations of the specific target sequence in the original DNA mixture. If the DNA mixtures are cDNAs synthesized from RNAs isolated from different tissues or cells, the relative abundances of the specific mRNA from which the target sequence was derived can be determined for the respective tissues or cells. This direct proportionality between the concentration of the PCR™ products and the relative mRNA abundances is only true in the linear range of the PCR™ reaction.

The final concentration of the target DNA in the plateau portion of the curve is determined by the availability of reagents in the reaction mix and is independent of the original concentration of target DNA. Therefore, the first condition that must be met before the relative abundances of a mRNA species can be determined by RT-PCR™ for a collection of RNA populations is that the concentrations of the amplified PCR™ products must be sampled when the PCR™ reactions are in the linear portion of their curves.

The second condition that must be met for an RT-PCR™ experiment to successfully determine the relative abundances of a particular mRNA species is that relative concentrations of the amplifiable cDNAs must be normalized to some independent standard. The goal of an RT-PCR™ experiment is to determine the abundance of a particular mRNA species relative to the average abundance of all mRNA species in the sample. In the experiments described below, mRNAs for β-actin, asparagine synthetase and lipocortin II were used as external and internal standards to which the relative abundance of other mRNAs are compared.

Most protocols for competitive PCR™ utilize internal PCR™ standards that are approximately as abundant as the target. These strategies are effective if the products of the PCR™ amplifications are sampled during their linear phases. If the products are sampled when the reactions are approaching the plateau phase, then the less abundant product becomes relatively over represented. Comparisons of relative abundances made for many different RNA samples, such as is the case when examining RNA samples for differential expression, become distorted in such a way as to make differences in relative abundances of RNAs appear less than they actually are. This is not a significant problem if the internal standard is much more abundant than the target. If the internal standard is more abundant than the target, then direct linear comparisons can be made between RNA samples.

The above discussion describes theoretical considerations for an RT-PCR™ assay for clinically derived materials. The problems inherent in clinical samples are that they are of variable quantity (making normalization problematic), and that they are of variable quality (necessitating the co-amplification of a reliable internal control, preferably of larger size than the target). Both of these problems are overcome if the RT-PCR™ is performed as a relative quantitative RT-PCR™ with an internal standard in which the internal standard is an amplifiable cDNA fragment that is larger than the target cDNA fragment and in which the abundance of the mRNA encoding the internal standard is roughly 5–100 fold higher than the mRNA encoding the target. This assay measures relative abundance, not absolute abundance of the respective mRNA species.

Other studies may be performed using a more conventional relative quantitative RT-PCR™ assay with an external standard protocol. These assays sample the PCR™ products in the linear portion of their amplification curves. The number of PCR™ cycles that are optimal for sampling must be empirically determined for each target cDNA fragment. In addition, the reverse transcriptase products of each RNA population isolated from the various tissue samples must be carefully normalized for equal concentrations of amplifiable cDNAs. This consideration is very important since the assay measures absolute mRNA abundance. Absolute mRNA abundance can be used as a measure of differential gene expression only in normalized samples. While empirical determination of the linear range of the amplification curve and normalization of cDNA preparations are tedious and time consuming processes, the resulting RT-PCR™ assays can be superior to those derived from the relative quantitative RT-PCR™ assay with an internal standard.

One reason for this advantage is that without the internal standard/competitor, all of the reagents can be converted into a single PCR™ product in the linear range of the amplification curve, thus increasing the sensitivity of the assay. Another reason is that with only one PCR™ product, display of the product on an electrophoretic gel or another display method becomes less complex, has less background and is easier to interpret.

(viii) Chip Technologies

Specifically contemplated by the present inventors are chip-based DNA technologies such as those described by Hacia et al. (1996) and Shoemaker et al. (1996). Briefly, these techniques involve quantitative methods for analyzing large numbers of genes rapidly and accurately. By tagging genes with oligonucleotides or using fixed probe arrays, one can employ chip technology to segregate target molecules as high density arrays and screen these molecules on the basis of hybridization. See also Pease et al. (1994); Fodor et al. (1991).

B. Immunodiagnosis

Antibodies of the present invention can be used in characterizing the TS10q23.3 content of healthy and diseased tissues, through techniques such as ELISAs and Western blotting. This may provide a screen for the presence or absence of malignancy or as a predictor of future cancer.

The use of antibodies of the present invention, in an ELISA assay is contemplated. For example, anti-TS10q23.3 antibodies are immobilized onto a selected surface, preferably a surface exhibiting a protein affinity such as the wells of a polystyrene microtiter plate. After washing to remove incompletely adsorbed material, it is desirable to bind or coat the assay plate wells with a non-specific protein that is known to be antigenically neutral with regard to the test antisera such as bovine serum albumin (BSA), casein or solutions of powdered milk. This allows for blocking of non-specific adsorption sites on the immobilizing surface and thus reduces the background caused by non-specific binding of antigen onto the surface.

After binding of antibody to the well, coating with a non-reactive material to reduce background, and washing to remove unbound material, the immobilizing surface is contacted with the sample to be tested in a manner conducive to immune complex (antigen/antibody) formation.

Following formation of specific immunocomplexes between the test sample and the bound antibody, and subsequent washing, the occurrence and even amount of immunocomplex formation may be determined by subjecting same to a second antibody having specificity for TS10q23.3 that differs the first antibody. Appropriate conditions preferably include diluting the sample with diluents such as BSA, bovine gamma globulin (BGG) and phosphate buffered saline (PBS)/Tween®. These added agents also tend to assist in the reduction of nonspecific background. The layered antisera is then allowed to incubate for from about 2 to about 4 hr, at temperatures preferably on the order of about 25° to about 27° C. Following incubation, the antisera-contacted surface is washed so as to remove non-immunocomplexed material. A preferred washing procedure includes washing with a solution such as PBS/Tween®, or borate buffer.

To provide a detecting means, the second antibody will preferably have an associated enzyme that will generate a color development upon incubating with an appropriate chromogenic substrate. Thus, for example, one will desire to contact and incubate the second antibody-bound surface with a urease or peroxidase-conjugated anti-human IgG for a period of time and under conditions which favor the development of immunocomplex formation (e.g., incubation for 2 hr at room temperature in a PBS-containing solution such as PBS/Tween®).

After incubation with the second enzyme-tagged antibody, and subsequent to washing to remove unbound material, the amount of label is quantified by incubation with a chromogenic substrate such as urea and bromocresol purple or 2,2'-azino-di-(3-ethyl-benzthiazoline) -6-sulfonic acid (ABTS) and $H_2O_2$, in the case of peroxidase as the enzyme label. Quantitation is then achieved by measuring the degree of color generation, e.g., using a visible spectrum spectrophotometer.

The preceding format may be altered by first binding the sample to the assay plate. Then, primary antibody is incubated with the assay plate, followed by detecting of bound primary antibody using a labeled second antibody with specificity for the primary antibody.

The steps of various other useful immunodetection methods have been described in the scientific literature, such as, e.g., Nakamura et al. (1987; incorporated herein by reference). Immunoassays, in their most simple and direct sense, are binding assays. Certain preferred immunoassays are the various types of radioimmunoassays (RIA) and immunobead capture assay. Immunohistochemical detection using tissue sections also is particularly useful. However, it will be readily appreciated that detection is not limited to such techniques, and Western blotting, dot blotting, FACS analyses, and the like also may be used in connection with the present invention.

The antibody compositions of the present invention will find great use in immunoblot or Western blot analysis. The antibodies may be used as high-affinity primary reagents for the identification of proteins immobilized onto a solid support matrix, such as nitrocellulose, nylon or combinations thereof. In conjunction with immunoprecipitation, followed by gel electrophoresis, these may be used as a single step reagent for use in detecting antigens against which secondary reagents used in the detection of the antigen cause an adverse background. Immunologically-based detection methods for use in conjunction with Western blotting include enzymatically-, radiolabel-, or fluorescently-tagged secondary antibodies against the toxin moiety are considered to be of particular use in this regard. U.S. patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody or a biotin/avidin ligand binding arrangement, as is known in the art.

V. Methods for Screening Active Compounds

The present invention also contemplates the use of TS10q23.3 and active fragments, and nucleic acids coding therefor, in the screening of compounds for activity in either stimulating TS10q23.3 activity, overcoming the lack of TS10q23.3 or blocking the effect of a mutant TS10q23.3 molecule. These assays may make use of a variety of different formats and may depend on the kind of "activity" for which the screen is being conducted. Contemplated functional "read-outs" include binding to a compound, inhibition of binding to a substrate, ligand, receptor or other binding partner by a compound, phosphatase activity, antiphosphatase activity, phosphorylation of TS10q23.3, dephosphorylation of TS10q23.3, inhibition or stimulation of cell-to-cell signaling, growth, metastasis, cell division, cell migration, soft agar colony formation, contact inhibition, invasiveness, angiogenesis, apoptosis, tumor progression or other malignant phenotype.

The polypeptide of the invention may also be used for screening compounds developed as a result of combinatorial library technology. Combinatorial library technology provides an efficient way of testing a potential vast number of different substances for ability to modulate activity of a polypeptide. Such libraries and their use are known in the art. The use of peptide libraries is preferred. See, for example, WO 97/02048.

Briefly, a method of screening for a substance which modulates activity of a polypeptide may include contacting one or more test substances with the polypeptide in a suitable reaction medium, testing the activity of the treated polypeptide and comparing that activity with the activity of the polypeptide in comparable reaction medium untreated with the test substance or substances. A difference in activity between the treated and untreated polypeptides is indicative of a modulating effect of the relevant test substance or substances.

Prior to or as well as being screened for modulation of activity, test substances may be screened for ability to interact with the polypeptide, e.g., in a yeast two-hybrid system (e.g., Bartel et al., 1993; Fields and Song, 1989; Chevray and Nathans, 1992; Lee et al., 1995). This system may be used as a coarse screen prior to testing a substance for actual ability to modulate activity of the polypeptide. Alternatively, the screen could be used to screen test substances for binding to an KVLQT1 or KCNE1 specific binding partner, or to find mimetics of the KVLQT1 or KCNE1 polypeptide.

Following identification of a substance which modulates or affects polypeptide activity, the substance may be investigated further. Furthermore, it may be manufactured and/or used in preparation, i.e., manufacture or formulation, or a composition such as a medicament, pharmaceutical composition or drug. These may be administered to individuals.

Thus, the present invention extends in various aspects not only to a substance identified using a nucleic acid molecule as a modulator of polypeptide activity, in accordance with what is disclosed herein, but also a pharmaceutical composition, medicament, drug or other composition comprising such a substance, a method comprising administration of such a composition comprising such a substance, a method comprising administration of such a composition to a patient, e.g., for treatment (which may include preventative treatment) of LQT, use of such a substance in the manufacture of a composition for administration, e.g., for treatment of LQT, and a method of making a pharmaceutical composition comprising admixing such a substance with a pharmaceutically acceptable excipient, vehicle or carrier, and optionally other ingredients.

A. In Vitro Assays

In one embodiment, the invention is to be applied for the screening of compounds that bind to the TS10q23.3 molecule or fragment thereof. The polypeptide or fragment may be either free in solution, fixed to a support, expressed in or on the surface of a cell. Either the polypeptide or the compound may be labeled, thereby permitting determining of binding.

In another embodiment, the assay may measure the inhibition of binding of TS10q23.3 to a natural or artificial substrate or binding partner. Competitive binding assays can be performed in which one of the agents (TS10q23.3, binding partner or compound) is labeled. Usually, the polypeptide will be the labeled species. One may measure the amount of free label versus bound label to determine binding or inhibition of binding.

Another technique for high throughput screening of compounds is described in WO 84/03564. Large numbers of small peptide test compounds are synthesized on a solid substrate, such as plastic pins or some other surface. The peptide test compounds are reacted with TS10q23.3 and washed. Bound polypeptide is detected by various methods.

Purified TS10q23.3 can be coated directly onto plates for use in the aforementioned drug screening techniques. However, non-neutralizing antibodies to the polypeptide can be used to immobilize the polypeptide to a solid phase. Also, fusion proteins containing a reactive region (preferably a terminal region) may be used to link the TS10q23.3 active region to a solid phase.

Various cell lines containing wild-type or natural or engineered mutations in TS10q23.3 can be used to study various functional attributes of TS10q23.3 and how a candidate compound affects these attributes. Methods for engineering mutations are described elsewhere in this document, as are naturally-occurring mutations in TS10q23.3 that lead to, contribute to and/or otherwise cause malignancy. In such assays, the compound would be formulated appropriately, given its biochemical nature, and contacted with a target cell. Depending on the assay, culture may be required. The cell may then be examined by virtue of a number of different physiologic assays. Alternatively, molecular analysis may be performed in which the function of TS10q23.3, or related pathways, may be explored. This may involve assays such as those for protein expression, enzyme function, substrate utilization, phosphorylation states of various molecules including TS10q23.3, cAMP levels, mRNA expression (including differential display of whole cell or polyA RNA) and others.

B. In Vivo Assays

The present invention also encompasses the use of various animal models. Here, the identity seen between human and mouse TS10q23.3 provides an excellent opportunity to examine the function of TS10q23.3 in a whole animal system where it is normally expressed. By developing or isolating mutant cells lines that fail to express normal TS10q23.3, one can generate cancer models in mice that will be highly predictive of cancers in humans and other mammals. These models may employ the orthotopic or systemic administration of tumor cells to mimic primary and/or metastatic cancers. Alternatively, one may induce cancers in animals by providing agents known to be responsible for certain events associated with malignant transformation and/or tumor progression. Finally, transgenic animals (discussed below) that lack a wild-type TS10q23.3 may be utilized as models for cancer development and treatment.

Treatment of animals with test compounds will involve the administration of the compound, in an appropriate form, to the animal. Administration will be by any route the could be utilized for clinical or non-clinical purposes, including but not limited to oral, nasal, buccal, rectal, vaginal or topical. Alternatively, administration may be by intratracheal instillation, bronchial instillation, intradermal, subcutaneous, intramuscular, intraperitoneal or intravenous injection. Specifically contemplated are systemic intravenous injection, regional administration via blood or lymph supply and intratumoral injection.

Determining the effectiveness of a compound in vivo may involve a variety of different criteria. Such criteria include, but are not limited to, survival, reduction of tumor burden or mass, arrest or slowing of tumor progression, elimination of tumors, inhibition or prevention of metastasis, increased activity level, improvement in immune effector function and improved food intake.

C. Rational Drug Design

The goal of rational drug design is to produce structural analogs of biologically active polypeptides or compounds with which they interact (agonists, antagonists, inhibitors, binding partners, etc.). By creating such analogs, it is possible to fashion drugs which are more active or stable than the natural molecules, which have different susceptibility to alteration or which may affect the function of various other molecules. In one approach, one would generate a three-dimensional structure for TS10q23.3 or a fragment thereof. This could be accomplished by x-ray crystallograph, computer modeling or by a combination of both approaches. An alternative approach, "alanine scan," involves the random replacement of residues throughout molecule with alanine, and the resulting affect on function determined.

It also is possible to isolate a TS10q23.3 specific antibody, selected by a functional assay, and then solve its crystal structure. In principle, this approach yields a pharmacore upon which subsequent drug design can be based. It is possible to bypass protein crystallograph altogether by generating anti-idiotypic antibodies to a functional, pharmacologically active antibody. As a mirror image of a mirror image, the binding site of anti-idiotype would be expected to be an analog of the original antigen. The anti-idiotype could then be used to identify and isolate peptides from banks of chemically- or biologically-produced peptides. Selected peptides would then serve as the pharmacore. Anti-idiotypes may be generated using the methods described herein for producing antibodies, using an antibody as the antigen.

Thus, one may design drugs which have improved TS10q23.3 activity or which act as stimulators, inhibitors, agonists, antagonists or TS10q23.3 or molecules affected by TS10q23.3 function. By virtue of the availability of cloned TS0q23.3 sequences, sufficient amounts of TS10q23.3 can be produced to perform crystallographic studies. In addition, knowledge of the polypeptide sequences permits computer employed predictions of structure-function relationships.

A substance identified as a modulator of polypeptide function may be peptide or non-peptide in nature. Non-peptide "small molecules" are often preferred for many in vivo pharmaceutical uses. Accordingly, a mimetic or mimic of the substance (particularly if a peptide) may be designed for pharmaceutical use.

The designing of mimetics to a known pharmaceutically active compound is a known approach to the development of pharmaceuticals based on a "lead" compound. This might be desirable where the active compound is difficult or expensive to synthesize or where it is unsuitable for a particular method of administration, e.g., pure peptides are unsuitable active agents for oral compositions as they tend to be quickly degraded by proteases in the alimentary canal. Mimetic design, synthesis and testing is generally used to avoid randomly screening large numbers of molecules for a target property.

There are several steps commonly taken in the design of a mimetic from a compound having a given target property. First, the particular parts of the compound that are critical and/or important in determining the target property are determined. In the case of a peptide, this can be done by systematically varying the amino acid residues in the peptide, e.g., by substituting each residue in turn. Alanine scans of peptide are commonly used to refine such peptide motifs. These parts or residues constituting the active region of the compound are known as its "pharmacophore".

Once the pharmacophore has been found, its structure is modeled according to its physical properties, e.g., stereochemistry, bonding, size and/or charge, using data from a range of sources, e.g., spectroscopic techniques, x-ray diffraction data and NMR. Computational analysis, similarity mapping (which models the charge and/or volume of a pharmacophore, rather than the bonding between atoms) and other techniques can be used in this modeling process.

In a variant of this approach, the three-dimensional structure of the ligand and its binding partner are modeled. This can be especially useful where the ligand and/or binding partner change conformation on binding, allowing the model to take account of this in the design of the mimetic.

A template molecule is then selected onto which chemical groups which mimic the pharmacophore can be grafted. The template molecule and the chemical groups grafted onto it can conveniently be selected so that the mimetic is easy to synthesize, is likely to be pharmacologically acceptable, and does not degrade in vivo, while retaining the biological activity of the lead compound. Alternatively, where the mimetic is peptide-based, further stability can be achieved by cyclizing the peptide, increasing its rigidity. The mimetic or mimetics found by this approach can then be screened to see whether they have the target property, or to what extent they exhibit it. Further optimization or modification can then be carried out to arrive at one or more final mimetics for in vivo or clinical testing.

VI. Methods for Treating 10q23.3 Related Malignancies

The present invention also involves, in another embodiment, the treatment of cancer. The types of cancer that may be treated, according to the present invention, is limited only by the involvement of TS10q23.3. By involvement, it is not even a requirement that TS10q23.3 be mutated or abnormal—the overexpression of this tumor suppressor may actually overcome other lesions within the cell. Thus, it is contemplated that a wide variety of tumors may be treated using TS10q23.3 therapy, including cancers of the brain (glioblastoma, astrocytoma, oligodendroglioma, ependymomas), lung, liver, spleen, kidney, lymph node, pancreas, small intestine, blood cells, colon, stomach, breast, endometrium, prostate, testicle, ovary, skin, head and neck, esophagus, bone marrow, blood or other tissue.

In many contexts, it is not necessary that the tumor cell be killed or induced to undergo normal cell death or "apoptosis." Rather, to accomplish a meaningful treatment, all that is required is that the tumor growth be slowed to some degree. It may be that the tumor growth is completely blocked, however, or that some tumor regression is achieved. Clinical terminology such as "remission" and "reduction of tumor" burden also are contemplated given their normal usage.

A. Genetic Based Therapies

One of the therapeutic embodiments contemplated by the present inventors is the intervention, at the molecular level, in the events involved in the tumorigenesis of some cancers. Specifically, the present inventors intend to provide, to a cancer cell, an expression construct capable of providing TS10q23.3 to that cell. Because the sequence homology between the human, mouse and dog genes, any of these nucleic acids could be used in human therapy, as could any of the gene sequence variants discussed above which would encode the same, or a biologically equivalent polypeptide. The lengthy discussion of expression vectors and the genetic elements employed therein is incorporated into this section by reference. Particularly preferred expression vectors are viral vectors such as *adenovirus*, adeno-associated virus, *herpesvirus*, vaccinia virus and retrovirus. Also preferred is liposomally-encapsulated expression vector.

Those of skill in the art are well aware of how to apply gene delivery to in vivo and ex vivo situations. For viral vectors, one generally will prepare a viral vector stock. Depending on the kind of virus and the titer attainable, one will deliver $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$ or $1 \times 10^{12}$ infectious particles to the patient. Similar figures may be extrapolated for liposomal or other non-viral formulations by comparing relative uptake efficiencies. Formulation as a pharmaceutically acceptable composition is discussed below.

Various routes are contemplated for various tumor types. The section below on routes contains an extensive list of possible routes. For practically any tumor, systemic delivery is contemplated. This will prove especially important for attacking microscopic or metastatic cancer. Where discrete tumor mass may be identified, a variety of direct, local and regional approaches may be taken. For example, the tumor may be directly injected with the expression vector. A tumor bed may be treated prior to, during or after resection. Following resection, one generally will deliver the vector by a catheter left in place following surgery. One may utilize the tumor vasculature to introduce the vector into the tumor by injecting a supporting vein or artery. A more distal blood supply route also may be utilized.

In a different embodiment, ex vivo gene therapy is contemplated. This approach is particularly suited, although not limited, to treatment of bone marrow associated cancers. In an ex vivo embodiment, cells from the patient are removed and maintained outside the body for at least some period of time. During this period, a therapy is delivered, after which the cells are reintroduced into the patient; hopefully, any tumor cells in the sample have been killed.

Autologous bone marrow transplant (ABMT) is an example of ex vivo gene therapy. Basically, the notion behind ABMT is that the patient will serve as his or her own bone marrow donor. Thus, a normally lethal dose of irradiation or chemotherapeutic may be delivered to the patient to kill tumor cells, and the bone marrow repopulated with the patients own cells that have been maintained (and perhaps expanded) ex vivo. Because, bone marrow often is contaminated with tumor cells, it is desirable to purge the bone marrow of these cells. Use of gene therapy to accomplish this goal is yet another way TS10q23.3 may be utilized according to the present invention.

Gene transfer systems known in the art may be useful in the practice of the gene therapy methods of the present invention. These include viral and nonviral transfer methods. A number of viruses have been used as gene transfer vectors or as the basis for repairing gene transfer vectors, including papovaviruses (e.g., SV40, Madzak et al., 1992), adenovirus (Berkner, 1992; Berkner et al., 1988; Gorziglia and Kapikian, 1992; Quantin et al., 1992; Rosenfeld et al., 1992; Wilkinson and Akrigg, 1992; Stratford-Perricaudet et al., 1990; Schneider et al., 1998), vaccinia virus (Moss, 1992; Moss, 1996), adeno-associated virus (Muzyczka, 1992; Ohi et al., 1990; Russell and Hirata, 1998), herpesviruses including HSV and EBV (Margolskee, 1992; Johnson et al., 1992; Fink et al., 1992; Breakefield and Geller, 1987; Freese et al., 1990; Fink et al., 1996), lentiviruses (Naldini et al., 1996), Sindbis and Semliki Forest virus (Berglund et al., 1993), and retroviruses of avian (Bandyopadhyay and Temin, 1984; Petropoulos et al., 1992), murine (Miller, 1992; Miller et al., 1985; Sorge et al., 1984; Mann and Baltimore, 1985; Miller et al., 1988), and human origin (Shimada et al., 1991; Helseth et al., 1990; Page et al., 1990; Buchschacher and Panganiban, 1992).

Nonviral gene transfer methods known in the art include chemical techniques such as calcium phosphate coprecipitation (Graham and van der Eb, 1973; Pellicer et al., 1980); mechanical techniques, for example microinjection (Anderson et al., 1980; Gordon et al., 1980; Brinster et al., 1981; Costantini and Lacy, 1981); membrane fusion-mediated transfer via liposomes (Felgner et al., 1987; Wang and Huang, 1989; Kaneda et al., 1989; Stewart et al., 1992; Nabel et al., 1990; Lim et al., 1991); and direct DNA uptake and receptor-mediated DNA transfer (Wolff et al., 1990; Wu et al., 1991; Zenke et al., 1990; Wu et al., 1989; Wolff et al., 1991; Wagner et al., 1990; Wagner et al., 1991; Cotten et al., 1990; Curiel et al., 1992; Curiel et al., 1991). Viral-mediated gene transfer can be combined with direct in vivo gene transfer using liposome delivery, allowing one to direct the viral vectors to the tumor cells and not into the surrounding nondividing cells. Alternatively, the retroviral vector producer cell line can be injected into tumors (Culver et al., 1992). Injection of producer cells would then provide a continuous source of vector particles. This technique has been approved for use in humans with inoperable brain tumors.

In an approach which combines biological and physical gene transfer methods, plasmid DNA of any size is combined with a polylysine-conjugated antibody specific to the adenovirus hexon protein, and the resulting complex is bound to an adenovirus vector. The trimolecular complex is then used to infect cells. The adenovirus vector permits efficient binding, internalization, and degradation of the endosome before the coupled DNA is damaged. For other techniques for the delivery of adenovirus based vectors see Schneider et al. (1998) and U.S. Pat. Nos. 5,691,198; 5,747,469; 5,436,146 and 5,753,500.

Liposome/DNA complexes have been shown to be capable of mediating direct in vivo gene transfer. While in standard liposome preparations the gene transfer process is nonspecific, localized in vivo uptake and expression have been reported in tumor deposits, for example, following direct in situ administration (Nabel, 1992).

Expression vectors in the context of gene therapy are meant to include those constructs containing sequences sufficient to express a polynucleotide that has been cloned therein. In viral expression vectors, the construct contains viral sequences sufficient to support packaging of the construct. If the polynucleotide encodes a TS10q23.3 gene, expression will produce the corresponding protein. If the polynucleotide encodes an antisense polynucleotide or a ribozyme, expression will produce the antisense polynucleotide or ribozyme. Thus in this context, expression does not require that a protein product be synthesized. In addition to the polynucleotide cloned into the expression vector, the vector also contains a promoter functional in eukaryotic cells. The cloned polynucleotide sequence is under control of this promoter. Suitable eukaryotic promoters include those described above. The expression vector may also include sequences, such as selectable markers and other sequences described herein.

B. Immunotherapies

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

According to the present invention, it is unlikely that TS10q23.3 could serve as a target for an immune effector given that (i) it is unlikely to be expressed on the surface of the cell and (ii) that the presence, not absence, of TS10q23.3 is associated with the normal state. However, it is possible that particular mutant forms of TS10q23.3 may be targeted by immunotherapy, either using antibodies, antibody conjugates or immune effector cells.

A more likely scenario is that immunotherapy could be used as part of a combined therapy, in conjunction with TS10q23.3-targeted gene therapy. The general approach for combined therapy is discussed below. Generally, the tumor cell must bear some marker that is amenable to targeting, i.e., is not present on the majority of other cells. Many tumor marker exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155.

Immunoconjugates. The invention further provides immunotoxins in which an antibody that binds to a cancer marker, such as a mutant TS10q23.3, is linked to a cytotoxic agent. Immunotoxin technology is fairly well-advanced and known to those of skill in the art. Immunotoxins are agents in which the antibody component is linked to another agent, particularly a cytotoxic or otherwise anticellular agent, having the ability to kill or suppress the growth or cell division of cells.

As used herein, the terms "toxin" and "toxic moiety" are employed to refer to any cytotoxic or otherwise anticellular agent that has such a killing or suppressive property. Toxins are thus pharmacologic agents that can be conjugated to an antibody and delivered in an active form to a cell, wherein they will exert a significant deleterious effect.

The preparation of immunotoxins is, in general, well known in the art (see, e.g., U.S. Pat. No. 4,340,535, incorporated herein by reference). It also is known that while IgG based immunotoxins will typically exhibit better binding capability and slower blood clearance than their Fab' counterparts, Fab' fragment-based immunotoxins will generally exhibit better tissue penetrating capability as compared to IgG based immunotoxins.

Exemplary anticellular agents include chemotherapeutic agents, radioisotopes as well as cytotoxins. Example of chemotherapeutic agents are hormones such as steroids; antimetabolites such as cytosine arabinoside, fluorouracil, methotrexate or aminopterin; anthracycline; mitomycin C; vinca alkaloids; demecolcine; etoposide; mithramycin; or alkylating agents such as chlorambucil or melphalan.

Preferred immunotoxins often include a plant-, fungal- or bacterial-derived toxin, such as an A chain toxin, a ribosome inactivating protein, α-sarcin, aspergillin, restirictocin, a ribonuclease, diphtheria toxin or pseudomonas exotoxin, to mention just a few examples. The use of toxin-antibody constructs is well known in the art of immunotoxins, as is their attachment to antibodies. Of course, combinations of the various toxins could also be coupled to one antibody molecule, thereby accommodating variable or even enhanced cytotoxicity.

One type of toxin for attachment to antibodies is ricin, with deglycosylated ricin A chain being particularly preferred. As used herein, the term "ricin" is intended to refer to ricin prepared from both natural sources and by recombinant means. Various 'recombinant' or 'genetically engineered' forms of the ricin molecule are known to those of skill in the art, all of which may be employed in accordance with the present invention.

Deglycosylated ricin A chain (dgA) is preferred because of its extreme potency, longer half-life, and because it is economically feasible to manufacture it a clinical grade and scale (available commercially from Inland Laboratories, Austin, Tex.). Truncated ricin A chain, from which the 30 N-terminal amino acids have been removed by Nagarase (Sigma), also may be employed.

Linking or coupling one or more toxin moieties to an antibody may be achieved by a variety of mechanisms, for example, covalent binding, affinity binding, intercalation, coordinate binding and complexation. Preferred binding methods are those involving covalent binding, such as using chemical cross-linkers, natural peptides or disulfide bonds.

The covalent binding can be achieved either by direct condensation of existing side chains or by the incorporation of external bridging molecules. Many bivalent or polyvalent agents are useful in coupling protein molecules to other proteins, peptides or amine functions. Examples of coupling agents are carbodiimides, diisocyanates, glutaraldehyde, diazobenzenes, and hexamethylene diamines. This list is not intended to be exhaustive of the various coupling agents known in the art but, rather, is exemplary of the more common coupling agents that may be used.

In preferred embodiments, it is contemplated that one may wish to first derivatize the antibody, and then attach the toxin component to the derivatized product. As used herein, the term "derivatize" is used to describe the chemical modification of the antibody substrate with a suitable cross-linking agent. Examples of cross-linking agents for use in this manner include the disulfide-bond containing linkers SPDP (N-succinimidyl-3-(2-pyridyldithio)propionate) and SMPT (4-succinimidyl-oxycarbonyl-α-methyl-α(2-pyridyldithio)toluene).

Biologically releasable bonds are particularly important to the realization of a clinically active immunotoxin in that the toxin moiety must be capable of being released from the antibody once it has entered the target cell. Numerous types of linking constructs are known, including simply direct disulfide bond formation between sulfhydryl groups contained on amino acids such as cysteine, or otherwise introduced into respective protein structures, and disulfide linkages using available or designed linker moieties.

Numerous types of disulfide-bond containing linkers are known which can successfully be employed to conjugate toxin moieties to antibodies, however, certain linkers are generally preferred, such as, for example, sterically hindered disulfide bond linkers are preferred due to their greater stability in vivo, thus preventing release of the toxin moiety prior to binding at the site of action. A particularly preferred cross-linking reagent is SMPT, although other linkers such as SATA, SPDP and 2-iminothiolane also may be employed.

Once conjugated, it will be important to purify the conjugate so as to remove contaminants such as unconjugated A chain or antibody. It is important to remove unconjugated A chain because of the possibility of increased toxicity. Moreover, it is important to remove unconjugated antibody to avoid the possibility of competition for the antigen between conjugated and unconjugated species. In any event, a number of purification techniques have been found to provide conjugates to a sufficient degree of purity to render them clinically useful.

In general, the most preferred technique will incorporate the use of Blue-Sepharose with a gel filtration or gel permeation step. Blue-Sepharose is a column matrix composed of Cibacron Blue 3GA and agarose, which has been found to be useful in the purification of immunoconjugates. The use of Blue-Sepharose combines the properties of ion exchange with A chain binding to provide good separation of conjugated from unconjugated binding. The Blue-Sepharose allows the elimination of the free (non conjugated) antibody from the conjugate preparation. To eliminate the free (unconjugated) toxin (e.g., dgA) a molecular exclusion chromatography step may be used using either conventional gel filtration procedure or high performance liquid chromatography.

After a sufficiently purified conjugate has been prepared, one will generally desire to prepare it into a pharmaceutical composition that may be administered parenterally. This is done by using for the last purification step a medium with a suitable pharmaceutical composition. Such formulations will typically include pharmaceutical buffers, along with excipients, stabilizing agents and such like. The pharmaceutically acceptable compositions will be sterile, non-immunogenic and non-pyrogenic. Details of their preparation are well known in the art and are further described herein. It will be appreciated that endotoxin contamination should be kept minimally at a safe level, for example, less that 0.5 ng/mg protein.

Suitable pharmaceutical compositions in accordance with the invention will generally comprise from about 10 to about 100 mg of the desired conjugate admixed with an acceptable pharmaceutical diluent or excipient, such as a sterile aqueous solution, to give a final concentration of about 0.25 to about 2.5 mg/ml with respect to the conjugate.

As mentioned above, the antibodies of the invention may be linked to one or more chemotherapeutic agents, such as anti-tumor drugs, cytokines, antimetabolites, alkylating agents, hormones, nucleic acids and the like, which may thus be targeted to a TS10q23.3 expressing cancer cell using the antibody conjugate. The advantages of antibody-conjugated agents over their non-antibody conjugated counterparts is the added selectivity afforded by the antibody.

In analyzing the variety of chemotherapeutic and pharmacologic agents available for conjugating to an antibody, one may wish to particularly consider those that have been previously shown to be successfully conjugated to antibodies and to function pharmacologically. Exemplary antineoplastic agents that have been used include doxorubicin, daunomycin, methotrexate, vinblastine. Moreover, the attachment of other agents such as neocarzinostatin, macromycin, trenimon and α-amanitin has also been described. The lists of suitable agents presented herein are, of course, merely exemplary in that the technology for attaching pharmaceutical agents to antibodies for specific delivery to tissues is well established.

Thus, it is generally believed to be possible to conjugate to antibodies any pharmacologic agent that has a primary or secondary amine group, hydrazide or hydrazine group, carboxyl alcohol, phosphate, or alkylating group available for binding or cross-linking to the amino acids or carbohydrate groups of the antibody. In the case of protein structures, this is most readily achieved by means of a cross linking agent, as described above for the immunotoxins. Attachment also may be achieved by means of an acid labile acyl hydrazone or cis aconityl linkage between the drug and the antibody, or by using a peptide spacer such as L-Leu-L-Ala-L-Leu-L-Ala, between the γ-carboxyl group of the drug and an amino acid of the antibody.

C. Protein Therapy

Another therapy approach is the provision, to a subject, of TS10q23.3 polypeptide, active fragments, synthetic peptides, mimetics or other analogs thereof. The protein may be produced by recombinant expression means or, if small enough, generated by an automated peptide synthesizer. Formulations would be selected based on the route of administration and purpose including, but not limited to, liposomal formulations and classic pharmaceutical preparations.

D. Combined Therapy with Immunotherapy, Traditional Chemo- or Radiotherapy

Tumor cell resistance to DNA damaging agents represents a major problem in clinical oncology. One goal of current cancer research is to find ways to improve the efficacy of chemo- and radiotherapy. One way is by combining such traditional therapies with gene therapy. For example, the herpes simplex-thymidine kinase (HS-tk) gene, when delivered to brain tumors by a retroviral vector system, successfully induced susceptibility to the antiviral agent ganciclovir (Culver et al., 1992). In the context of the present invention, it is contemplated that TS10q23.3 replacement therapy could be used similarly in conjunction with chemo- or radiotherapeutic intervention. It also may prove effective to combine TS10q23.3 gene therapy with immunotherapy, as described above.

To kill cells, inhibit cell growth, inhibit metastasis, inhibit angiogenesis or otherwise reverse or reduce the malignant phenotype of tumor cells, using the methods and compositions of the present invention, one would generally contact a "target" cell with a TS10q23.3 expression construct and at least one other agent. These compositions would be provided in a combined amount effective to kill or inhibit proliferation of the cell. This process may involve contacting the cells with the expression construct and the agent(s) or factor(s) at the same time. This may be achieved by contacting the cell with a single composition or pharmacological formulation that includes both agents, or by contacting the cell with two distinct compositions or formulations, at the same time, wherein one composition includes the expression construct and the other includes the agent.

Alternatively, the gene therapy treatment may precede or follow the other agent treatment by intervals ranging from minutes to weeks. In embodiments where the other agent and expression construct are applied separately to the cell, one would generally ensure that a significant period of time did not expire between the time of each delivery, such that the agent and expression construct would still be able to exert an advantageously combined effect on the cell. In such instances, it is contemplated that one would contact the cell with both modalities within about 12–24 hours of each other and, more preferably, within about 6–12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either TS10q23.3 or the other agent will be desired. Various combinations may be employed, where TS10q23.3 is "A" and the other agent is "B", as exemplified below:

A/B/A B/A/B B/B/A A/A/B B/A/A A/B/B B/B/B/A B/B/A/B

A/A/B/B A/B/A/B A/B/B/A B/B/A/A B/A/B/A B/A/A/B B/B/B/A

A/A/A/B B/A/A/A A/B/A/A A/A/B/A A/B/B/B B/A/B/B B/B/A/B

Other combinations are contemplated. Again, to achieve cell killing, both agents are delivered to a cell in a combined amount effective to kill the cell.

Agents or factors suitable for use in a combined therapy are any chemical compound or treatment method that induces DNA damage when applied to a cell. Such agents and factors include radiation and waves that induce DNA damage such as, γ-irradiation, X-rays, UV-irradiation, microwaves, electronic emissions, and the like. A variety of chemical compounds, also described as "chemotherapeutic agents," function to induce DNA damage, all of which are intended to be of use in the combined treatment methods disclosed herein. Chemotherapeutic agents contemplated to be of use, include, e.g., adriamycin, 5-fluorouracil (5FU), etoposide (VP-16), camptothecin, actinomycin-D, mitomycin C, cisplatin (CDDP) and even hydrogen peroxide. The invention also encompasses the use of a combination of one or more DNA damaging agents, whether radiation-based or actual compounds, such as the use of X-rays with cisplatin or the use of cisplatin with etoposide. In certain embodiments, the use of cisplatin in combination with a TS10q23.3 expression construct is particularly preferred as this compound.

In treating cancer according to the invention, one would contact the tumor cells with an agent in addition to the expression construct. This may be achieved by irradiating the localized tumor site with radiation such as X-rays, UV-light, γ-rays or even microwaves. Alternatively, the tumor cells may be contacted with the agent by administering to the subject a therapeutically effective amount of a pharmaceutical composition comprising a compound such as, adriamycin, 5-fluorouracil, etoposide, camptothecin, actinomycin-D, mitomycin C, or more preferably, cisplatin. The agent may be prepared and used as a combined therapeutic composition, or kit, by combining it with a TS10q23.3 expression construct, as described above.

Agents that directly cross-link nucleic acids, specifically DNA, are envisaged to facilitate DNA damage leading to a synergistic, antineoplastic combination with TS10q23.3. Agents such as cisplatin, and other DNA alkylating agents may be used. Cisplatin has been widely used to treat cancer, with efficacious doses used in clinical applications of 20 mg/m$^2$ for 5 days every three weeks for a total of three courses. Cisplatin is not absorbed orally and must therefore be delivered via injection intravenously, subcutaneously, intratumorally or intraperitoneally.

Agents that damage DNA also include compounds that interfere with DNA replication, mitosis and chromosomal segregation. Such chemotherapeutic compounds include adriamycin, also known as doxorubicin, etoposide, verapamil, podophyllotoxin, and the like. Widely used in a clinical setting for the treatment of neoplasms, these compounds are administered through bolus injections intravenously at doses ranging from 25–75 mg/m$^2$ at 21 day intervals for adriamycin, to 35–50 mg/m$^2$ for etoposide intravenously or double the intravenous dose orally.

Agents that disrupt the synthesis and fidelity of nucleic acid precursors and subunits also lead to DNA damage. As such a number of nucleic acid precursors have been developed. Particularly useful are agents that have undergone extensive testing and are readily available. As such, agents such as 5-fluorouracil (5-FU), are preferentially used by neoplastic tissue, making this agent particularly useful for targeting to neoplastic cells. Although quite toxic, 5-FU, is applicable in a wide range of carriers, including topical, however intravenous administration with doses ranging from 3 to 15 mg/kg/day being commonly used.

Other factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage DNA, on the precursors of DNA, the replication and repair of DNA, and the assembly and maintenance of chromosomes. Dosage ranges for X-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells.

The skilled artisan is directed to "Remington's Pharmaceutical Sciences" 15th Edition, chapter 33, in particular pages 624–652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

The inventors propose that the regional delivery of TS10q23.3 expression constructs to patients with 10q23.3-linked cancers will be a very efficient method for delivering a therapeutically effective gene to counteract the clinical disease. Similarly, the chemo- or radiotherapy may be directed to a particular, affected region of the subjects body. Alternatively, systemic delivery of expression construct and/or the agent may be appropriate in certain circumstances, for example, where extensive metastasis has occurred.

In addition to combining TS10q23.3-targeted therapies with chemo- and radiotherapies, it also is contemplated that combination with other gene therapies will be advantageous. For example, targeting of TS10q23.3 and p53 or p16 mutations at the same time may produce an improved anti-cancer treatment. Any other tumor-related gene conceivably can be targeted in this manner, for example, p21, Rb, APC, DCC, NF-1, NF-2, BCRA2, p16, FHIT, WT-1, MEN-I, MEN-II, BRCA1, VHL, FCC, MCC, ras, myc, neu, raf, erb, src, fms, jun, trk, ret, gsp, hst, bcl and abl.

It also should be pointed out that any of the foregoing therapies may prove useful by themselves in treating a TS10q23.3. In this regard, reference to chemotherapeutics and non-TS10q23.3 gene therapy in combination should also be read as a contemplation that these approaches may be employed separately.

E. Formulations and Routes for Administration to Patients

Where clinical applications are contemplated, it will be necessary to prepare pharmaceutical compositions—expression vectors, virus stocks, proteins, antibodies and drugs—in a form appropriate for the intended application. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions of the present invention comprise an effective amount of the vector to cells, dissolved or dispersed in a pharmaceutically acceptable carrier or aqueous medium. Such compositions also are referred to as inocula. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well know in the art. Except insofar as any conventional media or agent is incompatible with the vectors or cells of the present invention, its use in therapeutic compositions is contemplated. Supplementary active ingredients also can be incorporated into the compositions.

The active compositions of the present invention may include classic pharmaceutical preparations. Administration of these compositions according to the present invention will be via any common route so long as the target tissue is available via that route. This includes oral, nasal, buccal, rectal, vaginal or topical. Alternatively, administration may be by orthotopic, intradermal, subcutaneous, intramuscular, intraperitoneal or intravenous injection. Such compositions would normally be administered as pharmaceutically acceptable compositions, described supra.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral administration the polypeptides of the present invention may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

VII. Transgenic Animals/Knockout Animals

In one embodiment of the invention, transgenic animals are produced which contain a functional transgene encoding a functional TS10q23.3 polypeptide or variants thereof. Transgenic animals expressing TS10q23.3 transgenes, recombinant cell lines derived from such animals and transgenic embryos may be useful in methods for screening for and identifying agents that induce or repress function of TS10q23.3. Transgenic animals of the present invention also can be used as models for studying indications such as cancers.

In one embodiment of the invention, a TS10q23.3 transgene is introduced into a non-human host to produce a transgenic animal expressing a human or murine TS10q23.3 gene. The transgenic animal is produced by the integration of the transgene into the genome in a manner that permits the expression of the transgene. Methods for producing transgenic animals are generally described by Wagner and Hoppe (U.S. Pat. No. 4,873,191; which is incorporated herein by reference), Brinster et al. 1985; which is incorporated herein by reference in its entirety) and in "Manipulating the Mouse Embryo; A Laboratory Manual" 2nd edition (eds., Hogan, Beddington, Costantimi and Long, Cold Spring Harbor Laboratory Press, 1994; which is incorporated herein by reference in its entirety).

It may be desirable to replace the endogenous TS10q23.3 by homologous recombination between the transgene and the endogenous gene; or the endogenous gene may be eliminated by deletion as in the preparation of "knock-out" animals. Typically, a TS10q23.3 gene flanked by genomic sequences is transferred by microinjection into a fertilized egg. The microinjected eggs are implanted into a host female, and the progeny are screened for the expression of the transgene. Transgenic animals may be produced from the fertilized eggs from a number of animals including, but not limited to reptiles, amphibians, birds, mammals, and fish. Within a particularly preferred embodiment, transgenic mice are generated which overexpress TS10q23.3 or express a mutant form of the polypeptide. Alternatively, the absence of a TS10q23.3 in "knock-out" mice permits the study of the effects that loss of TS10q23.3 protein has on a cell in vivo. Knock-out mice also provide a model for the development of TS10q23.3-related cancers.

Methods for producing knockout animals are generally described by Shastry (1995, 1998) and Osterrieder and Wolf (1998). The production of conditional knockout animals, in which the gene is active until knocked out at the desired time is generally described by Feil et al. (1996), Gagneten et al. (1997) and Lobe and Nagy (1998). Each of these references is incorporated herein by reference.

As noted above, transgenic animals and cell lines derived from such animals may find use in certain testing experiments. In this regard, transgenic animals and cell lines capable of expressing wild-type or mutant TS10q23.3 may be exposed to test substances. These test substances can be screened for the ability to enhance wild-type TS10q23.3 expression and or function or impair the expression or function of mutant TS10q23.3.

EXAMPLES

The following examples are included to demonstrate preferred embodiments of the invention. It should be appreciated by those of skilled the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

Homozygous Deletions in Glioma Cell Lines

Figure 1:
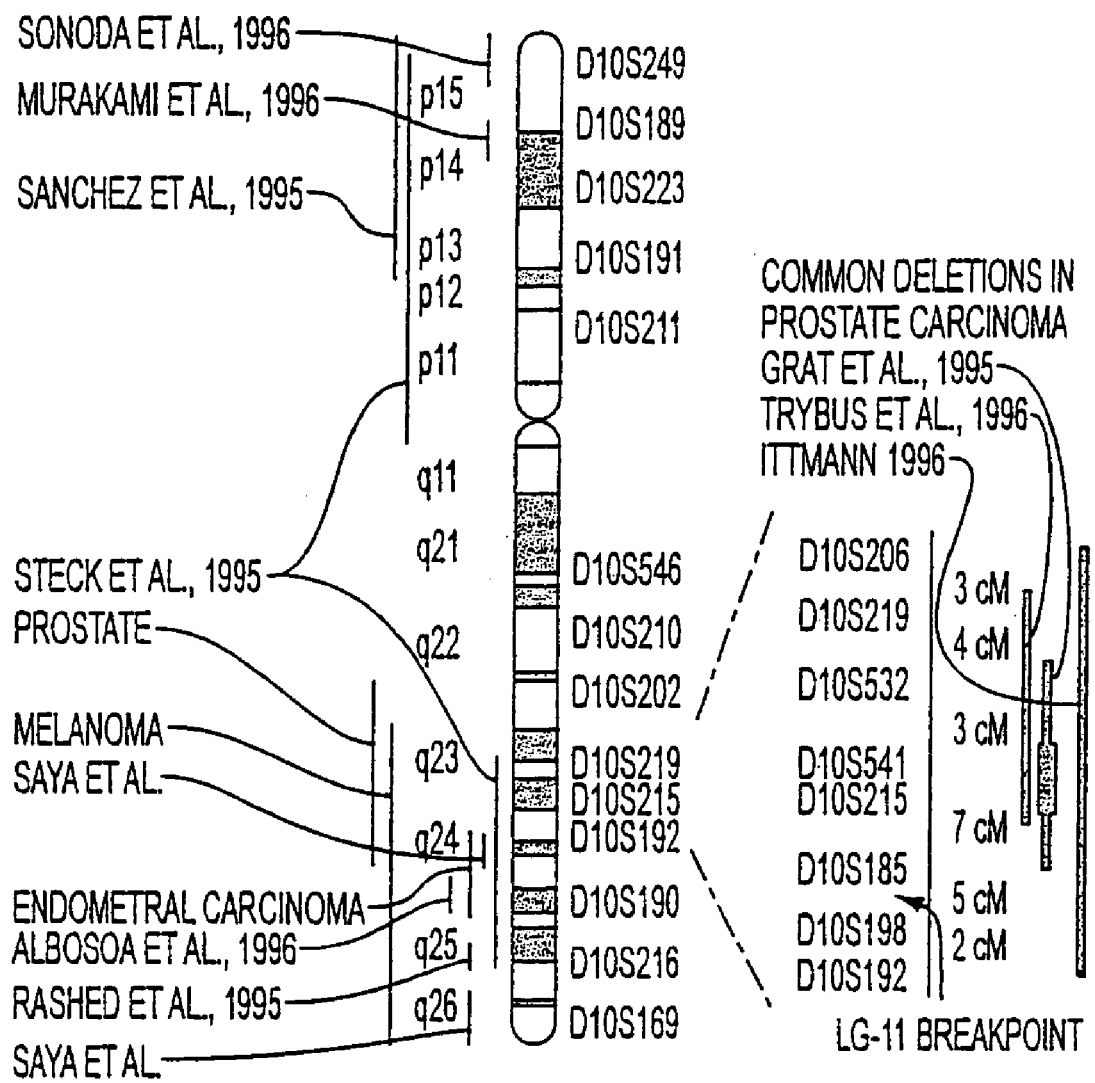
FIG. 1.—Localization of Candidate Tumor Suppressor Loci on Human Chromosome 10. Various loci on the human chromosome 10 have been implicated as possible sites for tumor suppressing activity. These locations, and the reporting group, are depicted.
Figure 2:
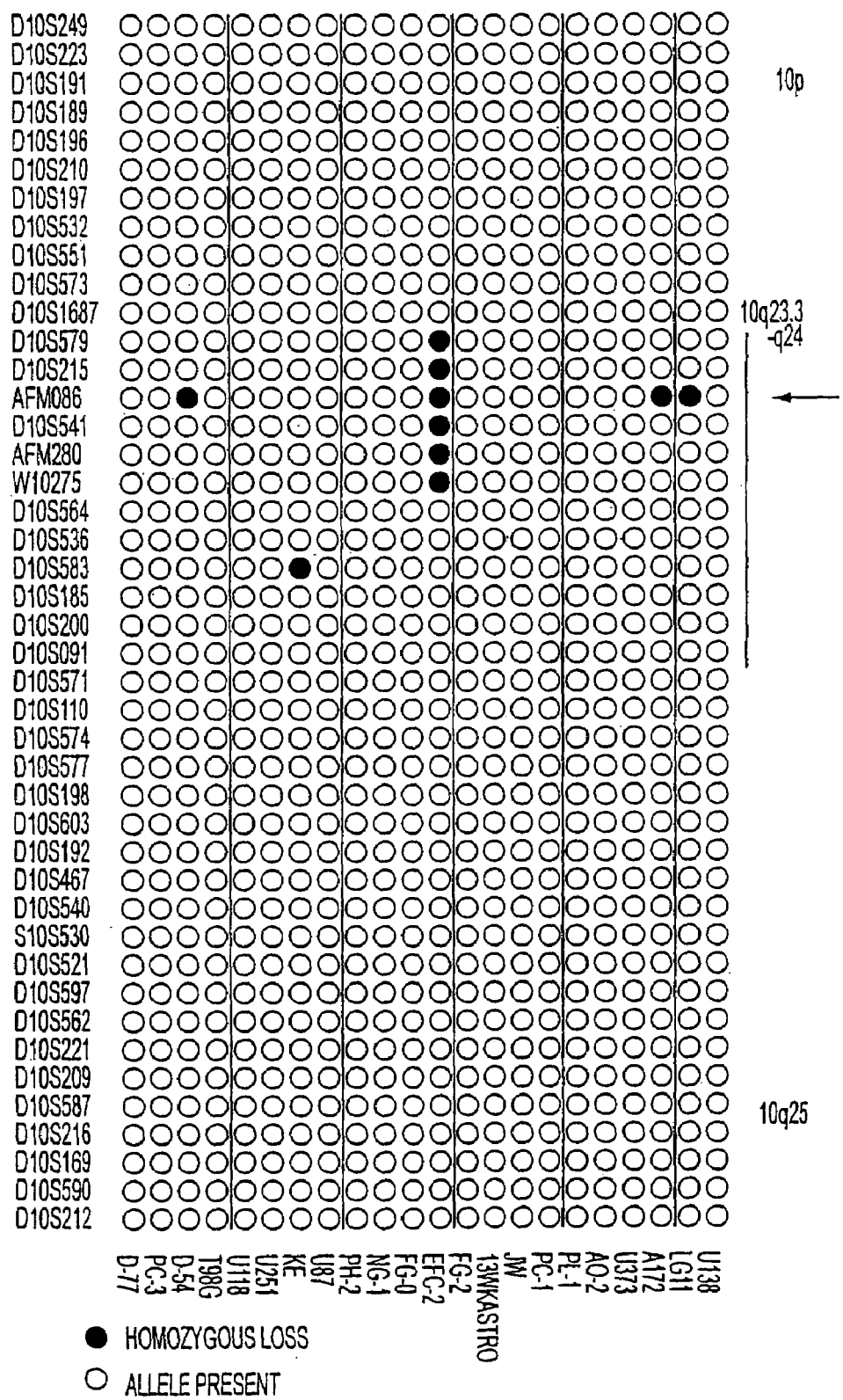
FIG. 2.—Illustration of Homozygous Deletions in Glioma Cell Lines. Various glioma cell lines were screened for the presence of deletions in both copies of loci on chromosome 10. Loci are indicated on the vertical axis and cell lines are listed across the horizontal axis. Homozygous loss is indicated by a darkened oval. The glioma cell lines D54, EFC-2, A172 and LG11 were examined for the presence of marker AFMA086WG9 (AFM086). The marker was shown to be deleted in multiplexed polymerase chain reactions using several additional chromosome 10 polymorphic alleles in independent reactions. Allele D10S196 is shown as the control for the PCR™ reaction. EFC-2 cells showed homozygous deletion of 4 contiguous markers (see FIG. 2).

The inventors have examined DNA from a series of 21 glioma cell lines and primary cultures, along with normal cells, to identify homozygous deletions of genomic material on chromosome 10. Markers were chosen for their approximate location at or near previously implicated regions (FIG. 1). The cells analyzed were generated in the Department of Neuro-Oncology UTMDACC (LG11, EFC-2, PL-1, PC-1, JW, FG-2, FG-0, NG-1, PH-2, KE, PC-3, and D77), were commercially available (U138, A172, U373, U87, U251, U118, and T98G), or obtained from collaborators (13 wk astro, D54-MG). Markers were obtained from Research Genetics, Huntsville, Ala., or synthesized from reported sequence. Once cell line, EFC-2, revealed a large homozygous deletion associated with four markers surrounding D10S215 (FIG. 2). This deletion was also observed by FISH using YAC 746h6, which maps to the region. Three other cell lines (D-54, A172, and LG11) also demonstrated homozygous deletions at AFM086, thereby strongly implicating the region to contain a putative tumor suppressor gene (FIG. 2). Deletions in PCR™ reactions were performed in the presence of two primer pairs (multiplexed) to assure appropriate amplification conditions. All deletions were confirmed by (at least) triplicate reactions. This same region has also been implicated in prostate carcinoma (Gray et al., 1995). Homozygous deletions in cell lines also have been used to define a tumor suppressor gene locus at 3p21.3 in small cell lung carcinoma (Daly et al., 1993; Kok et al., 1994; Wei et al., 1996).

Example 2

Retention of 10q Loci in Suppressed Hybrid Cells

Figure 3:
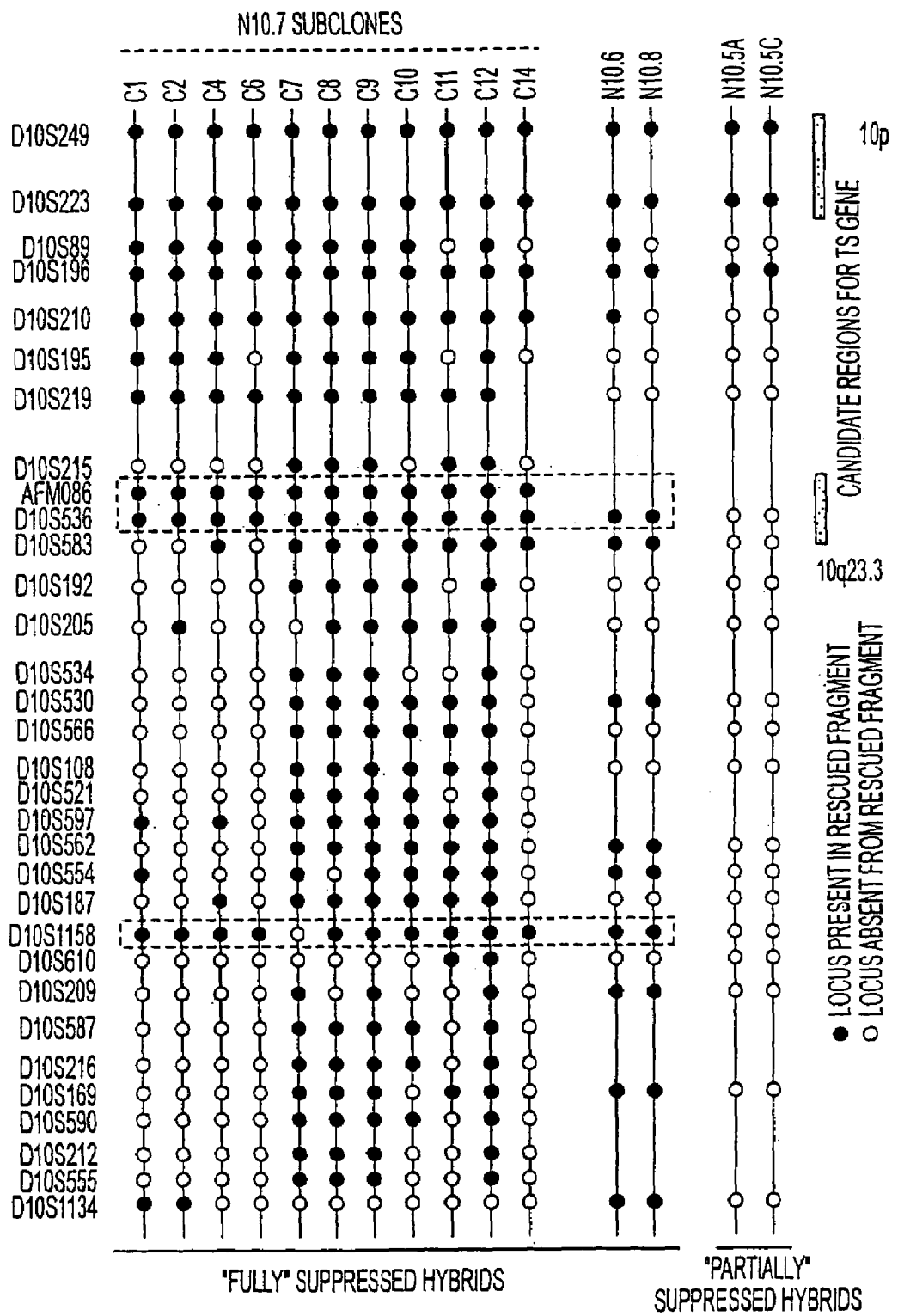
FIG. 3.—Illustration of Regions of Chromosome 10: Presence or Absence of DNA Microsatellite Markers in Hybrid Clone. Regions of chromosome 10 presence (solid circle) or absence (open circle) of DNA corresponding to chromosome 10 specific microsatellite markers from eleven subclones of the somatic cell hybrid clone U251.N10.7 that were transferred into mouse A9 cells are illustrated. The U251.N10.6 and U251.N10.8 somatic cell hybrids are fully suppressed clones, exhibiting no or little growth in soft agarose, and the U251.10.5A and C subclones are partially suppressed (Steck et al., 1995). The difference between the fully suppressed clones and the partially suppressed clones provides a functional localization of the tumor suppressor gene. The possible regions that contain the tumor suppressor gene are indicated by the hatched boxes. The hatched box at 10q23.3 overlaps with the homozygous deletions and region implicated by allelic deletion analysis (see FIG. 2 and FIG. 4).

The inventors' second strategy was to examine the regions of chromosome 10 that were retained in suppressed hybrid clones, but absent in the revertant clones. This analysis extended the inventors' previous study, showing the presence of two tumor suppressor loci on chromosome 10 and analyzing the regions that were retained. Hybrids retaining all or portions of 10q failed to grow in soft agarose and in nude mice ("fully" suppressed clones), while hybrid cells that lost the majority of the inserted chromosome 10q grew in soft agarose, but were nontumorigenic ("partially" suppressed clones; Steck et al., 1995; FIG. 3, right side). Original clones U251N10.6, N10.7, and N10.8 previously were shown to retain only fragments of 10q (Pershouse et al., 1993; Steck et al., 1995). Using additional informative microsatellite markers, three retained regions were identified in all three suppressed clones; a 22 cM region from D10S219 to D10S110, a 14 cM region from D10S192 to D10S187, and a 18 cM region from D10S169 through D10S1134 (FIG. 3).

To bypass this limitation, the originally transferred neomycin resistance-tagged chromosome 10 from hybrid U251.N10.7 was "rescued" by microcell-mediated chromosome transfer into mouse A9 cells. This allows all human microsatellite markers to be informative for the presence of chromosome 10. The basis for this analysis is that all "fully"

suppressed subclones should retain a common region and this region is deleted in the "partially" suppressed subclones. An additional impetus was that N10.7 displayed considerable heterogeneity in the size of chromosome 10 retained, as determined by FISH using chromosome 10 specific probes. Also, hybrid cells used for this rescue were first assayed for soft agarose growth and showed no colony formation. The mouse hybrids containing the transferred human chromosome 10 all contained the short arm of chromosome 10. The same region was retained in the "partially" suppressed clones (N10.5a–j) that grew in soft agarose (Steck et al., 1995), thus excluding this region (10pter-10q11) as containing the 10q tumor suppressor gene. Examination of the retained regions of 10q illustrated considerable heterogeneity (FIG. 3). The majority of clones showed either partial or extensive deletions of 10q23–26. Only two regions were retained in all the subclones examined. The most centromeric region retained involved the markers D10S210 and D10S219. However, these markers were absent in the original N10.6 and/or N10.8 clones, excluding this region (FIG. 3). The other region was centromeric of D4S536 but telomeric of D10S215 (~4 cM). The markers AFM086 and D10S536 were retained in all clones examined (boxed region in FIG. 3). These markers were absent in the partially suppressed clones (N10.5a–j). These results demonstrate that a common region, surrounding AFM086, is retained in all hybrid cells that are phenotypically suppressed. This same region is deleted in several glioma cell lines.

This analysis has several limitations. First, the rescued clones cannot be analyzed for biological activity, therefore any changes in chromosome 10 which may have occurred during or after transfer could not be detected. To partially address this concern, the inventors' analysis was performed as soon as the clones were able to be harvested. Furthermore, retention of this portion of the chromosome may only "correct" an in vitro artifactual deletion. Consequently, allelic deletion studies were performed to determine if this region was involved in gliomas. Also, an alternative region was suggested by this analysis at D10S1158, where all the clones but one (C7) retained this region. However, the retained region at AFM086 also exhibited homozygous deletions, thereby being implicated by two alternative methods as compared to D10S1158. It is also interesting to note that the tumor suppressor gene region appears to be preferentially retained, while the remainder of 10q is fragmented.

Example 3

Allelic Deletion Analysis of 10q

Figure 4:
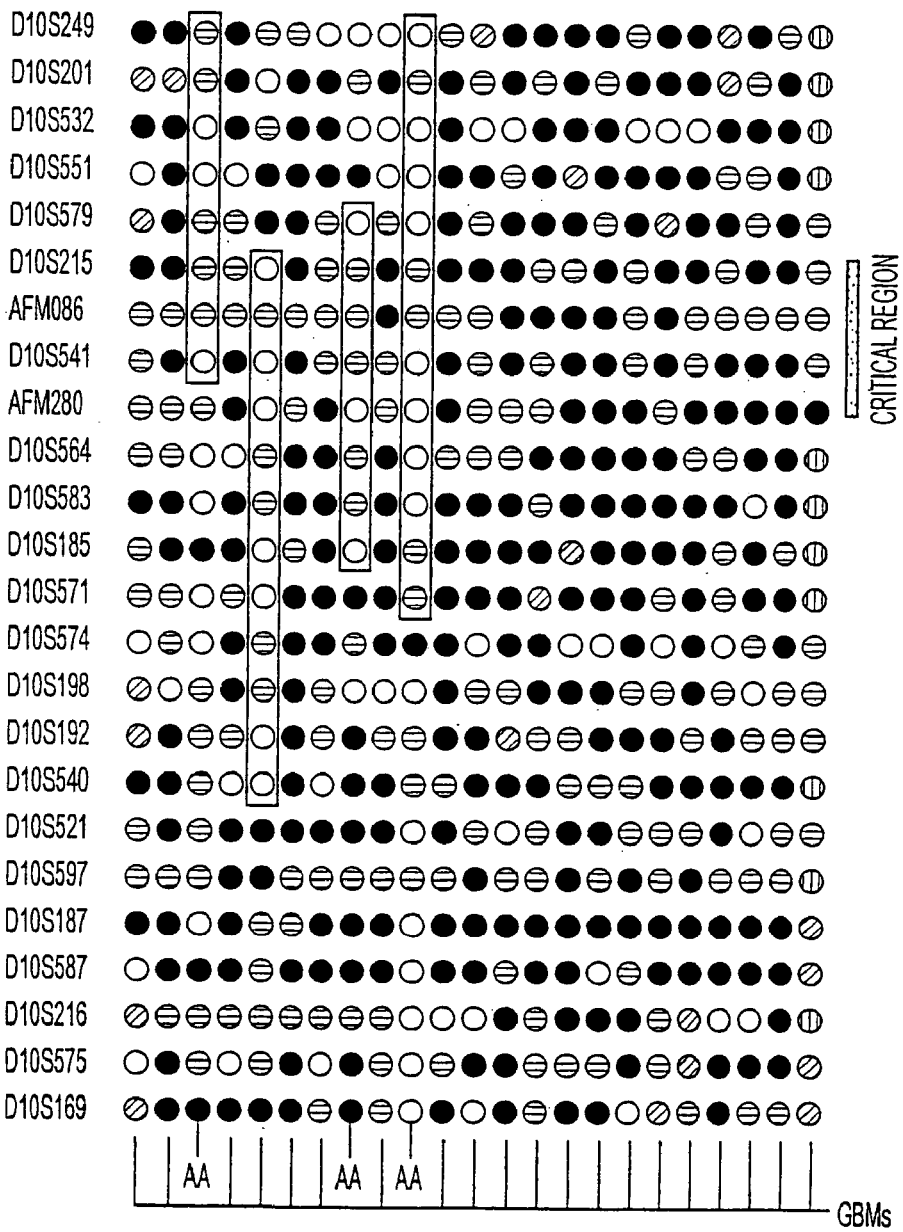
FIG. 4.—Deletion Map of Chromosome 10 in Human Gliomas. The region bounded by the markers D10S551 to D10S583 are located in a 10 cM region. The microsatellites are shown in their order of most probably linkage and mapped to their approximate chromosomal location based on the radiation hybrid map as described by Gyapay et al., 1994. The region of chromosome 101 that is not involved in anaplastic astrocytomas and one glioma is shown in the boxed regions of the tumor. The critical region defined from the homozygous deletion analysis and not excluded by this analysis is shown by the solid bar on the right side.

An allelic deletion study was performed on DNA from a series of 53 glioma specimens and corresponding patient lymphocytes using microsatellite markers specific for chromosome 10. This study was undertaken to determine if our critical region also was involved in glioma specimens. Extensive deletions were observed in the majority of specimens derived from GBM, with 30 of 38 GBMs exhibiting deletion of most or all of chromosome 10 markers. Less extensive deletions were observed in the majority if specimens derived from anaplastic astrocytomas, while infrequent deletions were observed in astrocytomas and most oligodendrogliomas (FIG. 4 and data not shown). The majority of markers used in this analysis mapped to 10q23–26 (Gyapay et al., 1994). Similar to other studies, a common region of deletion could not be convincingly demonstrated, due to the large deletions in most GBM samples (Fults et al., 1993; Rasheed et al., 1995).

However, for the GBM specimens examined, all but one tumor sample (#9; FIG. 4) revealed deletions involving the region from D10S579 to D10S541. Furthermore, only one AA showed a deletion at the inventors' critical region, and no astrocytomas. Two oligodendrogliomas exhibited deletions within the critical region, but both were diagnosed as malignant. This study presents several possibilities. First, the deletions involving the inventors' critical region occur predominantly in GBMs and not in lower grade tumors. This would imply that loss of the tumor suppressor gene on chromosome 10q in the inventors' critical region would represent a genetic alteration associated with progression to GBM. In support of this hypothesis, even though deletions occur on 10q in lower grade tumors, no common region of deletion on 10q was identified for these specimens. This observations would, again, support the inventors' previous suggestion that deletion of the 10q tumor suppressor gene is predominantly associated with GBMs and not all deletions on 10q affect the tumor suppressor gene. The region D10S216 to D10S587, showed extensive deletions, but several GBMs exhibited retention of heterozygosity at this region (tumors #2, #9, #13, #26; FIG. 4). Also, if low grade tumors are excluded from their study, the inventors' region is implicated in all GBMs. This combination of independent approaches strongly suggests a 10q tumor suppressor gene maps to the region D10S215 to D10S541, specifically at AFM086.

Example 4

Mapping of Candidate Tumor Suppressor Gene Region

Figure 8:
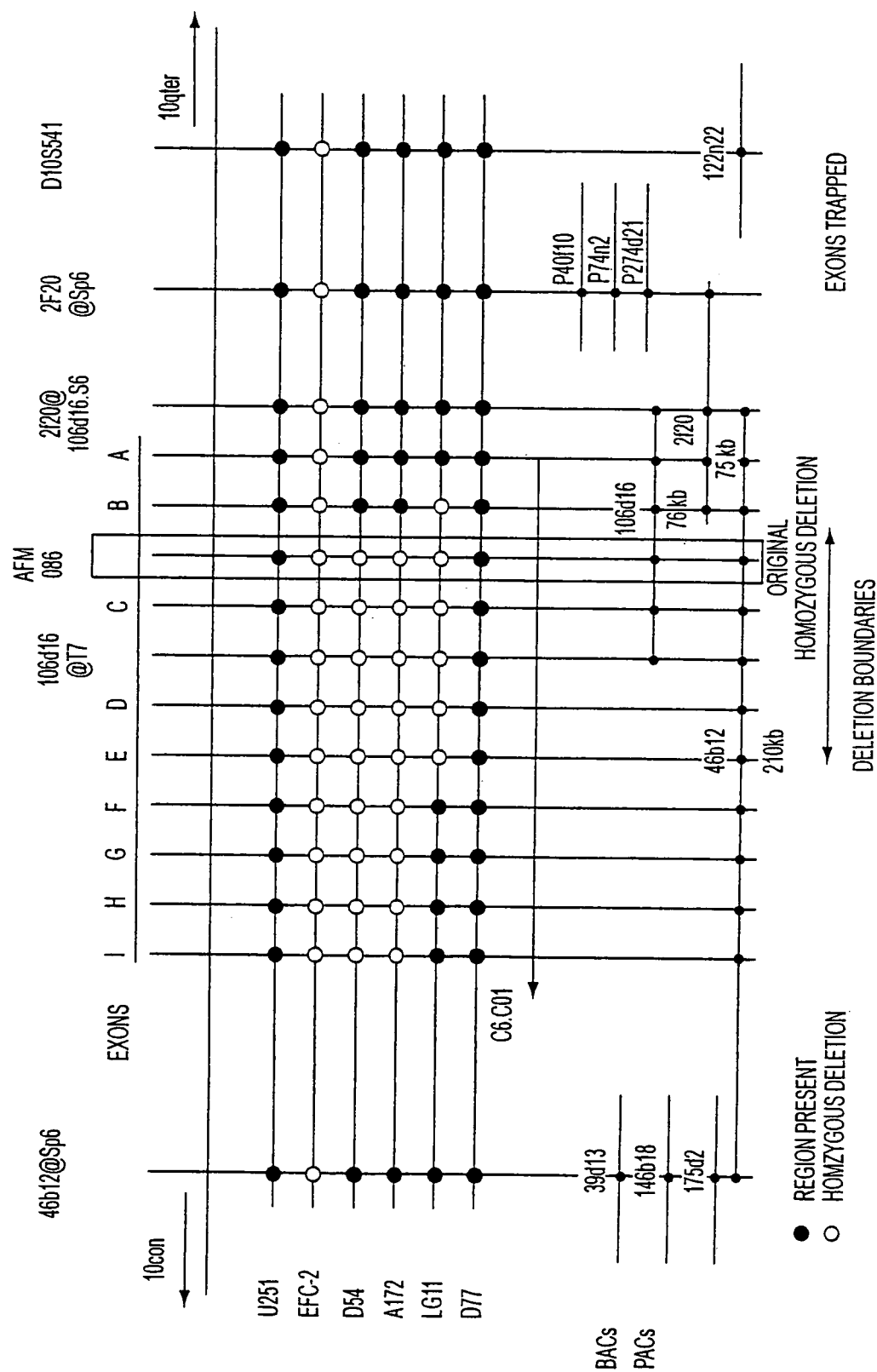
FIG. 8.—Deletional Analysis of 10q23.3. Glioma line initially indicated as having homozygous deletions in 10q23.3 were reanalyzed for the presence of the TS10q23.3 gene. Darkened oval indicates that the gene region is present; open oval indicates a homozygous deletion in the gene region. *—indicates exons trapped.

The critical region the inventors have identified is centered at AFM086 and is bordered by D10S215 and S10S541 (FIGS. 2 and 8). This region is relatively small, being contained within several individual YACs (787d7; 746h8; 934d3). FISH painting with YAC 746h8 on EFC-2 metaphase spreads shows that the homozygous deletion is contained within the YAC as the YAC was partially observed and adjacent YACs on both sides were present. Bacterial artificial chromosomes (BACs) or PACs for all markers in the region have been isolated (FIG. 8). The BAC contig of the region was constructed from end sequences of BACs mapping to the region. Several notable features have been identified. First, two overlapping BACs were identified (46b12 and 2f20) and verify the genomic integrity of 106d16. Second, a Not I site was identified at one end of the BACs. The presence of the Not I site and coincident restriction digestion with SacII, EagI, and BssHII suggest the presence of a CpG island within 106d16.

Figure 5:
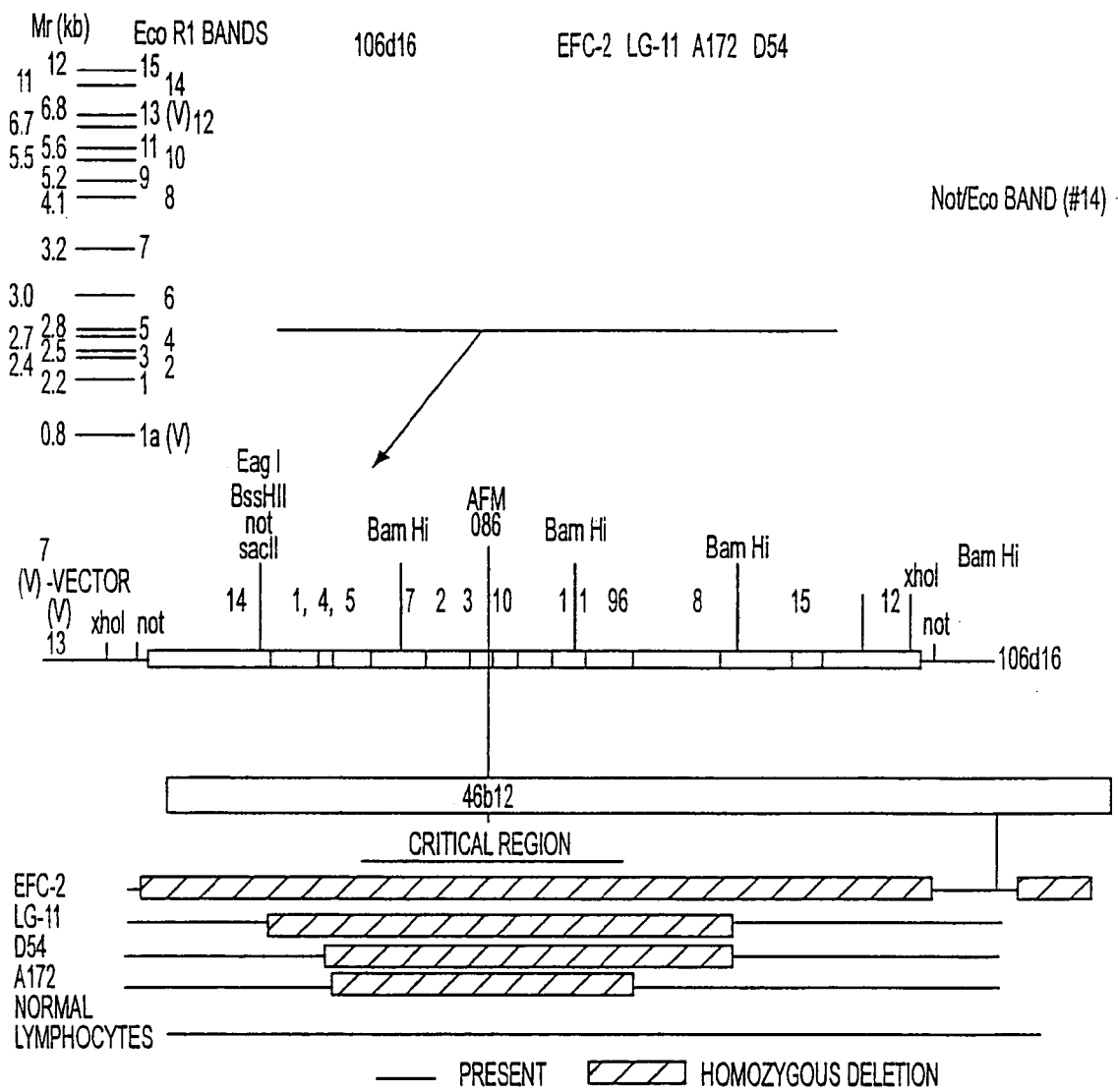
FIG. 5.—Mapping of BAC106d16. Mapping of the BAC designated 106d16, and demonstration of homozygous deletion by Southern blotting is illustrated. The partial restriction map of 106d16 is depicted. The illustration of the blot shows the homozygous deletion of Eco band #14 (Mr approx. 11 kb) in EFC-2 cells.

The EcoRI fragments from BAC 106d16 were used to examine the extent of the homozygous deletions, by Southern blotting, in the glioma cells that were previously shown to have homozygously deleted AFM086 (FIGS. 2 and 5). The right side (EcoRI fragment 14) contains the probable CpG island and is present in three of the four cell lines. A NotI/EcoRI (#3) fragment was used as a probe on a Southern blot containing several BACs and the glioma cell line (FIG. 2). Deletions to the telomeric side (right side) have not been detected using probes from 46b12, except for EFC-2 cells. However, additional homozygous deletions have been observed in the cells within the region defined by 106d16 (~65 kb). A homozygous deletion for band 3 is observed for LG11 and EFC-2 cells, but not the additional glioma cells or normal controls. 106d16 (band 12) has been observed to be present in all cells (EFC-2 exhibits an altered migrating band), suggesting the homozygous deletion is contained entirely within 106d16.

Example 5

Identification of Expressed Genes within the Critical Region

EcoRI fragments from BAC 106d 16 were generated and size separated by agarose gel electrophoresis. Individual bands or pools of similar sized bands were ligated into pSPL3 (GIBCO, Gaithersburg, Md.). Putative exons were identified as described by the manufacturer. Two exons were properly spliced into the trapping vector. The exons were derived from band pool 2, 3, 4, 5 and band 7. The sequence of the trapped exons was determined and defined by the known trapping vector sequence. Using BLAST searches of expressed sequence tag (dbEST) database, five potential expressed sequence tags (ESTs) were identified. Two ESTs (gb/H92038, AA009519) were observed to contain either one or both of the exons (albeit one EST was in the wrong orientation).

Sequencing primers were generated from the ESTs and used to define putative exon-intron boundaries using BAC46b12 as a template. Nine exons were identified. Sequence differences between the ESTs and the genomic template were corrected. All the exons were contained within BAC 46b12. Primers were generated from the intron sequences adjacent to the exons to form amplicon units for each exon. Two of the exons were corresponded to the trapped exons from the BAC 106d16 EcoRI sequences. The sequence of the gene is shown in FIG. 6. The predicted amino acid reading was defined by the presence of an ATG start site, TGA and TAA stop codons in frame, the presence of multiple stop codons in all three reading frames elsewhere in the sequence, nine splicing sites, and the presence of Kozak signals near the initiation site. The 403 amino acid sequence is shown in FIG. 7 and FIG. 9. The predicted molecular weight is 47,122 with a pI of 5.86.

A possible functional role for the protein product is suggested by its sequence homology to several protein motifs. A critical motif from residues 88 to 98 [IHCK-AGKGRTG](SEQ ID NO:28) has an exact match for the conserved catalytic domain of a protein tyrosine phosphatase [(I/V)HCxAGxxR(S/T)G] (SEQ ID NO:29; Denu et al., 1996). Several other motifs were identified that would agree with the phosphatase function for the tumor suppressor gene.

Amplicons (PCR™ products generated from various regions of the gene) were generated from random primed cDNA. The amplicons sequence corresponded to the DNA sequence. Non-overlapping amplicons were used to probe Northern blots of normal tissue derived from various organs (Clontech, Palo Alto, Calif.; multitissue blots). All amplicons identified a major band at 5.5 to 6 kb on the Northern blots and several minor bands. The message was expressed in all tissues examined (heart, brain, placenta, lung, liver skeletal muscle, kidney, pancreas, spleen, thymus, prostate, testes, ovary, small intestine, colon and peripheral blood lymphocytes).

Example 6

Mutational Analysis

The mutational analyses have initially proceeded on two fronts. First, the glioma cell lines initially shown to have homozygous deletions were analyzed for the presence of the candidate gene. As shown in FIG. 8, all of the cell lines that exhibited deletion of AFM086 had homozygous deletions of multiple exons of the candidate gene. Furthermore, the deletions occurred in the middle of the gene, thus defining the deletion boundaries (similar deletions in all cell lines) between exons 2 and 7. Deletions that affect the middle of the gene further indicate that the identified gene represents the gene targeted for mutation.

Preliminary analysis for sequence mutations was also performed on a series of glioma cell lines. Mutations and/or deletions were observed in all but three glioma cell lines examined (Table 5). Reference to base number in the table references the exon, not the entire sequences, i.e., the 98th base of exon 7 for U251.

TABLE 5

IDENTIFIED MUTATIONS IN CANDIDATE GENE

| | Cells | Cell Type | Mutation | Predicted Effect |
|---|---|---|---|---|
| 1 | U87 | glioma | splice junction exon 3: G + 1 > T | splicing variant |
| 2 | U138 | glioma | splicing site exon 8; G + 1 > T | splicing variant |
| 3 | U251 | glioma | 2 bp addition exon 7; 98 ins TT | |
| 4 | U373 | glioma | frame shift exon 7 | |
| 5 | EFC-2 | glioma | -all exons | no product |
| 6 | D54 | glioma | -exons 3–9 | no product |
| 7 | A172 | glioma | -exons 3–9 | no product |
| 8 | LG11 | glioma | -exons 2–9 | no product |
| 9 | T98G | glioma | missense exon 2; T46→G | leu > arg |
| 10 | KE | glioma | missense exon 2; G28→A | gly > glu |
| 11 | F60 | glioma | terminal mutation exon 8; C202→T | terminal stop |
| 12 | D77 | glioma | no mutation (heterogeneous for 10q | |
| 13 | PC-3 | low grade | no mutation | |
| 14 | PH-2 | low grade | no mutation | |
| 15 | nLnCap | prostate | deletion exon 1, 16–17 del AA; mutation exon 2, C53→T | silent |

Also, deletions of exons were found in LnCap, a prostate cell line. The glioma cells that failed to show a mutation/deletion were derived from low grade tumors (PC-3 and PH-2) where no allelic deletion of chromosome 10 is expected and has been observed for these cells. The other cells (D77) were a primary cell culture, and chromosome 10 was shown to be heterozygous from a 1 bp polymorphism within the gene. A breast cancer cell line also showed a mutation. This initial analysis supports the inventors' conclusion that loss of a 10q tumor suppressor gene represents a critical molecular marker for glioblastoma and disease progression.

Example 7

Analysis of TS10Q23.3 Mutations in Cancer Specimens and Tumor Cell Lines

In a more extensive study, the inventors report the incidence of TS10q23.3 mutations in 342 primary tumor specimens and 164 tumor cell lines (TCLs), which exhibit apparent LOH across the TS10q23.3 locus, from various cancer types. Out of 75 TCLs that displayed apparent loss of heterozygosity (LOH) across the TS10q23.3 locus, the inventors found ten homozygous deletions that removed coding portions of TS10q23.3, along with one frameshift, one nonsense and seven missense variants. In contrast, out of 84 primary tumors prescreened for LOH, the inventors only detected a frameshift lesion, a nonsense mutation, a splicing variant and a missense variant. Of interest, the expression of TS10q23.3 message was shown to be significantly reduced in high grade glioblastomas compared to normal brain tissues.

Methods

LOH Analysis: Total genomic DNA was purified from frozen specimens or deparaffinized sections. Total genomic DNA was purified from cancer cell lines using the Easy-DNA kit (Invitrogen, San Diego, Calif.). LOH analysis was performed as previously described (Teng et al., 1996; Steck et al., 1995). The polymorphic short tandem repeat markers used in this study were: D10S1687 (heterozygosity index, H.I.=0.81; Ldb (Collins et al., 1996) radiation map location from p-telomere, R.L.=85 Mb), D10S579 (H.I.=0.59; R.L.=86.4 Mb), D10S541 (H.I.=0.78; R.L.=86.5 Mb), AFM280WE1 (H.I.=not determined; R.L.=87 Mb), AFMA114XB1 (H.I.=0.70; R.L.=91.9 Mb) and D10S1753 (H.I.=0.74; R.L.=92.48 Mb). TS10q23.3 as defined by AFM086WE1 is at 86.5 Mb. LOH was assessed in primary tumor specimens, in the majority of cases, by quantitatively comparing STR marker amplicons generated from tumor and normal DNAs of each individual tested. In the case of TCLs and some primary tumors, LOH was assessed on the basis of combined apparent hemizygosity of AFMA114XB1, D10S541 and D10S1753; the likelihood that all three of these STR markers are homozygous in a given sample is less than 0.017.

Homozygous Deletion Screen: Using the cell line genomic DNAs as templates, nested PCR™ amplifications were performed with either TaqPlus (Strategene, La Jolla, Calif.) or AmpliTaq Gold (Perkin Elmer, Foster City, Calif.). The primers used for generating TS10q23.3 and MMK4 amplicons, and the PCR™ conditions used, are as described below. Twenty μl of the secondary reactions were fractionated on 2–3% Nu Sieve (FMC Bioproducts) agarose gels and subsequently visualized.

Mutation screen: The inventors performed nested PCR™ amplifications on genomic DNAs of tumor specimens or TCLs, and screened the resulting amplicons for sequence variants according to the procedures of Steck et al., (1997) with several modifications. First, exon 6 was screened with a single secondary amplicon amplified using the exon 6 FB-RR primer pair. Second, after a primary amplification of exon 8 using FA-RP primers, the exon was screened as two secondary amplicons using the following FB-RQ and FC-RR primers:

```
CA6.ex8.FB                              (SEQ ID NO:33)
GTTTTCCCAGTCACGACGAGGTGACAGATTTTCTTTTTA

CA6.ex8.RQ                              (SEQ ID NO:34)
AGGAAACAGCTATGACCATTCGGTTGGCTTTGTCTTTA

CA6.ex8.FC                              (SEQ ID NO:35)
GTTTTCCCAGTCACGACGCATTTGCAGTATAGAGCGT
```

```
-continued
CA6.ex8.RR                              (SEQ ID NO:36)
AGGAAACAGCTATGACCATAGCTGTACTCCTAGAATTA
```

Third, since mononucleotide runs in certain introns caused poor dye-primer sequencing, the inventors obtained dye-terminator sequence data on secondary amplicons exon 8 FB-RQ and exon 9 FB-RR using the nested primers 5'-TTTTTTTTTAGGACAAAATGTTTC-3' (SEQ ID NO:37) and 5'-AATTCAGACTTTTGTAATTTGTG-3' (SEQ ID NO:38), respectively. The inventors obtained greater than 90% coverage of the TS10q23.3 coding sequence for all samples screened; all mutations were confirmed by sequencing a newly amplified product.

RT-PCR™ Expression: Messenger RNA was isolated from frozen sections of 10 normal tissue and 10 high normal tissue and 10 high grade gliobastoma specimens. Frozen sections (5 μm, 20 each) were cut and used to isolate mRNA (Micro-Fast Track; Invitrogen, San Diego, Calif.). Adjacent sections were histologically examined and the sections were shown to contain predominantly normal or tumor cells. Normal sections were obtained from regions that free from tumor during the normal course of therapeutic craniotomies. Complementary DNA was made using Superscript II and primers to amplify TS10q23.3 corresponding to −28 to 347 or 345 to 1232 of the coding region. The primers used were:

```
M5'F:
TCCTTTTTCTTCAGCCACAG          (SEQ ID NO:39)

M5' R:
ATTGCTGCAACATGATTGTC;         (SEQ ID NO:40)

M3'F:
TGACAATCATGTTGCAGCA;          (SEQ ID NO:41)

F3'R:
TTTATTTTCATGGTGTTTTATCC.      (SEQ ID NO:42)
```

The PCR™ conditions were similar to those previously described except the annealing step was performed at 53° C.

Characterization of a TS10q23.3 Pseudogene: DNA fragments were amplified from a human fetal brain cDNA library using Pfu polymerase and a nested PCR™ strategy. The initial χ μl reaction contained 100 ng of cDNA. The primer pair used in the first round of amplification were CTTCAGCCACAGGCTCCCAGAC (SEQ ID NO:43) and GGTGTTTTATCCCTCTTG (SEQ ID NO:44), after which the reaction was diluted 20-fold and reamplified with CGGGATCCATGACAGCCATCATCAAAGAGATC (SEQ ID NO:45) and CGGAATTCTCAGACTTTTGTAATTG (SEQ ID NO:46) primers. The PCR™ conditions used were an initial denaturation step at 94° C. for 5 min followed by 30 cycles of 94° C. for 45 s, 55° C. for 30 s, and 72° C. for 1 min. To determine the chromosomal location of this pseudogene, the inventors performed radiation hybrid mapping using the Genebridge 4 panel (Genome Systems) and the following primer pair designed to generate a specific 303 bp product from the pseudogene but not TS10q23.3: ATCCTCAGTTTGTGGTCTGC (SEQ ID NO:47) and GAGCGTGCAGATAATGACAA (SEQ ID NO:48). Using this STS, the inventors determined that the pseudogene was located at about 160 cR on chromosome 9. Additionally, the inventors have isolated two bacterial artificial clones (BACs), 145c22 and 188122, that carry this pseudogene and have confirmed its genomic DNA sequence. Comparison of TS10q23.3 coding sequence to that of the pseudogene revealed the following base differences: T2G, C89T, T202C, T242C, G248A, A258G, G397A, A405T, G407A, T531C, T544G, C556G, A672G, C700T, A705G, C720T C900T and A942G. The nucleotide sequence for the human TS10q23.3 pseudogene is set forth in SEQ ID NO:64.

Since TS10q23.3 appears to encode a tumor suppressor gene, the inventors' initial step toward identifying new mutations in this gene was to prescreen primary tumors and TCLs for LOH within this region of 10q23. Altogether 342 primary tumor specimens and 164 TCLs were examined for LOH using polymorphic short tandem repeat markers on chromosome 10 located near the TS10q23.3 locus (Table 6). In this panel of samples, the inventors observed LOH in primary tumor specimens at frequencies ranging from 20% in colon specimens to 75% in glioblastoma multiforms (GBMs), with an overall LOH frequency of ~49%. For TCLs with sample sizes greater than nine, the incidence of LOH varied from 28% (colon) to 82% (GBMs), with an overall frequency of ~46%.

To search for coding variants of TS10q23.3 in primary tumors, the inventors sequenced amplicons consisting of the exons and flanking splice junctions of this gene amplified from tumor DNAs that displayed LOH. A caveat of this approach is that it fails to identify regulatory mutations that affect the expression levels of this gene. In addition, this screen excludes the possibility of finding mutant homozygotes and compound heterozygotes but the incidence of these kinds of mutants is presumably low. Previously, the inventors reported that the incidence of TS10q23.3 coding variants in glioblastomas, breast and kidney carcinomas were 6/26 (23%), 2/14 (14%) and 1/4, respectively (Steck et al., 1997). In this study, out of 84 primary tumors exhibiting LOH surrounding the TS10q23.3 locus, the inventors detected a frameshift mutation (breast carcinoma), a nonsense mutation (pediatric GBM), a splicing variant (pediatric GBM) and a missense variant (melanoma; Table 7).

TABLE 6

LOH ANALYSES OF TUMOR SPECIMENS AND TUMOR CELL LINES

| Tumor Type | Tumor Specimens LOH/screened[1] | Sequenced[2,3] | Tumor Cell Lines LOH/screened[1] | Sequenced[2,4] |
|---|---|---|---|---|
| Brain (Gliomas) | 40/53[5] (75%) | 26[5] | 9/11[5] (82%) | 7[5] |
| Pediatric brain | 5/7 | 7 (2) | — | — |
| Bladder | — | — | 3/4 | 2 |
| Breast | 32/67[5] (48%) | 31[5] | 14/22 (64%) | 13 |
| Cecum | — | — | 1/6 | 1 |
| Colon | 3/15[6] (20%) | 1 | 7/25 (28%) | 7 |
| Duodenum | — | — | 1/1 | 1 |
| Endometrial | 6/13 (46%) | 0 | — | — |
| Head and neck | 9/14 (64%) | 9 | — | — |
| Kidney | 8/20[3] (40%) | 8[3] | — | — |
| Leukemia | — | — | 11/23 (48%) | 11 |
| Lung | 10/27 (37%) | 7 | 7/17 (41%) | 6 |
| Lymphoma | — | — | 2/3 | 2 |
| Melanoma | 10/21 (48%) | 15 | 7/14 (50%) | 3 |
| Neuroblastoma | — | — | 0/3 | — |
| Ovarian | 10/19 (52%) | 9 | 3/8 | 3 |
| Pancreatic | 7/19 (37%) | 0 | 5/12 (42%) | 5 |
| Prostate | 10/24 (42%) | 8 (2) | 1/1[7] | — |
| Retinoblastoma | — | — | 0/2 | — |
| Sarcomas | 4/16 (25%) | 6 (2) | — | — |
| Submaxillary gland | — | — | 1/1 | 1 |
| Testis | — | — | 3/5 | 3 |
| Thyroid | 6/17 (35%) | 2 | 0/2 | — |
| Uterine | — | — | 0/4 | — |
| Metastatic[8] | 6/10 (60%) | 8 (2) | — | — |
| Total | 166/342[5] (49%) | 137 (8)[5,9] | 75/164 (46%) | 65 |

[1]LOH percentage was only calculated for sample sizes greater than nine.
[2]Samples that amplified and sequenced successfully (>90% coding sequence screened).
[3]The number of non-LOH samples that were sequenced are shown in parentheses. Certain primary tumor DNAs, particularly pancreatic and endometrial carcinomas, were isolated from microdissected paraffin-embedded sections and failed to sequence at >90% coverage due to poor template quality.
[4]All TCLs screened displayed apparent LOH. TCLs with homozygous deletions in the coding portion of TS10q23.3 were not screened by sequencing.
[5]These totals include samples that were previously reported by Steck et al. (1997).
[6]Five of these colon samples consisted of cancers that had metastasized to the liver, although the liver metastases exhibited no LOH.
[7]The prostate line, NCIH660 (TCL10F4), was characterized by Li et al. (1997) and shown to be homozygously deleted from exons 2–9 of TS10q23.3.
[8]These metastatic tumor specimens originated from adenocarcinomas, a sarcoma, a renal cell carcinoma and a melanoma. The metastatic lesions were to the lung, except the melanoma which was to the groin.
[9]Of these 137 specimens analyzed by sequencing, 45 had been reported (Steck et al., 1997), 8 were non-LOH and 84 displayed LOH.

TABLE 7

TS10q23.3 Variants Identified in Primary Tumors and Tumor Cell Lines

| Sample | Type | Mutation | Exon/intron | Codon | Predicted Effect |
|---|---|---|---|---|---|
| PGT-2 | Pediatric glioma[1] | G > T at −1 | intron 2 | — | splicing variant |
| MT-1 | Melanoma[1] | CC112-113TT | exon 2 | 38 | Pro > Phe |
| TCL10B1 | Breast | T323G | exon 5 | 108 | Leu > Arg |
| TCL10H2 | Leukemia | T331C | exon 5 | 111 | Trp > Arg |
| TCL11E12 | Glioblastoma | T335G | exon 5 | 112 | Leu > Arg |
| PGT-5 | Pediatric glioma[1] | C388T | exon 5 | 130 | Arg > Stop |
| TCL10A7 | Breast | G407A | exon 5 | 136 | Cys > Tyr |
| TCL10F5 | Submaxillary Gland | T455C | exon 5 | 152 | Leu > Pro |
| TCL10H8 | Leukemia | C517T | exon 6 | 173 | Arg > Cys |
| TCL10F7 | Testis | G518C | exon 6 | 173 | Arg > Pro |
| TCL11F5 | Glioblastoma | C697T | exon 7 | 233 | Arg > Stop |
| BT-88 | Breast[1,2] | 705 del A | exon 7 | 235 | protein truncation |
| TCL10A3 | Breast | 823 del G | exon 7 | 275 | protein truncation |

[1]Primary tumor specimens.
[2]Analysis of corresponding normal DNA has shown that the TS10q23.3 mutation of this primary breast tumor sample is somatic. Similar analysis of the TS10q23.3 alterations in the other three primary tumor specimens was not possible because corresponding normal DNAs were not available. The inventors have, however, determined that all nine primary tumor mutations previously observed by Steck et al., (1997) arose somatically.

In addition to primary tumors, the inventors examined a set of tumor cell lines for alterations in the TS10q23.3 gene. These TCLs permitted the inventors to investigate cancer types that were not represented in the panel of primary tumors screened, including leukemia, lymphoma, neuroblastoma, retinoblastoma, as well as bladder, testis and uterine cancers. Out of the 75 TCLs exhibited LOH, the inventors identified ten homozygous deletions that affected the coding regions of TS10q23.3 (FIG. 13A and FIG. 13B). The homozygous deletions were present in TCLs from astrocytomas (1/1), bladder carcinoma (1/3), breast carcinoma (1/14), glioblastoma (2/8), lung carcinoma (1/7), melanoma (4/7) and prostate carcinoma (1/2). Whereas two of the cell lines had lost all nine TS10Q23.3 exons, the other eight TCLs had homozygously deleted different coding portions of the gene. Analysis of the remaining 65 TCLs revealed one frameshift, one nonsense and seven non-conservative missense variants (Table 7).

Figure 13C:
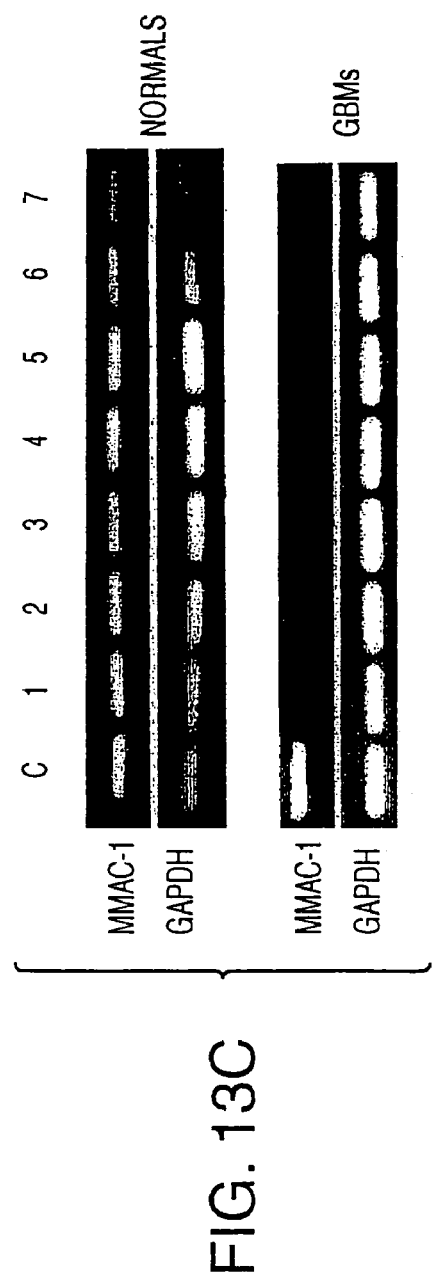
FIG. 13C. Homozygous deletion of the TS10Q23.3 gene in human tumor cell lines and TS10Q23.3 mRNA expression levels in primary glioblastomas. Expression of TS10Q23.3 message in human normal brain and GBM specimens as detected by RT-PCR™ analysis. The 5' terminal amplicon of TS10Q23.3 is shown. The lanes shown include a control amplicon (C) from PL-1 low grade glioma cDNA, along with seven normal and tumor specimens. Six of the 10 GBMs examined were examined for LOH surrounding the TS10Q23.3 locus and TS10Q23.3 gene alterations. All six samples exhibited LOH but no mutations were detected when the inventors screened their DNAs by sequencing. The expression levels of GADPH message was used to control for equivalent template quantities and qualities.
Figure 13D:
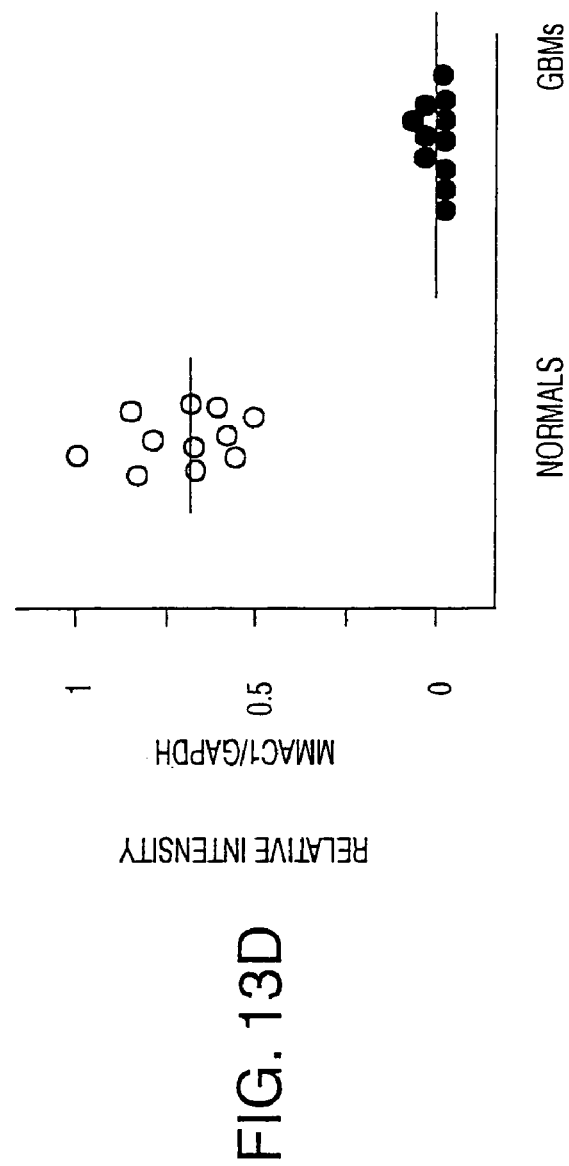
FIG. 13D. Homozygous deletion of the TS10Q23.3 gene in human tumor cell lines and TS10Q23.3 mRNA expression levels in primary glioblastomas. Ratio of the RT-PCR™ amplicon intensities of TS10Q23.3 to GADPH for every normal and GBM specimen.

Due to the relatively low frequency of observed TS10q23.3 mutations in primary tumors compared to that observed in TCLs, the inventors examined the expression of TS10q23.3 in a series of ten GBM and ten normal specimens. All normal samples exhibited expression of TS10q23.3, while none of the GBMs exhibited significant expression of this message (FIG. 13C and FIG. 13D). Weak signals were observed in certain samples upon prolonged exposure, although the inventors could not distinguish whether these levels of message were detected due to contamination of normal cells in the sections or low TS10q23.3 expression within the tumor cells. However, this observation suggests that the altered expression of TS10q23.3 may potentially play a role in the tumorigenesis of these GBMs. The mechanism(s) of inhibition of TS10q23.3 expression and the level of TS10q23.3 expression in other types of primary tumors are currently under investigation.

The inventors have investigated a large panel of primary tumors and TCLs, prescreened for LOH, for alterations in TS10q23.3. In this set of 84 primary tumors, the inventors only detected four potential inactivating TS10q23.3 mutations. Taken together with the inventors' previous findings (Steck et al., 1997), 8/31 (26%) primary glioblastomas, 3/31 (10%) primary breast, 1/8 (13%) primary kidney and 1/11 (9%) primary melanoma tumors showed TS10q23.3 alterations. Interestingly, two of the five pediatric GBMs exhibited TS10q23.3 alterations that should lead to the expression of non-functional protein, suggesting that further analysis of TS10q23.3 involvement in this childhood disease is warranted. In the set of 75 TCLs, the inventors observed a total of 19 putative inactivating TS10q23.3 mutations.

The actual incidence of TS10q23.3 mutations in the different cancer types will likely be between the frequency observed in primary tumors and that observed for the TCLs. The inventors' findings show that in comparison to primary tumors, TCLs harbor a significantly higher incidence of mutations in TS10q23.3 (Table 6). A similar observation has been reported by Spruck et al. for mutations of p16 in bladder cancers (Spruck III, et al., 1994). This discrepancy is likely due to one or more of the following possibilities. First, in order to be successfully cultured in vitro, tumor cells may require certain combinations of genetic lesions that are acquired in vivo. Second, mutation events in TS10q23.3 may confer a growth advantage or cause clonal selection during the passaging of TCLs in vitro. Third, the substantially reduced expression of TS10q23.3 observed in 10/10 primary GBM specimens suggest that certain tumors may not have coding mutations in this gene but may instead express diminished levels of functional TS10q23.3. And fourth, normal cell contamination and specimen heterogeneity of primary tumors may prevent the detection of homozygous deletions, a mutational mechanism observed for a significant number of TCLs at the TS10q23.3 locus. In control experiments, it was determined that even the presence of 5% contaminating normal tissue DNA within the tumor samples will prevent the identification of homozygous deletions using these procedures. Thus, the presence of homozygous deletions affecting TS10q23.3 in primary tumors could easily be underestimated by the inventors' analysis and will require alternative approaches to evaluate their occurrence. However, an additional complication is the presence of an apparently unspliced TS10q23.3 pseudogene, located on chromosome 9q; the coding sequence of TS10q23.3 differs from this putative pseudogene in 16/1209 bases (see Methods).

Figure 14:
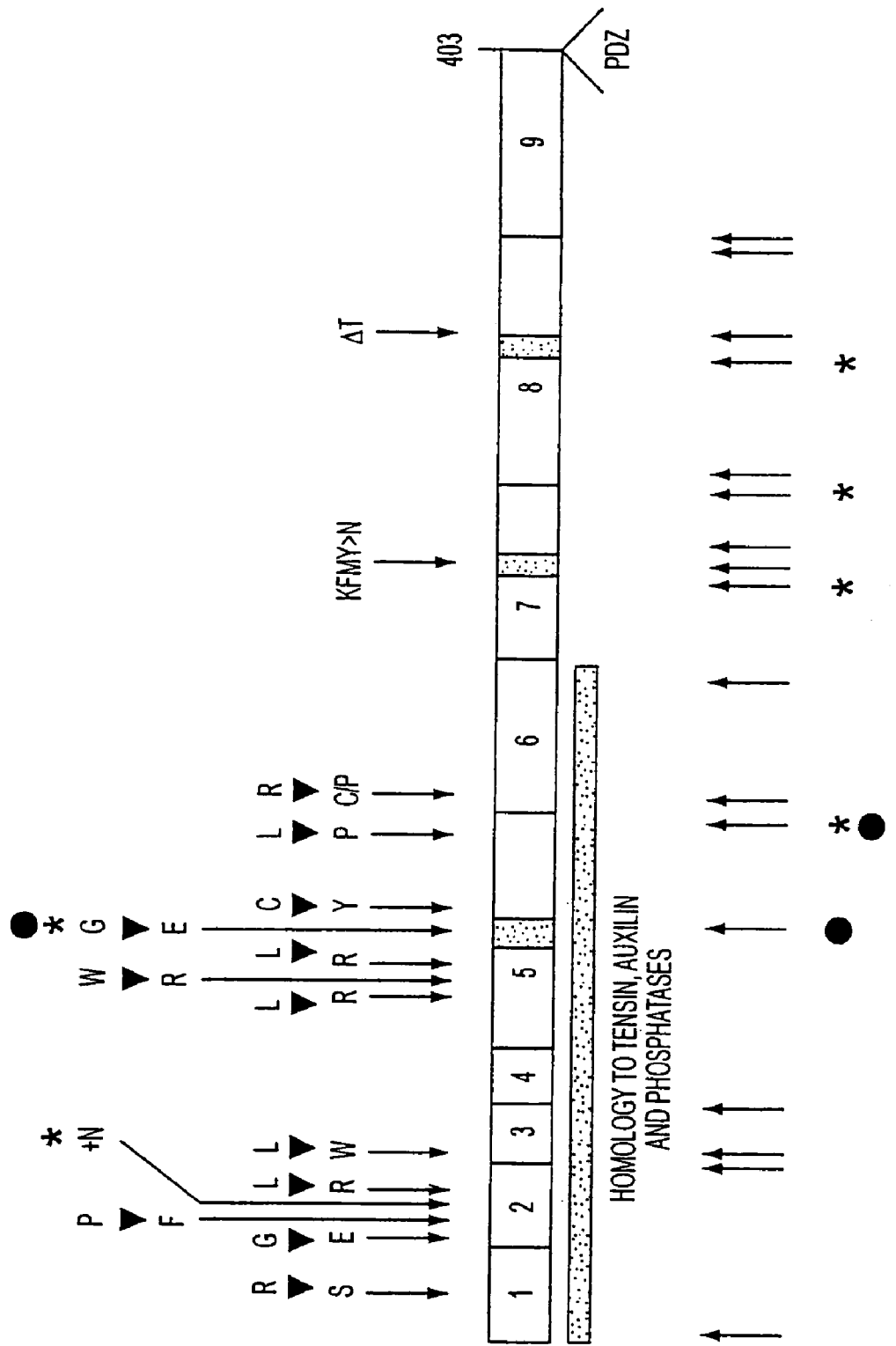
FIG. 14. Representation of the putative functional domains of TS10Q23.3 and the location of identified alterations. The N-terminal half of TS10Q23.3 is homologous to phosphatases, as well as the cytoskeletal proteins, tensin and auxilin (brown box). Also shown are the locations of the core phosphatase domain (red box), three potential tyrosine phosphorylation sites (blue boxes) and two potential serine phosphorylation sites (yellow boxes). The PDZ motif, ITKV, is located at the C-terminus of the protein. Shown are TS10Q23.3 variants identified by Steck et al. (1997), Li et al., (1997), and Liaw et al. (1997), and alterations detected in this study; blue arrows mark missense substitutions, black arrows indicate in-frame insertions or deletions, green arrows mark potential splicing variants, and red arrows represent frameshift or nonsense mutations that result in TS10Q23.3 truncations. Asterisks indicate germline mutations that were detected in Cowden's patients (Liaw et al., 1997), while the closed circles indicate lesions that have been observed in two presumably independent DNA samples.

A compilation of TS10q23.3 alterations shows that the spectrum of variants is diverse (FIG. 14). All of the non-conservative missense substitutions identified are found in the N-terminal portion of TS10q23.3 within its putative phosphatase domain. In contrast, the lesions that result in the truncation of TS10q23.3 are distributed throughout the gene. If all of the truncated forms of TS10q23.3 are nonfunctional, then the data indicate that the carboxy-terminal region of TS10q23.3 is essential for the expression of active protein. This is consistent with the notion that the potential phosphorylation sites and PDZ motif are important for TS10q23.3 function. Alternatively, the sequences of the C-terminal region of this protein may be required for proper folding. Of interest, the only germline mutations in TS10q23.3 reported to date have been detected in individuals with Cowden's syndrome (Liaw et al., 1997); all other primary tumor TS10q23.3 variants characterized have arisen somatically (Table 7). The diversity of the TS10q23.3 alterations observed predict that many distinct lesions of this gene exist in the population. Overall, the data suggest that TS10q23.3 is a tumor suppressor that plays a significant role in the genesis of many types of cancers.

Example 8

Role of TS10q23.3 Mutations in Early Onset Breast Cancer: Causative in Association with Cowden's Syndrome and Excluded in Brca1-negative Cases Methods Clinical Materials: Blood samples were obtained after informed consent from individuals with Cowden's syndrome. An aliquot was used for DNA extraction, while peripheral blood mononuclear cells were purified from a second sample and used to generate an EBV-transformed lymphoblastoid cell line. The diagnosis of CS was made using the International Cowden's Consortium CD diagnostic criteria (Nelen et al., 1996). For individuals with early onset breast cancer, the sample consists of 63 women who developed breast cancer before age 35 (average age at diagnosis is 27.7 yrs), did not have a clinical diagnosis of CS, and who had previously been shown not to carry clearly deleterious mutations in BRCA1 (5 women in the sample carried missense polymorphisms of unknown significance). These women are a subset of a sample of 798 unrelated individuals from 20 collaborating institutions, chosen from families which were generally at an elevated risk of carrying BRCA1 mutations. Most families were chosen because of multiple cases of breast cancer, early age of breast cancer diagnosis, and incidence of ovarian cancer, as these conditions have been previously shown to be associated with germline mutations of BRCA1. Some of the families extended to second degree relatives. All samples from institutions in the United States were collected from individuals participating in research studies on the genetics of breast cancer. A1 samples from institutions outside of the United States were collected according to the appropriate guidelines concerning research involving human subjects imposed by the institution's equivalent authorities. Only one representative from each family was included in the sample, and no families known to be linked by genetic markers to BRCA1 were included. This is a heterogeneous sample which represents the diversity amongst patients who present at high-risk clinics as opposed to the more controlled sampling done for family or population studies. This has directed the inventors' analyses towards methods which do not require that sample frequencies of subgroups reflect frequencies in the general population. Therefore the inventors can assess, for example, the probability that a woman with breast cancer diagnosed at age 30 carries a deleterious BRCA1 or TS10q23.3 (also referred to as MMAC1) mutation, but the inventors cannot estimate the frequency of such women in the general population. All the samples used in the TS10Q23.3 study were stripped of identifiers.

DNA Extraction: After informed consent was obtained, patients' genomic DNA was extracted from whole blood or lymphoblastoid cell lines using Q1Aamp blood Maxi Kit. Concentration was measured by $OD_{250}$ and purity was checked by the ratio of $OD_{260}/OD_{280}$.

Genotyping: Primer pairs for the chromosome 10 locus were obtained from Research Genetics. The forward strand primer was end-labeled in the presence of $^{33}$P-γATP and polynucleotide kinase. PCR™ reactions were performed in a total reaction volume of 30 microliters. The reactions consisted of 10 mM of each primer, 200 mM of deoxynucleotides, 1.5 units of Taq DNA polymerase and 50 ng of genomic DNA. PCR™ was performed for 35 cycles with 45 seconds denaturation at 94° C., 45 seconds annealing at 55° C. and 1 min elongation at 72° C. A final 10 min elongation was used. PCR™ reactions were stopped by addition of 20 microliters of stop solution (95% formamide, 1 mM EDTA, 0.25% bromophenol blue, 0.25% xylene cyanol). Then reactions were denatured for 5 min at 94° C. and the products were separated on a 8% denaturing polyacrylamide gel. Allele sizes were determined by comparing to the SequaMark (Research Genetics) which was included as a size standard on the gels.

Linkage Analysis: Two-point linkage analysis was performed using MLINK. Individuals below 20 years were considered as unknown. Disease gene frequency was set equal to 0.000001 and marker allele frequencies were estimated using ILINK. Both MLINK and ILINK are from the LINKAGE package Version 5.2 (Lathtop et al., 1984). Reconstruction of the most probable haplotypes in family D was obtained using GENEHUNTER (Kruglyak et al., 1996). Pedigrees were drawn using Cyrillic Version 2.02.

Results

Cowden's syndrome (CS) (Lloyd and Dermis, 1963), or multiple hamartoma syndrome (Weary et al., 1972), is an autosomal dominant disorder associated with the development of hamartomas and benign tumors in a variety of tissues, including the skin, the thyroid, the breast, the colon and the brain. It has been suggested that women with CS are at increased risk for breast cancer (Brownstein et al., 1978) and, as in other susceptibility syndromes, they appear to develop breast cancer at an early age. CS is also associated with a specific skin lesion, the trichilemmoma (tumor of the follicular infundibulum), and thus this breast cancer susceptibility syndrome can be recognized by the presence of a cutaneous biomarker (Brownstein et al., 1977; 1978). The inventors have studied in detail the clinical and pathological findings in this syndrome and have demonstrated that the mean age of presentation with malignant breast disease in CS is 46 years, with the age range of presentation with breast cancer in affected women from 33 to 74 years. Moreover, very few of the women with CS that the inventors studied had a family history of breast cancer. Of interest, men with CS appear not to be at increased risk for the development of breast cancer (Brownstein et al., 1978). The inventors have also shown that women with CS develop exuberant benign breast disease and frequently report a history of multiple breast biopsies prior to the development of breast cancer. The history of skin disease and benign breast disease can therefore allow identification of affected individuals prior to the development of breast cancer in this high risk population.

It has been previously demonstrated that a locus for CS exists on chromosome 10 (Nelen et al., 1996). In that study, a total of 12 families were examined resulting in the identification of the Cowden critical interval between markers D10S215 and D10S564. Certain affected individuals in these families had CS and Lhermette-Duclos disease (LDD) (Nelen et al., 1996; Liaw et al., 1997), a rare brain disorder characterized by a dysplastic gangliocytoma of the cerebellum (Albrecht et al., 1992). Fine mapping of this area refined this initial result (Liaw et al., 1997), supporting a location for the CS gene between markers D10S215 and D10S541. More recently, affected individuals in four families with CS have been shown to have germline mutations (Liaw et al., 1997) in a gene known as PTEN (Li et al., 1997), TS10Q23.3 (Steck et al., 1997) or TEP1 (Li et al., 1997) which is located in the Cowden critical interval on chromosome 10. Of interest, the predicted TS10q23.3 protein contains sequence motifs with significant homology to the catalytic domain of protein phosphatases, and to the cytoskeletal proteins, tensin and auxillin (Li et al., 1997; Steck et al., 1997). Moreover, coding region mutations in TS10q23.3 were observed in human tumors or tumor cell lines of the breast, brain, prostate and kidney (Li et al., 1997; Steck et al., 1997). While the function of this gene is unknown, it is likely that TS10q23.3 plays a role in the control of cell proliferation and its loss of function is important in the development of human tumors.

Linkage Analysis and Mutation Screening in CS Kindreds

Figure 15:
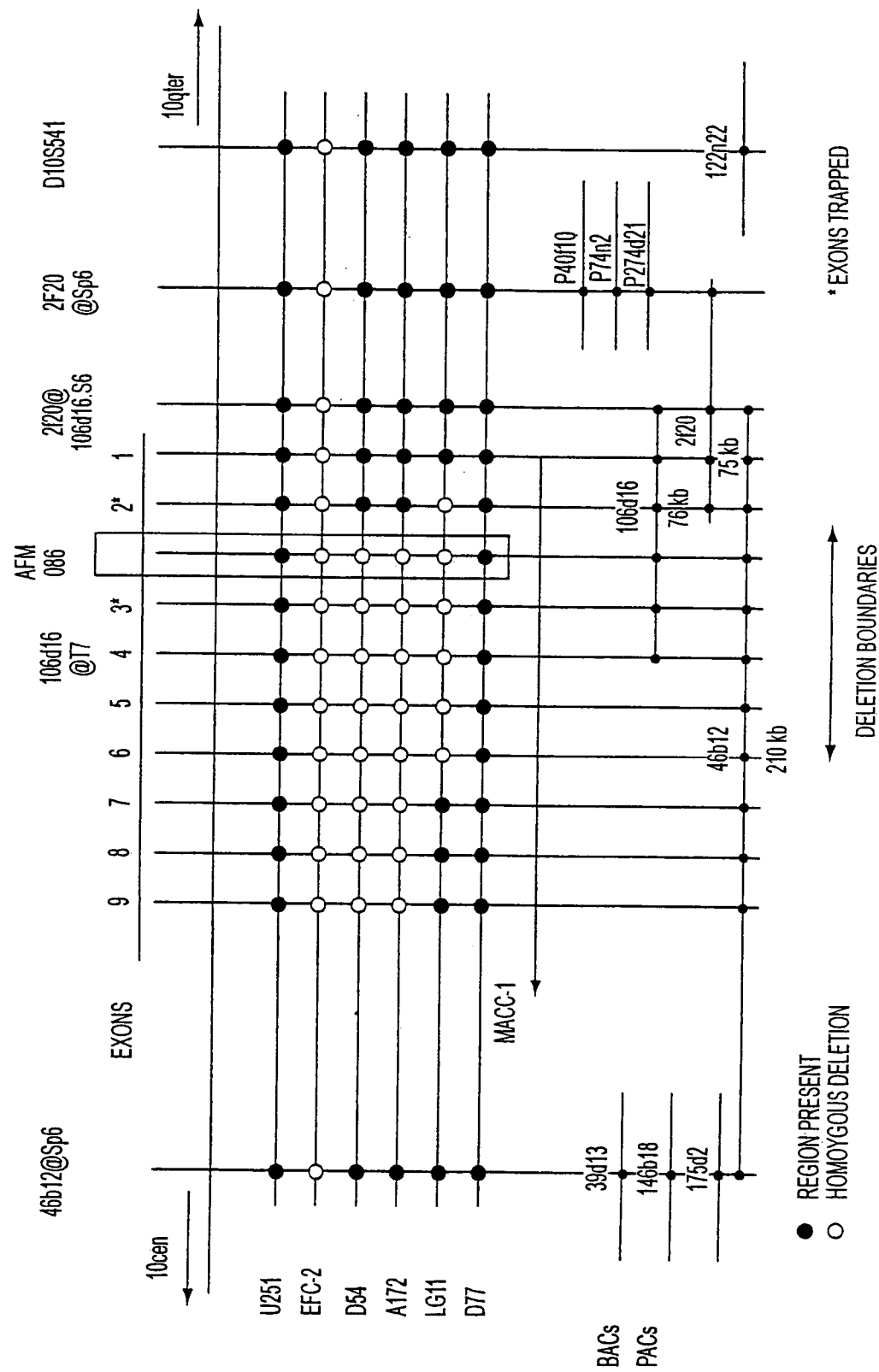
FIG. 15. Haplotype construction with markers on chromosome 10 in four families with CS.

In order to extend the observations indicating a CS locus on chromosome 10, the inventors performed a two point linkage analysis using five markers located in the Cowden critical interval, on four families with clinical evidence of CS (Nelen et al., 1996). All families were examined in detail and the diagnosis of this syndrome was made using the international Cowden's Consortium CD diagnostic criteria (Nelen et al., 1996). Two small families displayed positive LOD scores that could not exclude linkage to three loci on chromosome 10 (see family A and B, Table 8). Two other families with clinical findings identical to those described above, showed significant negative lod-scores for some of the markers in this region (families C and D, Table 8). A heterogeneity test also was performed which gave non-significant results. These findings were confirmed by the haplotypes construction (FIG. 15). In particular, in family C, individual 2 transmits to both her affected children the haplotype inherited from her unaffected father. Finally, in family D, individuals 2 and 20 have inherited a haplotype different from one of their affected relatives.

TABLE 8

Twopoint Analysis of CD Families with CA Repeat Markers

|  | 0.0 | 0.01 | 0.05 | 0.1 | 0.2 | 0.3 | 0.4 |
|---|---|---|---|---|---|---|---|
| FAMILY A |  |  |  |  |  |  |  |
| D10S579 | 0.00 | 0.00 | 0.00 | 0.00 | 0.00 | 0.00 | 0.00 |
| D10S215 | 0.30 | 0.30 | 0.28 | 0.26 | 0.20 | 0.15 | 0.08 |
| D10S541 | 0.00 | 0.00 | 0.00 | 0.00 | 0.00 | 0.00 | 0.00 |
| D10S1739 | 0.30 | 0.30 | 0.28 | 0.26 | 0.20 | 0.15 | 0.08 |

TABLE 8-continued

Twopoint Analysis of CD Families with CA Repeat Markers

|  | 0.0 | 0.01 | 0.05 | 0.1 | 0.2 | 0.3 | 0.4 |
|---|---|---|---|---|---|---|---|
| D10S564 | 0.30 | 0.30 | 0.28 | 0.26 | 0.20 | 0.15 | 0.08 |
| FAMILY B |  |  |  |  |  |  |  |
| D10S579 | 0.00 | 0.00 | 0.00 | 0.00 | 0.00 | 0.00 | 0.00 |
| D10S215 | 0.30 | 0.29 | 0.26 | 0.21 | 0.13 | 0.06 | 0.02 |
| D10S541 | 0.00 | 0.00 | 0.00 | 0.00 | 0.00 | 0.00 | 0.00 |
| D10S1739 | 0.30 | 0.29 | 0.26 | 0.21 | 0.13 | 0.06 | 0.02 |
| D10S564 | 0.30 | 0.29 | 0.26 | 0.21 | 0.13 | 0.06 | 0.02 |
| FAMILY C |  |  |  |  |  |  |  |
| D10S579 | 0.00 | 0.00 | 0.00 | 0.00 | 0.00 | 0.00 | 0.00 |
| D10S215 | −infinity | −3.40 | −2.00 | −1.40 | −0.80 | −0.44 | −0.19 |
| D10S541 | 0.00 | 0.00 | 0.00 | 0.00 | 0.00 | 0.00 | 0.00 |
| D10S1739 | −0.05 | −0.06 | −0.09 | −0.13 | −0.16 | −0.15 | −0.09 |
| D10S564 | −infinity | −3.40 | −2.00 | −1.40 | −0.80 | −0.44 | −0.19 |
| FAMILY D |  |  |  |  |  |  |  |
| D10S579 | −infinity | −1.52 | −0.28 | 0.11 | 0.28 | 0.19 | 0.05 |
| D10S215 | −infinity | −1.58 | −0.33 | 0.07 | 0.25 | 0.18 | 0.05 |
| D10S541 | −infinity | −1.44 | −0.39 | 0.01 | 0.22 | 0.18 | 0.06 |
| D10S1739 | −2.20 | −0.45 | 0.14 | 0.32 | 0.35 | 0.23 | 0.08 |
| D10S564 | −0.03 | 0.08 | 0.30 | 0.38 | 0.35 | 0.22 | 0.07 |

TABLE 9

| Mutation | Exon/Intron | Predicted Effect |
|---|---|---|
| 1. 791insAT | Exon 7 | Frameshift |
| 2. 915del13 | Exon 8 | Frameshift |
| 3. 137ins3 | Exon 2 | One amino acid insertion (Asn) |

Using a PCR™ and sequencing based approach, the inventors examined the 9 exons and associated splice junctions of TS10Q23.3, using the described primers (Steck et al., 1997), in 16 affected individuals from these 4 families. Of interest, 4 of these 16 individuals had breast cancer, and 2 of the 4 had breast cancer prior to the age of 40. The inventors failed to detect mutations in the coding sequence in these 16 individuals from these 4 families with the classic symptoms and signs of CS.

Mutational Analysis in Individuals with CS

Figure 16:
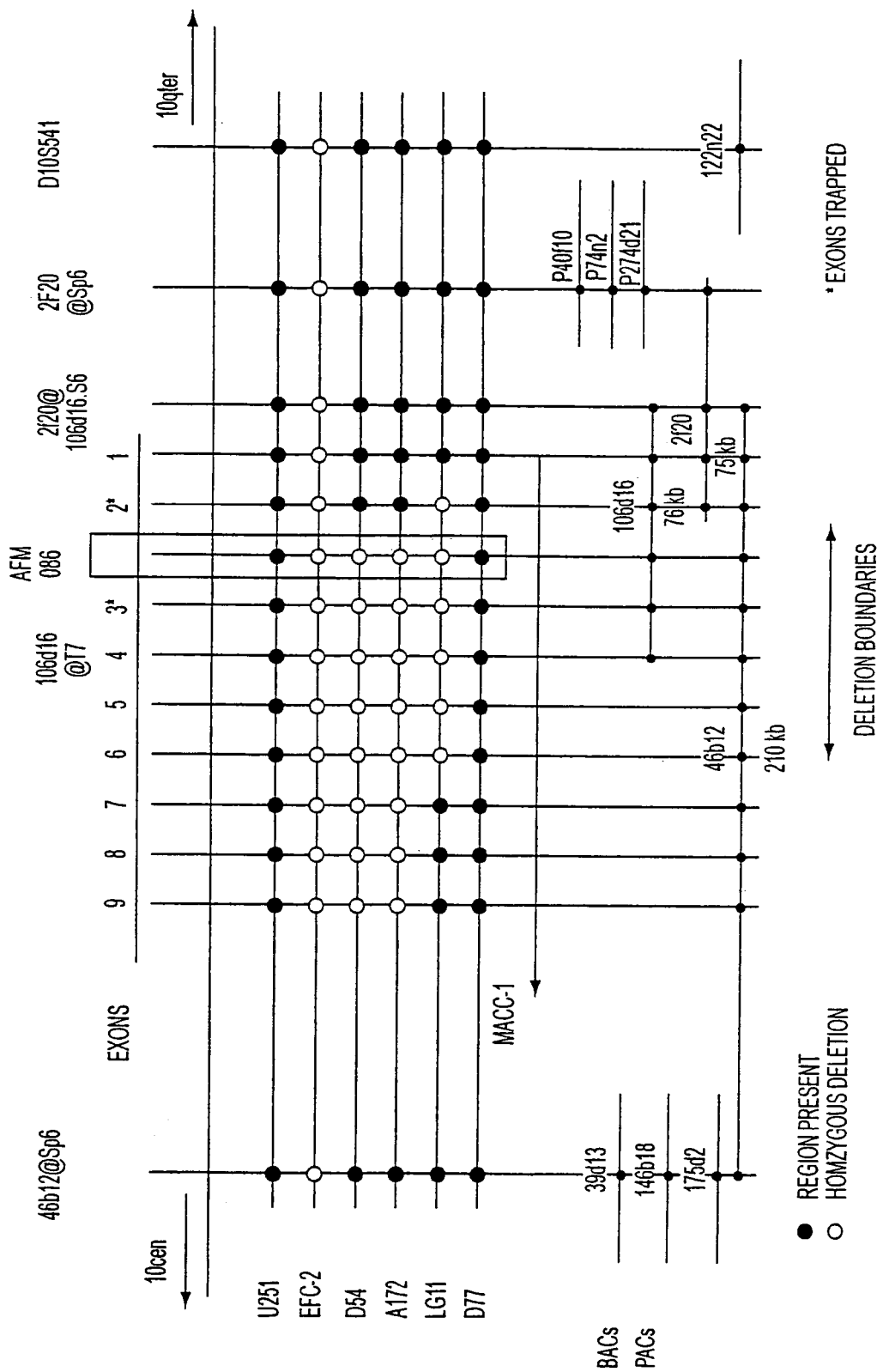
FIG. 16. DNA Sequencing of TS10Q23.3 in a family with CS and early onset breast cancer. The affected mother (black circle) demonstrates a 2 base pair insertion (AT) in exon 5, which is not seen in her unaffected brother (open square). Her affected daughter has inherited the AT insertion.

The inventors then screened a set of 31 affected individuals from 23 families with CS whose kindreds had not been used in the inventors' linkage studies. Of the 31 individuals, 13 were related individuals from 5 families. Thus, a total of 23 unrelated probands were screened. A single affected female (Walton et al., 1986) demonstrated a frameshift mutation in exon 7 of the coding sequence (see FIG. 16). Specifically, the inventors demonstrated an AT insertion after nucleotide 791 (791insAT), thus resulting in a frameshift and downstream premature termination codon. Of interest, this woman developed mammogram negative breast cancer at the age of 36, which was discovered at the time of prophylactic mastectomy (Walton et al., 1986). The proband had an unaffected brother, as well as an affected daughter. Direct sequencing of exon 7 in these individuals demonstrated the presence of the identical mutation in the affected daughter (FIG. 16) and the absence of the mutation in the unaffected brother. In studying a second individual with CS and early onset breast cancer (age 33), the inventors demonstrated a three base insertion in exon 2 (137ins3), resulting in the insertion of a single amino acid (Asn). Finally, in another woman with bilateral breast cancer and endometrial cancer, the inventors identified a 13 base pair frame shift deletion in exon 8 (915de112). These data demonstrate 3 more mutant alleles of TS10Q23.3 that are associated with CS (Liaw et al., 1997), and in particular, with CS and breast cancer (Brownstein et al., 1978). However, in 27 individuals from 20 families, the inventors did not detect mutations in the coding sequences of TS10Q23.3. In this population, 7 of these individuals had breast cancer, although all of these women developed breast cancer after the age of 40. One of these 7 individuals had bilateral breast cancer. In total, therefore, combining the family data, as well as these individuals, the inventors detected coding sequence mutations in 4 individuals from 3 CS families, but did not detect coding sequence alterations (i.e., missense or silent variants) in 43 other individuals from 24 families with CS.

Mutational Analysis in Women with Early Onset Breast Cancer

A strong case has been made for the existence of a genetic mechanism regulating breast tumor formation in early onset breast cancer (the development of breast cancer before the age of 40) (Claus et al., 1990). As CS is inherited in an autosomal dominant fashion, the genetic mechanisms regulating the development of breast cancer in this population may also play a role in the development of early onset breast cancer. Since the inventors detected germline TS10Q23.3 mutations in CS associated with early onset breast cancer, and mutations in this gene occur at relatively high frequency in breast tumors and breast tumor cell lines (Steck et al., 1997, Li et al., 1997), the inventors wanted to further investigate the role of germline TS10Q23.3 mutations in early onset breast cancer. In an effort to bias the inventors towards a sample set potentially enriched in germline TS10Q23.3 mutations, the inventors sequenced the gene in 63 women who developed breast cancer before age 35 (average age at diagnosis 27.7 years), did not appear to have a clinical diagnosis of CS, and who had previously been shown not to carry dearly deleterious mutations in BRCA1 (5 women in the sample carried missense polymorphisms of unknown significance). No coding sequence alterations were detected in the 9 exons of TS10Q23.3 in this sample set. In contrast, using the exact same mutation detection and analysis criteria on a similarly ascertained set of non-Ashkenazi breast cancer affecteds (without exclusion of BRCA1 carriers), the inventors would expect to detect 7 deleterious mutations and 5 missense polymorphisms of unknown significance in BRCA1. Furthermore, outside of the 4 CS patients carrying germ line mutations in TS10Q23.3 described above, the inventors have detected no sequence polymorphisms in the coding sequence of this gene in more than 200 germline chromosomes, and in fact find only one sequence difference (silent) between the human and chimpanzee sequences. If the frequency of coding and proximal splice junction sequence variants in TS10Q23.3 were 5% in the population from which this sample was drawn, then the inventors would have had a 95% chance of detecting one or more such variant.

Discussion

Cowden's syndrome is distinct among autosomal dominant genetic syndromes that predispose to the development of breast cancer as it has a unique cutaneous biomarker, the trichilemmoma (Brownstein et al., 1997; 1978). Furthermore, women with CS frequently give a history of multiple breast biopsies for benign breast disease prior to the development of breast cancer. Most of these women did not have a family history of breast cancer. To date, the most well described association of CS with organ specific cancer susceptibility is the female breast (Brownstein et al., 1977). Other organ systems that appear to develop cancer with increased frequency in these individuals such as the thyroid. In contrast to other autosomal breast cancer susceptibility syndromes, such as the one associated with mutations in BRCA1 (Ford et al., 1995), the development of ovarian cancer in this syndrome is quite rare. However, CS shares with these syndromes an earlier age of onset of breast cancer, as well as an increased likelihood of bilateral breast cancer. Previous observations demonstrated linkage of CS to chromosome 10q22–23 (Nelen et al., 1996). Furthermore, it is also now evident that mutations in a gene (Liaw et al., 1997) known as PTEN (Li et al., 1997), TS10Q23.3 (Steck et al., 1997) or TEP1 (Li and Sun, 1997) found in the Cowden's critical interval on chromosome 10, are associated with CS individuals (Liaw et al., 1997).

In the observations reported here, the inventors identify 3 new germline mutations in the coding sequence of TS10Q23.3 associated with CS, and specifically in individuals with CS and breast cancer. In two, related individuals with CS, the inventors described a frameshift mutation in exon 7, resulting in a premature termination codon, that is identical in an affected mother and her affected daughter. This TS10Q23.3 mutation appears to be associated with early onset breast cancer, as one of the two affected individuals developed breast cancer at age 36. In a third affected individual, the inventors identified a 13 base pair deletion in exon 8. While this individual did not develop breast cancer at an early age, she had a history of bilateral breast cancer. Of interest, she also developed endometrial cancer while on tamoxifen. Given that endometrial cancer has been associated with CS (Starink et al., 1986) and with tamoxifen use (Fornander et al., 1989), the contribution of both risk factors to the development of disease in this one women is unknown. However, this raises the possibility that the subpopulation of women who develop endometrial cancer while on tamoxifen may have CS and/or mutations in TS10Q23.3. Finally, the inventors identified a 3 base insertion in exon 2 in a another woman who developed breast cancer at the age of 33.

In the set of CS individuals that the inventors studied, the inventors detected germline TS10Q23.3 mutations in 4 individuals from 3 families, but did not observe any coding sequence alterations in the remaining 43 individuals from 24 unrelated families. These data supported the inventors' limited linkage information, suggesting that all CS families may not link to the locus identified on chromosome 10. While the studies the inventors performed do not rule out mutations in the 5' regulatory regions or in the 3' untranslated region of TS10Q23.3, or other mechanisms that alter its expression level, such as methylation silencing, as being associated with CS, both the linkage data and the DNA sequencing results support the idea that the CS may be genetically heterogeneous. Tuberous sclerosis, another autosomal dominant disorder associated with the formation of hamartomas in the skin and other organs, has been shown to be genetically heterogeneous with distinct loci located at chromosome 9q34 (Haines et al., 1991) and chromosome 16p13.3 (Kandt et al., 1992). The inventors' results indicate that this also may be true for CS. Why this was not demonstrated in the initial observations is not clear, but could be due to the ethnic backgrounds of the initial families examined (Nelen et al., 1996; Liaw et al., 1997). Moreover, certain of these individuals presented with CS and Lhermette-Duclos disease, which the inventors have never seen in a CS proband or in a CS family (Nelen et al., 1996; Liaw et al., 1997).

A strong case has been made for the existence of a genetic mechanism regulating breast tumor formation in early onset breast cancer (Claus et al., 1990). Indeed, early onset breast cancer has been associated with mutations in the BRCA1 (Miki et al., 1994) and BRCA2 (Wooster et al., 1995). CS is associated with early onset breast cancer, and the cancer is usually ductal carcinoma (Brownstein et al., 1977; Brownstein et al., 1978). Rachel Cowden, for whom the syndrome is named, apparently died of breast cancer at age 31 (Lloyd and Dennis, 1963; Brownstein et al., 1978). As described herein, the inventors have identified TS10Q23.3 mutations in 2 CS individuals with early onset breast cancer, as well as in 1 with bilateral breast cancer. However, when the inventors searched for germline TS10Q23.3 mutations in a subgroup of women with early onset breast cancer, lacking the signs of CS and previously shown to have wild-type sequences of BRCA1, the inventors failed to detect any sequence variants. These data suggest that germline mutations in TS10Q23.3 occur infrequently in at least this subpopulation of early onset breast cancer cases.

Example 9

Suppression of Tumorigenicity of Glioblastoma Cells by Adenovirus-mediated MMAC1/PTEN Gene Transfer Additional studies were designed to further evaluate the function of MMAC1/PTEN as a tumor suppressor. A replication-defective adenovirus (MMCB) was constructed for efficient, transient transduction of MMAC1 into tumor cells. The data presented in this Example support an in vivo tumor suppression activity of MMAC1/PTEN, and suggests that in vivo gene transfer with this recombinant adenoviral vector will be useful in cancer gene therapy.

Materials and Methods

Cell Lines: The MMAC1-mutated glioblastoma cell line U87MG was obtained from the American Type Culture Collection (ATCC). Cells were maintained in culture medium (DME/10% FBS/1% L-glutamine) in a humidified atmosphere containing 7% $CO_2$ at 37° C. 293 embryonic kidney cells were also obtained from ATCC and were grown in DME culture medium supplemented with 10% FBS.

RT-PCR analysis: Total RNA was isolated from U87MG cells (Tri Reagent, Molecular Research Center) per manufacturer's instructions. RNA was reverse-transcribed using MuLV-RT (RNA PCR kit, Perkin-Elmer), random hexamer and other kit reagents, followed by PCR using primers MAC1.6f (5'-CTG CAG AAA GAC TTG AAG GCG TA-3', SEQ ID NO:58) and MAC1.6r (5'-GCC CCG ATG TAA TAA ATA TGC AC-3') (SEQ ID NO:59) matching sequences in MMAC1 exons 2 and 5, respectively. Amplification conditions were 95° C. denaturation for 1 min, then (95° C., 15"; 55° C., 30") for 25 cycles, then 72° C. for 5 min. The expected normal product size was 317 bp. The abnormal band from U87MG was cut out from an agarose gel, purified (UltraClean, Mo Bio Labs), and directly sequenced using an automated sequencing system (ABI 373A, Perkin Elmer).

Viruses: A recombinant adenovirus containing wild-type p53 (FTCB) was constructed as described previously (Wills et al., 1994). The genome of this vector has deletions of the E1 and E3 regions and protein IX gene, and expresses the transgene under control of the human cytomegalovirus (CMV) immediate early promoter/enhancer. The MMAC1/PTEN vector MMCB was constructed in exactly the same manner except that p53 was replaced with a cDNA encoding full-length MMAC1 (Steck et al., 1997). The control vector GFCB was constructed to match MMCB except for its transgene, enhanced green fluorescent protein (Clontech). Another matching control vector, ZZCB, was constructed without a transgene. The BGCA control vector expressing E. coli LacZ driven by the CMV promoter was constructed in a genome with partial E4 deletion in addition to deletions of E1, E3, and protein IX (Wang et al., 1997) because of packaging size constraints. All viruses were grown in 293 cells and purified by DEAE column chromatography as described (Huyghe et al., 1995). Virus particle concentrations were determined by Resource Q HPLC (Shabram et al., 1997), and the primary structure of all transgenes was verified by automated sequencing of viral DNA.

Immunodetection of MMAC1 protein: Cell monolayers were infected for 24 hr with GFCB or MMCB at various viral particle numbers per milliliter of growth medium (pn/ml). Virus-containing solutions were removed at 24 hr and cells were either harvested at this time or refed with growth medium and collected at later time points. Cells were harvested by scraping into cold phosphate-buffered saline (PBS), centrifuged and washed once more in cold PBS, then freeze-thawed and resuspended in lysis buffer [50 mM MOPS. pH 7.0, 150 mM NaCl, 1% NP-40, 5% glycerol, 0.4 mM EDTA and supplemented with 1 mM DTT and 1× Complete Protease Inhibitor Cocktail (Boehringer Mannheim)]. Cell lysates were clarified by centrifugation at 10,000×g for 15 min, and supernatants were normalized for protein content. Samples were resolved by SDS-PAGE using pre-cast 8% TRIS-glycine gels (Novex), then transferred to poly(vinylidene difluoride) membranes (Immobilon-P) for Western blotting. Membranes were blocked with TBST containing 5% skim milk, and then blotted with anti-MMAC1 rabbit polyclonal antibody (BL74), followed by donkey and rabbit IgG conjugated with horseradish peroxidase (Amersham). MMAC1 was detected by chemiluminescence (HCL kit, Pierce) using Kodak XAR-5 film.

FACS infectivity assay: U87MG cells were plated at $2×10^5$ cells/well in 6-well plates and incubated overnight, then infected with GFCB at concentrations ranging from $1×10^5$ to $1×10^9$ particles/ml for 24 hr. Cells were harvested by trypsinization and assayed by flow cytometry (Becton Dickenson FACScan) for green fluorescence (525 nm peak detection, filter FL-I). Cells were gated on forward and side scatter, and a cutoff of fluorescence intensity was established such that ~99% of uninfected cells were negative. The percentage of GFCB-infected cells with greater fluorescence than this cutoff was then determined, representing a minimum estimate of the percentage of infected cells.

$^3$H-thymidine incorporation assay: Cells were plated at $5×10^3$ cells/well in 96-well microtiter plates (Costar) and incubated overnight. Dilutions of ZZCB, GFCB, FTCB and MMCB in medium ranging from $5×10^6$ to $1×10^9$ particles/ml were added in triplicate to the cell monolayers and then incubated for 24 hr. Virus-containing solutions were removed at 24 hr after infection and replaced with new tissue culture medium for an additional 24 hr. Cells were treated with 1 µCi of $^3$H-thymidine per well 4 hr prior to harvesting. Cell were harvested onto glass-fiber filters, and incorporation of $^3$H-thymidine was determined using liquid scintillation (Top Count, Packard). Results are plotted as percentages of buffer-treated control (mean±SD).

Cell count/viability assay: Subconfluent monolayers of U87MG cells were infected in triplicate with MMCB or GFCB adenovirus at various concentrations for 24 hr, after which supernatants was replaced with fresh tissue culture medium for 48 addition hr. Cells were then harvested by trypsinization, and viable cells were counted by the trypan blue exclusion method using a hemocytometer.

Soft agar colony formation assay: U87MG cells infected as above with $5\times10^6$, $5\times10^7$ or $5\times10^8$ particles/fill for 24 hr were suspended in tissue culture medium containing 0.35% agar and layered in triplicate onto 0.7% agar in 35 mm tissue culture wells. Cultures were incubated in a humidified atmosphere containing 7% $CO_2$ at 37° C. with overlying tissue culture medium that was replaced every five days. Colony growth was assessed at 14 days post infection.

Tumorigenicity assay: U87MG cells were plated at a density of $1\times10^7$ cells per T225 flask. After overnight incubation, cell monolayers were infected with $5\times10^7$ or $5\times10^8$ particles/ml of adenoviruses GFCB, FTCB, BGCA or MMCB for 24 hr. Infected or uninfected cells were harvested by trypsinization, washed in medium, counted in the presence of Trypan Blue, and injected subcutaneously ($5\times10^6$ viable cells per flank) into athymic nu/nu female mice (Simonsen Labs). Mice were scored for tumors at 21 or 30 days; tumor diameters in 3 dimensions were measured with Vernier calipers, and tumor volumes were calculated as their product.

Results and Discussion

U87MG human glioblastoma cells (Ponten and Macintyre, 1968) were chosen for study based on their reported MMAC1 mutation (Steck et al., 1997), soft agar colony-forming ability and subcutaneous tumorigenicity in nude mice. An abnormally small RT-PCR product derived from U87MG RNA using primers in exons 2 and 5 (see Methods section above in Example 9) was found to lack exon 3 by sequencing, in agreement with the intron 3 splice donor site mutation (Steck et al., 1997). Although exon 3 contains 45 bp (15 codons) and an in-frame readthrough product is possible, the missing residues encode a conserved alpha helix in the native protein, and their loss ablated growth-inhibitory activity as measured by Fumari et al., (1997).

Figure 17:
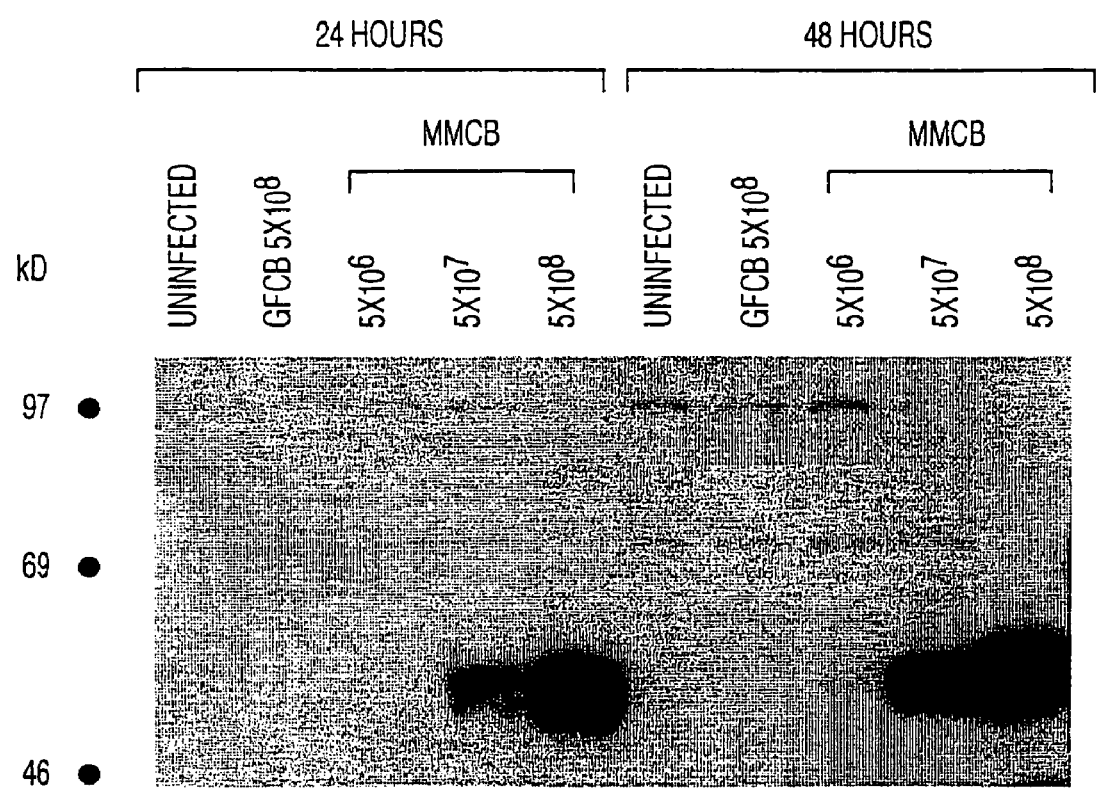
FIG. 17. Exogenous MMAC1 protein expression. U87MG cells were infected with MMCB or GFCB at the indicated concentrations (particle numbers/ml) for 24 hr, then lysates were prepared immediately (24 hr) or 24 hr later (48 hr). Western blotting was performed as described in Methods. Protein size markers are shown at left. MMAC1 protein migrated at approximately 55 kD in agreement with Li et al., 1997.

The purified recombinant MMAC1-containing adenovirus (MMCB) was characterized for transgene expression in U87MG cells by Western blotting of cell lysates with a rabbit polyclonal antibody (FIG. 17). Endogenous MMAC1 protein was not detected in uninfected or control virus-infected cells, but was detected in a dose-dependent fashion in MMCB-infected cells by the end of the 24 hr infection period, as well as at 48 hr, 72 hr and 96 hr (FIG. 17). This study verified the efficient transduction and acute expression of exogenous MMAC1 protein in U87MG glioma cells as well as validating its detection by Western blotting with antibody BL74.

Infectivity of U87MG cells was assessed quantitatively by FACS analysis using a recombinant adenovirus identical to MMCB except for its transgene, which encoded green fluorescent protein (FIG. 18). The expected sigmoidal infectivity curve was obtained, from which it was estimated that 85–90% of cells were infected at a viral dose of $5\times10^7$ particles/ml for 24 hr. Of note is that the dosing parameters used herein are not based on the plaque-forming unit or its derivative, multiplicity of infection, it has previously been shown that adenoviral concentration and infection time are the primary determinants of in vitro transduction (Nyberg-Hoffman et al., 1997).

Figure 19A:
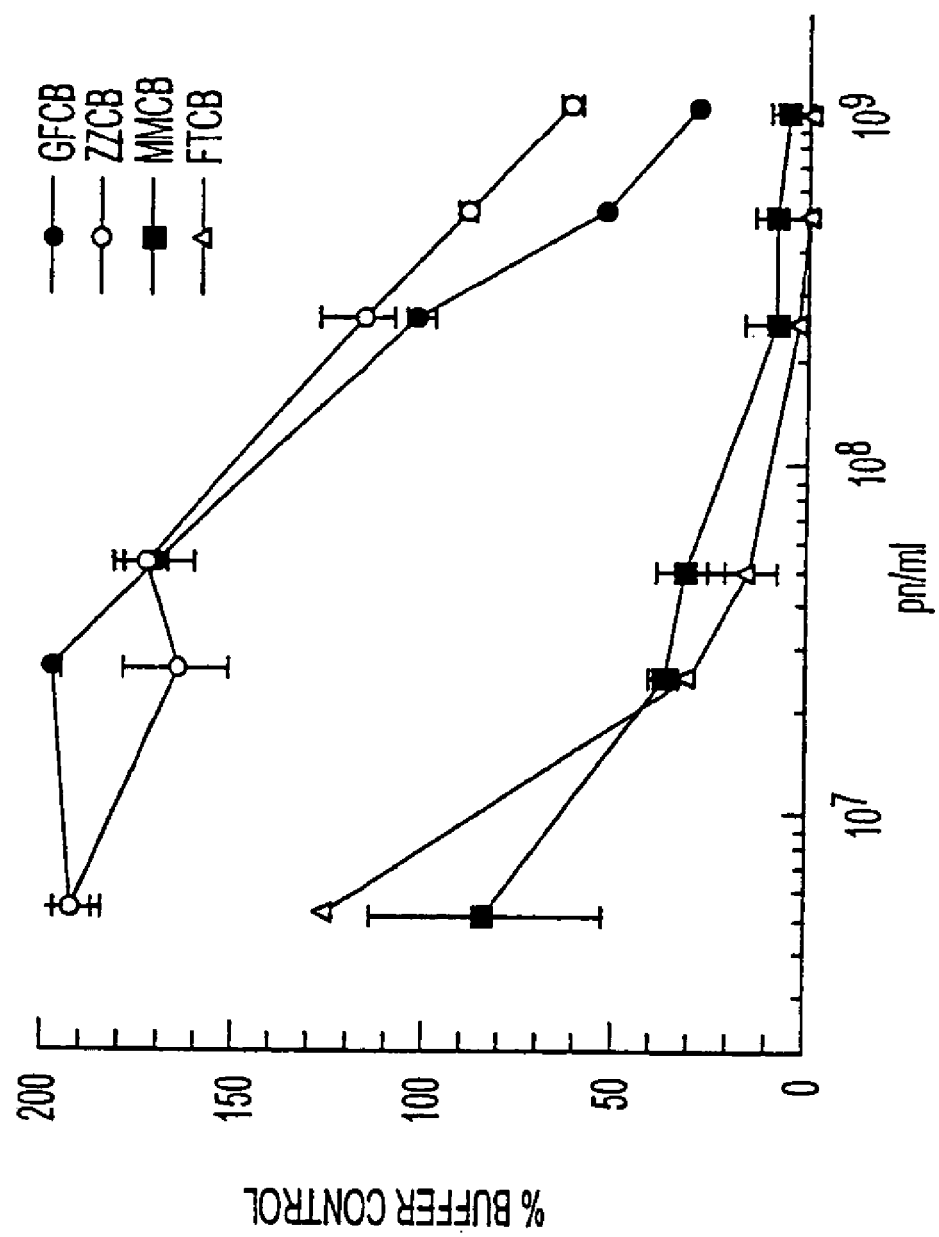
FIG. 19A and FIG. 19B. Inhibition of in vitro proliferation by MMCB.

In vitro proliferation of MMCB vs. control-Ad infected U87MG cells was measured by $^3$H-thymidine uptake over a range of viral concentrations (FIG. 19A), U87MG was differentially inhibited by MMCB compared to two control adenoviruses (GFCB and ZZCB) over most viral doses; at high adenovirus concentrations (e.g. $1\times10^9$ particles/ml), a nonspecific inhibitory effect predominated, as has been noted before in some cell lines (Harris et al., 1995). Inhibition of DNA synthesis by MMCB was comparable to that induced by adenoviral p53 gene transfer (FTCB; FIG. 19A).

Figure 19B:
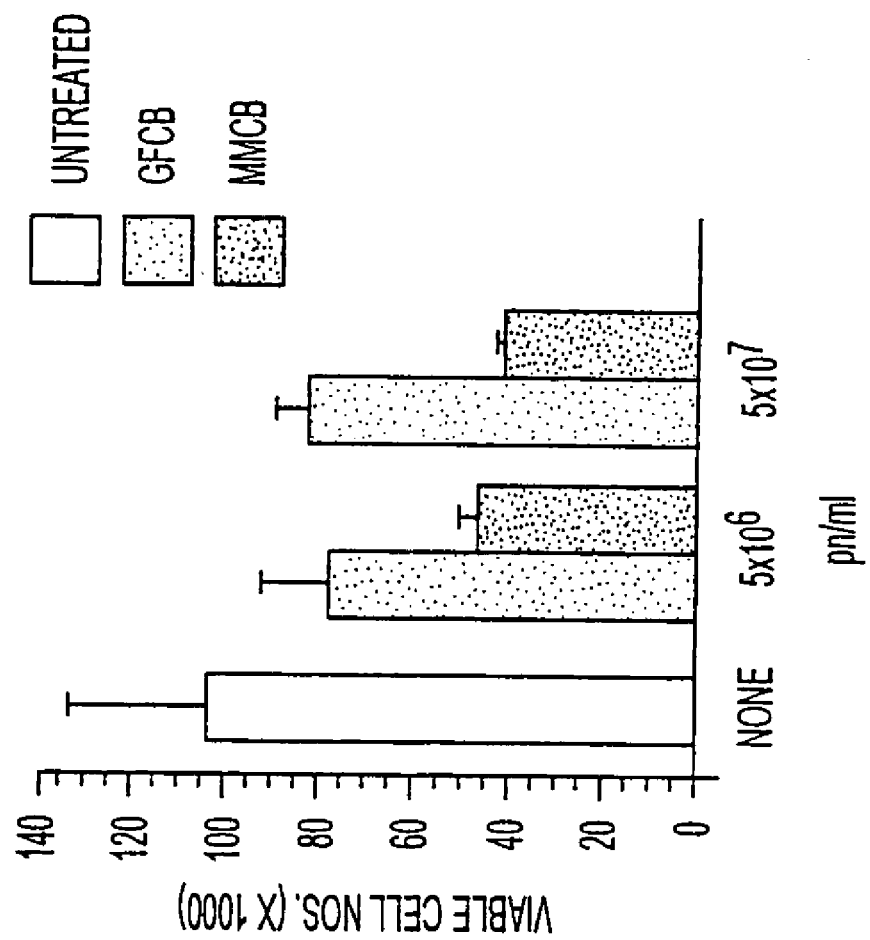

Growth inhibition was confirmed in a second in vitro assay by counting viable cells at 72 hr after the start of infection (FIG. 19B), MMCB reduced cell numbers at this time point by about 50% compared to GFCB at equal doses. This inhibition was comparable in magnitude to that observed using transient plasmid transfection (Furnari et al., 1997). MMCB and GFCB infected cultures had similar viability rates at 72 hr and morphological evidence of cell death, such as cell blebbing or nuclear fragmentation, was not seen with MMCB treatment.

Figure 20:
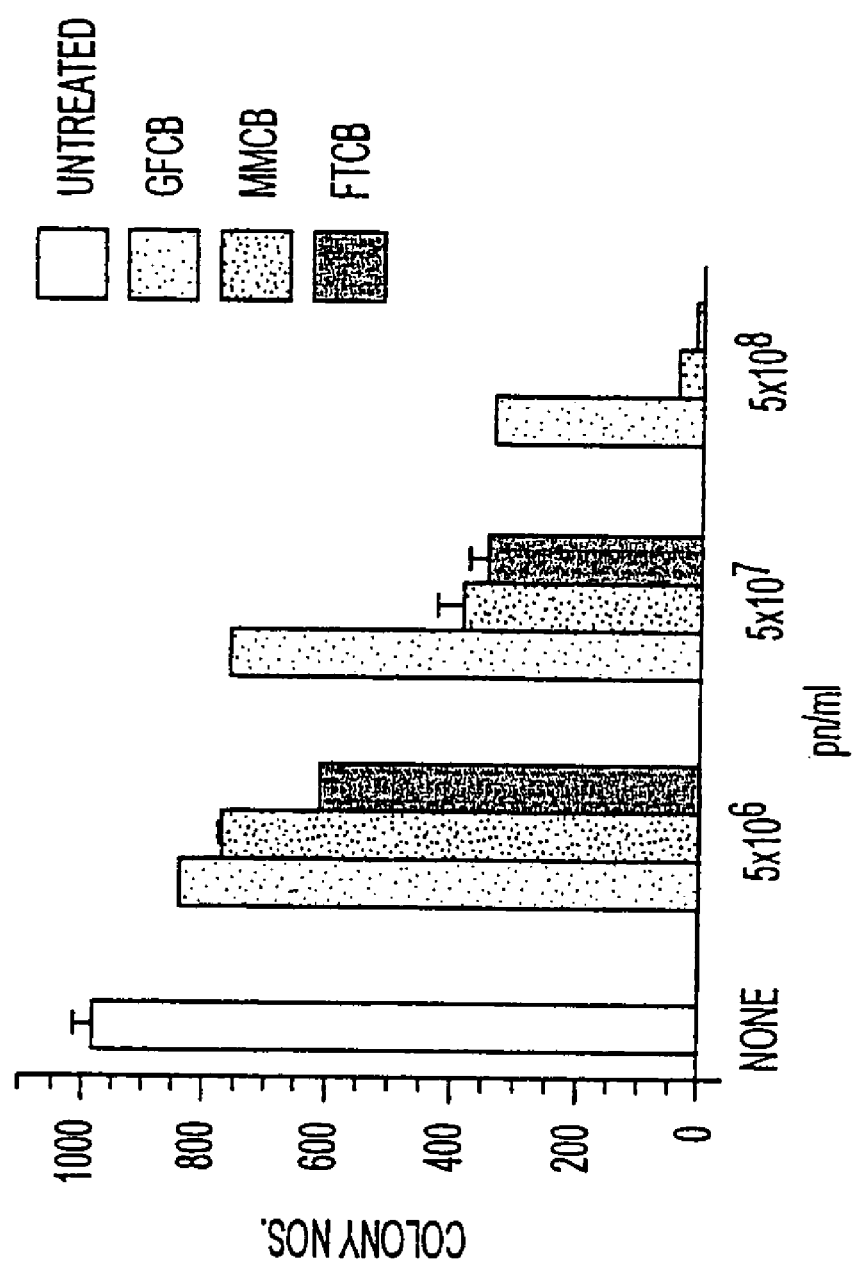
FIG. 20. Soft-agar colony formation. U87MG cells were infected with GFCB, MMCB or FTCB at the indicated concentrations for 24 hr. Mean colony numbers±S.D. are plotted. pn/ml: adenovirus particle numbers per ml.

Effects of MMAC1 on anchorage-independent growth were assessed as well by colony formation in soft agar following transduction by MMCB vs. GFCB or FTCB. The latter was included in order to validate the assay with an established tumor suppressor gene. At a dose of $5\times10^7$ particles/ml for 24 hr, colony formation with MMCB or FTCB was inhibited by approximately 50% compared to the GFCB control, whereas a >85% inhibition (relative to GFCB) could be achieved at $5\times10^8$/ml of either MMCB or FFCB (FIG. 20). Therefore, a dose-dependent, gene-specific effect of MMAC1 was evident in this in vitro assay.

Two tumorigenicity assays were performed with $5\times10^6$ MMCB-infected U87MG cells per injection compared to the same number of cells infected by three different control Ads: GFCB (green fluorescent protein in matching $\Delta EI/\Delta E3$ background), FTCB (p53 in matching $\Delta EI/\Delta E3$ background), and BGCA (LacZ in $\Delta E1/\Delta E3/\Delta E4$ background) (Table 10). Differences between experiments 1 and 2 included the use of two dose levels vs. one, and termination at 21 vs. 30 days, respectively. MMCB-infected U87 cells were completely nontumorigenic at 21 or 30 days with the exception of three very small tumors (~10 $mm^3$) at the lower dose level in Experiment 1. Tumors formed in all 39 mice injected with uninfected or control-Ad infected cells. Reporter gene-containing control-Ads, GFCB and BGCA, had some activity in reducing average tumor size compared to buffer-treated cells, a nonspecific "adenoviral effect" previously noted by the inventors (Wills et al., 1994; Harris et al., 1995). The p53-containing Ad had a more dramatic effect on average tumor size (~68 $mm^3$), yet tumors still formed in 6 of 6 mice. These results are consistent with the growth-inhibitory effects of p53 adenovirus gene transfer in U87MG cells reported elsewhere, even though these cells contain p53 alleles with the wild-type sequence (Gomez-Manzani et al., 1996; Kock et al., 1996). In any case, these data indicate a gene-specific tumor suppression activity of MMCB in U87MG cells at moderate viral doses.

Using a recombinant adenoviral gene transfer system, an in vitro growth inhibition activity of MMAC1/PTEN in U87MG cells was shown. The use of a recombinant adenovirus was helpful in circumventing the known technical difficulty of studying tumor cells stably expressing potentially growth-inhibiting proteins such as MMAC1. A specific tumor suppression activity of MMAC1 was most clearly detected in the in vivo assay, supporting the importance of the tumorigenicity assay in determining tumor suppression function. These data support a role for MMAC1 inactivation in glioblastoma tumorigenesis, and further suggest that MMAC1/PTEN gene transfer in vivo may be considered as a potential cancer therapy approach.

While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference:

Albarosa et al., *Am. J. Genet.*, 58: 1260–1267, 1996.
Albrecht, et al, *Cancer,* 70: 869–875, 1992.
Anderson W F, et al. (1980). *Proc. Natl. Acad. Sci. USA* 77: 5399–5403.
Arcone et al., *Nuc. Acids Res.* 16(8): 3195–3207, 1988.
Baichwal and Sugden, In: *Gene Transfer*, Kucherlapati R, ed., New York, Plenum Press, pp. 117–148, 1986.
Bandyopadhyay P K and Temin H M (1984). *Mol. Cell. Biol.* 4: 749–754.
Barany and Merrifield, The Peptides, Gross and Meienhofer, eds., Academic Press, New York, pp. 1–284, 1979.
Bartel P L, et al. (1993). "Using the 2-hybrid system to detect protein-protein interactions." In *Cellular Interactions in Development: A Practical Approach*, Oxford University Press, pp. 153–179.
Bartlett et al., *Proc. Natl. Acad. Sci. USA*, 93: 8852–8857, 1996.
Batterson and Roizman, *J. Virol.*, 46: 371–377, 1983.
Bellus, *J. Macromol. Sci. Pure Appl. Chem*, A311: 1355–1376, 1994.
Benvenisty and Neshif, *Proc. Nat. Acad. Sci. USA*, 83: 9551–9555, 1986.
Berglund P, et al. (1993). *Biotechnology* 11: 916–920.
Berkner K L, et al. (1988). *BioTechniques* 6: 616–629.
Berkner K L (1992). *Curr. Top. Microbiol. Immunol.* 158: 39–66.
Berns and Bohenzky, *Adv. Virus Res.*, 32: 243–307, 1987.
Berns and Giraud, *Curr. Top. Microbiol. Immunol.*, 218: 1–23, 1996.
Berns, *Microbiol Rev.*, 54: 316–329, 1990.
Bertran, et al., *J Virol.*, 70 (10) 6759–6766, 1996.
Bianchi et al., *Nature Genetics*, 6: 185–192, 1994.
Bigner et al., *Cancer Res.*, 48: 405–411, 1988.
Bishop, J. M., *Cell*, 64: 2351–248, 1991.
Boring et al., *Cancer Statistics*, 1994 CA, 43: 7–26, 1994.
Breakefield X O and Geller A I (1987). *Mol. Neurobiol.* 1: 337–371.
Brinster R L, et al. (1981). *Cell* 27: 223–231.
Brinster et al., *Proc. Nat'l Acad. Sci. USA*, 82: 4438–4442, 1985.
Brownstein, et al., *JAMA*, 238: 26, 1977.
Brownstein, et al, *Cancer*, 41: 2393–2398, 1978.
Buchschacher G L and Panganiban A T (1992). *J. Virol.* 66: 2731–2739.
Campbell et al., *J. Mol. Biol.*, 180: 1–19, 1984.
Capaldi et al., *Biochem. Biophys. Res. Comm.*, 76: 425, 1977
Carter et al., *Proc. Natl. Acad. Sci. USA*, 87: 8751–8755, 1990.
Chang et al., *Hepatology,* 14: 124A, 1991.
Chen and Okayama, *Mol. Cell Biol.*, 7: 2745–2752, 1987.
Chevray P M and Nathans D N (1992). *Proc. Natl. Acad. Sci. USA* 89: 5789–5793.
Claus, et al., *Am. J. Epidemiol.*, 131: 961–972, 1990.
Coffin, Retroviridae and Their Replication. In: *Virology*, Fields et al., eds., Raven Press, New York, pp. 1437–1500, 1990.
Cohen, P., *Bioessays,* 61–583–588, 1994.
Collet et al., *Proc. Natl. Acad. Sci. USA,* 75: 2021–2024, 1978.
Compton J (1991). *Nature* 350: 91–92.
Cook et al., *Cell,* 27: 487–496, 1981.
Costantini F and Lacy E (1981). *Nature* 294: 92–94.
Cotten M, et al. (1990). *Proc. Natl. Acad. Sci. USA* 87: 4033–4037.
Couch et al., *Am. Rev. Resp. Dis.,* 88: 394–403, 1963.
Coupar et al., *Gene,* 68: 1–10, 1988
Culver et al., *Science,* 256: 1550–1552, 1992.
Curiel D T, et al. (1991). *Proc. Natl. Acad. Sci. USA* 88: 8850–8854.
Curiel D T, et al. (1992). *Hum. Gene Ther.* 3: 147–154.
Daly et al., *Oncogene* 8: 1721–1729, 1993.
Dani, et al., *J. Biol. Chem.*, 264: 10119–10125, 1989.
Davey et al., EPO No. 329 822.
DeLuca et al., *J. Virol.,* 56: 558–570, 1985.
Denu et al., *Cell* 87: 361–364, 1996.
Dubensky et al., *Proc. Nat. Acad. Sci. USA,* 81: 7529–7533, 1984.
El-Azouzi et al., *Proc. Natl. Acad. Sci. USA,* 86: 7186–7190, 1989.
Elroy-Stein et al., *Proc. Nat'l Acad. Sci. USA,* 1989.
EP 329 822, Davey et al.
Fahy E, et al. (1991). *PCR Methods Appl.* 1: 25–33.
Fanning and Anderson, *Curr Biol,* 6: 11, 1385–1388, 1996.
Fearron and Vogelstein, *Cell*, 61: 759–767, 1990.
Fechheimer et al., *Proc. Natl. Acad. Sci. USA,* 84: 8463–8467, 1987.
Feil et al., *Proc. Natl. Acad. Sci. USA* 93: 10887–10890, 1996.
Felgner P L, et al. (1987). *Proc. Natl. Acad. Sci. USA* 84: 7413–7417.
Ferkol et al., "*FASEB J.*, 7: 1081–1091, 1993.
Fields S and Song O-K (1989). *Nature* 340: 245–246.
Fink D J, et al. (1992). *Hum. Gene Ther.* 3: 11–19.
Fink D J, et al. (1996). *Ann. Rev. Neurosci.* 19: 265–287.
Fodor et al., *Science,* 251: 767–773, 1991.
Ford, et al., *Am. J. Hum. Genet.,* 57: 1457–1462, 1995.
Fornander et al., *Lancet,* 1, 8630: 117–120, 1989.
Forster and Symons, *Cell,* 49: 211–220, 1987.
Foulds, *J. Chronic Dis.,* 8: 2–37, 1958.
Fraley et al., *Proc. Natl. Acad. Sci. USA,* 76: 3348–3352, 1979.
Freese A, et al. (1990). *Biochem. Pharmacol.* 40: 2189–2199.
Freifelder, *Physical Biochemistry Applications to Biochemistry and Molecular Biology,* 2nd ed. Wm. Freeman and Co., New York, N.Y., 1982.
Freshner, Animal Cell Culture: A Practical Approach, 2nd ed., Oxford/New York, IRL Press, Oxford University Press, 1992.
Friedmann, *Science,* 244: 1275–1281, 1989.
Friedman T (1991). In *Therapy for Genetic Diseases*, T. Friedman, ed., Oxford University Press, pp. 105–121.
Frohman, In: *PCR Protocols: A Guide To Methods And Applications*, Academic Press, N.Y., 1990.
Fujimoto et al., *Genomics,* 4: 210–214, 1989.

Fults and Pedone, *Genes Chromosom. Cancer* 7: 173–177, 1993.
Fults et al., *Cancer Res.*, 50: 5784–5789, 1990.
Fumari et al., *Proc. Natl. Acad. Sci. USA*, 94: 12479–12484, 1997
GB Application 2 202 328
Ganeten et al., *Nucl. Acids Res.* 25: 3326–3331, 1997.
Gefter et al., *Somatic Cell Genet.*, 3: 231–236, 1977.
Gerlach et al., *Nature London*, 328: 802–805, 1987.
Ghosh-Choudhury et al., *EMBO J.*, 6: 1733–1739, 1987.
Ghosh and Bachhawat, In: *Liver Diseases, Targeted Diagnosis and Therapy Using Specific Receptors and Ligands*. Wu et al., eds., Marcel Dekker, New York, pp. 87–104, 1991.
Gingeras et al., PCT Application WO 88/10315,
Glorioso et al., *Ann. Rev. Microbiol*, 49: 675–710, 1995.
Goding, 1986, In: *Monoclonal Antibodies: Principles and Practice*, 2d ed., Academic Press, Orlando, Fla., pp. 60–61, and 71–74, 1986.
Gomez-Foix et al., *J. Biol. Chem.*, 267: 25129–25134, 1992.
Gomez-Manzani et al., *Cancer Res*, 6: 694–699, 1996.
Gopal, *Mol. Cell Biol.*, 5: 1188–1190, 1985.
Gordon J W, et al. (1980). *Proc. Natl. Acad. Sci. USA* 77: 7380–7384.
Gorziglia M and Kapikian A Z (1992). *J. Virol.* 66: 4407–4412.
Gossen and Bujard, *Proc. Natl. Acad. Sci. USA*, 89: 5547–5551, 1992.
Gossen et al., *Science*, 268: 1766–1769, 1995.
Graham and Prevec, In: *Methods in Molecular Biology: Gene Transfer and Expression Protocol*, E. J. Murray, ed., Humana Press, Clifton, N.J., 7: 109–128, 1991.
Graham and van der Eb, *Virology*, 52: 456–467, 1973.
Graham et al., *J. Gen. Virol.*, 36: 59–72, 1977.
Gray et al., *Cancer Res.*, 55: 4800–4803, 1995.
Grunhaus and Horwitz, *Seminar in Virology*, 3: 237–252, 1992.
Gyapay et al., *Nat. Genet.*, 7: 246–339, 1994.
Hacia et al., *Nature Genetics*, 14: 441–447, 1996.
Haines et al., *Am. J. Hum. Genet.*, 49: 764–772, 1991.
Hardie and Hanks, In: The Protein Kinase Facts Book, 1995
Harland and Weintraub, *J. Cell Biol.*, 101: 1094–1099, 1985.
Harlow and Lane, Antibodies: A Laboratory manual, Cold Spring Harbor Laboratory, 1988.
Harris et al., *Cancer Gene Ther.*, 3: 121–130, 1995.
Helseth E, et al. (1990). *J. Virol.* 64: 2416–2420.
Henson et al., *Ann. Neurol.*, 36: 714–721, 1994.
Herbst et al., *Cancer Res.*, 54: 3111–3114, 1994.
Hermonat and Muzycska, *Proc. Nat. Acad. Sci. USA*, 81: 6466–6470, 1984.
Hersdorffer et al., *DNA Cell Biol.*, 9: 713–723, 1990.
Herz and Gerard, *Proc. Nat'l Acad. Sci. USA*, 90: 2812–2816, 1993.
Holland et al., *Virology*, 101: 10–18, 1980.
Honess and Roizman, *J. Virol.*, 14: 8–19, 1974.
Honess and Roizman, *J. Virol.*, 16: 1308–1326, 1975.
Hoon et al., J. Urol., 150(6):2013–2018, 1993.
Horwich, et al., *J. Virol.*, 64: 642–650, 1990.
Hunt et al., *Proc. Natl. Acad. Sci. USA*, 83: 3786–3790, 1986.
Hunter, *Cell*, 64–249–270, 1991.
Huyghe et al., *Hum. Gene Ther.*, 6: 1403–1416, 1995.
Innis et al., *PCR Protocols*, Academic Press, Inc., San Diego Calif., 1990.
Ittmann, *Cancer Res.*, 56: 2143–2147, 1996.
James et al., *Cancer Res.*, 48: 5546–5551, 1988.
Johnson P A, et al. (1992). *J. Virol.* 66: 2952–2965.
Johnson et al., Peptide Turn Mimetics" IN: *Biotechnology And Pharmacy*, Pezzuto et al., eds., Chapman and Hall, New York, 1993.
Joki et al., *Human Gene Ther.*, 6: 1507–1513, 1995.
Jones and Shenk, Cell, 13:181–188, 1978.
Jones, et al., *Genes Chromosomes Cancer*, 9: 2, 119–123, 1994.
Kageyama et al., *J. Biol. Chem.*, 262(5): 2345–2351, 1987.
Kamb et al., *Science*, 264: 436–440, 1984.
Kaneda Y, et al. (1989). *J. Biol. Chem.* 264: 12126–12129.
Kandt et al., *Nature Genet.*, 2: 3741, 1992.
Kaneda et al., *Science*, 243: 375–378, 1989.
Karlbom et al., *Hum. Genet.*, 92: 169–174, 1993.
Karlsson et al., *EMBO J.*, 5: 2377–2385, 1986.
Kato et al., *J. Biol. Chem.*, 266: 3361–3364,1991.
Kearns et al., *Gene Ther.*, 3: 748–755, 1996.
Kim and Cook, *Proc. Natl. Acad. Sci. USA*, 84: 8788–8792, 1987.
Kimmelman et al., *Genomics* 34: 250–254, 1996.
Klein et al., *Nature*, 327: 70–73, 1987.
Kock et al., *Int. J. Cancer*, 67: 808–815, 1996.
Kohler and Milstein, *Eur. J. Immunol.*, 6: 511–519, 1976.
Kohler and Milstein, *Nature*, 256: 495497, 1975.
Kok et al., *Cancer Res.* 54: 4183–4187, 1994.
Komiya et al., *Genes Chromo. Cancer* 17: 245–253, 1996.
Korhonen, et al., Blood, 86(5): 1828–1835, 1995.
Kotin and Berns, *Virol.*, 170: 460–467, 1989.
Kotin et al., *Genomics*, 10: 831–834, 1991.
Kotin et al., *Proc. Natl. Acad. Sci. USA*, 87: 2211–2215, 1990.
Kruglyak, et al., *Am. J. Hum. Genet.*, 58: 347–1363, 1996.
Kwoh et al., *Proc. Nat. Acad. Sci. USA*, 86: 1173, 1989.
Kyte and Doolittle, *J. Mol. Biol.*, 157, 1: 105–132, 1982.
Lathrop, et al., *Proc. Natl. Acad. Sci. USA*, 81: 3443–3446, 1984.
Le Gal La Salle et al., *Science*, 259: 988–990, 1993.
Lee et al., *Science*, 235: 1394–1399, 1987.
Lee J E, et al. (1995). *Science* 268: 836–844.
Levin et al., In: *Cancer: Principles & Practice of Oncology*, 4th ed., DeVita et al, eds., J.B. Lippincott Co., Philadelphia, 1993.
Levrero et al., *Gene*, 101: 195–202, 1991.
Li and Sun, *Cancer Res.*, 57: 2124–2129, 1997.
Li et al., *Science*, 275: 1943–1947, 1997.
Liaw et al., *Nature Genet.*, 16: 64–67, 1997.
Lim C S, et al. (1991). *Circulation* 83: 2007–2011.
Lloyd and Dennis, *Ann. Intern. Med.*, 58: 136–142, 1963.
Lobe and Nagy, *Bioessays*, 20: 200–208, 1998.
Macejak and Sarnow, *Nature*, 353: 90–94, 1991.
Madzak C, et al. (1992). *J. Gen. Virol.* 73: 1533–1536.
Manipulating the Mouse Embryo: A Laboratory Manual, 2nd ed., Hogan et al., eds., Cold Spring Harbor Laboratory Press, 1994.
Mann R and Baltimore D (1985). *J. Virol.* 54: 401–407.
Mann et al., *Cell*, 33: 153–159, 1983.
Margolskee R F (1992). *Curr. Top. Microbiol. Immunol.* 158: 67–95.
Markowitz et al., *J. Virol.*, 62: 1120–1124, 1988.
Merrifield, *Science*, 232: 341–347, 1986.
Michel and Westhof, *J. Mol. Biol.*, 216: 585–610, 1990.
Miki et al., *Science*, 266: 66–71, 1994.
Miller et al., PCT Application WO 89/06700
Miller A D, et al. (1988). *J. Virol.* 62: 4337–4345.
Miller A D (1992). *Curr. Top. Microbiol. Immunol.* 158: 1–24.
Miller A D, et al. (1985). *Mol. Cell. Biol.* 5: 431–437.
Mizukami et al., *Virology*, 217: 124–130, 1996.

Morita et al., *Cancer Res.*, 51: 5817–5820, 1991.
Moss B (1992). *Curr. Top. Microbiol. Immunol.* 158: 25–38.
Moss B (1996). *Proc. Natl. Acad. Sci. USA* 93: 11341–11348.
Mulligan, *Science*, 260: 926–932, 1993.
Murakami et al., *Cancer Res.*, 56: 2157–2160, 1996.
Muzyczka N (1992). *Curr. Top. Microbiol. Immunol.* 158: 97–129.
Myers, EP 0273085
Nabel E G, et al. (1990). *Science* 249: 1285–1288.
Nabel (1992). *Hum. Gene Ther.* 3: 399–410.
Nakamura et al., In: Handbook of Experimental Immunology (4th Ed.), Weir, E., Herzenberg, L. A., Blackwell, C., Herzenberg, L. (eds). Vol. 1, Chapter 27, Blackwell Scientific Publ., Oxford, 1987.
Naldini L, et al. (1996). *Science* 272: 263–267.
Nelen et al., *Nature Genet.*, 13: 114–116, 1996.
Nicolas and Rubenstein, In: *Vectors: A survey of molecular cloning vectors and their uses*, Rodriguez and Denhardt (eds.), Stoneham: Butterworth, pp. 493–513, 1988.
Nicolau and Sene, *Biochem. Biophys. Acta*, 721: 185–190, 1982.
Nicolau et al., *Methods Enzymol.*, 149: 157–176, 1987.
Nihei et al., *Genes Chromosom. Cancer*, 14: 112–119, 1995.
Nishi et al., *Oncogene*, 6: 1555–1559, 1991.
Nyberg-Hoffman et al., *Nat. Medicine*, 7: 808–811, 1997.
Ohara et al., *Proc. Nat'l Acad. Sci. USA*, 86: 5673–5677, 1989.
Ohi S, et al. (1990). *Gene* 89: 279–282.
Olivierio et al., *EMBO J.*, 6(7): 1905–1912, 1987.
Osterrieder and Wolf, *Rev. Sci. Tech.* 17: 351–364, 1998.
Ostrove et al., *Virology*, 113: 532–533, 1981.
Page K A, et al. (1990). *J. Virol.* 64: 5270–5276.
Pape and Kim, *Mol. Cell. Biol.*, 974–982, 1989.
Paskind et al., *Virology*, 67: 242–248, 1975.
PCT/US87/00880
PCT/US89/01025
PCT published application WO 93/07282
PCT Published Application WO 97/02048
Pease et al., *Proc. Natl. Acad. Sci. USA*, 91: 5022–5026, 1994.
Peiffer et al., *Cancer Res.*, 55: 1922–1926, 1995.
Pelletier and Sonenberg, *Nature*, 334: 320–325, 1988.
Pellicer A, et al. (1980). *Science* 209: 1414–1422.
Perales et al., *Proc. Natl. Acad. Sci.* 91: 4086–4090, 1994.
Pershouse et al., *Cancer Res.* 53: 5043–5050, 1993.
Petersen et al., *Brit. J. Cancer* 75: 79–86, 1997.
Petropoulos C J, et al. (1992). *J. Virol.* 66: 3391–3397.
Pignon et al., *Hum. Mutat.*, 3: 126–132, 1994.
Poli and Cortese, *Proc. Natl. Acad. Sci. USA*, 86: 8202–8206, 1989.
Ponnazhagan et al., *Hum. Gene Ther.*, 8:275–284, 1997a.
Ponnazhagan et al., *J. Gen. Virol.*, 77: 1111–1122, 1996.
Post et al., *Cell*, 24: 555–565, 1981.
Potter et al., *Proc. Nat. Acad. Sci. USA*, 81: 7161–7165, 1984.
Prowse and Baumann, *Mol Cell Biol*, 8(1): 42–51, 1988.
Quantin B, et al. (1992). *Proc. Natl. Acad. Sci. USA* 89: 2581–2584.
Racher et al., *Biotechnology Techniques*, 9: 169–174, 1995.
Ragot et al., *Nature*, 361: 647–650, 1993.
Ransom et al., *Genes Chromosom. Cancer* 5: 357–374, 1992.
Rasheed et al., *Genes Chromo. Cancer*, 5: 75–82, 1992.
Rasheed et al., *Oncogene*, 11: 2243–2246, 1995.
Reinhold-Hurek and Shub, *Nature*, 357: 173–176, 1992.
Remington's Pharmaceutical Sciences, 15th ed., pp. 1035–1038 and 1570–1580.
Rempel et al., *Cancer Res.*, 53: 2386–2392, 1993.
Renan, *Radiother. Oncol.*, 19: 197–218, 1990.
Rich et al., *Hum. Gene Ther.*, 4: 461–476, 1993.
Ridgeway, In: *Vectors: A survey of molecular cloning vectors and their uses*, Rodriguez R L, Denhardt D T, ed., Stoneham:Butterworth, pp. 467–492, 1988.
Rippe et al., *Mol. Cell Biol.*, 10: 689–695, 1990.
Ritland et al., *Genes. Chromo. Cancer*, 12: 277–282, 1995.
Rosenfeld et al., In vivo transfer of the human cystic fibrosis transmembrane conductance regulator gene to the airway epithelium. *Cell*, 68: 143–155, 1992.
Rosenfeld et al., *Science*, 252: 431–434, 1991.
Rosenfeld M A, et al. (1992). *Cell* 68: 143–155.
Roux et al., *Proc. Nat'l Acad. Sci. USA*, 86: 9079–9083, 1989.
Rubio et al., *Cancer Res.*, 54: 45–47, 1994.
Russell D and Hirata R (1998). *Nature Genetics* 18: 323–328.
Russell and Rubinstein, In: *Pathology of Tumors of the Nervous System*, 5th ed., Williams and Wilkins, eds., pp. 82–219, 1989.
Sambrook et al., In: *Molecular Cloning: A Laboratory Manual*, 2d Ed., Cold Spring Harbor Laboratory Press, Cold Spring Harbor, N.Y., 1989.
Samulski et al, *EMBO J.*, 10: 3941–3950, 1991.
Sanchez et al., *Proc. Natl. Acad. Sci. USA*, pp. 2551–2556, 1996.
Sanchez, et al., *Mil Med.*, 160: 8, 416–419, 1995.
Saras and Heldin C H, *Trends Biochem Sci.* 21, 12 455–458, 1996.
Sarver et al., *Science*, 247: 1222–1225, 1990.
Scanlon et al., *Proc Natl Acad Sci USA*, 88: 10591–10595, 1991.
Scheck and Coons, *Cancer Res.*, 53: 5605–5609, 1993.
Schneider G, et al. (1998). *Nature Genetics* 18: 180–183.
Shabram et al., "*Hum. Gene Ther.*, 8: 453–465, 1997.
Shastry, *Experientia* 51: 1028–1039,1995.
Shastry, *Mol. Cell. Biochem.* 181: 163–179, 1998.
Shimada T, et al. (1991). *J. Clin. Invest.* 88: 1043–1047.
Shoemaker et al., *Nature Genetics* 14: 450–456, 1996.
Smith and Moss, *Gene*, 25: 21–28, 1983.
Songyang et al., *J Biol. Chem.* 270(44): 26029–26032, 1995
Sonoda et al., *Cancer Res.*, 55: 2166–2168, 1995.
Sorge J, et al. (1984). *Mol. Cell. Biol.* 4: 1730–1737.
Spargo C A, et al. (1996). *Mol. Cell. Probes* 10: 247–256.
Speigelman, et al., *J. Biol. Chem.*, 264(3), 1811–1815, 1989.
Spruck, et al., *Nature,:* 370: 6486, 183–184, see also Comment in Nature 1994 Jul. 21, 370, 6486: 180 1994
Srivastava et al., *J. Virol.*, 45: 555–564, 1983.
Starink, et al., *Clin. Genet.*, 29: 222–233, 1986.
Steck and Saya, *Curr. Opin Oncol.*, 3: 3, 476–484, 1991.
Steck et al., *Genes Chromosom. Cancer* 712: 255–261, 1995.
Steck et al., *Nature Genet.*, 15: 356–362, 1997.
Stewart and Young, Solid Phase Peptide Synthesis, 2d. ed., Pierce Chemical Co., 1984.
Stewart M J, et al. (1992). *Hum. Gene Ther.* 3: 267–275.
Stratford-Perricaudet and Perricaudet, Gene transfer into animals: the promise of adenovirus In: *Human Gene Transfer*, O. Cohen-Haguenauer et al., eds., John Libbey Eurotext, France, pp. 51–61, 1991.
Stratford-Perricaudet et al., *Hum. Gene. Ther.*, 1: 241–256, 1990.
Tam et al., *J. Am. Chem. Soc.*, 105: 6442, 1983.
Tavtigian et al., *Nature Genet.*, 12: 333–337, 1996.

Temin, In: *Gene Transfer*, Kucherlapati (ed.), New York: Plenum Press, pp. 149–188, 1986.
Teng et al., "*Cancer Res.,* 57: 5221–5225, 1997.
Tonks and Neel, *Cell* 87: 3, 365–368, see also Comment in Cell 1996 Nov. 1, 87, 3: 361–4, 1996.
Top et al., *J. Infect. Dis.,* 124: 155–160, 1971.
Trybus et al., *Cancer Res.* 56: 2263–2267, 1996.
Tur-Kaspa et al., *Mol. Cell Biol.,* 6: 716–718, 1986.
U.S. Pat. No. 4,554,101
U.S. Pat. No. 4,683,195
U.S. Pat. No. 4,683,202
U.S. Pat. No. 4,800,159
U.S. Pat. No. 4,873,191, Wagner and Hoppe
U.S. Pat. No. 4,883,750
U.S. Pat. No. 5,252,479
U.S. Pat. No. 5,270,184
U.S. Pat. No. 5,279,721
U.S. Pat. No. 5,354,855
U.S. Pat. No. 5,409,818
U.S. Pat. No. 5,436,146
U.S. Pat. No. 5,455,166
U.S. Pat. No. 5,672,344
U.S. Pat. No. 5,691,198
U.S. Pat. No. 5,747,469
U.S. Pat. No. 5,753,500.
Varmus et al., *Cell,* 25: 23–36, 1981.
Vogelstein, et al., *Genes Chromosomes Cancer,* 2: 2, 159–162, 1990.
von Deimling, et al., *J Neurosurg,* 77: 2, 295–301, 1992.
von Deimling et al., *Int. J. Cancer,* 57: 676–680, 1994.
Voullaire et al., *Am. J. Hum. Genet.,* 52: 1153–1163, 1993.
Wagner and Hoppe U.S. Pat. No. 4,873,191
Wagner et al., *Proc. Natl. Acad. Sci.* 87, 9: 3410–3414, 1990.
Wagner E, et al. (1991). *Proc. Natl. Acad. Sci. USA* 88: 4255–4259.
Wagner et al., *Science,* 260: 1510–1513, 1993.
Walker et al., *Proc. Natl. Acad. Sci. USA,* 89: 392–396, 1992a.
Walker G T, et al., (1992b). *Nucl. Acids Res.* 20: 1691–1696.
Walther and Stein, *J. Mol. Med.,* 74: 379–392, 1996.
Walton, et al., *Surgery,* 99: 82–86, 1986.
Wang C Y and Huang L (1989). *Biochemistry* 28: 9508–9514.
Wang et al., *Cancer Res.,* 57: 351–354, 1997.
Weary, et al., *Arch. Dermatol.,* 106: 682–690, 1972.
Wei et al., *Cancer Res.* 56: 1487–1494, 1996.
Weinberg, *Biochemistry,* 28: 8263–8269, 1989.
Wilkinson G W and Akrigg A (1992). *Nucleic Acids Res.* 20: 2233–2239.
Wills et al., *Human Gene Therapy,* 5: 1079–1088, 1994.
Wilson et al., *Mol. Cell. Biol.,* 6181–6191, 1990.
Wolff J A, et al. (1990). *Science* 247: 1465–1468.
Wolff J A, et al. (1991). *BioTechniques* 11: 474–485.
Wong et al., *Gene,* 10: 87–94, 1980.
Wong et al., *Proc. Natl. Acad. Sci. USA,* 84: 6899–6903, 1987.
Wooster et al., *Nature,* 378: 789–792, 1995.
Wu and Wu, *Biochemistry,* 27: 887–892, 1988.
Wu and Wu, *J. Biol. Chem.,* 262: 4429–4432, 1987.
Wu and Wu, *Adv. Drug Delivery Rev.,* 12: 159–167, 1993.
Wu et al., *Genomics,* 4: 560, 1989.
Wu C H, et al. (1989). *J. Biol. Chem.* 264: 16985–16987.
Wu G Y, et al. (1991). *J. Biol. Chem.* 266: 14338–14342.
Yamaguchi et al., *Proc. Natl. Acad. Sci. USA,* 91: 484–488, 1994.
Yang et al., *Proc. Natl. Acad. Sci. USA,* 87: 9568–9572, 1990.
Zechner et al., *Mol. Cell. Biol.,* 2394–2401, 1988.
Zelenin et al., *FEBS Lett.,* 280: 94–96, 1991.
Zenke M, et al. (1990). *Proc. Natl. Acad. Sci. USA* 87: 3655–3659.

What is claimed is:

1. A method for determining the presence or absence of PTEN in a cancer cell comprising the steps of (i) obtaining a sample from a subject; and (ii) determining the expression of a functional PTEN in said cancer cell of said sample wherein said PTEN encodes a protein having the amino acid sequence of SEQ ID NO:2 and said cancer cell is selected from the group consisting of a lung cancer cell, an endometrial cancer cell, a colon cancer cell, a head and neck cancer cell, and a breast cancer cell.

2. The method of claim 1 wherein said cancer is lung cancer.

3. The method of claim 1 wherein said cancer is endometrial cancer.

4. The method of claim 1 wherein said cancer is colon cancer.

5. The method of claim 1 wherein said cancer is head and neck cancer.

6. The method of claim 1 wherein said cancer is breast cancer.

7. The method of claim 1 wherein said sample is a tissue or fluid sample.

8. The method of claim 1 wherein said determining comprises assaying for a PTEN nucleic acid in said sample.

9. The method of claim 8 further comprising subjecting the sample to conditions suitable to amplify said PTEN nucleic acid.

10. The method of claim 1 wherein said determining comprises sequencing, wild-type oligonucleotide hybridization, or RNase protection.

11. The method of claim 10 wherein said wild-type oligonucleotide hybridization comprises configuring the wild-type oligonucleotide in an array, chip or wafer.

12. The method of claim 1 wherein said determining step comprises determining the DNA sequence of PTEN in said sample.

13. The method of claim 1 wherein said determining step comprises contacting said sample with an antibody that binds immunologically to PTEN.

14. The method of claim 13 wherein said antibody is a monoclonal antibody.

15. The method of claim 1 wherein said determining step comprises immunohistochemical detection of PTEN in tissue sections.

16. The method of claim 15 wherein said tissue section is from a tumor sample.

17. The method of claim 16 wherein said tumor sample is selected from the group consisting of lung tumor, colon tumor, breast tumor, endometrial tumor, and head and neck tumor.

18. The method of claim 12 wherein said tumor sample is a lung cancer tumor sample.

19. The method of claim 12 wherein said tumor sample is a colon cancer tumor sample.

20. The method of claim 12 wherein said tumor sample is a breast cancer tumor sample.

21. The method of claim 12 wherein said tumor sample is an endometrial cancer tumor sample.

22. The method of claim 12 wherein said tumor sample is a head and neck cancer tumor sample.

23. The method of claim 1 wherein said determining step comprises comparing the expression of PTEN in a cancer sample with the expression of PTEN in a non-cancer sample.

24. A method for determining the presence or absence of PTEN in a cancer cell comprising the steps of (i) obtaining a sample from a subject; (ii) contacting said sample with an antibody that binds immunologically to PTEN; and (iii) detecting the binding of said antibody to said PTEN wherein said PTEN encodes a protein having the amino acid sequence of SEQ ID NO:2 and said cancer cell is selected from the group consisting of a lung cancer cell, an endometrial cancer cell, a colon cancer cell, a head and neck cancer cell, and a breast cancer cell.

25. The method of claim 24 wherein said cancer is lung cancer.

26. The method of claim 24 wherein said cancer is endometrial cancer.

27. The method of claim 24 wherein said cancer is colon cancer.

28. The method of claim 24 wherein said cancer is head and neck cancer.

29. The method of claim 24 wherein said cancer is breast cancer.

30. The method of claim 24 wherein said sample is a tissue or fluid sample.

31. The method of claim 24 wherein said antibody is a monoclonal antibody.

32. The method of claim 31 wherein said monoclonal antibody comprises a detectable label.

33. The method of claim 32 wherein said detectable label is selected from a fluorescent label, a chemiluminescent label, a radiolabel, or an enzyme label.

34. A method for determining if both alleles of PTEN in a sample are altered comprising
   (a) obtaining a sample from a patient;
   (b) determining if the sample has lost one allele of PTEN; and
   (c) determining if the sample has an alteration in the other allele of PTEN,
wherein if said sample has lost one allele and the other allele is altered then both alleles of PTEN are altered wherein said PTEN encodes a protein having the amino acid sequence of SEQ ID NO:2 and said sample is selected from the group consisting of a lung cancer sample, an endometrial cancer sample, a colon cancer sample, a head and neck cancer sample, and a breast cancer sample.

35. The method of claim 34 wherein said sample comprises a cancer cell.

36. The method of claim 34 wherein said sample is a tumor specimen.

37. The method of claim 34 wherein said tumor specimen is a lung cancer tumor specimen.

38. The method of claim 34 wherein said tumor specimen is an endometrial cancer tumor specimen.

39. The method of claim 34 wherein said tumor specimen is a colon cancer tumor specimen.

40. The method of claim 34 wherein said tumor specimen is a head and neck cancer tumor specimen.

41. The method of claim 34 wherein said tumor specimen is a breast cancer tumor specimen.

42. A method for detecting a PTEN alteration comprising the steps of (i)obtaining a sample from a subject and (ii) determining if PTEN is altered in said sample, wherein said PTEN encodes a protein having the amino acid sequence of SEQ ID NO:2, wherein said sample is selected from the group consisting of a lung cancer sample, an endometrial sample, a colon cancer sample, a head and neck cancer sample and a breast cancer sample, and wherein said PTEN alterations are selected from the group consisting of a deletion, an insertion, a frameshift and a point mutation.

43. The method of claim 42 wherein said tumor sample is a lung cancer tumor sample.

44. The method of claim 42 wherein said tumor sample is an endometrial cancer tumor sample.

45. The method of claim 42 wherein said tumor sample is a colon cancer tumor sample.

46. The method of claim 42 wherein said tumor sample is a head and neck cancer tumor sample.

47. The method of claim 42 wherein said tumor sample is a breast cancer tumor sample.

48. The method of claim 42 wherein said determining comprises sequencing, mutant-oligonucleotide hybridization, SSCP™ or RNase protection.

49. The method of claim 48 wherein said mutant-oligonucleotide hybridization comprises configuring the wild-type oligonucleotide in an array, chip or wafer.

* * * * *

UNITED STATES PATENT AND TRADEMARK OFFICE
CERTIFICATE OF CORRECTION

PATENT NO. : 7,129,040 B2 Page 1 of 1
APPLICATION NO. : 10/979642
DATED : October 31, 2006
INVENTOR(S) : Steck et al.

It is certified that error appears in the above-identified patent and that said Letters Patent is hereby corrected as shown below:

Title page Item [56]
Other Publications (page 2), Col. 2, line 37, please add --WILSON et al., "2.2 Mb of contiguous nucleotide sequence from chromosome III of *C. elegans*", *Nature*, 1994, 368:32-38.--

Signed and Sealed this

Tenth Day of July, 2007

JON W. DUDAS
*Director of the United States Patent and Trademark Office*